(12) United States Patent
Shalek et al.

(10) Patent No.: US 11,844,800 B2
(45) Date of Patent: Dec. 19, 2023

(54) METHODS AND COMPOSITIONS FOR PREDICTING AND PREVENTING RELAPSE OF ACUTE LYMPHOBLASTIC LEUKEMIA

(71) Applicants: Massachusetts Institute of Technology, Cambridge, MA (US); Dana-Farber Cancer Institute, Inc., Boston, MA (US)

(72) Inventors: Alexander K. Shalek, Cambridge, MA (US); Peter Winter, Cambridge, MA (US); David Weinstock, Boston, MA (US); Mark Murakami, Boston, MA (US); Scott Manalis, Cambridge, MA (US); Andrew Navia, Cambridge, MA (US); Jennyfer Galvez-Reyes, Cambridge, MA (US)

(73) Assignees: Massachusetts Institute of Technology, Cambridge, MA (US); Dana-Farber Cancer Institute, Inc., Boston, MA (US)

( * ) Notice: Subject to any disclaimer, the term of this patent is extended or adjusted under 35 U.S.C. 154(b) by 397 days.

(21) Appl. No.: 17/085,650

(22) Filed: Oct. 30, 2020

(65) Prior Publication Data

US 2021/0128557 A1 May 6, 2021

Related U.S. Application Data

(60) Provisional application No. 62/928,091, filed on Oct. 30, 2019.

(51) Int. Cl.
| | |
|---|---|
| *A61K 31/506* | (2006.01) |
| *C07K 16/28* | (2006.01) |
| *A61K 45/06* | (2006.01) |
| *A61K 31/403* | (2006.01) |
| *A61K 31/427* | (2006.01) |
| *A61K 31/5383* | (2006.01) |
| *A61K 31/44* | (2006.01) |
| *A61P 35/02* | (2006.01) |

(52) U.S. Cl.
CPC .......... *A61K 31/506* (2013.01); *A61K 31/403* (2013.01); *A61K 31/427* (2013.01); *A61K 31/44* (2013.01); *A61K 31/5383* (2013.01); *A61K 45/06* (2013.01); *A61P 35/02* (2018.01); *C07K 16/2887* (2013.01)

(58) Field of Classification Search
None
See application file for complete search history.

(56) References Cited

U.S. PATENT DOCUMENTS

| | | |
|---|---|---|
| 5,143,854 A | 9/1992 | Fodor et al. |
| 5,288,644 A | 2/1994 | Beavis et al. |
| 5,324,633 A | 6/1994 | Fodor et al. |
| 5,427,930 A | 6/1995 | Birkenmeyer et al. |
| 5,432,049 A | 7/1995 | Fischer et al. |
| 5,470,710 A | 11/1995 | Weiss et al. |
| 5,492,806 A | 2/1996 | Drmanac et al. |
| 5,503,980 A | 4/1996 | Cantor |
| 5,510,270 A | 4/1996 | Fodor et al. |
| 5,525,464 A | 6/1996 | Drmanac et al. |
| 5,547,839 A | 8/1996 | Dower et al. |
| 5,580,732 A | 12/1996 | Grossman et al. |
| 5,661,028 A | 8/1997 | Foote |
| 5,686,281 A | 11/1997 | Roberts |
| 5,744,311 A | 4/1998 | Fraiser et al. |
| 5,800,992 A | 9/1998 | Fodor et al. |
| 5,843,728 A | 12/1998 | Seed et al. |
| 5,851,828 A | 12/1998 | Seed et al. |
| 5,906,936 A | 5/1999 | Eshhar et al. |
| 5,912,170 A | 6/1999 | Seed et al. |
| 5,912,172 A | 6/1999 | Eshhar et al. |
| 6,004,811 A | 12/1999 | Seed et al. |
| 6,025,134 A | 2/2000 | Sooknanan |
| 6,027,889 A | 2/2000 | Barany et al. |
| 6,033,881 A | 3/2000 | Himmler et al. |
| 6,284,240 B1 | 9/2001 | Seed et al. |
| 6,392,013 B1 | 5/2002 | Seed et al. |

(Continued)

FOREIGN PATENT DOCUMENTS

| | | |
|---|---|---|
| EP | 0 320 308 A2 | 6/1989 |
| EP | 0 785 280 A2 | 7/1997 |

(Continued)

OTHER PUBLICATIONS

Cetin et al., Nature Commuications (2017), 8(1), pp. 1-12.*
Abdelmoez, et al., "SINC-Seq: Correlation of Transient Gene Expressions Between Nucleus and Cytoplasm Reflects Single-Cell Physiology", Genome Biology, vol. 19, Article No. 66, Jun. 6, 2018, 11 pages.
Abudayyeh, et al., "C2C2 is a Single-Component Programmable RNA-Guided RNA-Targeting CRISPR Effector", Science, vol. 353, No. 6299, Aug. 5, 2016, 23 pages.
Abudayyeh, et al., "RNA Targeting with CRISPR-Cas13a", Nature, vol. 550, No. 7675, Oct. 12, 2017, 30 pages.

(Continued)

*Primary Examiner* — Brian J Davis
(74) *Attorney, Agent, or Firm* — F. Brent Nix, Esq.; Johnson, Marcou, Isaacs & Nix, LLC; Carin R. Miller, Esq.

(57) ABSTRACT

Described in exemplary embodiments herein are methods, compositions, and kits for diagnosing, prognosing, monitoring, treating and/or preventing a hemopoietic malignancy and/or relapse thereof in a subject. In some embodiments, the methods can include determining an average cellular mass of cells in a sample from the subject and/or detecting one or more molecular signatures in one or more of the cells. In some embodiments, treatment includes administering one or more BCR-ABL tyrosine kinase inhibitors or a pharmaceutical formulation thereof, one or more pre-BCR signaling pathway inhibitors or a pharmaceutical formulation thereof, one or more p38 MAPK inhibitors or a pharmaceutical formulation thereof; or any combination thereof.

11 Claims, 20 Drawing Sheets

Specification includes a Sequence Listing.

(56) References Cited

U.S. PATENT DOCUMENTS

| | | |
|---|---|---|
| 6,410,014 B1 | 6/2002 | Seed et al. |
| 6,479,626 B1 | 11/2002 | Kim et al. |
| 6,489,458 B2 | 12/2002 | Hackett et al. |
| 6,534,261 B1 | 3/2003 | Cox et al. |
| 6,607,882 B1 | 8/2003 | Cox et al. |
| 6,746,838 B1 | 6/2004 | Choo et al. |
| 6,753,162 B1 | 6/2004 | Seed et al. |
| 6,794,136 B1 | 9/2004 | Eisenberg et al. |
| 6,824,978 B1 | 11/2004 | Cox et al. |
| 6,866,997 B1 | 3/2005 | Choo et al. |
| 6,903,185 B2 | 6/2005 | Kim et al. |
| 6,933,113 B2 | 8/2005 | Case |
| 6,979,539 B2 | 12/2005 | Cox et al. |
| 7,013,219 B2 | 3/2006 | Case et al. |
| 7,030,215 B2 | 4/2006 | Liu et al. |
| 7,148,203 B2 | 12/2006 | Hackett et al. |
| 7,160,682 B2 | 1/2007 | Hackett et al. |
| 7,220,719 B2 | 5/2007 | Case et al. |
| 7,241,573 B2 | 7/2007 | Choo et al. |
| 7,241,574 B2 | 7/2007 | Choo et al. |
| 7,446,190 B2 | 11/2008 | Sadelain et al. |
| 7,585,849 B2 | 9/2009 | Liu et al. |
| 7,595,376 B2 | 9/2009 | Kim et al. |
| 7,741,465 B1 | 6/2010 | Eshhar et al. |
| 7,985,739 B2 | 7/2011 | Kay et al. |
| 8,021,867 B2 | 9/2011 | Smith et al. |
| 8,088,379 B2 | 1/2012 | Robbins et al. |
| 8,119,361 B2 | 2/2012 | Smith et al. |
| 8,119,381 B2 | 2/2012 | Smith et al. |
| 8,124,369 B2 | 2/2012 | Smith et al. |
| 8,129,134 B2 | 3/2012 | Smith et al. |
| 8,133,697 B2 | 3/2012 | Smith et al. |
| 8,163,514 B2 | 4/2012 | Smith et al. |
| 8,211,422 B2 | 7/2012 | Eshhar et al. |
| 8,227,432 B2 | 7/2012 | Hackett et al. |
| 8,399,645 B2 | 3/2013 | Campana et al. |
| 8,697,854 B2 | 4/2014 | Schendel et al. |
| 8,906,682 B2 | 12/2014 | June et al. |
| 8,911,993 B2 | 12/2014 | June et al. |
| 8,916,381 B1 | 12/2014 | June et al. |
| 8,975,071 B1 | 3/2015 | June et al. |
| 9,027,388 B2 | 5/2015 | Babcock et al. |
| 9,101,584 B2 | 8/2015 | June et al. |
| 9,102,760 B2 | 8/2015 | June et al. |
| 9,102,761 B2 | 8/2015 | June et al. |
| 9,134,294 B2 | 9/2015 | Manalis et al. |
| 9,181,527 B2 | 11/2015 | Sentman |
| 9,233,125 B2 | 1/2016 | Davila et al. |
| 9,790,490 B2 | 10/2017 | Zhang et al. |
| 11,021,740 B2 | 6/2021 | Abudayyeh et al. |
| 2010/0104509 A1 | 4/2010 | King et al. |
| 2013/0071414 A1 | 3/2013 | Dotti et al. |
| 2015/0368342 A1 | 12/2015 | Wu et al. |
| 2015/0368360 A1 | 12/2015 | Liang et al. |
| 2016/0046724 A1 | 2/2016 | Brogdon et al. |
| 2016/0129109 A1 | 5/2016 | Davila et al. |
| 2016/0166613 A1 | 6/2016 | Spencer et al. |
| 2016/0175359 A1 | 6/2016 | Spencer et al. |
| 2017/0283504 A1 | 10/2017 | Wiltzius et al. |
| 2018/0085444 A1 | 3/2018 | Morgan et al. |
| 2018/0274017 A1 | 9/2018 | Abudayyeh et al. |
| 2018/0298445 A1 | 10/2018 | Abudayyeh et al. |
| 2018/0305773 A1 | 10/2018 | Abudayyeh et al. |

FOREIGN PATENT DOCUMENTS

| | | |
|---|---|---|
| EP | 0 373 203 B2 | 2/2007 |
| WO | 90/01069 A1 | 2/1990 |
| WO | 92/15322 A1 | 9/1992 |
| WO | 95/21265 A1 | 8/1995 |
| WO | 96/31622 A1 | 10/1996 |
| WO | 97/10365 A1 | 3/1997 |
| WO | 97/27317 A1 | 7/1997 |
| WO | 03/020763 A2 | 3/2003 |
| WO | 2004/033685 A1 | 4/2004 |
| WO | 2004/044004 A2 | 5/2004 |
| WO | 2004/074322 A1 | 9/2004 |
| WO | 2005/113595 A2 | 12/2005 |
| WO | 2005/114215 A2 | 12/2005 |
| WO | 2006/000830 A2 | 1/2006 |
| WO | 2006/125962 A2 | 11/2006 |
| WO | 2008/038002 A2 | 4/2008 |
| WO | 2008/039818 A2 | 4/2008 |
| WO | 2011/146862 A1 | 11/2011 |
| WO | 2012/058460 A2 | 5/2012 |
| WO | 2012/079000 A1 | 6/2012 |
| WO | 2013/039889 A1 | 3/2013 |
| WO | 2013/040371 A2 | 3/2013 |
| WO | 2013/044225 A1 | 3/2013 |
| WO | 2013/154760 A1 | 10/2013 |
| WO | 2013/166321 A1 | 11/2013 |
| WO | 2013/176915 A1 | 11/2013 |
| WO | 2014/011987 A1 | 1/2014 |
| WO | 2014/018863 A1 | 1/2014 |
| WO | 2014/059173 A2 | 4/2014 |
| WO | 2014/083173 A1 | 6/2014 |
| WO | 2014/093622 A2 | 6/2014 |
| WO | 2014/134165 A1 | 9/2014 |
| WO | 2014/172606 A1 | 10/2014 |
| WO | 2014/184744 A1 | 11/2014 |
| WO | 2014/191128 A1 | 12/2014 |
| WO | 2014/204725 A1 | 12/2014 |
| WO | 2014/210353 A2 | 12/2014 |
| WO | 2015/057834 A1 | 4/2015 |
| WO | 2015/057852 A1 | 4/2015 |
| WO | 2015/158671 A1 | 10/2015 |
| WO | 2015/187528 A1 | 12/2015 |
| WO | 2016/000304 A1 | 1/2016 |
| WO | 2016/011210 A2 | 1/2016 |
| WO | 2016/014789 A2 | 1/2016 |
| WO | 2016/040476 A1 | 3/2016 |
| WO | 2016/070061 A1 | 5/2016 |
| WO | 2016/106236 A1 | 6/2016 |
| WO | 2016/149661 A1 | 9/2016 |
| WO | 2016/168584 A1 | 10/2016 |
| WO | 2016/205711 A1 | 12/2016 |
| WO | 2016/205749 A1 | 12/2016 |
| WO | 2016/205764 A1 | 12/2016 |
| WO | 2017/070605 A1 | 4/2017 |
| WO | 2017/106657 A1 | 6/2017 |
| WO | 2017/127807 A1 | 7/2017 |
| WO | 2017/164936 A1 | 9/2017 |
| WO | 2017/184768 A1 | 10/2017 |
| WO | 2017/184786 A1 | 10/2017 |
| WO | 2017/189308 A1 | 11/2017 |
| WO | 2017/211900 A1 | 12/2017 |
| WO | 2017/219027 A1 | 12/2017 |
| WO | 2018/028647 A1 | 2/2018 |
| WO | 2018/035387 A1 | 2/2018 |
| WO | 2018/035388 A1 | 2/2018 |
| WO | 2018/107129 A1 | 6/2018 |
| WO | 2018/170333 A1 | 9/2018 |
| WO | 2018/170340 A1 | 9/2018 |
| WO | 2018/191388 A1 | 10/2018 |
| WO | 2018/191553 A1 | 10/2018 |
| WO | 2018/194963 A1 | 10/2018 |
| WO | 2018/213708 A1 | 11/2018 |
| WO | 2018/213726 A1 | 11/2018 |
| WO | 2019/005866 A1 | 1/2019 |
| WO | 2019/005884 A1 | 1/2019 |
| WO | 2019/005886 A1 | 1/2019 |
| WO | 2019/018423 A1 | 1/2019 |
| WO | 2019/051318 A1 | 3/2019 |
| WO | 2019/060746 A1 | 3/2019 |
| WO | 2019/071048 A1 | 4/2019 |
| WO | 2019/071051 A1 | 4/2019 |
| WO | 2019/084063 A1 | 5/2019 |
| WO | 2019/126577 A2 | 6/2019 |
| WO | 2019/126709 A1 | 6/2019 |
| WO | 2019/126716 A1 | 6/2019 |
| WO | 2019/126762 A2 | 6/2019 |
| WO | 2019/126774 A1 | 6/2019 |

(56) References Cited

FOREIGN PATENT DOCUMENTS

| WO | 2020/033601 A1 | 2/2020 |
|----|----------------|--------|
| WO | 2020/131862 A1 | 6/2020 |

OTHER PUBLICATIONS

Acevedo, et al., "Mutational and Fitness Landscapes of an RNA Virus Revealed Through Population Sequencing", Nature, vol. 505, Jan. 30, 2014, 686-690.
Ackerman, et al., "Massively Multiplexed Nucleic Acid Detection with Cas13", Nature, vol. 582, Apr. 29, 2020, 277-282.
Agathanggelou, et al., "Expression of Immune Regulatory Molecules in Epstein-Barr Virus-Associated Nasopharyngeal Carcinomas with Prominent Lymphoid Stroma. Evidence for a Functional Interaction between Epithelial Tumor Cells and Infiltrating Lymphoid Cells", The American Journal of Pathology, vol. 147, No. 4, Oct. 1995, 1152-1160.
Angermueller, et al., "Parallel Single-Cell Sequencing Links Transcriptional and Epigenetic Heterogeneity", Nature Methods, vol. 13, No. 3, Mar. 2016, 11 pages.
Anzalone, et al., "Search-and-replace Genome Editing Without Double-Strand Breaks or Donor DNA", Nature, vol. 576, No. 7785, Dec. 5, 2019, 149-157.
Appleby, et al., "New Technologies for Ultra-High Throughput Genotyping in Plants", Methods in Molecular Biology, vol. 513, 2009, 19-39.
Assarsson, et al., "Homogenous 96-plex PEA Immunoassay Exhibiting High Sensitivity, Specificity, and Excellent Scalability", PLoS One, vol. 9, Issue 4, Apr. 2014, 11 pages.
Atschul, et al., "Basic Local Alignment Search Tool", Journal of Molecular Biology, vol. 215, 1990, 403-410.
Baba, et al., "Highly Enhanced Expression of CD70 on Human T-Lymphotropic Virus Type 1-Carrying T-Cell Lines and Adult T-Cell Leukemia Cells", Journal of Virology, vol. 82, No. 8, Apr. 2008, 3843-3852.
Baerwald, et al., "Rapid and Accurate Species Identification for Ecological Studies and Monitoring Using CRISPR-Based Sherlock", Molecular Ecology Resources, vol. 20, 2020, 961-970.
Barnes, et al., "Deployable CRISPR-Cas13a Diagnostic Tools to Detect and Report Ebola and Lassa Virus Cases in Real-time", Nature Communications, vol. 11, No. 4131, Aug. 17, 2020, 10 pages.
Bartel, et al., "MicroRNAs: Genomics,Biogenesis, Mechanism, and Function", Cell, vol. 116, No. 2, Jan. 23, 2004, 281-297.
Batista, et al., "Detecting Pathogens with Zinc-Finger, TALE and CRISPR-Based Programmable Nucleic Acid Binding Proteins", Journal of Microbiological Methods, vol. 152, Aug. 2, 2018, 98-104.
Becht, et al., "Dimensionality Reduction for Visualizing Single-Cell Data Using UMAP", Nature Biotechnology, vol. 37, No. 1, Jan. 2019, 38-44.
Becht, et al., "Evaluation of UMAP as an Alternative to T-SNE for Single-Cell Data", bioRxiv, Apr. 10, 2018, 10 pages.
Bell, et al., "Live Cell Genomics: RNA Exon-Specific RNA-Binding Protein Isolation", Methods in Molecular Biology, vol. 1324, 2015, 457-468.
Berdeja, et al., "Durable Clinical Responses in Heavily Pretreated Patients with Relapsed/Refractory Multiple Myeloma: Updated Results from a Multicenter Study of bb2121 Anti-Bcma Car T Cell Therapy", Blood, vol. 130, Dec. 7, 2017, 16 pages.
Besser, et al., "Clinical Responses in a Phase II Study Using Adoptive Transfer of Short-term Cultured Tumor Infiltration Lymphocytes in Metastatic Melanoma Patients", Clinical Cancer Research, vol. 16, No. 9, May 1, 2010, 2646-2655.
Bhargava, et al., "Quantitative Transcriptomics Using Designed Primer-based Amplification", Scientific Reports, vol. 3, No. 1740, Apr. 29, 2013, 9 pages.
Bian, et al., "Single-cell Multiomics Sequencing and Analyses of Human Colorectal Cancer", Science, vol. 362, Issue 6418, Nov. 30, 2018, 4 pages.

Binan, et al., "Live Single-Cell Laser Tag", Nature Communications, vol. 7, No. 11636, May 20, 2016, 8 pages.
Binz, et al., "Engineering Novel Binding Proteins from Nonimmunoglobulin Domains", Nature Biotechnology, vol. 23, No. 10, Oct. 6, 2005, 1257-1268.
Biswas, et al., "CRISPRTarget: Bioinformatic Prediction and Analysis of crRNA Targets", RNA Biology, vol. 10, No. 5, May 2013, 817-827.
Boch, et al., "Breaking the Code of DNA Binding Specificity of TAL-type III Effectors", Science, vol. 326, No. 5959, Dec. 11, 2009, 1509-1512.
Bondeson, et al., "Targeted Protein Degradation by Small Molecules", Annual Review of Pharmacology and Toxicology, vol. 57, Jan. 6, 2017, 107-123.
Boni, et al., "Adoptive Transfer of Allogeneic Tumor-Specific T Cells Mediates Effective Regression of Large Tumors Across Major Histocompatibility Barriers", Blood, vol. 112, No. 12, Dec. 1, 2008, 4746-4754.
Budde, et al., "Combining a CD20 Chimeric Antigen Receptor and an Inducible Caspase 9 Suicide Switch to Improve the Efficacy and Safety of T Cell Adoptive Immunotherapy for Lymphoma", PLOS One, vol. 8, Issue 12, Dec. 17, 2013, 10 pages.
Buenrostro, et al., "Single-Cell Chromatin Accessibility Reveals Principles of Regulatory Variation", Nature, vol. 523, Jun. 17, 2015, 486-490.
Byun, et al., "BCR-ABL Translocation as a Favorable Prognostic Factor in Elderly Patients With Acute Lymphoblastic Leukemia in the Era of Potent Tyrosine Kinase Inhibitors", Haematologica, vol. 102, No. 5, May 2017, 187-190.
Cao, et al., "Comprehensive Single Cell Transcriptional Profiling of a Multicellular Organism by Combinatorial Indexing", Available at: BioRxiv https://doi.org/10.1101/104844, Feb. 2, 2017, 35 pages.
Cao, et al., "Comprehensive Single-cell Transcriptional Profiling of a Multicellular Organism", Science, vol. 357, No. 6352, Aug. 18, 2017, 661-667.
Cao, et al., "Joint Profiling of Chromatin Accessibility and Gene Expression in Thousands of Single Cells", Science, vol. 361, No. 6409, Sep. 28, 2018, 14 pages.
Carlson, et al., "MIPSTR: A Method for Multiplex Genotyping of Germline and Somatic STR Variation Across Many Individuals", Genome Research, vol. 25, 2015, 750-761.
Casasent, et al., "Multiclonal Invasion in Breast Tumors Identified by Topographic Single Cell Sequencing", Cell, vol. 172, Jan. 11, 2018, 205-217.e12.
Chahlavi, et al., "Glioblastomas Induce T-Lymphocyte Death by Two Distinct Pathways Involving Gangliosides and CD70", Cancer Research, vol. 65, No. 12, Jun. 15, 2005, 5428-5438.
Chen, et al., "Single Cell RNA-Seq Technologies and Related Computational Data Analysis", Frontiers in Genetics, vol. 10, No. 317, Apr. 5, 2019, 13 pages.
Chen, et al., "Single-Cell Whole-Genome analyses by Linear Amplification via Transposon Insertion", Science, vol. 356, Issue 6334, Apr. 14, 2017, 189-194.
Chubiz, et al., "FREQ-Seq: A Rapid, Cost-Effective, Sequencing-Based Method to Determine Allele Frequencies Directly from Mixed Populations", PLOS One, vol. 7, No. 10, Oct. 2012, 9 pages.
Clark, et al., "ScNMT-seq Enables Joint Profiling of Chromatin Accessibility DNA Methylation and Transcription in Single Cells", Nature Communications, vol. 9, Article No. 781, 2018, 9 pages.
Cokus, et al., "Shotgun Bisulphite Sequencing of the Arabidopsis Genome Reveals DNA Methylation Patterning", Nature, vol. 452, No. 7184, Mar. 13, 2008, 215-219.
Cooper, et al., "T-Cell Clones can be Rendered Specific for CD19: Toward the Selective Augmentation of the Graft-Versus-B-Lineage Leukemia Effect", Blood, vol. 101, No. 4, Feb. 15, 2003, 1637-1644.
Cox, et al., "RNA Editing with CRISPR-Cas13", Science, vol. 358, No. 6366, Nov. 24, 2017, 1019-1027.
Cusanovich, et al., "Multiplex Single Cell Profiling of Chromatin Accessibility by Combinatorial Cellular Indexing", Science, vol. 348, No. 6237, May 22, 2015, 11 pages.

(56) References Cited

OTHER PUBLICATIONS

Dar, et al., "Allogeneic Chimeric Antigen Receptor T Cells Targeting B Cell Maturation Antigen", American Association for Cancer Research (AACR) Annual meeting Poster, 2018, 1 page.
Datlinger, et al., "Pooled CRISPR Screening with Single-cell Transcriptome Readout", Nature Methods, vol. 14, No. 3, Mar. 2017, 297-301.
De Puig, et al., "Point-of-Care Devices to Detect Zika and Other Emerging Viruses", Annual Review of Biomedical Engineering, vol. 22, 2020, 371-386.
De Vis, et al., "Flow Cytometric Immunophenotyping of Leukemia Cells in Clotted Blood and Bone Marrow", Journal of Immunological Methods, vol. 137, 1991, 193-197.
Dean, et al., "Rapid Amplification of Plasmid and Phage DNA Using Phi29 DNA Polymerase and Multiply-Primed Rolling Circle Amplification", Genome Research, vol. 11, 2001, 1095-1099.
Deng, et al., "Targeted Bisulfite Sequencing Reveals Changes in DNA Methylation Associated With Nuclear Reprogramming", Nature Biotechnology, vol. 27, Mar. 29, 2009, 353-360.
Dey, et al., "Integrated Genome and Transcriptome Sequencing of the Same Cell", Nature Biotechnolgy, vol. 33, No. 3, Mar. 2015, 285-289.
Di Stasi, et al., "Inducible Apoptosis as a Safety Switch for Adoptive Cell Therapy", The New England Journal of Medicine, vol. 365, No. 18, Nov. 3, 2011, 1673-1683.
Doench, et al., "Optimized sgRNA Design to Maximize Activity and Minimize Off-Target Effects of CRISPR-Cas9", Nature Biotechnology, vol. 34, No. 2, Feb. 2016, 184-191.
Dong, et al., "Accurate Identification of Single-Nucleotide Variants in Whole Genome-Amplified Single Cells", Nature Methods, Mar. 20, 2017, 6 pages.
Down, et al., "A Bayesian Deconvolution Strategy for Immunoprecipitation-based DNA Methylome Analysis", Nature Biotechnology, vol. 26, No. 7, Jun. 2008, 779-785.
Doyon, et al., "Enhancing Zinc-Finger-Nuclease Activity With Improved Obligate Heterodimeric Architectures", Nature Methods, vol. 8, No. 1, Jan. 2011, 74-79.
Dudley, et al., "Adoptive Cell Transfer Therapy Following Non-Myeloablative but Lymphodepleting Chemotherapy for the Treatment of Patients With Refractory Metastatic Melanoma", Journal of Clinical Oncology, vol. 23, No. 10, Apr. 1, 2005, 2346-2357.
Dudley, et al., "Cancer Regression and Autoimmunity in Patients After Clonal Repopulation with Antitumor Lymphocytes", Science, vol. 298, No. 55494, Oct. 25, 2002, 850-854.
Esvelt, et al., "Orthogonal Cas9 Proteins for RNA-Guided Gene Regulation and Editing", Nature Methods, vol. 10, No. 11, Nov. 2013, 19 pages.
Eyquem, et al., "Targeting a CAR to the TRAC Locus with CRISPR/Cas9 Enhances Tumour Rejection", Nature, vol. 543, No. 7643, Mar. 2, 2017, 113-117.
Fan, et al., "Combinatorial Labeling of Single Cells for Gene Expression Cytometry", Science, vol. 347, Issue 6222, Feb. 6, 2015, 10 pages.
Fan, et al., "Single-Cell RNA-Seq Transcriptome Analysis of Linear and Circular RNAs in Mouse Preimplantation Embryos", Genome Biology, vol. 16, No. 148, 2015, 17 pages.
Fisher, et al., "Transforming Activities of the Nup98-kmt2a Fusion Gene Associated With Myelodysplasia and Acute Myeloid Leukemia", Haematologica, vol. 105, No. 7, Jul. 2020, 1857-1867.
Fox, et al., "Applications of Ultra-high-Throughput Sequencing", Methods of Molecular Biology, vol. 553, 2009, 79-108.
Frei, et al., "Highly Multiplexed Simultaneous Detection of RNAs and Proteins in Single Cells", Nature Methods, vol. 13, No. 3, Mar. 2016, 269-275.
Friedman, et al., "Effective Targeting of Multiple B-Cell Maturation Antigen-Expressing Hematological Malignances by Anti-B-Cell Maturation Antigen Chimeric Antigen Receptor T Cells", Human Gene Therapy, vol. 29, No. 5, May 2018, 585-601.
Gao, et al., "Engineered Cpf1 Enzymes with Altered PAM Specificities", BioRxiv, doi: http://dx.doi.org/10.1101/091611, Dec. 4, 2016, 17 pages.
Gao, et al., "Nanogrid Single-Nucleus RNA Sequencing Reveals Phenotypic Diversity in Breast Cancer", Nature Communications, vol. 8, No. 228, 2017, 12 pages.
Gaudelli, et al., "Programmable Base Editing of A•T to G•C in Genomic DNA without DNA Cleavage", Nature, vol. 551, No. 7681, Nov. 23, 2017, 464-471.
Gebauer, et al., "Engineered Protein Scaffolds as next-Generation Antibody Therapeutics", Current Opinion in Chemical Biology, vol. 13, No. 3, Jun. 2009, 245-255.
Geiss, et al., "Direct Multiplexed Measurement of Gene Expression with Color-coded Probe Pairs", Nature Biotechnology, vol. 26, No. 3, Mar. 2008, 317-325.
Georgiadis, et al., "Long Terminal Repeat CRISPR-CAR-Coupled "Universal" T Cells Mediate Potent Anti-leukemic Effects", Molecular Therapy, vol. 26, No. 5, May 2, 2018, 1215-1227.
Gierahn, et al., "Seq-Well: Portable, Low-Cost RNA Sequencing of Single Cells at High Throughput", Nature Methods, vol. 14, No. 4, Apr. 2017, 8 pages.
Gill, et al., "Biopharmaceutical Drug Discovery Using Novel Protein Scaffolds", Current Opinion in Biotechnology, vol. 17, No. 6, Dec. 2006, 653-658.
Gleditzsch, et al., "PAM Identification by CRISPR-Cas Effector Complexes: Diversified Mechanisms and Structures", RNA Biology, vol. 16. No. 4, 2019, 504-517.
Godin, et al., "Using Buoyant Mass to Measure the Growth of Single Cells", Nature Methods, vol. 7, May 2010, 387-390.
Gole, et al., "Massively Parallel Polymerase Cloning and Genome Sequencing of Single Cells Using Nanoliter Microwells", Nature Biotechnology, vol. 31, No. 12, Nov. 10, 2013, 1126-1132.
Gootenberg, et al., "Multiplexed and Portable Nucleic Acid Detection Platform with Cas13, Cas12a, and Csm6", Science, vol. 360, No. 6387, XP055664590, Apr. 27, 2018, 439-444.
Gootenberg, et al., "Nucleic Acid Detection with CRISPR-Cas13a/C2c2", Science, vol. 356, No. 6336, Apr. 28, 2017, 438-442.
Greco, et al., "Improving the Safety of Cell Therapy with the TK-Suicide Gene", Frontiers in Pharmacology, vol. 6, No. 95, May 5, 2015, 13 pages.
Grindberg, et al., "RNA-sequencing from Single Nuclei", Proceedings of the National Academy of Sciences of the United States of America, vol. 110, No. 49, Dec. 3, 2013, 19802-19807.
Grissa, et al., "CRISPRFinder: A Web Tool to Identify Clustered Regularly Interspaced Short Palindromic Repeats", Nucleic Acids Research, vol. 35, 2007, W52-W57.
Gu, et al., "Preparation of Reduced Representation Bisulfite Sequencing Libraries for Genome-scale DNA Methylation Profiling", Nature Protocols, vol. 6, Mar. 18, 2011, 468-481.
Guan, et al., "Detection, Isolation, and Stimulation of Quiescent Primitive Leukemic Progenitor Cells From Patients With Acute Myeloid Leukemia (AML)", Blood, vol. 101, No. 8, Apr. 15, 2003, 3142-3149.
Habib, et al., "Div-Seq: Single-Nucleus RNA-Seq Reveals Dynamics of Rare Adult Newborn Neurons", Science, vol. 353, No. 6302, Aug. 26, 2016, 925-928.
Habib, et al., "Massively Parallel Single-Nucleus RNA-seq with DroNc-seq", Nature Methods, vol. 14, No. 10, Oct. 2017, 955-958.
Han, et al., "Mapping the Mouse Cell Atlas by Microwell-Seq", Cell, vol. 172, Feb. 22, 2018, 1091-1107.e17.
Han, et al., "SIDR: Simultaneous Isolation and Parallel Sequencing of Genomic DNA and Total RNA from Single Cells", Genome Research, vol. 28, 2018, 75-87.
Harris, et al., "Comparison of Sequencing-based Methods to Profile DNA Methylation and Identification of Monoallelic Epigenetic Modifications", Nature Biotechnology, vol. 28, Sep. 19, 2010, 1097-1105.
Hashimshony, et al., "CEL-Seq: Single-Cell RNA-Seq by Multiplexed Linear Amplification", Cell Reports, vol. 2, No. 3, Sep. 27, 2012, 666-673.
Hayashi, et al., "Single-Cell Full-Length Total RNA Sequencing Uncovers Dynamics of Recursive Splicing and Enhancer RNAs", Nature Communications, vol. 9, 2018, 16 pages.

(56) References Cited

OTHER PUBLICATIONS

Head, et al., "Library Construction for Next-Generation Sequencing: Overviews and Challenges", Biotechniques, vol. 56, No. 2, Feb. 1, 2014, 61-77.
Hiatt, et al., "Single Molecule Molecular Inversion Probes for Targeted, High-Accuracy Detection of Low-Frequency Variation", Genome Research, vol. 23, 2013, 843-854.
Hinrichs, et al., "Exploiting the Curative Potential of Adoptive T-Cell Therapy for Cancer", Special Issue: Adoptive Immunotherapy for Cancer, vol. 257, Issue 1, Dec. 13, 2013, 56-71.
Hou, et al., "Single-Cell Triple Omics Sequencing Reveals Genetic, Epigenetic and Transcriptomic Heterogeneity in Hepatocellular Carcinomas", Cell Research, vol. 26, No. 3, Mar. 2016, 16 pages.
Houot, et al., "T-Cell-Based Immunotherapy: Adoptive Cell Transfer and Checkpoint Inhibition", Cancer Immunology Research, vol. 3, No. 10, Oct. 2015, 1115-1122.
Hsu, et al., "Development and Applications of CRISPR-Cas9 for Genome Engineering", Cell, Leading Edge Review, vol. 157,, Jun. 5, 2014, 1262-1278.
Hughes, et al., "Highly Efficient, Massively-Parallel Single-Cell RNA-Seq Reveals Cellular States and Molecular Features of Human Skin Pathology", Retrieved as on Jun. 10, 2020:—https://doi.org/10.1101/689273, Jul. 2, 2019, 51 pages.
Hughes, et al., "Transfer of a TCR Gene Derived from a Patient with a Marked Antitumor Response Conveys Highly Active T-Cell Effector Functions", Human Gene Therapy, vol. 16, No. 4, Apr. 2005, 457-472.
Hunter, et al., "High Levels of Soluble Immunoregulatory Receptors in Patients with WaldenströM's Macroglobulinemia", Blood, vol. 104, Issue 11, Nov. 16, 2004, 4881.
Imashimizu, et al., "Direct Assessment of Transcription Fidelity by High-Resolution RNA Sequencing", Nucleic Acids Research, vol. 41, No. 19, Aug. 7, 2013, 9090-9104.
Imelfort, et al., "De Novo Sequencing of Plant Genomes Using Second-Generation Technologies", Briefings in Bioinformatics, vol. 10, No. 6, May 4, 2009., 609-618.
Irving, et al., "Engineering Chimeric Antigen Receptor T-Cells for Racing in Solid Tumors: Don't Forget the Fuel", Frontiers in Immunology, vol. 8, Article 267, Apr. 3, 2017, 19 pages.
Islam, et al., "Characterization of the Single-Cell Transcriptional Landscape by Highly Multiplex RNA-Seq", Genome Research, vol. 21, No. 7, Jul. 2011, 1160-1167.
Iwasaki, et al., "Sprint: A Cas13a-based Platform for Detection of Small Molecules", Nucleic Acids Research, vol. 48, No. 17, Aug. 14, 2020, 16 pages.
Jabbour, et al., "Chronic Myeloid Leukemia: 2018 Update on Diagnosis, Therapy and Monitoring", American Journal of Hematology, vol. 93, No. 3, Mar. 2018, 442-459.
Jain, et al., "BCR-ABL1-like B-Acute Lymphoblastic Leukemia/Lymphoma: A Comprehensive Review", Archives of Pathology & Laboratory Medicine, vol. 144, No. 2, Feb. 2020, 150-155.
Jaitin, et al., "Massively Parallel Single-Cell RNA-Seq for Marker-Free Decomposition of Tissues into Cell Types", Science, vol. 343, Issue 6172, Feb. 2014, 776-779.
Jensen, et al., "Design and Implementation of Adoptive Therapy with Chimeric Antigen Receptor-Modified T Cells", Immunological Reviews, vol. 257, No. 1, Jan. 2014, 127-144.
Jiang, et al., "CRISPR-Assisted Editing of Bacterial Genomes", Nature Biotechnology, vol. 31, No. 3, Mar. 2013, 233-239.
Jin, et al., "CD70, A Novel Target of Car T-Cell Therapy for Gliomas", Neuro-Oncology, vol. 20, No. 1, Jan. 10, 2018, 55-65.
Johnson, et al., "Gene Therapy with Human and Mouse T-Cell Receptors Mediates Cancer Regression and Targets Normal Tissues Expressing Cognate Antigen", Blood, vol. 114, No. 3, Jul. 16, 2009, 535-546.
Joung, et al., "Point-of-Care Testing for COVID-19 Using Sherlock Diagnostics", medRxiv, May 8, 2020, 21 pages.
Junker, et al., "CD70: A New Tumor Specific Biomarker for Renal Cell Carcinoma", The Journal of Urology, vol. 173, Issue 6, Jun. 2005, 2150-2153.
Kalisky, et al., "Genomic Analysis at the Single-Cell Level", Annual Review of Genetics, vol. 45, 2011, 431-445.
Kalisky, et al., "Single-Cell Genomics", Nature Methods, vol. 8, No. 4, Apr. 2011, 311-314.
Kalos, et al., "T Cells with Chimeric Antigen Receptors Have Potent Antitumor Effects and Can Establish Memory in Patients with Advanced Leukemia", Science Translational Medicine, vol. 3, No. 95, Aug. 10, 2011, 21 pages.
Kamta, et al., "Advancing Cancer Therapy with Present and Emerging Immuno-Oncology Approaches", Frontiers in Oncology, vol. 7, Article 64, Apr. 18, 2017, 15 pages.
Kim, et al., "Chimeric Restriction Endonuclease", Proceedings of the National Academy of Sciences, vol. 91, No. 3, 1994, 883-887.
Kim, et al., "Hybrid Restriction Enzymes: Zinc Finger Fusions to Fok I Cleavage Domain", Proceedings of the National Academy of Sciences, vol. 93 No. 3, Feb. 1996, 1156-1160.
Kimmerling, et al., "Linking Single-cell Measurements of Mass, Growth Rate, and Gene Expression", Genome Biology, vol. 19, No. 207, Nov. 27, 2018, 13 pages.
Kinde, et al., "Detection and Quantification of Rare Mutations with Massively Parallel Sequencing", Proceedings of the National Academy of Sciences of the United States of America, vol. 108, No. 23, Jun. 7, 2011, 9530-9535.
Kivioja, et al., "Counting Absolute Number of Molecules Using Unique Molecular Identifiers", Nature Methods, vol. 9, 2012, 72-74.
Klein, et al., "Droplet Barcoding for Single-Cell Transcriptomics Applied to Embryonic Stem Cells", Cell, vol. 161, No. 5, May 21, 2015, 1187-1201.
Kleinstiver, et al., "Engineered Crispr-Cas9 Nucleases with Altered Pam Specificities", Nature, vol. 523, No. 7561, Jul. 23, 2015, 481-485.
Klompe, et al., "Transposon-encoded CRISPR-Cas Systems Direct RNA-guided DNA Integration", Nature, vol. 571, Jul. 11, 2019, 219-225.
Kochenderfer, et al., "Construction and Preclinical Evaluation of an Anti-CD19 Chimeric Antigen Receptor", Journal of Immunotherapy, vol. 32, No. 7, Sep. 2009, 689-702.
Koide, et al., "Monobodies: Antibody Mimics Based on the Scaffold of the Fibronectin Type III Domain", Methods in Molecular Biology, vol. 352, 2007, 95-109.
Kolmar, Harald, "Alternative Binding Proteins: Biological Activity and Therapeutic Potential of Cystine-knot Miniproteins", The FEBS Journal, vol. 275, No. 11, Jun. 2008, 2684-2690.
Komor, et al., "Programmable Editing of a Target Base in Genomic DNA without Double-Stranded DNA Cleavage", Nature, vol. 533, No. 7603, May 19, 2016, 420-424.
Koonin, et al., "Origins and Evolution of CRISPR-Cas Systems", Philosophical Transactions of the Royal Society of London, vol. 374, No. 1772, May 13, 2019, 16 pages.
Kooreman, et al., "Autologous iPSC-Based Vaccines Elicit Antitumor Responses In Vivo", Cell Stem Cell, vol. 22, No. 4, Apr. 5, 2018, 34 pages.
Lagos-Quintana, et al., "Identification of Novel Genes Coding for Small Expressed RNAs", Science, vol. 294, No. 5543, Oct. 26, 2001, 853-858.
Lagos-Quintana, et al., "Identification of Tissue-Specific MicroRNAs from Mouse", Current Biology, vol. 12, No. 9, Apr. 30, 2002, 735-739.
Lagos-Quintana, et al., "New MicroRNAs from Mouse and Human", RNA, vol. 9, No. 2, Feb. 9, 2003, 175-179.
Lai, et al., "Modular PROTAC Design for the Degradation of Oncogenic BCR-ABL", Angewandte Chemie International Edition, vol. 55, No. 2, Jan. 11, 2016, 807-810.
Lake, et al., "Integrative Single-Cell Analysis of Transcriptional and Epigenetic States in the Human Adult Brain", Nature Biotechnology, vol. 36, No. 1, Dec. 11, 2017, 70-80.
Lan, et al., "Droplet Barcoding for Massively Parallel Single-Molecule Deep Sequencing", Nature Communications, vol. 7, Article No. 11784, Jun. 29, 2016, 10 pages.
Lau, et al., "An Abundant Class of Tiny RNAs with Probable Regulatory Roles in Caenorhabditis Elegans", Science, vol. 294, No. 5543, Oct. 26, 2001, 858-862.

(56) References Cited

OTHER PUBLICATIONS

Lee, et al., "An Extensive Class of Small RNAs in Caenorhabditis Elegans", Science, vol. 294, No. 5543, Oct. 26, 2001, 862-864.
Legut, et al., "CRISPR-Mediated TCR Replacement Generates Superior Anticancer Transgenic T Cells", Blood, vol. 131, No. 3, Jan. 18, 2018, 311-322.
Lens, et al., "Demethylation of the Same Promoter Sequence Increases CD70 Expression in Lupus T Cells and T Cells Treated with Lupus-Inducing Drugs", The Journal of Immunology, vol. 174, 2005, 6212-6219.
Leung, et al., "SNES: Single Nucleus Exome Sequencing", Genome Biology, vol. 16, 2015, 9 pages.
Li, et al., "Adoptive Cell Therapy With CD4+ T Helper 1 Cells and CD8+ Cytotoxic T Cells Enhances Complete Rejection of an Established Tumour, Leading to Generation of Endogenous Memory Responses to Non-Targeted Tumour Epitopes", Clinical & Translational Immunology, vol. 6, No. 10, Oct. 20, 2017, 10 pages.
Li, et al., "Base Editing With a Cpf1-cytidine Deaminase Fusion", Nature Biotechnology, vol. 36, Apr. 2018, 324-327.
Li, et al., "Single-Cell Multi-Omics Sequencing of Human Early Embryos", Nature Cell Biology,, Jun. 18, 2018, 15 pages.
Lim, et al., "The MicroRNAs of Caenorhabditis Eegans", Genes & Development, vol. 17, No. 8, Apr. 15, 2003, 991-1008.
Lim, et al., "Vertebrate MicroRNA Genes", Science, vol. 299, No. 5612, Mar. 7, 2003, 1540 page.
Lino, et al., "Delivering CRISPR: A Review of the Challenges and Approaches", Drug Delivery, vol. 25, No. 1, May 7, 2018, 1234-1257.
Lister, et al., "Human DNA Methylomes at Base Resolution Show Widespread Epigenomic Differences", Nature, vol. 462, No. 7271, Nov. 19, 2009, 315-322.
Liu, et al., "Engineering Cell Signaling Using Tunable CRISPR-Cpf1-based Transcription Factors", Nature Communications, vol. 8, No. 2095, Dec. 13, 2017, 8 pages.
Lovatt, et al., "Transcriptome in Vivo Analysis (TIVA) of Spatially Defined Single Cells in Intact Live Mouse and Human Brain Tissue", Nature Methods, vol. 11, No. 2, Jul. 2014, 22 pages.
Luo, et al., "Single Cell Methylomes Identify Neuronal Subtypes and Regulatory Elements in Mammalian Cortex", Science, vol. 357, No. 6351, Aug. 11, 2017, 600-604.
Macaulay, et al., "G&T-seq: Parallel Sequencing of Single-Cell Genomes and Transcriptomes", Nature Methods, vol. 12, No. 6, Jun. 2015, 519-522.
Macosko, et al., "Highly Parallel Genome-Wide Expression Profiling of Individual Cells Using Nanoliter Droplets", Cell, vol. 161, No. 5, May 21, 2015, 1202-1214.
Maher, et al., "Human T-Lymphocyte Cytotoxicity and Proliferation directed by a Single Chimeric TCRzeta /CD28 Receptor", Nature Biotechnology, vol. 20, No. 1, Jan. 2002, 70-75.
Makarova, et al., "Classification and Nomenclature of CRISPR-Cas Systems: Where from Here?", The CRISPR Journal, vol. 1, No. 5, 2018, 325-336.
Makarova, et al., "Evolutionary Classification of CRISPR-Cas Systems: A Burst of Class 2 and Derived Variants", Nature Reviews Microbiology, vol. 18, Feb. 2020, 67-83.
Margulies, et al., "Genome Sequencing in Open Microfabricated High Density Picoliter Reactors", Nature, vol. 437, No. 7057, Sep. 15, 2005, 376-380.
Marraffini, et al., "Self Vs. Non-Self Discrimination During CRISPR RNA-Directed Immunity", Nature, vol. 463, No. 7280, Jan. 28, 2010, 568-571.
Martin-Orozco, et al., "T Helper 17 Cells Promote Cytotoxic T Cell Activation in Tumor Immunity", Immunity, vol. 31, Nov. 20, 2009, 787-798.
Maus, et al., "Adoptive Immunotherapy for Cancer or Viruses", Annual Review of Immunology, vol. 32, Jan. 9, 2014, 189-225.
Mcginnis, et al., "MULTI-Seq: Sample Multiplexing for Single-Cell RNA Sequencing Using Lipid-Tagged Indices", Nature Methods, vol. 16, Jul. 2019, 619-626.

Meissner, et al., "Reduced Representation Bisulfite Sequencing for Comparative High-resolution DNA Methylation Analysis", Nucleic Acids Research, vol. 33, No. 18, Oct. 13, 2005, 5868-5877.
Michlits, et al., "CRISPR-UMI: single-cell lineage tracing of pooled CRISPR-Cas9 screens", Nature Methods, vol. 14, No. 12, Oct. 16, 2017, 1191-1197.
Mimitou, et al., "Expanding the CITE-seq tool-kit: Detection of proteins, transcriptomes, clonotypes and CRISPR perturbations with multiplexing, in a single assays", vol. 16, No. 5, 2019, 409-412.
Mojica, et al., "Short Motif Sequences Determine the Targets of the Prokaryotic CRISPR Defence System", Microbiology, vol. 155, 2009, 733-740.
Mooijman, et al., "Single-Cell 5hmC Sequencing Reveals Chromosome-Wide Cell-to-Cell Variability and Enables Lineage Reconstruction", Nature Biotechnology, vol. 34, No. 8, Jun. 27, 2016, 852-856.
Morgan, et al., "Cancer Regression in Patients After Transfer of Genetically Engineered Lymphocytes", Science, vol. 314, No. 5796, Oct. 6, 2006, 126-129.
Morozova, et al., "Applications of next-generation sequencing technologies in functional genomics", Genomics, vol. 92, Aug. 24, 2008., 255-264.
Moscou, et al., "A Simple Cipher Governs DNA Recognition by TAL Effectors", Science, vol. 326, Issue 5959, Dec. 11, 2009, 1501 page.
Mouhieddine, et al., "Immunotherapy in Multiple Myeloma: The Era of CAR T Cell Therapy", The Hematologist, vol. 15, Issue 3, May-Jun. 2018.
Mulqueen, et al., "Highly Scalable Generation of DNA Methylation Profiles in Single Cells", Nature Biotechnology, vol. 36, No. 5, Jun. 2018, 16 pages.
Muranski, et al., "Tumor-Specific Th17-Polarized Cells Eradicate Large Established Melanoma", Blood, vol. 112, No. 2, Jul. 15, 2008, 362-373.
Myhrvold, et al., "Field-Deployable Viral Diagnostics Using CRISPR-Cas13", Science, vol. 360, Apr. 27, 2018, 444-448.
Myllykangas, et al., "Efficient Targeted Resequencing of Human Germline and Cancer Genomes by Oligonucleotide-Selective Sequencing", Nature Biotechnology, vol. 29, No. 11, Oct. 23, 2011, 1024-1027.
Nagano, et al., "Single-cell Hi-C Reveals Cell-to-cell Variability in Chromosome Structure", Nature, vol. 502, Oct. 3, 2013, 59-64.
Nishida, et al., "Targeted Nucleotide Editing Using Hybrid Prokaryotic and Vertebrate Adaptive Immune Systems", Science, vol. 353, Issue. 6305, Sep. 16, 2016, 35 pages.
Nishimasu, et al., "Crystal Structure of Cas9 in Complex with Guide RNA and Target DNA", Cell, vol. 156, Feb. 27, 2014, 935-949.
Nixon, et al., "Engineered Protein Inhibitors of Proteases", Current Opinion in Drug Discovery and Development, vol. 9, No. 2, Apr. 2006 , 261-268—Abstract only.
Nygren, Per-Ake, "Alternative Binding Proteins: Affibody Binding Proteins Developed From a Small Three-helix Bundle Scaffold", The FEBS Journal, vol. 275, No. 11, Jun. 2008, 2668-2676.
Padalia, et al., "Allogeneic CRISPR Engineered Anti-CD70 CAR-T Cells Demonstrate Potent Preclinical Activity Against Both Solid and Hematological Cancer Cells", American Association for Cancer Research (AACR) Annual meeting Poster, 2018, 1 page.
Park, et al., "CD70 as a Target for Chimeric Antigen Receptor T Cells in Head and Neck Squamous Cell Carcinoma", Oral Oncology, vol. 78, Mar. 2018, 145-150.
Patchsung, et al., "Clinical Validation of a Cas13-based Assay for the Detection of SARS-COV-2 RNA", Nature Biomedical Engineering, vol. 4, Aug. 26, 2020, 1140-1149.
Pattanayak, et al., "High-Throughput Profiling of Off-Target DNA Cleavage Reveals RNA-Programmed Cas9 Nuclease Specificity", Nature biotechnology, vol. 31, No. 9, Sep. 2013, 839-843.
Peters, et al., "Recruitment of CRISPR-Cas Systems by Tn7-Like Transposons", Proceedings of the National Academy of Sciences, vol. 114, No. 35, 2017, E7358-E7366.
Petri, et al., "Sherlock and DETECTR Open a New Frontier in Molecular Diagnostics", The CRISPR Journal, vol. 1, No. 3, 2018, 209-211.

(56) References Cited

OTHER PUBLICATIONS

Picelli, et al., "Full-Length RNA-Seq from Single Cells using Smart-seq2", Nature Protocols, vol. 9, No. 1, Jan. 2, 2014, 171-181.
Picelli, et al., "Smart-Seq2 for Sensitive Full-Length Transcriptome Profiling in Single Cells", Nature methods, vol. 10, Issue 11, Sep. 22, 2013, 5 pages.
Plessy, et al., "Linking Promoters to Functional Transcripts in Small Samples with nanoCAGE and CAGEscan", Nature Methods, vol. 7, No. 7, Jun. 13, 2010, 528-534.
Poirot, et al., "Multiplex Genome-Edited T-cell Manufacturing Platform for "Off-the-Shelf" Adoptive T-cell Immunotherapies", Cancer Research, vol. 75, Issue 18, Sep. 2015, 3853-3864.
Puram, et al., "Single-Cell Transcriptomic Analysis of Primary and Metastatic Tumor Ecosystems in Head and Neck Cancer", Cell, vol. 171, No. 7, Dec. 14, 2017, 1611-1624.
Qasim, et al., "Molecular Remission of Infant B-ALL after Infusion of Universal Talen Gene-Edited CAR T Cells", Science Translational Medicine, vol. 9, No. 374, Jan. 25, 2017, 8 pages.
Qui, et al., "Mutation Detection Using Surveyor Nuclease", Biotechniques, vol. 36, No. 4, 2004, 702-707.
Rajasagi, et al., "Systematic Identification of Personal Tumor-Specific Neoantigens in Chronic Lymphocytic Leukemia", Blood, vol. 124, No. 3, Jul. 17, 2014, 453-462.
Ramani, et al., "Massively Multiplex Single-Cell Hi-C", Nature Methods, vol. 14, No. 3, Mar. 2017, 13 pages.
Ramos, et al., "An Inducible Caspase 9 Suicide Gene to Improve the Safety of Mesenchymal Stromal Cell Therapies", Stem Cells, vol. 28, No. 6, Jun. 8, 2010, 1107-1115.
Ramskold, et al., "Full-Length mRNA-Seq from Single Cell Levels of RNA and Individual Circulating Tumor Cells", Nature Biotechnology, vol. 30, No. 8, Aug. 2012, 20 pages.
Ran, et al., "Double Nicking by RNA-Guided CRISPR Cas9 for Enhanced Genome Editing Specificity", Cell, vol. 154, No. 6, Sep. 12, 2013, 1380-1389.
Rees, et al., "Base Editing: Precision Chemistry on the Genome and Transcriptome of Living Cells", Nature Reviews Genetics, vol. 19, No. 12, Dec. 2018, 770-788.
Ren, et al., "Multiplex Genome Editing to Generate Universal CAR T Cells Resistant to PD1 Inhibition", Clinical Cancer Research, vol. 23, No. 9, May 1, 2017, 2255-2266.
Restifo, et al., "Adoptive Immunotherapy for Cancer: Harnessing the T Cell Response", Nature Reviews Immunology, vol. 12, No. 4, Apr. 1, 2012, 269-281.
Ronaghi, et al., "Real-Time DNA Sequencing Using Detection of Pyrophosphate Release", Analytical Biochemistry, vol. 242, No. 1, Nov. 1996, 84-89.
Rosenberg, et al., "Adoptive Cell Transfer as Personalized Immunotherapy for Human Cancer", Science, vol. 348, No. 6230, Apr. 2015, 62-68.
Rosenberg, et al., "Scaling Single Cell Transcriptomics Through Split Pool Barcoding", Available at:Bio Rxiv http://dx.doi.org/10.1101/105163, Feb. 2, 2017, 13 pages.
Rosenberg, et al., "Single-Cell Profiling of the Developing Mouse Brain and Spinal Cord with Split-Pool Barcoding", Science, vol. 360, No. 6385, Mar. 15, 2018, 8 pages.
Rotem, et al., "High-Throughput Single-Cell Labeling (Hi-SCL) for RNA-Seq Using Drop-Based Microfluidics", PLOS One, May 22, 2015, 14 pages.
Rotem, et al., "Single-cell Chip-seq Reveals Cell Subpopulations Defined by Chromatin State", Nature Biotechnology, vol. 33, No. 11, Nov. 2015, 1165-1172.
Ruggiero, et al., "High-Resolution Analysis of the Human T-Cell Receptor Repertoire", Nature Communications, vol. 6, No. 8081, Sep. 1, 2015, 7 pages.
Sadelain, Michael, "Eliminating Cells Gone Astray", The New England Journal of Medicine, vol. 365, Nov. 3, 2011, 1735-1737.
Salesse, et al., "BCR/ABL: From Molecular Mechanisms of Leukemia Induction to Treatment of Chronic Myelogenous Leukemia", Oncogene, vol. 21, Dec. 9, 2002, 8547-8559.
Sasagawa, et al., "Quartz-Seq: A Highly Reproducible and Sensitive Single-Cell RNA Sequencing Method, Reveals Non-Genetic Gene-Expression Heterogeneity", Genome Biology, vol. 14, No. R31, 2013, 17 pages.
Sasagawa, et al., "Quartz-Seq2: A High-Throughput Single-Cell RNA-Sequencing Method That Effectively Uses Limited Sequence Reads", Genome Biology, vol. 19, No. 29, 2018, 24 pages.
Satija, et al., "Spatial Reconstruction of Single-Cell Gene Expression Data", Nature Biotechnology, vol. 33, No. 5, May 2015, 32 pages.
Schmitt, et al., "Detection of Ultra-Rare Mutations by Next-generation Sequencing", PNAS, vol. 109, No. 36, Sep. 4, 2012, 14508-14513.
Schneider, et al., "DNA Sequencing With Nanopores", Nature Biotechnology, vol. 30, Apr. 10, 2012, 326-328.
Seth-Smith, et al., "Generating Whole Bacterial Genome Sequences of Low-Abundance Species from Complex Samples with IMS-MDA", Nature Protocols, vol. 8, No. 12, Nov. 7, 2013, 2404-2412.
Shendure, et al., "Accurate Multiplex Polony Sequencing of an Evolved Bacterial Genome", Science, vol. 309, Sep. 9, 2005, 1728-1732.
Sheng, et al., "Effective Detection of Variation in Single-Cell Transcriptomes using MATQ-seq", Nature Methods, vol. 14, No. 3, Jan. 16, 2017, 7 pages.
Shiroguchi, et al., "Digital RNA Sequencing Minimizes Sequence Dependent Bias and Amplification Noise with Optimized Single-Molecule Barcodes", Proceedings of the National Academy of Sciences, vol. 109, No. 4, Jan. 24, 2012, 1347-1352.
Shishkin, et al., "Simultaneous Generation of Many RNA-Seq Libraries in a Single Reaction", Nature Methods, vol. 12, No. 4, Mar. 2, 2015, 323-325.
Shmakov, et al., "Discovery and Functional Characterization of Diverse Class 2 CRISPR-Cas Systems", Molecular Cell, vol. 60, No. 3, Nov. 5, 2015, 385-397.
Shmakov, et al., "Diversity and Evolution of Class 2 CRISPR-Cas Systems", Nature Reviews Microbiology, vol. 15, No. 3, Mar. 2017, 30 pages.
Silverman, et al., "Multivalent Avimer Proteins Evolved by Exon Shuffling of a Family of Human Receptor Domains", Nature Biotechnology, vol. 23, No. 12, Dec. 2005, 1556-1561.
Skerra, Arne, "Alternative Binding Proteins: Anticalins—Harnessing the Structural Plasticity of the Lipocalin Ligand Pocket to Engineer Novel Binding Activities", The FEBS Journal, vol. 275, No. 11, Jun. 2008, 2677-2683.
Skerra, Arne, "Alternative Non-Antibody Scaffolds for Molecular Recognition", Current Opinion in Biotechnology, vol. 18, Issue 4, Aug. 2007, 295-304.
Skerra, Arne, "Engineered Protein Scaffolds for Molecular Recognition", Journal of Molecular Recognition, vol. 13, No. 4, 2000, 167-187.
Smallwood, et al., "Single-cell Genome-wide Bisulfite Sequencing for Assessing Epigenetic Heterogeneity", Nature Methods, vol. 11, No. 8, Aug. 2014, 817-820.
Smargon, et al., "Cas13b Is a Type VI-B CRISPR-Associated RNA-Guided RNase Differentially Regulated by Accessory Proteins Csx27 and Csx28", Molecular Cell, vol. 65, No. 4, Feb. 16, 2017, 30 pages.
Soumillon, et al., "Characterization of Directed Differentiation by High-Throughput Single-Cell RNA-Seq", BioRxiv Preprint, Mar. 5, 2014, 13 pages.
Stoeckius, et al., "Simultaneous Epitope and Transcriptome Measurement in Single Cells", Nature Methods, vol. 14, No. 9, Jul. 31, 2017, 865-868.
Strecker, et al., "RNA-Guided DNA Insertion with CRiSPR-Associated Transposes", Science, 10/1126/science.aax9181, 2019, 12 pages.
Stumpp, et al., "DARPins: A New Generation of Protein Therapeutics", Drug Discovery Today, vol. 13, No. 15-16, Aug. 2008, 695-701.
Sugapriya, et al., "BCR-ABL Translocation in Pediatric Acute Lymphoblastic Leukemia in Southern India", Indian Journal of Hematology and Blood Transfusion, vol. 28, No. 1, Jan.-Mar. 2012, 37-41.

(56) References Cited

OTHER PUBLICATIONS

Suzuki, et al., "In Vivo Genome Editing via CRISPR/Cas9 Mediated Homology-Independent Targeted Integration", Nature, vol. 540, Dec. 2016, 144-149.
Swiech, et al., "In Vivo Interrogation of Gene Function in the Mammalian Brain Using CRISPR-Cas9", Nature Biotechnology, vol. 33, No. 1, 2014, 102-106.
Tan, et al., "Three-dimensional Genome Structures of Single Diploid Human Cells", Science, vol. 361, No. 6405, Aug. 31, 2018, 924-928.
Tang, et al., "mRNA-Seq Whole-Transcriptome Analysis of a Single Cell", Nature Methods, vol. 6, No. 5, May 2009, 377-382.
Tang, et al., "RNA-Seq Analysis to Capture the Transcriptome Landscape of a Single Cell", Nature Protocols, vol. 5, No. 3, Mar. 2010, 516-535.
Thomsen, et al., "Fixed Single-cell Transcriptomic Characterization of Human Radial Glial Diversity", Nature Methods, vol. 13, No. 1, Jan. 2016, 87-93.
Trombetta, et al., "Preparation of Single Cell RNA-Seq Libraries for Next Generation Sequencing", Current Protocols in Molecular Biology, vol. 107, Jul. 2014, 25 pages.
Turchaninova, et al., "Pairing of T-Cell Receptor Chains via Emulsion PCR", European Journal of Immunology, vol. 43, 2013, 2507-2515.
Upton, et al., "Ubiquitous L1 Mosaicism in Hippocampal Neurons", Cell, vol. 161, Apr. 9, 2015, 228-239.
Vangah, et al., "CRISPR-Based Diagnosis of Infectious and Noninfectious Diseases", Biological Procedures Online, vol. 22, No. 22, Sep. 14, 2020, 14 pages.
Vitak, et al., "Sequencing Thousands of Single-Cell Genomes with Combinatorial Indexing", Nature Methods, vol. 14, No. 3, Mar. 2017, 302-308.
Von Essen, et al., "Constitutive and Ligand-Induced TCR Degradation", Journal of Immunology, vol. 173, No. 1, Jul. 1, 2004, 384-393.
Wang, et al., "Clonal Evolution in Breast Cancer Revealed by Single Nucleus Genome Sequencing", Nature, vol. 512, Aug. 14, 2014, 155-160.
Wu, et al., "Detecting Activated Cell Populations Using Single-Cell RNA-Seq", Neuron, vol. 96, No. 2, Oct. 11, 2017, 313-329.
Yang, et al., "Engineering and Optimising Deaminase Fusions for Genome Editing", Nature Communications, vol. 7, Article No. 13330, Nov. 2, 2016, 11 pages.
Yang, et al., "Purinostat Mesylate Is a Uniquely Potent and Selective Inhibitor of Hdacs for the Treatment of BCR-ABL-Induced B-cell Acute Lymphoblastic Leukemia", Clinical Cancer Research, vol. 25, No. 24, Dec. 15, 2019, 7527-7539.
Zacharakis, et al., "Immune Recognition of Somatic Mutations Leading to Complete Durable Regression in Metastatic Breast Cancer", Nature Medicine, vol. 24, No. 6, Jun. 4, 2018, 724-730.
Zanini, et al., "Single-Cell Transcriptional Dynamics of Flavivirus Infection", Elife, vol. 7:e32942, Feb. 16, 2018, 21 pages.
Zetche, et al., "A Split Cas9 Architecture for Inducible Genome Editing and Transcription Modulation", Nature Biotechnology, vol. 33, No. 2, Feb. 2015, 139-142.
Zetsche, et al., "Cpf1 is a Single RNA-Guided Endonuclease of a Class 2 CRISPR-Cas System", Cell, vol. 163, No. 3, Oct. 22, 2015, 759-771.
Zhang, et al., "Efficient Construction of Sequence-Specific TAL Effectors for Modulating Mammalian Transcription", Nature Biotechnology, vol. 29, No. 2, Feb. 2011, 149-153.
Zheng, et al., "Haplotyping Germline and Cancer Genomes with High-Throughput Linked-Read Sequencing", Nature Biotechnology, vol. 34, No. 3, Mar. 2016, 303-311.
Zheng, et al., "Massively Parallel Digital Transcriptional Profiling of Single Cells", Nature Communications, vol. 8, No. 14049, Jan. 16, 2017, 12 pages.
Zhou, et al., "Discovery of a Small-molecule Degrader of Bromodomain and Extra-terminal (BET) Proteins With Picomolar Cellular Potencies and Capable of Achieving Tumor Regression", Journal of Medicinal Chemistry, vol. 61, No. 2, Jan. 25, 2018, 462-481.
Zhou, et al., "Leukemia Stem Cells: the Root of Chronic Myeloid Leukemia", Protein cell, vol. 6, No. 6, Jun. 2015, 403-412.
Zhou, et al., "Long-Term Outcome after Haploidentical Stem Cell Transplant and Infusion of T Cells Expressing the Inducible Caspase 9 Safety Transgene", Blood, vol. 123, No. 25, Jun. 19, 2014, 3895-3905.
Zilberman, et al., "Genome-wide Analysis of DNA Methylation Patterns", Development, vol. 134, No. 22, Nov. 2007, 3959-3965.
Zilionis, et al., "Single-cell Barcoding and Sequencing Using Droplet Microfluidics", Nature Protocols, vol. 12, No. 1, Jan. 2017, 44-73.
Zong, et al., "Genome-Wide Detection of Single-Nucleotide and Copy-Number Variations of a Single Human Cell", Science, vol. 338, Dec. 21, 2012, 1622-1626.
Leenay et al., "Identifying and Visualizing Functional PAM Diversity across CRISPR-Cas Systems", Molecular Cell, 62, Apr. 7, 2016, 137-147.
Levy et al., "Cytosine and adenine base editing of the Brain, Liver, Retina, Heart and Skeletal Muscle of Mice via adeno-associated Viruses", Nature Biomedical Engineering, 2020, 18 pages.
Yang et al., "Regulatory T Cells Generated Early in Life Play a Distinct Role in Maintaining Self-Tolerance", Science, 348(6234), May 2015, pp. 589-594.

* cited by examiner

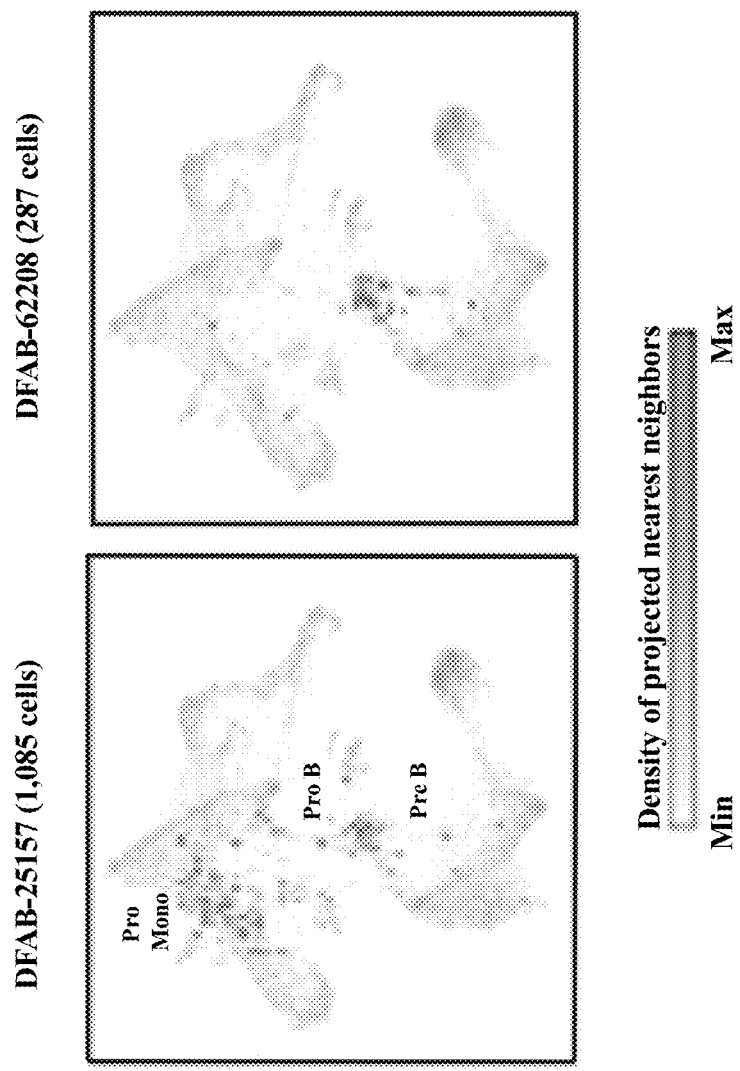

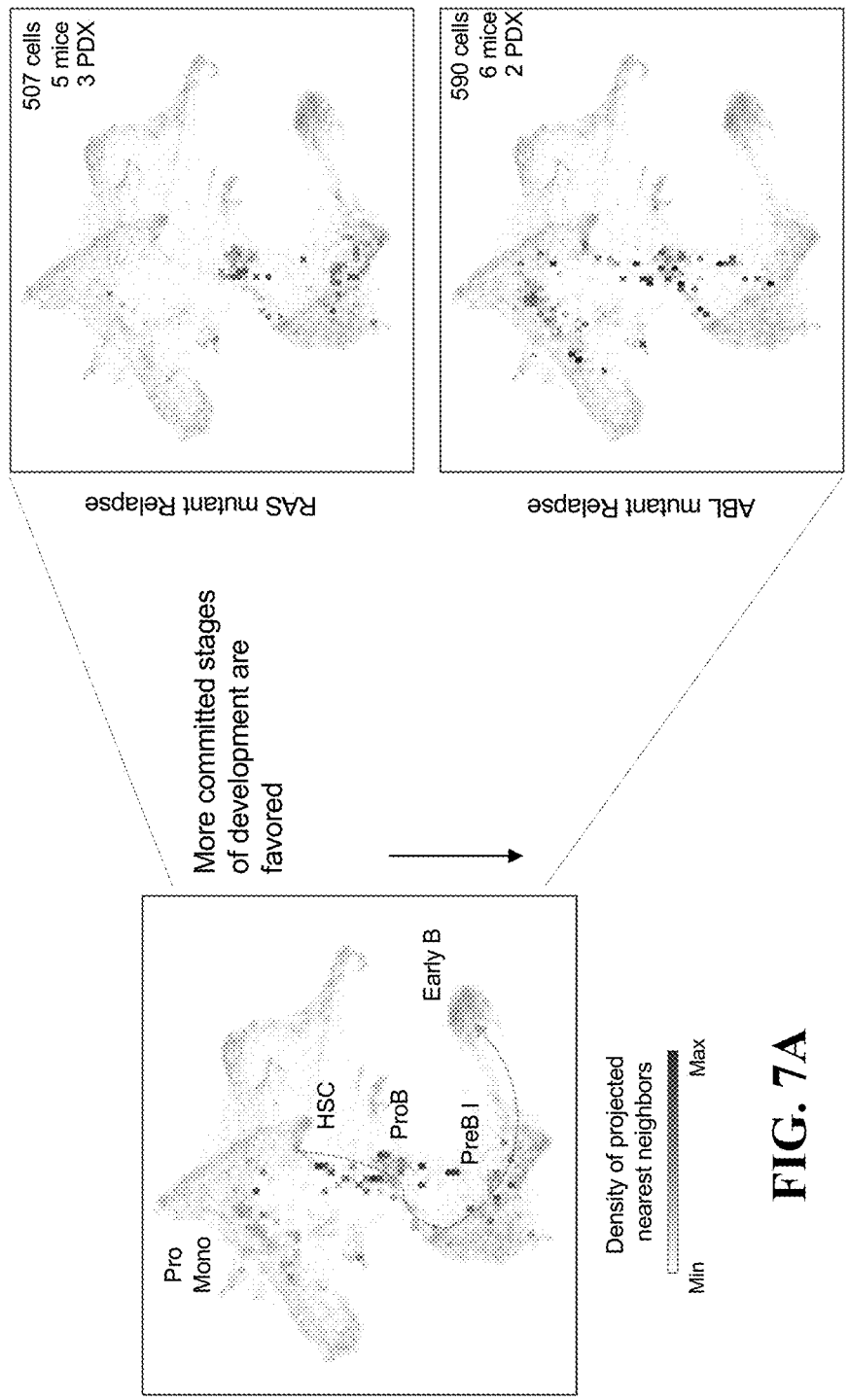

METHODS AND COMPOSITIONS FOR PREDICTING AND PREVENTING RELAPSE OF ACUTE LYMPHOBLASTIC LEUKEMIA

CROSS-REFERENCE TO RELATED APPLICATIONS

This application claims the benefit of U.S. Provisional Application No. 62/928,091, filed Oct. 30, 2019, the entire contents of which are hereby fully incorporated herein by reference.

STATEMENT REGARDING FEDERALLY SPONSORED RESEARCH

This invention was made with government support under Grant No. CA217377 awarded by National Institutes of Health. The government has certain rights in the invention.

REFERENCE TO AN ELECTRONIC SEQUENCE LISTING

This application contains a sequence listing filed in electronic form as an ASCII.txt file entitled BROD-4910US_ST25.txt, created on Oct. 29, 2020 and having a size of 11,634 bytes (12 KB on disk). The contents of the electronic sequence listing is herein incorporated by reference in its entirety.

TECHNICAL FIELD

The subject matter disclosed herein is generally directed to methods and compositions for predicting and preventing relapse of hematopoietic malignant diseases.

BACKGROUND

Although many novel therapeutics have been developed for cancer treatment, the majority of cancer patients undergo relapse and metastasis. Following initial treatments, cancer patients can have different outcomes, including minimal residual disease (MRD), negative MRD (complete remission), or disease progression. Depending on intrinsic and extrinsic factors such as genomic and genetic makeups of cancer cells, the length of MRD varies greatly. While some patients can have a very long time of MRD phase, unfortunately some patients experience a short period of MRD phase followed by disease relapse.

One characteristic of cancer is the high heterogeneity in cell types in tumor and its microenvironment. The heterogeneity in cancer cell types starts at the beginning of tumorigenesis and continues to exist during treatment and after relapse. Methods for isolating, enumerating, and characterizing cancer cells at multiple time points, including MRD, would greatly help monitor treatment efficacy and improve patient's survival. However, current methods for enumeration and molecular characterization of cancer cells at MRD are insufficient for predicting therapeutic response and often insensitive for functionally significant subclones. For hematopoietic malignant diseases, studies at single-cell level have shed light on the insight of treatment response and survival prognosis. However, because of the limited availability of cancer samples at MRD, little information is available on the biology of cancer cells at MRD at single-cell level, particularly on the cancer cells that escape from MRD phase and develop to disease relapse. Effective methods for predicting and preventing relapse from MRD phase are urgently needed for developing clinical strategies to prevent the occurrence of relapse.

Citation or identification of any document in this application is not an admission that such a document is available as prior art to the present invention.

SUMMARY

In certain embodiments, methods and compositions are provided for predicting and preventing relapse of B-cell acute lymphoblastic leukemia (ALL). In some embodiments, the methods for predicting the risk of relapse of B-cell ALL is performed at the phase of minimal residual disease (MRD) or earlier phase. In some embodiments, the compositions for preventing relapse of B-cell ALL are a combination of tyrosine kinase inhibitor (TKI) with inhibitors of pre-BCR signaling pathway and/or p38 MAPK inhibitors.

In certain embodiments, the methods disclosed herein for predicting the risk of relapse of B-cell ALL comprise an integrative biophysical measurements and transcriptome measurements at single-cell level. In some embodiments, the biophysical measurements include measuring the cellular mass and stiffness of single leukemic cells in a population before and after treatment, during MRD phase, or after relapse. Biophysical property metrics at least provide the advantages of rapid turnaround time, easy interpretation, and the ability to map to clinically relevant phenotypes. Furthermore, measurement of biophysical properties at single-cell level requires only minimal amount of sample input, which fits the situation of disease at MRD phase in which usually very limited amount of tumor samples are available.

In certain embodiments, the methods disclosed herein comprise transcriptomic profiling single leukemic cells at MRD phase, and identifying distinct profiles associated with relapse of B-cell ALL. In certain embodiments, the distinct profiles of leukemic cells are integrated to the cellular mass of the same cells, so that each leukemic cell is measured for its cellular mass followed by transcriptomic profile.

In certain embodiments, the methods disclosed herein comprise MRD modules that are composed of cellular mass, transcriptomic profile, and mutation status of genes involved in specific signaling pathways. By comparing the MRD module type of a subject with B-cell MRD to those derived from respective references, the risk of relapse of the subject can be evaluated. In some embodiments, the mutations of genes include those involved in STAT5 signaling pathway and ERK signaling pathway. In some embodiment, mutations of genes such as ABL1 phase in patients who are treated with BCR-ABL inhibitor ABL001 (asciminib) indicate the patient has a high risk of early-onset relapse. In some embodiments, mutations of genes such as KRAS and NRAS in patients who are treated with ponatinib or other BCR-ABL tyrosine kinase inhibitors (TKIs) indicate the patient has a risk of late-onset relapse.

In some embodiments, the methods disclosed herein can be used not only for predicting the risk of relapse of B-cell ALL, but also for predicting the risk of relapse of other hematopoietic malignancies, including chronic myeloid leukemia (C-L), T-cell ALL, acute myeloid leukemia, and lymphoid lymphomas.

In some embodiments, the compositions disclosed herein provide effective treatments for B-cell ALL. In some embodiments, treating B-cell ALL patients with ponatinib can substantially increase the survival time. In some embodiments, treating B-cell ALL patients with a combination of ponatinib and inhibitors of pre-BCR signaling pathways can significantly prevent relapse of the disease. In some embodiments, treating B-cell ALL patients with a combination of ponatinib and p38 MAPK inhibitors can significantly prevent relapse of the disease. In some embodiments, treating B-cell ALL patients with a combination of ponatinib or other BCR-ABL TKIs, pre-BCR signaling pathway inhibitors, and p38 MAPK inhibitors can significantly prevent relapse of the disease.

In some embodiments, the agents used as pre-BCR signaling pathway can be acting to block the proximal or distal or both signaling pathways. In some embodiments, the agents used for inhibiting p38 MAPK can be inhibitors against any component of the pathway or the p38 protein or gene expression.

The present invention provides many advantages and unexpected results over the current methods and compositions for predicting and preventing relapse of B-cell ALL. One of the advantages is that the methods and compositions target the MRD phase, a specific phase that some resistant cell clones will develop to disease relapse. The methods disclosed herein require only minimal tumor samples to produce evaluation of relapse risk. The combination therapy provides an effective approach to treat patients who are resistant or less sensitive to ABL001 or ponatinib or other BCR-ABL TKIs therapies.

Described in certain exemplary embodiments herein are methods of treating or preventing hematopoietic malignancy relapse in a subject in need thereof, comprising:
  a. prognosing hematopoietic malignancy relapse in the subject in need thereof by determining an average cellular mass of the plurality of cells using the cellular mass of each individual cell of the plurality of cells, wherein an average cellular mass equal to or greater than a defined threshold indicates a low risk of hematopoietic malignancy relapse and an average cellular mass less than a defined threshold indicates a high risk of hematopoietic malignancy relapse; and
  b. administering, to a subject in need thereof of having a high risk of early-onset hematopoietic malignancy relapse, or both, a therapeutically effective amount of
    i. one or more BCR-ABL tyrosine kinase inhibitors or a pharmaceutical formulation thereof;
    ii. one or more pre-BCR signaling pathway inhibitors or a pharmaceutical formulation thereof,
    iii. one or more p38 MAPK inhibitors or a pharmaceutical formulation thereof; or
    iv. any combination thereof.

In certain exemplary embodiments, determining the average cellular mass of the plurality of cells comprises measuring a cellular mass of each individual cell in the plurality of cells and calculating an average cellular mass of the plurality cells based on the measured cellular mass of each of the individual cells in the plurality of cells.

In certain exemplary embodiments, the cellular mass of each individual cell is measured using a suspended microchannel resonator.

In certain exemplary embodiments, (a) an average cellular mass of 20-80 pg indicates a low risk of relapse, and an average cellular mass between about 0-20 pg indicates a high risk of relapse; (a) an average cellular mass of 20-60 pg indicates a low risk of relapse, and an average cellular mass between about 5-20 pg indicates a high risk of relapse; or (a) an average cellular mass of 20-35 pg indicates a low risk of relapse, and an average cellular mass between about 10-20 pg indicates a high risk of relapse.

In certain exemplary embodiments, the hematopoietic malignancy is a B-cell malignancy, a T-cell malignancy, or a myeloid-cell malignancy.

In certain exemplary embodiments, the hematopoietic malignancy is acute lymphoblastic leukemia (ALL), chronic myeloid leukemia (CML), or both.

In certain exemplary embodiments, the ALL is B-cell ALL.

In certain exemplary embodiments, one or more B-cell ALL cells have a BCR-ABL translocation.

In certain exemplary embodiments, (a) the one or more BCR-ABL tyrosine kinase inhibitors comprise imatinib, dasatinib, nilotinib, bosutinib, ponatinib, bafetinib, rebastinib, tozasertib, danusertib, HG-7-85-01, GNF-2, GNF-5, Compound 2, asciminib, or a combination thereof; (b) the one or more pre-BCR signaling inhibitors comprise fostamatinib, ibrutinib, duvelisib, idelalisib, dasatinib, entospletinib, cerdulatinib, TAK-659, RG7666, apitolisib, LY3023414, gedatolisib, bimiralisib, SF-1126, copanlisib, buparlisib, tenalisib, taselisib, KA2237, alpelisib, parsaclisib, umbralisib, fimepinostat, rigosertib, dactolisib, BGT-226, DS-7423, PF-04691502, PKI-179, pictilisib, PX-866, TG100-115, AZD8835, WX-037, a genetic modifying agent capable of inhibiting or deleting one or more components of the pre-BCR signaling pathway, or a combination thereof; (c) the one or more p38 MAPK inhibitors comprise losmapimod, talmapimod, SB203580, VX-702, VX-745, pamapimod, dilmapimod, doramapimod, BMS-582949, ARRY-797, PH797804, SCIO-469, SD-0006, AMG-548, ralimetinib (LY2228820), SB239063, Skepinone-L, SB202190, TAK715, a genetic modifying agent capable of inhibiting or deleting one or more components of the p38 signaling pathway, or a combination thereof, or (d) any combination thereof.

In certain example embodiments, the sample is obtained from peripheral blood or bone marrow of the subject in need thereof.

In certain exemplary embodiments, the subject in need thereof is in the minimal residual disease phase of the hematopoietic malignancy.

Described in certain exemplary embodiments herein are methods of treating or preventing hematopoietic malignancy relapse in a subject in need thereof, comprising: (a) determining a molecular signature of one or more cells in the plurality of cells, wherein the molecular signature comprises (i) a quiescent signature characterized by high TNF-α/NF-kB score and/or low HSF1/p38 score, and cycling signature characterized by high pre-BCR score, wherein a quiescent signature indicates a low risk of relapse, and a cycling signature indicates a high risk of relapse; (ii) an ABL1, KRAS, and NRAS gene mutation status, wherein a mutation or mutations in ABL1 gene indicates low risk and/or late-onset of relapse, and a mutation or mutations in KRAS and/or NRAS genes indicate a high risk and/or early-onset of relapse; or (iii) both; and (b) administering, to a subject in need thereof of having a high risk of, a risk of early-onset hematopoietic malignancy relapse, or both, a therapeutically effective amount of (i) one or more BCR-ABL tyrosine kinase inhibitors or a pharmaceutical formulation thereof, (ii) one or more pre-BCR signaling pathway inhibitors or a pharmaceutical formulation thereof; (iii) one or more p38 MAPK inhibitors or a pharmaceutical formulation thereof; or (iv) any combination thereof.

In certain exemplary embodiments, the hematopoietic malignancy is a B-cell malignancy, a T-cell malignancy, or a myeloid-cell malignancy.

In certain exemplary embodiments, the hematopoietic malignancy is acute lymphoblastic leukemia (ALL), chronic myeloid leukemia (CML), or both.

In certain exemplary embodiments, the ALL is B-cell ALL.

In certain exemplary embodiments, one or more B-cell ALL cells have a BCR-ABL translocation.

In certain exemplary embodiments, (a) the one or more BCR-ABL tyrosine kinase inhibitors comprise imatinib, dasatinib, nilotinib, bosutinib, ponatinib, bafetinib, rebastinib, tozasertib, danusertib, HG-7-85-01, GNF-2, GNF-5, Compound 2, asciminib, or a combination thereof; (b) the one or more pre-BCR signaling inhibitors comprise fostamatinib, ibrutinib, duvelisib, idelalisib, dasatinib, entospletinib, cerdulatinib, TAK-659, RG7666, apitolisib, LY3023414, gedatolisib, bimiralisib, SF-1126, copanlisib, buparlisib, tenalisib, taselisib, KA2237, alpelisib, parsaclisib, umbralisib, fimepinostat, rigosertib, dactolisib, BGT-226, DS-7423, PF-04691502, PKI-179, pictilisib, PX-866, TG100-115, AZD8835, WX-037, a genetic modifying agent capable of inhibiting or deleting one or more components of the pre-BCR signaling pathway, or a combination thereof, (c) the one or more p38 MAPK inhibitors comprise losmapimod, talmapimod, SB203580, VX-702, VX-745, pamapimod, dilmapimod, doramapimod, BMS-582949, ARRY-797, PH797804, SCIO-469, SD-0006, AMG-548, ralimetinib (LY2228820), SB239063, Skepinone-L, SB202190, TAK715, a genetic modifying agent capable of inhibiting or deleting one or more components of the p38 signaling pathway, or a combination thereof, or (d) any combination thereof.

In certain exemplary embodiments, the sample is obtained from peripheral blood or bone marrow of the subject in need thereof.

In certain exemplary embodiments, the subject in need thereof is in the minimal residual disease phase of the hematopoietic malignancy.

Described in certain exemplary embodiments herein are methods of treating or preventing hematopoietic malignancy or hematopoietic malignancy relapse comprising: administering, to a subject optionally identified as having a high risk of hematopoietic malignancy relapse or early-onset of haemopoietic malignancy relapse or identified as having a hematopoietic malignancy, a therapeutically effective amount of (a) one or more BCR-ABL tyrosine kinase inhibitors or a pharmaceutical formulation thereof, (b) one or more pre-BCR signaling pathway inhibitors or a pharmaceutical formulation thereof; (c) one or more p38 MAPK inhibitors or a pharmaceutical formulation thereof; or (d) any combination thereof.

In certain exemplary embodiments, (a) the one or more BCR-ABL tyrosine kinase inhibitors comprise imatinib, dasatinib, nilotinib, bosutinib, ponatinib, bafetinib, rebastinib, tozasertib, danusertib, HG-7-85-01, GNF-2, GNF-5, Compound 2, asciminib, or a combination thereof; (b) the one or more pre-BCR signaling inhibitors comprise fostamatinib, ibrutinib, duvelisib, idelalisib, dasatinib, entospletinib, cerdulatinib, TAK-659, RG7666, apitolisib, LY3023414, gedatolisib, bimiralisib, SF-1126, copanlisib, buparlisib, tenalisib, taselisib, KA2237, alpelisib, parsaclisib, umbralisib, fimepinostat, rigosertib, dactolisib, BGT-226, DS-7423, PF-04691502, PKI-179, pictilisib, PX-866, TG100-115, AZD8835, WX-037, a genetic modifying agent capable of inhibiting or deleting one or more components of the pre-BCR signaling pathway, or a combination thereof, (c) the one or more p38 MAPK inhibitors comprise losmapimod, talmapimod, SB203580, VX-702, VX-745, pamapimod, dilmapimod, doramapimod, BMS-582949, ARRY-797, PH797804, SCIO-469, SD-0006, AMG-548, ralimetinib (LY2228820), SB239063, Skepinone-L, SB202190, TAK715, a genetic modifying agent capable of inhibiting or deleting one or more components of the p38 signaling pathway, or a combination thereof, or (d) any combination thereof.

In certain exemplary embodiments, a subject is identified as having a high risk of haemopoietic malignancy relapse when an average cellular mass of a plurality of cells in a sample obtained from the subject is less than a defined threshold.

In certain exemplary embodiments, the average cellular mass of the plurality of cells is (a) between about 0-20 pg; (b) between about 5-20 pg; or (c) between about 10-20 pg.

In certain exemplary embodiments, the average cellular mass of the plurality of cells is determined by measuring a cellular mass of each individual cell in the plurality of cells and calculating an average cellular mass of the plurality cells based on the measured cellular mass of each of the individual cells in the plurality of cells.

In certain exemplary embodiments, the cellular mass of each individual cell is measured using a suspended microchannel resonator.

In certain exemplary embodiments, a subject is identified as having a high risk of haemopoietic malignancy relapse when one or more cells of a plurality of cells in a sample obtained from the subject has a cycling gene expression signature.

In certain exemplary embodiments, a subject is identified as having a high risk of haemopoietic malignancy relapse when one or more cells of a plurality of cells in a sample obtained from the subject has one or more gene mutations in KRAS, NRAS, or a combination thereof.

In certain exemplary embodiments, the subject is in the acute response phase of treatment for the hematopoietic malignancy.

In certain exemplary embodiments, the subject is in the minimal residual disease phase of the hematopoietic malignancy.

In certain exemplary embodiments, the haemopoietic malignancy is a B-cell malignancy, a T-cell malignancy, or a myeloid-cell malignancy.

In certain exemplary embodiments, the haemopoietic malignancy is acute lymphoblastic leukemia (ALL), chronic myeloid leukemia (CML), or both.

In certain exemplary embodiments, administering comprises administering a therapeutically effective amount of one or more BCR-ABL tyrosine kinase inhibitors or a pharmaceutical formulation thereof and a therapeutically effective amount of one or more pre-BCR inhibitors or a pharmaceutical formulation thereof.

In certain exemplary embodiments, wherein administering comprises administering a therapeutically effective amount of one or more BCR-ABL tyrosine kinase inhibitors or a pharmaceutical formulation thereof and a therapeutically effective amount of one or more p38 MAPK inhibitors or a pharmaceutical formulation thereof.

In certain exemplary embodiments, the method further comprises administering an amount of an additional therapeutic agent, wherein the additional therapeutic agent is an anti-CD20 agent.

In certain exemplary embodiments, the anti-CD20 agent comprises an anti-CD20 antibody or fragment thereof.

In certain exemplary embodiments, the anti-CD20 antibody comprises rituximab, ofatumumab, obinutuzumab, ibritumomab tiuxetan, ocrelizumab, tositumomab, or a combination thereof.

Described in certain example embodiments herein are pharmaceutical formulations for treating a subject having a hematopoietic malignancy or treating or preventing a relapse thereof, comprising: (a) a therapeutically effective amount of one or more BCR-ABL inhibitors; (b) a therapeutically effective amount of one or more pre-BCR inhibitors; (c) a therapeutically effective amount of one or more p38 MAPK inhibitors; or (d) a combination thereof, and a pharmaceutically acceptable carrier.

In certain exemplary embodiments, (a) the one or more BCR-ABL tyrosine kinase inhibitors comprise imatinib, dasatinib, nilotinib, bosutinib, ponatinib, bafetinib, rebastinib, tozasertib, danusertib, HG-7-85-01, GNF-2, GNF-5, Compound 2, asciminib, or a combination thereof; (b) the one or more pre-BCR signaling inhibitors comprise fostamatinib, ibrutinib, duvelisib, idelalisib, dasatinib, entospletinib, cerdulatinib, TAK-659, RG7666, apitolisib, LY3023414, gedatolisib, bimiralisib, SF-1126, copanlisib, buparlisib, tenalisib, taselisib, KA2237, alpelisib, parsaclisib, umbralisib, fimepinostat, rigosertib, dactolisib, BGT-226, DS-7423, PF-04691502, PKI-179, pictilisib, PX-866, TG100-115, AZD8835, WX-037, a genetic modifying agent capable of inhibiting or deleting one or more components of the pre-BCR signaling pathway, or a combination thereof, and (c) the one or more p38 MAPK inhibitors comprise losmapimod, talmapimod, SB203580, VX-702, VX-745, pamapimod, dilmapimod, doramapimod, BMS-582949, ARRY-797, PH797804, SCIO-469, SD-0006, AMG-548, ralimetinib (LY2228820), SB239063, Skepinone-L, SB202190, TAK715, a genetic modifying agent capable of inhibiting or deleting one or more components of the p38 signaling pathway; (d) or any combination thereof.

Described in certain exemplary embodiments herein are kits for diagnosing, prognosing, monitoring, treating, and/or preventing a hematopoietic malignancy or a relapse thereof or a combination thereof in a subject, comprising one or more of the following: (a) one or more reagents for determining a cellular mass in an individual cell; (b) one or more reagents for determining a molecular signature in one or more cells; (c) a pharmaceutical formulation as described herein (see e.g. paragraphs [0052]-[0053] and elsewhere herein; or (d) any combination thereof; and instructions in a tangible medium of expression, wherein in the instructions provide direction for diagnosing, prognosing, monitoring, treating, or preventing a hematopoietic malignancy or relapse thereof in the subject in need thereof by performing, on one or more cells in a plurality of cells present in a sample obtained from the subject in need thereof, (a) determining an average cellular mass of the plurality of cells using the cellular mass of each individual cell of the plurality of cells, wherein an average cellular mass equal to or greater than a defined threshold indicates a low risk of hematopoietic malignancy relapse and an average cellular mass less than a defined threshold indicates a high risk of hematopoietic malignancy relapse; (b) determining a molecular signature of one or more cells in the plurality of cells, wherein the molecular signature comprises (i) a quiescent signature characterized by high TNF-α/NF-kB score and/or low HSF1/p38 score, and cycling signature characterized by high pre-BCR score, wherein a quiescent signature indicates a low risk of relapse, and a cycling signature indicates a high risk of relapse; (ii) an ABL1, KRAS, and NRAS gene mutation status, wherein a mutation or mutations in ABL1 gene indicates low risk and/or late-onset of relapse, and a mutation or mutations in KRAS and/or NRAS genes indicate a high risk and/or early-onset of relapse; or (iii) both; or (c) both; and where the instructions provide direction for treating a hematopoietic malignancy or a relapse thereof by administering, to the subject, (i) one or more BCR-ABL tyrosine kinase inhibitors or a pharmaceutical formulation thereof; (ii) one or more pre-BCR signaling pathway inhibitors or a pharmaceutical formulation thereof, (iii) one or more p38 MAPK inhibitors or a pharmaceutical formulation thereof; or (iv) any combination thereof.

In certain example embodiments, (a) the one or more BCR-ABL tyrosine kinase inhibitors comprise imatinib, dasatinib, nilotinib, bosutinib, ponatinib, bafetinib, rebastinib, tozasertib, danusertib, HG-7-85-01, GNF-2, GNF-5, Compound 2, asciminib, or a combination thereof, (b) the one or more pre-BCR signaling inhibitors comprise fostamatinib, ibrutinib, duvelisib, idelalisib, dasatinib, entospletinib, cerdulatinib, TAK-659, RG7666, apitolisib, LY3023414, gedatolisib, bimiralisib, SF-1126, copanlisib, buparlisib, tenalisib, taselisib, KA2237, alpelisib, parsaclisib, umbralisib, fimepinostat, rigosertib, dactolisib, BGT-226, DS-7423, PF-04691502, PKI-179, pictilisib, PX-866, TG100-115, AZD8835, WX-037, a genetic modifying agent capable of inhibiting or deleting one or more components of the pre-BCR signaling pathway, or a combination thereof, (c) wherein the one or more p38 MAPK inhibitors comprise losmapimod, talmapimod, SB203580, VX-702, VX-745, pamapimod, dilmapimod, doramapimod, BMS-582949, ARRY-797, PH797804, SCIO-469, SD-0006, AMG-548, ralimetinib (LY2228820), SB239063, Skepinone-L, SB202190, TAK715, a genetic modifying agent capable of inhibiting or deleting one or more components of the p38 signaling pathway; or (d) any combination thereof.

These and other aspects, objects, features, and advantages of the example embodiments will become apparent to those having ordinary skill in the art upon consideration of the following detailed description of example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

(FIG. 3A) Event free survival in 13 models of BCR-ABL mutant B-cell ALL treated with next generation ABL1 inhibitors (n=88 animals). Mice treated with ponatinib experience deep remissions followed by late relapse while ABL001 alone leads to significant earlier relapse. Vehicle vs. ABL001 p=0.014. Vehicle vs. Ponatinib p<0.001. Vehicle vs. Ponatinib+ ABL001 p<0.001. ABL001 vs. Ponatinib p<0.001. Ponatinib vs. Ponatinib+ ABL001 p=0.78. (FIG. 3B) Amplicon-based targeted sequencing for known resistance-associated mutations was performed on pretreatment and relapsed animals. Data from a pilot study including Nilotinib are shown and follow similar trends as ABL001. (FIG. 3C) Pathway reactivating mutations (STAT5 pathway, e.g. ABL1, STAT5A) enrich in relapses on ABL001 while alternative pathway mutations (mainly ERK pathway; e.g. KRAS, NRAS) enrich for arms containing ponatinib.

(FIG. 4A) Mutations as in FIG. 2, separated by PDX line. (FIG. 4B) Representative flow cytometry for an early (CD34+) and later marker (CD179b+) of canonical B cell development. ABL mutations occur in models from early stages, RAS in more mature.

(FIG. 5A) Visualization of cells (13,643, shaded by cell type) recovered from 8 separate donors using Seq-Well. Samples are flow-sorted for CFUL (HSCs and progenitors) as well as specific stages of B-cell development (n>=2 donors/cell type). (FIG. 5B) Heatmap showing select markers for normal populations. A Random Forest classifier was trained on these 13 normal cell types. (FIG. 5C) Random forest prediction scores for sorted Smart-seq2 cells from healthy bone marrow (top). Bottom plot shows the 20 nearest neighbors for each Smart-seq2 cell shown above projected onto the normal bone marrow KNN graph from (FIG. 5A). Heat indicates the density of projected cells per bin.

FIGS. 6A-6C—Developmentally aberrant expression states in B-cell ALL cells. (FIG. 6A) Projection of pretreatment nearest neighbors for malignant B cells from two PDX models onto normal cell types as in FIG. 3C. (FIG. 6B) Heatmap depicting genes (rows) highly correlated to each normal cell type prediction where at least 10 malignant cells were identified (n=30 genes/cell type; columns are single cells). Pro B-like malignant cells are down-samples for visualization porposes. (FIG. 6C). Scatterplots for MPO (myeloid lineage marker) and CD19 (B cell lineage marker) expression in single cells from either healthy bone marrow (left) or leukemic B cells (right). Each dot represents a single cell that was classified as a pro-monocyte by the Random Forest classifier. Top density plots show distribution of CD19 expression in each subset.

FIGS. 7A-7C—RAS mutations associate with later stages of development while ABL mutations skew towards less committed B cell phenotypes. (FIG. 7A) Nearest neighbor projections for pretreatment (left) vs relapse (right). (FIG. 7B) Relapses are split by mouse-level mutational calls from bulk targeted sequencing into ABL-altered (blue; multiple point mutants) or RAS-altered (green; NRAS and KRAS). (FIG. 7C) Heatmap showing genes (rows) highly correlated to normal cell type predictions in malignant cells. Shown are the 3 classes where the majority of cells are detected (n=30 genes/malignant cell type; columns are single relapse cells). Top mutational metadata bar indicates if that cell came from an animal where the indicated mutation was detected.

(FIG. 8A) Cross-correlational heatmap of genes differentially expressed at MRD in at least two models. (FIG. 8B) Signature scores for each MRD cell reveals quiescent and cycling subsets.

(FIGS. 13A and 13B) A schematic for the treatment study is shown. The bone marrow involvement at MRD is shown for mice received ponatinib alone or in combination with other agents. (FIGS. 13C-13D) A separate head-to-head comparison study shows that the combination of ponatinib and p38 MAPK inhibitor resulted in substantially lower levels of bone marrow involvement at MRD than the combination of ponatinib and ABL001.

Figure 1:
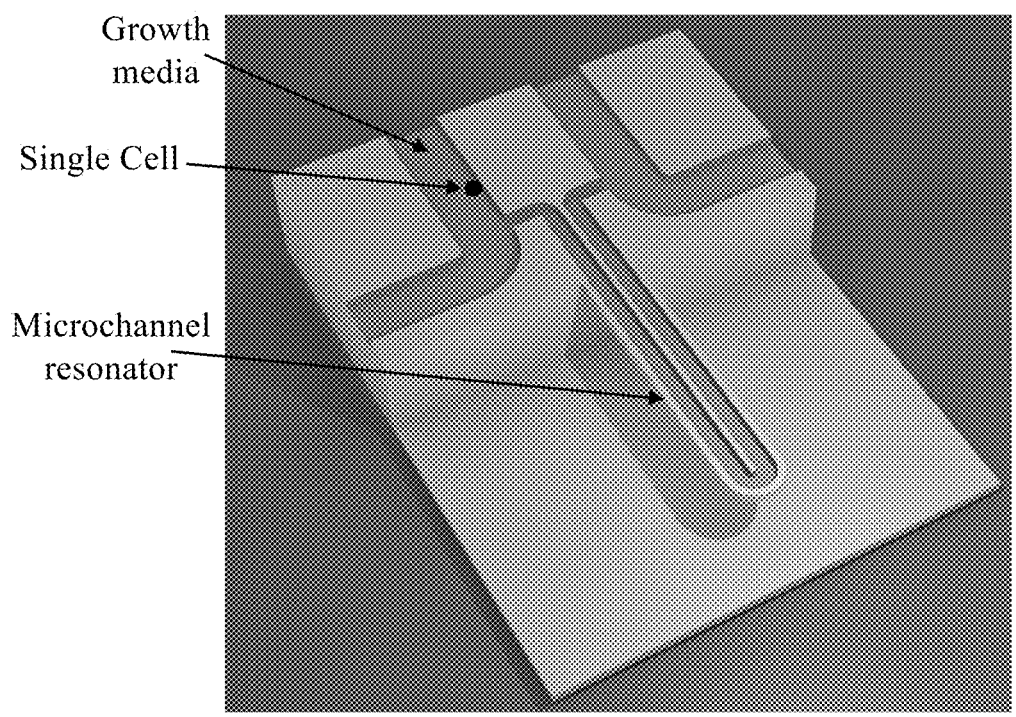
FIG. 1—A schematic showing the Suspended Microchannel Resonator (SMR) device. A resonant frequency shift is directly proportional to single-cell buoyant mass and is non-destructive to the cells.
Figure 1:
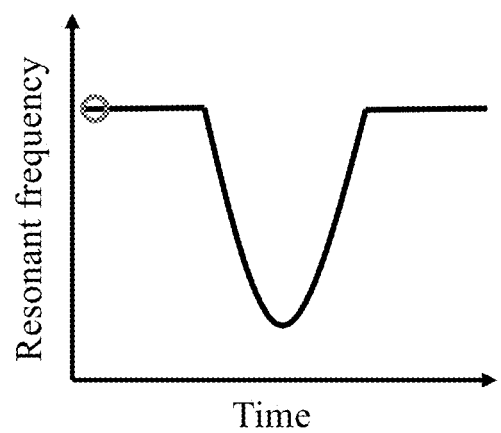

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R.I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a" "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader embodiments discussed herein. One embodiment described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment but may. Furthermore, the particular features, structures or characteristics may be combined in any suitable manner, as would be apparent to a person skilled in the art from this disclosure, in one or more embodiments. Furthermore, while some embodiments described herein include some, but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

Embodiments disclosed herein provides methods, compositions, and uses thereof for predicting and preventing relapse of hematopoietic malignancy. In some embodiments, the methods disclosed herein rely on assessing the state of B cell maturation, cellular biophysical properties, and mutation status of specific genes in leukemic cells to assess disease state and/or the likelihood of relapse before and during the treatment for hematopoietic malignancy. In some embodiments, an integrative approach is provided that uses biophysical parameters of single leukemic cells at single-cell level as an integrated biomarker to present a novel method with rapid readout, easy to interpret, cost-effective, low-dimensional data, single-cell resolution, and minimal sample input.

In some embodiments, the methods disclosed herein provide specific gene expression programs of leukemic cells that resemble the various developmental stages of normal hematopoietic cells. In some embodiments, the methods show a highly correlated gene expression program between leukemic cells and normal hematopoietic cells. In some embodiments, the methods show aberrant gene expression programs in leukemic cells in comparison to normal hematopoietic cells.

In some embodiments, pharmaceutical compositions and methods are provided for treating B-cell ALL and other hematopoietic malignancies. The pharmaceutical compositions and methods of treatment disclosed herein are based on the findings of the present invention that the relapse leukemic cells have distinct gene expression programs that can be targeted so as to prevent the relapse of disease.

Functional Biomarkers of Hematopoietic Malignancy and/or Relapse

Described herein are biomarkers of hematopoietic malignancy and/or relapse thereof. Such biomarkers can be used to diagnose, prognose, monitor, identify subjects having or at risk of hematopoietic malignancy and/or relapse. Exemplary embodiments of such methods are described in greater detail elsewhere herein. In some embodiments, the biomarker is a biophysical phenotype, such as a cell mass of one or more individual cells or an average cellular mass of a cell population. In some embodiments, the biomarker is a molecular signature (such as a gene signature, protein signature, or other signature). In some embodiments, the biomarker used include both a biophysical phenotype, such as cell mass, and a molecular signature, such as a gene expression signature. In some embodiments, the presence of a "low risk" biomarker can indicate that the time to relapse can be greater than 200, 250, 300, 400, 500, 600, 700, 800, 900, 1000, 2000, 3000, 4000, 5000, more than 5000, or more than 10,000 days. In some embodiments, the presence of a "high risk" biomarker can indicate that the time to relapse of less than 200, 150, 100, 80, 50, 40, 30, 20, 10, 5, or 2 days. In some embodiments, the presence of a "low risk" biomarker can indicate that the time to relapse for a B-cell ALL subject can be greater than 200, 250, 300, 400, 500, 600, 700, 800, 900, 1000, 2000, 3000, 4000, 5000, more than 5000, or more than 10,000 days. In some embodiments, the presence of a "high risk" biomarker can indicate that the time to relapse for a B-cell ALL subject is less than 200, 150, 100, 80, 50, 40, 30, 20, 10, 5, or 2 days.

The biomarkers of the present invention are useful in methods of identifying specific patient populations based on a detected level of expression, activity and/or function of one or more biomarkers. These biomarkers are also useful in monitoring subjects undergoing treatments and therapies for suitable or aberrant response(s) to determine efficaciousness of the treatment or therapy and for selecting or modifying therapies and treatments that would be efficacious in treating, delaying the progression of or otherwise ameliorating a symptom. The biomarkers provided herein are useful for selecting a group of patients at a specific state of a disease with accuracy that facilitates selection of treatments. Furthermore, the biomarkers provided herein are useful for predicting the relapse of patients suffering from hematopoietic malignancies comprising B-cell ALL, CML, T-cell ALL, AML, lymphoma, and other hematopoietic malignant diseases. Such methods are described in greater detail elsewhere herein.

The hematopoietic malignancy can be a lymphoid or myeloid malignancy. The hematopoietic malignancies may be any of lymphoid malignancies comprising B-cell ALL, T-cell ALL, chronic lymphoblastic leukemia (CLL), diffuse large B-cell lymphoma, follicular lymphoma, Burkitt's lymphoma, mantle cell lymphoma, marginal zone lymphoma, T-cell lymphoma, multiple myeloma, Hodgkin's lymphoma, and any other types of malignancies derived from lymphoid lineage. In some embodiments, the methods disclosed herein for predicting the risk of relapse can be used for any of the subtypes of the aforementioned lymphoid malignancies. In some embodiments, the hematopoietic malignancies can be any of myeloid malignancies comprising chronic myeloid leukemia (CML), acute myeloid leukemia (AML), myelodysplastic syndromes (MDS), myeloproliferative diseases (MPD), chronic neutrophilic leukemia, chronic eosinophilic leukemia, polycythemia vera, chronic idiopathic myelofibrosis, essential thrombocythemia, chronic myeloproliferative disease (unclassifiable), refractory anemia, refractory cytopenia with multilineage dysplasia (RCMD), mastocytosis, and any other types of malignancies derived from myeloid lineage. In some embodiments, the methods disclosed herein for predicting the risk of relapse can be used for any of the subtypes of the aforementioned myeloid malignancies.

In certain example embodiments, the hematopoietic malignancy is an acute lymphoblastic leukemia (ALL). In certain example embodiments, the ALL is a B-cell ALL. In certain other example embodiments, the ALL is a T-cell ALL. B-cell ALL comprises many distinct molecular subtypes, with 25% of B-cell ALL harboring BCR-ABL1 gene translocation. BCR-ABL1 gene fusion, also called Philadelphia chromosome (Ph+), is formed when part of chromosomes 9 and 22 break off and joined aberrantly so that the ABL1 gene located on chromosome 9 is translocated to the BCR gene on chromosome 22: t(9;22)(q34;q11). Three BCR-ABL1 fusion gene hybrids encode BCR-ABL1 protein isoforms p210, p190, and p230, which have persistently enhanced tyrosine kinase (TK) activity. These aberrantly activated kinases disturb downstream signaling pathways, causing enhanced proliferation, differentiation arrest, and resistance to cell death.

The biomarkers can be detected, such as by a method described in greater detail elsewhere herein, in any suitable biological sample. In some embodiments, the sample is a blood sample. In some embodiments, the sample is a peripheral blood sample. In some embodiments, the sample is a bone marrow sample.

Compared with the classical microscopic detection of residual leukemic cells, MRD is assessed by sensitive molecular and flow cytometric methods to more precisely monitor disease kinetics during and after treatment. MRD assessment can provide real-time information about tumor burden and response to therapy, noninvasive genomic profiling, and monitoring of clonal dynamics, allowing for many possible applications that could significantly affect the care of patients with leukemia. There is a strong correlation between MRD levels in bone marrow and the risk of relapse in childhood & adult leukemias. Bone marrow MRD (BM-MRD) level of >0.01% is considered as positive and a mid-induction MRD of >1% is associated with high risk of relapse. On the other hand, peripheral blood MRD (PB-MRD), as a replacement for BM-MRD, has been used clinically. In pediatric B-cell ALL, presence of PB-MRD is associated with a high relapse rate in comparison to cases which are PB-MRD negative. PB-MRD and BM-MRD levels in day 15 induction therapy of B-cell ALL cases are correlated. In some embodiments, a level of <1% in peripheral blood is considered PB-MRD. Despite achieving MRD, virtually all B-cell ALL cases relapse without highly intensive consolidation therapy, regardless the type of BCR-ABL1 inhibitors being used. Most relapses with activating mutations in the ABL1 catalytic domain (e.g. ABL1 T315I).

In some embodiments, different biological samples can be used for the methods disclosed herein. The biological samples may comprise peripheral blood, bone marrow, lymph nodes, tissues where malignant cells reside, cerebrospinal fluid (CSF), pleural effusion, or ascitic fluid. In some embodiments, the malignant cells are lymphoid leukemic cells. In some embodiments, the leukemic cells are B cell lineage lymphoblastic leukemic cells. In some embodiments, the malignant cells are myeloid leukemic cells. In some embodiments, the leukemic cells are isolated using conventional techniques, such as the method described in Guan et al., Blood 2003 101:3142-3149. In some embodiments, the leukemic cells can be prepared using other appropriate methods such as using flow cytometry, such as the method described in De Vis et al., J. Immunol Methods, 1991 137:193-197. In some embodiments, leukemic cells can be simply collected by centrifugation.

Biophysical Phenotype—Cell Mass

In some embodiments, the biomarker can be a biophysical phenotype of a cell or cell population. The term biophysical phenotype refers to a physical characteristic that is proxy for an underlying biological cell state or signature, such as a disease state, metabolic state, stress response, proliferation state, and the like. In some embodiments, the biophysical phenotype that is a biomarker for hematopoietic malignancy and/or relapse is the mass of a cell (i.e. cellular mass).

In some embodiments, an average cellular mass equal to or greater than a defined threshold indicates a low risk of hematopoietic malignancy relapse and an average cellular mass lower than a defined threshold indicates a high risk of hematopoietic malignancy relapse. In some embodiments, the methods may also include measuring cellular stiffness at single-cell level, and the stiffness metric can be integrated into the cellular mass metric to form an integrative biomarker.

Measuring Cellular Mass

In some embodiments, the methods disclosed herein comprise a step of detecting cellular mass of single cells. In certain example embodiments, the cellular mass can be detected using a device called Suspended Microchannel Resonator (SMR) as described in Godin et al., Nature Methods, 2010, 7:387-390 and patents U.S. Pat. Nos. 9,134, 294; 9,027,388. A schematic of the SMR device is shown in FIG. 1. The SMR enables the buoyant mass of cells as small as bacteria and as large as mammalian lymphocytes to be repeatedly measured. The SMR consists of a vacuum packed hollow microcantilever beam containing an embedded fluidic microchannel and is capable of weighing nanoparticles, bacterial cells, and sub-monolayers of adsorbed proteins with femtogram resolution (1 Hz bandwidth). As individual cells transit the microchannel, a shift in the resonant frequency of the SMR is observed that corresponds to the buoyant mass of the cell. A feedback algorithm is implemented that reverses the direction of fluid flow upon detecting a cell transiting through the SMR, thereby reintroducing the cell into the cantilever. Continuously alternating flow direction creates a dynamic trap that allows for consecutive buoyant mass measurements of the same cell. Since the cell fully exits the SMR prior to flow reversal, the baseline resonant frequency is acquired after each measurement, allowing compensation for drift arising from temperature variations or accretion on the walls of the microchannel. Dilute cultures of non-adherent cells in any desired growth medium can be loaded directly into the system. The dynamic trap is very stable when measuring polystyrene particles that are less than half the size of the channel height (3-15 μm). Such particles are trapped for more than 20 hours (>32,000 measurements). Sample concentration was the main limiting factor of the trapping duration. Low concentrations (≤107 ml$^{-1}$) decrease the probability of additional particles randomly drifting into the cantilever and becoming trapped along with the particle being measured. The maximal trapping duration for cells was typically shorter than for polystyrene particles and was dependent on the cell type. On average, E. coli and B. subtilis could be trapped for 500 sec and 300 sec, respectively, before being lost. Yeast and L1210 mouse lymphoblast cells could be trapped in excess of 30 minutes in a similar system as bacteria but with larger SMR channels. When living cells are trapped, growth is observed from the increasing amplitude of the resonant frequency peaks. Trapped cells are in an open system, as the suspended microchannel is in constant contact with the larger inlet and outlet channels, which act as reservoirs of nutrients. Diffusion and convection prevent local depletion of nutrients by the growing cell. Variability in the peak amplitudes limits the precision of this method and is mainly due to the trapped cell taking different flow paths as it turns the corners at the cantilever tip. Different flow paths, as well as increased interaction with the microchannel walls, may also explain why cells with irregular shapes escape the dynamic trap much more frequently than do polystyrene particles and round cells.

In certain embodiments, cellular mass can also be measured using methods comprising z-stack analysis, flow cytometry, and measurement with a Coulter counter. Cellular mass can be measured with quantitative phase microscopy. The gold standard for determining cell density is density gradient centrifugation, which is difficult to precisely calibrate and subjects cells to stresses that may lead to biological artifacts. Despite a multitude of instruments and techniques available for measuring cellular physical properties, few tools are capable of simultaneously measuring multiple physical properties and at the level of a single cell. SMR is the tool that can simultaneously measure multiple biophysical properties at single-cell level.

In some embodiments, the cellular mass may be assessed at one or more time points. For example, the cellular mass may be assessed prior to treatment, within 24 hours of initial treatment, at minimal residual disease (MRD) phase. In some embodiments, the methods disclosed herein are directed obtaining a sample at MRD phase. MRD is used to describe the low-level disease which is not detectable by conventional cytomorphology. In present invention, MRD in PDX models is defined as the period of treatment is greater than 20 days and less than 1% peripheral blood involvement.

In some embodiments, cellular mass is measured by transporting cells in suspension through an SMR, resulting in a transient shift in resonant frequency. When resonating in the second vibration mode, the SMR generates three peaks as the cell passes through the channel. The magnitude of the two side peaks is identical and independent of the flow path that a cell takes within the SMR, allowing the buoyant mass to be measured with a precision of 0.8% in normal medium and 1.5% in dense medium. For the two-fluid switching measurement, dense medium was obtained by adding 30% Opti-Prep (60% iodixanol in water with a density of 1.32 g/ml) to RPMI medium to achieve a density of 1.10 g/ml. Because Opti-Prep is isosmotic, the osmolarity of the dense medium was identical to that of the normal medium. Based on the buoyant mass of a cell measured in two fluids of different density, the volume, mass, and density can be calculated by the following Formula (1): $m_b = m_c(1-\rho_f \rho_c)$, where $m_b$ is 'the buoyant mass, $m_c$ is the absolute mass, $\rho_c$ is the density of a cell, and $\rho_f$ is the fluid density.

In some embodiments, the cellular mass (buoyant mass) of single cells from a sample is calculated for its mean value and is designated as average cellular mass. In some embodiments, the average cellular mass of cancer cells from each individual patient of a group of patients are evaluated against the patient's disease state, treatment efficacy, disease-free duration time, MRD duration time, and the onset of relapse.

In some embodiments, a modified SMR or SMR system is used to collect and/or measure the cellular mass of individual cells. In some embodiments, the modification is such that after cellular mass measurement is complete on an individual cell, the individual cell is captured in such a way that identifies the cell such that results of a subsequent cellular analysis performed on the same cell (e.g. detection of a molecular signature or biomarker) can be linked to a cell mass or other biophysical property of the cell. For example, in some embodiments the modification includes using peak detection in the final cantilever. Detection at this cantilever indicates a cell exiting the mass sensor array and triggers the motion of a three-dimensional motorized stage which positions a PCR tube containing lysis buffer to capture each single cell as it is flushed from the system. This enables measurements of the biophysical properties of mass and growth rate to be linked to genomic profiles-here RNA-seq- at the single-cell level.

Molecular Signatures and Biomarkers

In some embodiments, the biomarker is or includes one or more molecular signature or molecular biomarker. In some embodiments, a molecular signature of a hematopoietic malignancy and/or relapse can include a signature that indicates a quiescent/senescent (stemness) gene expression program, characterized by high expression levels of TNFa/ NF-kB pathways and subset of CDKN2A, and high expression levels of SNAI1, TNF, GADD45B, EGR1, and NFKBIZ, which can indicate a low risk of hematopoietic malignancy and/or relapse and/or indicate the subject can have a late-onset of hematopoietic malignancy relapse. In some embodiments, a subject whose malignant cells show a cycling program signature, characterized by high pre-BCR score and high levels of expression of IGLL1, VPREB3, CCND3, HMGN2, VPREB1, AURKB, CCNA2, HMGB2, PCNA, and TUBA1B can have a high risk of and/or early-onset of relapse. In some embodiments, a molecular signature in malignant cells that is indicative of a stress response program can have high expression levels of HSF1/p38 and high expression levels of genes HSPA1A, HSPA1B, HSP90AA1, BAG3, and DNAJA1, and indicates that the subject has a high risk of relapse and/or early-onset relapse.

In some embodiments, the presence of a "low risk" signature can indicate that the time to relapse can be greater than 200, 250, 300, 400, 500, 600, 700, 800, 900, 1000, 2000, 3000, 4000, 5000, more than 5000, or more than 10,000 days. In some embodiments, the presence of a "high risk" signature can indicate that the time to relapse of less than 200, 150, 100, 80, 50, 40, 30, 20, 10, 5, or 2 days. In some embodiments, the presence of a "low risk" signature can indicate that the time to relapse for a B-cell ALL subject can be greater than 200, 250, 300, 400, 500, 600, 700, 800, 900, 1000, 2000, 3000, 4000, 5000, more than 5000, or more than 10,000 days. In some embodiments, the presence of a "high risk" signature can indicate that the time to relapse for a B-cell ALL subject is less than 200, 150, 100, 80, 50, 40, 30, 20, 10, 5, or 2 days.

As used herein a "signature" may encompass any gene or genes, protein or proteins, or epigenetic element(s) whose expression profile or whose occurrence is associated with a specific cell type, subtype, or cell state of a specific cell type or subtype within a population of cells (e.g., malignant cells, immune evading tumor cells, immunotherapy resistant tumor cells, tumor infiltrating lymphocytes, and macrophages).

In certain embodiments, use of signature genes includes epigenetic modifications that may be detected or modulated. For ease of discussion, when discussing gene expression, any of gene or genes, protein or proteins, or epigenetic element(s) may be substituted. As used herein, the terms "signature", "expression profile", or "expression program" may be used interchangeably. It is to be understood that also when referring to proteins (e.g. differentially expressed proteins), such may fall within the definition of "gene" signature. Levels of expression or activity may be compared between different cells in order to characterize or identify for instance signatures specific for cell (sub)populations. Increased or decreased expression or activity or prevalence of signature genes may be compared between different cells in order to characterize or identify for instance specific cell (sub)populations. The detection of a signature in single cells may be used to identify and quantitate for instance specific cell (sub)populations. A signature may include a gene or genes, protein or proteins, or epigenetic element(s) whose expression or occurrence is specific to a cell (sub)population, such that expression or occurrence is exclusive to the cell (sub)population. A gene signature as used herein, may thus refer to any set of up- and/or down-regulated genes that are representative of a cell type or subtype. A gene signature as used herein, may also refer to any set of up- and/or down-regulated genes between different cells or cell (sub)populations derived from a gene expression profile. For example, a gene signature may comprise a list of genes differentially expressed in a distinction of interest.

The signature as defined herein (being it a gene signature, protein signature or other genetic or epigenetic signature) can be used to indicate the presence of a cell type, a subtype of the cell type, the state of the microenvironment of a population of cells, a particular cell type population or subpopulation, and/or the overall status of the entire cell (sub)population. Furthermore, the signature may be indicative of cells within a population of cells in vivo. The signature may also be used to suggest for instance particular therapies, or to follow up treatment, or to suggest ways to modulate immune systems. The signatures of the present invention may be discovered by analysis of expression profiles of single-cells within a population of cells from isolated samples (e.g. tumor samples), thus allowing the discovery of novel cell subtypes or cell states that were previously invisible or unrecognized. The presence of subtypes or cell states may be determined by subtype specific or cell state specific signatures. The presence of these specific cell (sub)types or cell states may be determined by applying the signature genes to bulk sequencing data in a sample. Not being bound by a theory the signatures of the present invention may be microenvironment specific, such as their expression in a particular spatio-temporal context. Not being bound by a theory, signatures as discussed herein are specific to a particular pathological context. Not being bound by a theory, a combination of cell subtypes having a particular signature may indicate an outcome. Not being bound by a theory, the signatures can be used to deconvolute the network of cells present in a particular pathological condition. Not being bound by a theory the presence of specific cells and cell subtypes are indicative of a particular response to treatment, such as including increased or decreased susceptibility to treatment. The signature may indicate the presence of one particular cell type or state. In one embodiment, the signatures are used to detect multiple cell states or hierarchies that occur in subpopulations of cells that are linked to particular pathological condition or linked to a particular outcome or progression of the disease, or linked to a particular response to treatment of the disease (e.g. resistance to immunotherapy).

The signature according to certain embodiments of the present invention may comprise or consist of one or more genes, proteins and/or epigenetic elements, such as for instance 1, 2, 3, 4, 5, 6, 7, 8, 9, 10 or more. In certain embodiments, the signature may comprise or consist of two or more genes, proteins and/or epigenetic elements, such as for instance 2, 3, 4, 5, 6, 7, 8, 9, 10 or more. In certain embodiments, the signature may comprise or consist of three or more genes, proteins and/or epigenetic elements, such as for instance 3, 4, 5, 6, 7, 8, 9, 10 or more. In certain embodiments, the signature may comprise or consist of four or more genes, proteins and/or epigenetic elements, such as for instance 4, 5, 6, 7, 8, 9, 10 or more. In certain embodiments, the signature may comprise or consist of five or more genes, proteins and/or epigenetic elements, such as for instance 5, 6, 7, 8, 9, 10 or more. In certain embodiments, the signature may comprise or consist of six or more genes, proteins and/or epigenetic elements, such as for instance 6, 7, 8, 9, 10 or more. In certain embodiments, the signature may comprise or consist of seven or more genes, proteins and/or epigenetic elements, such as for instance 7, 8, 9, 10 or more. In certain embodiments, the signature may comprise or consist of eight or more genes, proteins and/or epigenetic elements, such as for instance 8, 9, 10 or more. In certain embodiments, the signature may comprise or consist of nine or more genes, proteins and/or epigenetic elements, such as for instance 9, 10 or more. In certain embodiments, the signature may comprise or consist of ten or more genes, proteins and/or epigenetic elements, such as for instance 10, 11, 12, 13, 14, 15, or more. It is to be understood that a signature according to the invention may for instance also include genes or proteins as well as epigenetic elements combined.

In certain embodiments, a signature is characterized as being specific for a particular cell or cell (sub)population if it is upregulated or only present, detected or detectable in that particular cell or cell (sub)population, or alternatively is downregulated or only absent, or undetectable in that particular cell or cell (sub)population. In this context, a signature consists of one or more differentially expressed genes/proteins or differential epigenetic elements when comparing different cells or cell (sub)populations, including comparing different tumor cells or tumor cell (sub)populations (e.g., leukemic cells), as well as comparing tumor cells or tumor cell (sub)populations with other tumor cells or tumor cell (sub)populations. It is to be understood that "differentially expressed" genes/proteins include genes/proteins which are up- or down-regulated as well as genes/proteins which are turned on or off. When referring to up-or down-regulation, in certain embodiments, such up- or down-regulation is preferably at least two-fold, such as two-fold, three-fold, four-fold, five-fold, or more, such as for instance at least ten-fold, at least 20-fold, at least 30-fold, at least 40-fold, at least 50-fold, or more. Alternatively, or in addition, differential expression may be determined based on common statistical tests, as is known in the art.

As discussed herein, differentially expressed genes/proteins, or differential epigenetic elements may be differentially expressed on a single-cell level or may be differentially expressed on a cell population level. Preferably, the differentially expressed genes/proteins or epigenetic elements as discussed herein, such as constituting the gene signatures as discussed herein, when as to the cell population level, refer to genes that are differentially expressed in all or substantially all cells of the population (such as at least 80%, preferably at least 90%, such as at least 95% of the individual cells). This allows one to define a particular subpopulation of cells. As referred to herein, a "subpopulation" of cells preferably refers to a particular subset of cells of a particular cell type (e.g., resistant) which can be distinguished or are uniquely identifiable and set apart from other cells of this cell type. The cell subpopulation may be phenotypically characterized and is preferably characterized by the signature as discussed herein. A cell (sub)population as referred to herein may constitute of a (sub)population of cells of a particular cell type characterized by a specific cell state.

When referring to induction, or alternatively reducing or suppression of a particular signature, preferable is meant induction or alternatively reduction or suppression (or upregulation or downregulation) of at least one gene/protein and/or epigenetic element of the signature, such as for instance at least two, at least three, at least four, at least five, at least six, or all genes/proteins and/or epigenetic elements of the signature.

Various embodiments and embodiments of the invention may involve analyzing gene signatures, protein signature, and/or other genetic or epigenetic signature based on single-cell analyses (e.g., single-cell RNA sequencing) or alternatively based on cell population analyses, as is defined herein elsewhere.

The signature genes of the present invention were discovered by analysis of expression profiles of single-cells within a population of tumor cells, thus allowing the discovery of novel cell subtypes that were previously invisible in a population of cells within a tumor. The presence of subtypes may be determined by subtype specific signature genes. The presence of these specific cell types may be determined by applying the signature genes to bulk sequencing data in a patient. Not being bound by a theory, many cells that make up a microenvironment, whereby the cells communicate and affect each other in specific ways. As such, specific cell types within this microenvironment may express signature genes specific for this microenvironment. Not being bound by a theory the signature genes of the present invention may be microenvironment specific, such as their expression in a tumor. The signature genes may indicate the presence of one particular cell type. In one embodiment, the expression may indicate the presence of immunotherapy resistant cell types. Not being bound by a theory, a combination of cell subtypes in a subject may indicate an outcome (e.g., resistant cells, cytotoxic T cells, Tregs).

Detecting Molecular Signatures

In one embodiment, the signature genes, biomarkers, and/or cells expressing biomarkers may be detected or isolated by immunofluorescence, immunohistochemistry (IHC), fluorescence activated cell sorting (FACS), mass spectrometry (MS), mass cytometry (CyTOF), sequencing, whole genome sequencing, whole exome sequencing, RNA-seq, single-cell RNA-seq, quantitative RT-PCR, single-cell qPCR, FISH, RNA-FISH, MERFISH (multiplex (in situ) RNA FISH) and/or by in situ hybridization. Other methods including absorbance assays and colorimetric assays are known in the art and may be used herein. Detection may comprise primers and/or probes or fluorescently bar-coded oligonucleotide probes for hybridization to RNA (see e.g., Geiss G K, et al., Direct multiplexed measurement of gene expression with color-coded probe pairs. Nat Biotechnol. 2008 March;26(3):317-25). In certain embodiments, cancer is diagnosed, prognosed, or monitored. For example, a tissue sample may be obtained and analyzed for specific cell markers (IHC) or specific transcripts (e.g., RNA-FISH). In one embodiment, tumor cells are stained for cell subtype specific signature genes. In one embodiment, the cells are fixed. In another embodiment, the cells are formalin fixed and paraffin embedded. Not being bound by a theory, the presence of the tumor subtypes indicates outcome and personalized treatments.

The present invention also may comprise a kit with a detection reagent that binds to one or more biomarkers or can be used to detect one or more biomarkers.

Sequencing

In certain embodiments, sequencing is used to identify expression of genes or transcriptomes in single cells. In certain embodiments, sequencing comprises high-throughput (formerly "next-generation") technologies to generate sequencing reads. Methods for constructing sequencing libraries are known in the art (see, e.g., Head et al., Library construction for next-generation sequencing: Overviews and challenges. Biotechniques. 2014; 56(2): 61-77). A "library" or "fragment library" may be a collection of nucleic acid molecules derived from one or more nucleic acid samples, in which fragments of nucleic acid have been modified, generally by incorporating terminal adapter sequences comprising one or more primer binding sites and identifiable sequence tags. In certain embodiments, the library members (e.g., cDNA) may include sequencing adaptors that are compatible with use in, e.g., Illumina's reversible terminator method, long read nanopore sequencing, Roche's pyrosequencing method (454), Life Technologies' sequencing by ligation (the SOLiD platform) or Life Technologies' Ion Torrent platform. Examples of such methods are described in the following references: Margulies et al (Nature 2005

437: 376-80); Schneider and Dekker (Nat Biotechnol. 2012 Apr. 10; 30(4):326-8); Ronaghi et al (Analytical Biochemistry 1996 242: 84-9); Shendure et al (Science 2005 309: 1728-32); Imelfort et al (Brief Bioinform. 2009 10:609-18); Fox et al (Methods Mol. Biol. 2009; 553:79-108); Appleby et al (Methods Mol. Biol. 2009; 513:19-39); and Morozova et al (Genomics. 2008 92:255-64), which are incorporated by reference for the general descriptions of the methods and the particular steps of the methods, including all starting products, reagents, and final products for each of the steps.

As used herein the term "transcriptome" refers to the set of transcript molecules. In some embodiments, transcript refers to RNA molecules, e.g., messenger RNA (mRNA) molecules, small interfering RNA (siRNA) molecules, transfer RNA (tRNA) molecules, ribosomal RNA (rRNA) molecules, and complimentary sequences, e.g., cDNA molecules. In some embodiments, a transcriptome refers to a set of mRNA molecules. In some embodiments, a transcriptome refers to a set of cDNA molecules. In some embodiments, a transcriptome refers to one or more of mRNA molecules, siRNA molecules, tRNA molecules, rRNA molecules, in a sample, for example, a single cell or a population of cells. In some embodiments, a transcriptome refers to cDNA generated from one or more of mRNA molecules, siRNA molecules, tRNA molecules, rRNA molecules, in a sample, for example, a single cell or a population of cells. In some embodiments, a transcriptome refers to 25%, 50%, 55, 60, 65, 70, 75, 80, 85, 90, 91, 92, 93, 94, 95, 96, 97, 98, 99, 99.9, or 100% of transcripts from a single cell or a population of cells. In some embodiments, transcriptome not only refers to the species of transcripts, such as mRNA species, but also the amount of each species in the sample. In some embodiments, a transcriptome includes each mRNA molecule in the sample, such as all the mRNA molecules in a single cell.

In certain embodiments, the invention involves single-cell RNA sequencing (see, e.g., Kalisky, T., Blainey, P. & Quake, S. R. Genomic Analysis at the Single-Cell Level. Annual review of genetics 45, 431-445, (2011); Kalisky, T. & Quake, S. R. Single-cell genomics. Nature Methods 8, 311-314 (2011); Islam, S. et al. Characterization of the single-cell transcriptional landscape by highly multiplex RNA-seq. Genome Research, (2011); Tang, F. et al. RNA-Seq analysis to capture the transcriptome landscape of a single cell. Nature Protocols 5, 516-535, (2010); Tang, F. et al. mRNA-Seq whole-transcriptome analysis of a single cell. Nature Methods 6, 377-382, (2009); Ramskold, D. et al. Full-length mRNA-Seq from single-cell levels of RNA and individual circulating tumor cells. Nature Biotechnology 30, 777-782, (2012); and Hashimshony, T., Wagner, F., Sher, N. & Yanai, I. CEL-Seq: Single-Cell RNA-Seq by Multiplexed Linear Amplification. Cell Reports, Cell Reports, Volume 2, Issue 3, p666-673, 2012).

In certain embodiments, the present invention involves single-cell RNA sequencing (scRNA-seq). In certain embodiments, the invention involves plate based single cell RNA sequencing (see, e.g., Picelli, S. et al., 2014, "Full-length RNA-seq from single cells using Smart-seq2" Nature protocols 9, 171-181, doi:10.1038/nprot.2014.006).

In certain embodiments, the invention involves high-throughput single-cell RNA-seq where the RNAs from different cells are tagged individually, allowing a single library to be created while retaining the cell identity of each read. In this regard reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO2014210353A2; Zilionis, et al., 2017, "Single-cell barcoding and sequencing using droplet microfluidics" Nat Protoc. Jan;12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; Rosenberg et al., 2017, "Scaling single cell transcriptomics through split pool barcoding" bioRxiv preprint first posted online Feb. 2, 2017, doi: dx.doi.org/10.1101/105163; Rosenberg et al., "Single-cell profiling of the developing mouse brain and spinal cord with split-pool barcoding" Science 15 Mar. 2018; Vitak, et al., "Sequencing thousands of single-cell genomes with combinatorial indexing" Nature Methods, 14(3):302-308, 2017; Cao, et al., Comprehensive single-cell transcriptional profiling of a multicellular organism. Science, 357(6352):661-667, 2017; Gierahn et al., "Seq-Well: portable, low-costRNA sequencing of single cells at high throughput" Nature Methods 14, 395-398 (2017); and Hughes, et al., "Highly Efficient, Massively-Parallel Single-Cell RNA-Seq Reveals Cellular States and Molecular Features of Human Skin Pathology" bioRxiv 689273; doi: doi.org/10.1101/689273, all the contents and disclosure of each of which are herein incorporated by reference in their entirety.

In certain embodiments, the invention involves single nucleus RNA sequencing. In this regard reference is made to Swiech et al., 2014, "In vivo interrogation of gene function in the mammalian brain using CRISPR-Cas9" Nature Biotechnology Vol. 33, pp. 102-106; Habib et al., 2016, "Div-Seq: Single-nucleus RNA-Seq reveals dynamics of rare adult newborn neurons" Science, Vol. 353, Issue 6302, pp. 925-928; Habib et al., 2017, "Massively parallel single-nucleus RNA-seq with DroNc-seq" Nat Methods. 2017 October;14(10):955-958; and International patent application number PCT/US2016/059239, published as WO2017164936 on Sep. 28, 2017, which are herein incorporated by reference in their entirety.

In certain embodiments, dimension reduction is used to cluster single cells based on differentially expressed genes. In certain embodiments, the dimension reduction technique may be, but is not limited to, Uniform Manifold Approximation and Projection (UMAP) or t-SNE (see, e.g., Becht et al., Evaluation of UMAP as an alternative to t-SNE for single-cell data, bioRxiv 298430; doi.org/10.1101/298430; and Becht et al., 2019, Dimensionality reduction for visualizing single-cell data using UMAP, Nature Biotechnology volume 37, pages 38-44).

Other suitable single-cell sequencing techniques include, but are not limited to, those set forth in International Patent Publication No. WO2016/040476, Chen et al., Front. Genet., 5 Apr. 2019 | https://doi.org/10.3389/fgene.2019.00317, particularly at Table 1, scRNA-seq, SUPeR-seq, MATQ-seq, RamDA-seq, SINC-seq, ViscRNA-seq, UMI Methods, Digital RNA HiRes-SEQ, FREQ-SEQ RNAtag-Seq, MARS-Seq, Quartz-Seq, Quartz-Seq2, DP-Seq, Smart-Seq, Nano-Cage, Smart-Seq2, snRNA-Seq, FRISCR, SPLiT-seq, sci-RNA-seq, CEL-seq, STRT, TCR Chain pairing, TCR- LA-MC PCR, CirSeq, TIVA, PAIR, CLaP, CytoSeq, Drop-Seq, snDrop-Seq, DroNC-Seq, CITE-Seq, ECCITE-Seq, CROP-Seq, Mosaic-Seq, Act-Seq, Seq-Well, Microwell-seq, Nanogrid-SNRS, Multi-Seq, Hi-SCL, in-Drop, Nuc-Seq, Div-Seq, SCRB-Seq, smMIP, MIPSTR, MDA, IMS-MDA, MIDAS, SCMDA, MALBAC, SNES, LIANTI, Sci-DNA-Seq, CRISPR-UMI, TSCS, OS-Seq, Safe-SeqS, Duplex-Seq, snmC-Seq, scAba-Seq, sci-MET, scRC-Seq, scChIP-seq, scATAC-Seq, Drop-ChIP, scTHS-seq, sciHi-C, Dip-C, SMDB, SIDR, DR-Seq, G&T-Seq, scM&T-Seq, sci-CAR, scTrio-Seq, scTrio-Seq2, scNMT-seq, scCool-Seq, TruSeq PCR Free, TruSeqNano, AmpliSeq, TruSeq RNA, TruSeq small RNA, TruSeq stranded RNA, TruSeq RNA exome, TruSeq targeted RNA expression, Act-Seq (see e.g. Wu Y. E. et al. (2017) Neuron 96(2): 313-329); CEL-Seq (see e.g., Hashimshony T. et al. (2012) Cell Rep 2: 666-673); CirSeq (see e.g., Acevedo A. et al. (2014) Nature 505: 686-690); CITE-Seq (see e.g., Stoeckius M., et al. (2017) Nat Methods 14(9): 865-868); CLaP (see e.g., Binan L. et al. (2016) Nat Commun 7: 11636); CRISPR-UMI (see e.g., Michlits G. et al. (2017) Nat Methods 14(12): 1191-1197); CROP-Seq (see e.g., Datlinger P. et al. (2017) Nat Methods 14(3): 297-301); CytoSeq (see e.g., Fan H. C. et al. (2015) Science 347: 1258367); Digital RNA (see e.g., Shiroguchi K. et al. (2012) Proc Natl Acad Sci USA 109:1347-1352); Dip-C(see e.g., Tan L., et al. (2018) Science 361(6405): 924-928); Div-Seq (see e.g., Habib N. et al. (2016) Science 353(6302): 925-928); DP-Seq (see e.g., Bhargava V. et al. (2013) Sci Rep 3: 1740); DroNC-seq (see e.g., Habib N. et al. (2017) Nat Methods 14(10): 955-958); Drop-Seq (see e.g., Macosko E. Z. et al. (2015) Cell 161: 1202-1214); DR-Seq (see e.g., Dey S. S. et al. (2015) Nat Biotechnol 33: 285-9); Drop-ChIP (see e.g., Rotem A. et al. (2015) Nat Biotechnol 33: 1165-72); Duplex-Seq (see e.g., Schmitt M. W. et al. (2012) Proc Natl Acad Sci USA 109: 14508-14513); ECCITE-seq (see e.g., Mimitou E. P. et al. (2019) Nat Methods 16(5): 409-412); FREQ-Seq (see e.g., Chubiz L. M. et al. (2012) PLoS One 7: e47959); FRISCR (see e.g., Thomsen E. R. et al. (2016) Nat Methods 13: 87-93); G&T-seq (see e.g., Macaulay I. C. et al. (2015) Nat Methods 12: 519-522); HiRes-Seq (see e.g., Imashimizu M. et al. (2013) Nucleic Acids Res 41:9090-9104); Hi-SCL (see e.g., Rotem A. et al. (2015) PLoS One 10: e0116328); IMS-MDA (see e.g., Seth-Smith H. M. et al. (2013) Nat Protoc 8: 2404-2412); inDrop (see e.g., Klein A. M. et al. (2015) Cell 161: 1187-201); LIANTI (see e.g., Chen C. et al. (2017) Science 356(6334): 189-194); MALBAC (see e.g., Zong C. et al. (2012) Science 338: 1622-1626); MARS-seq (see e.g., Jaitin D. A. et al. (2014) Science 343:776-9); MATQ-seq (see e.g., Sheng K. et al. (2017) Nat Methods 14(3): 267-270); MDA (see e.g., Dean F. B. et al. (2001) Genome Res 11: 1095-1099); Microwell-seq (see e.g., Han X. et al. (2018) Cell 172(5): 1091-1107.e1017); MIDAS (see e.g., Gole J. et al. (2013) Nat Biotechnol 31:1126-32); MIPSTR (see e.g., Carlson K. D. et al. (2015) Genome Res 25: 750-761); Mosaic-seq (see e.g., Han X. et al. (2018) Cell 172(5): 1091-1107 e1017); MULTI-seq (see e.g., McGinnis C. S. et al. (2019) Nat Methods 16(7): 619-626); NanoCAGE (see e.g., Plessy C. et al. (2010) Nat Methods 7: 528-534); Nanogrid SNRS (see e.g., Gao R. et al. (2017) Nat Commun 8(1): 228); nuc-seq (see e.g., Wang Y. et al. (2014) Nature 512: 155-160); Nuc-Seq/SNES (see e.g., Leung M. L. et al. (2015) Genome Biology 16(1): 55); OS-Seq (see e.g., Myllykangas S. et al. (2011) Nat Biotechnol 29: 1024-1027); PAIR (see e.g., Bell T. J. et al. (2015) Methods Mol Biol 1324: 457-68); Quartz-Seq (see e.g., Sasagawa Y. et al. (2013) Genome Biol 14: R31); Quartz-Seq2 (see e.g., Sasagawa Y. et al. (2018) Genome Biology 19(1): 29); RamDA-seq (see e.g., Hayashi T. et al. (2018) Nature Communications 9(1): 619); RNAtag-Seq (see e.g., Shishkin A. A. et al. (2015) Nat Methods 12: 323-325); Safe-SeqS (see e.g., Kinde I. et al. (2011) Proc Natl Acad Sci USA 108: 9530-5); scABA-seq (see e.g., Mooijman D. et al. (2016) Nature Biotechnology 34: 852); scATAC-seq (see e.g., Buenrostro J. D. et al. (2015) Nature 523: 486-490 (Microfluidics)); scATAC-Seq (see e.g., Cusanovich D. A. et al. (2015) Science 348: 910-4 (Cell Index)); scChip-seq (see e.g., Rotem A. et al. (2015) Nat Biotechnol 33: 1165-72); scCool-seq (see e.g., Li L. et al. (2018) Nature Cell Biology 20(7): 847-858); sciHi-C(see e.g., Ramani V. et al. (2017) Nature Methods 14: 263); sci-CAR (see e.g., Cao J. et al. (2018) Science 361(6409): 1380); sci-DNA-seq (see e.g., Rosenberg A. B. et al. (2018) Science 360: 176-182); sci-MET (see e.g., Mulqueen R. M. et al. (2018) Nature Biotechnology 36: 428); sci-RNA-seq (see e.g., Cao J. et al. (2017) Science 357(6352): 661); SCMDA (see e.g., Dong X. et al. (2017) Nature Methods 14: 491); scM&T-seq (see e.g., Angermueller C. et al. (2016) Nature Methods 13: 229); scNMT-seq (see e.g., Clark S. J. et al. (2018) Nature Communications 9(1): 781 scRC-Seq Upton K. R. et al. (2015) Cell 161: 228-39); scRNA-seq (see e.g., Tang F. et al. (2009) Nat Methods 6: 377-82); SCRB-Seq Soumillon M. et al. (2014) bioRxiv: 003236); scTHS-seq (see e.g., Lake B. B. et al. (2018) Nature Biotechnology 36(1): 70-80); scTrio-seq (see e.g., Hou Y. et al. (2016) Cell Res 26: 304-19); scTrio-seq2 (see e.g., Bian S. et al. (2018) Science 362 (6418): 1060); Seq-Well (see e.g., Gierahn T. M., et al. (2017). Nat Methods 14(4): 395-398); SIDR (see e.g., Han K. Y. et al. (2018) Genome Research 28(1): 75-87); SINC-seq (see e.g., Abdelmoez M. N. et al. (2018) Genome Biology 19(1): 66); Smart-Seq (see e.g., Ramskold D. et al. (2012) Nat Biotechnol 30: 777-782); Smart-seq2 (see e.g., Picelli S. et al. (2013) Nat Methods 10: 1096-1098v); SMDB (see e.g., Lan F. et al. (2016) Nat Commun 7: 11784); smMIP (see e.g., Hiatt J. B. et al. (2013) Genome Res 23: 843-854); snDrop-seq (see e.g., Lake B. B. et al. (2018) Nature Biotechnology 36(1): 70-80); SNES (see e.g., Leung M. L. et al. (2015) Genome Biol 16: 55); snmC-Seq (see e.g., Luo C. et al. (2017) Science 357(6351): 600); snRNA-seq (see e.g., Grindberg R. V. et al. (2013) Proc Natl Acad Sci USA 110: 19802-7); SPLiT-seq (see e.g., Rosenberg A. B. et al. (2018) Science 360(6385): 176); STRT (see e.g., Islam S. et al. (2011) Genome Res 21: 1160-1167); SUPeR-seq (see e.g., Fan X. et al. (2015) Genome Biol 16: 148); TCR Chain Pairing (see e.g., Turchaninova M. A. et al. (2013) Eur J Immunol 43: 507-2515); TCR-LA-MC-PCR (see e.g., Ruggiero E. et al. (2015) Nat Commun 6: 8081); TIVA (see e.g., Lovatt D. et al. (2014) Nat Methods 11: 190-196); TSCS (see e.g., Casasent A. K. et al. (2018) Cell 172(1): 205-217.e212); UMI Method (see e.g., Kivioja T. et al. (2012) Nat Methods 9: 72-74); and viscRNA-seq (see e.g., Zanini F. et al. (2018) Elife 7: e32942) and combinations thereof, which can be adapted for use with the embodiments described herein.

In certain embodiments, a subject can be categorized based on signature genes or gene programs expressed by a tissue sample obtained from the subject. In certain embodiments, the tissue sample is analyzed by bulk sequencing. In certain embodiments, subtypes can be determined by determining the percentage of specific cell subtypes expressing the identified interacting genetic variants in the sample that contribute to the phenotype. In certain embodiments, gene expression associated with the cells are determined from bulk sequencing reads by deconvolution of the sample. For example, deconvoluting bulk gene expression data obtained from a tumor containing both malignant and non-malignant cells can include defining the relative frequency of a set of cell types in the tumor from the bulk gene expression data using cell type specific gene expression (e.g., cell types may be T cells, fibroblasts, macrophages, mast cells, B/plasma cells, endothelial cells, myocytes and dendritic cells); and defining a linear relationship between the frequency of the non-malignant cell types and the expression of a set of genes, wherein the set of genes comprises genes highly expressed by malignant cells and at most two non-malignant cell types, wherein the set of genes are derived from gene expression analysis of single cells in the tumor or the same tumor type, and wherein the residual of the linear relationship defines the malignant cell-specific (MCS) expression profile (see, e.g., WO 2018/191553; and Puram et al., Cell. 2017 Dec. 14; 171(7):1611-1624.e24).

MS Methods

Biomarker detection may also be evaluated using mass spectrometry methods. A variety of configurations of mass spectrometers can be used to detect biomarker values. Several types of mass spectrometers are available or can be produced with various configurations. In general, a mass spectrometer has the following major components: a sample inlet, an ion source, a mass analyzer, a detector, a vacuum system, and instrument-control system, and a data system. Difference in the sample inlet, ion source, and mass analyzer generally define the type of instrument and its capabilities. For example, an inlet can be a capillary-column liquid chromatography source or can be a direct probe or stage such as used in matrix-assisted laser desorption. Common ion sources are, for example, electrospray, including nanospray and microspray or matrix-assisted laser desorption. Common mass analyzers include a quadrupole mass filter, ion trap mass analyzer and time-of-flight mass analyzer. Additional mass spectrometry methods are well known in the art (see Burlingame et al., Anal. Chem. 70:647R-716R (1998); Kinter and Sherman, New York (2000)).

Protein biomarkers and biomarker values can be detected and measured by any of the following: electrospray ionization mass spectrometry (ESI-MS), ESI-MS/MS, ESI-MS/(MS)n, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), tandem time-of-flight (TOF/TOF) technology, called ultraflex III TOF/TOF, atmospheric pressure chemical ionization mass spectrometry (APCI-MS), APCI-MS/MS, APCI-(MS).sup.N, atmospheric pressure photoionization mass spectrometry (APPI-MS), APPI-MS/MS, and APPI-(MS).sup.N, quadrupole mass spectrometry, Fourier transform mass spectrometry (FTMS), quantitative mass spectrometry, and ion trap mass spectrometry.

Sample preparation strategies are used to label and enrich samples before mass spectroscopic characterization of protein biomarkers and determination biomarker values. Labeling methods include but are not limited to isobaric tag for relative and absolute quantitation (iTRAQ) and stable isotope labeling with amino acids in cell culture (SILAC). Capture reagents used to selectively enrich samples for candidate biomarker proteins prior to mass spectroscopic analysis include but are not limited to aptamers, antibodies, nucleic acid probes, chimeras, small molecules, an F(ab')$_2$ fragment, a single chain antibody fragment, an Fv fragment, a single chain Fv fragment, a nucleic acid, a lectin, a ligand-binding receptor, affibodies, nanobodies, ankyrins, domain antibodies, alternative antibody scaffolds (e.g. diabodies etc.) imprinted polymers, avimers, peptidomimetics, peptoids, peptide nucleic acids, threose nucleic acid, a hormone receptor, a cytokine receptor, and synthetic receptors, and modifications and fragments of these.

Immunoassays

Immunoassay methods are based on the reaction of an antibody to its corresponding target or analyte and can detect the analyte in a sample depending on the specific assay format. To improve specificity and sensitivity of an assay method based on immunoreactivity, monoclonal antibodies are often used because of their specific epitope recognition. Polyclonal antibodies have also been successfully used in various immunoassays because of their increased affinity for the target as compared to monoclonal antibodies. Immunoassays have been designed for use with a wide range of biological sample matrices. Immunoassay formats have been designed to provide qualitative, semi-quantitative, and quantitative results.

Quantitative results may be generated through the use of a standard curve created with known concentrations of the specific analyte to be detected. The response or signal from an unknown sample is plotted onto the standard curve, and a quantity or value corresponding to the target in the unknown sample is established.

Numerous immunoassay formats have been designed. ELISA or EIA can be quantitative for the detection of an analyte/biomarker. This method relies on attachment of a label to either the analyte or the antibody and the label component includes, either directly or indirectly, an enzyme. ELISA tests may be formatted for direct, indirect, competitive, or sandwich detection of the analyte. Other methods rely on labels such as, for example, radioisotopes ($I^{11}$) or fluorescence. Additional techniques include, for example, agglutination, nephelometry, turbidimetry, Western blot, immunoprecipitation, immunocytochemistry, immunohistochemistry, flow cytometry, Luminex assay, and others (see ImmunoAssay: A Practical Guide, edited by Brian Law, published by Taylor & Francis, Ltd., 2005 edition).

Exemplary assay formats include enzyme-linked immunosorbent assay (ELISA), radioimmunoassay, fluorescent, chemiluminescence, and fluorescence resonance energy transfer (FRET) or time resolved-FRET (TR-FRET) immunoassays. Examples of procedures for detecting biomarkers include biomarker immunoprecipitation followed by quantitative methods that allow size and peptide level discrimination, such as gel electrophoresis, capillary electrophoresis, planar electrochromatography, and the like.

Methods of detecting and/or quantifying a detectable label or signal generating material depend on the nature of the label. The products of reactions catalyzed by appropriate enzymes (where the detectable label is an enzyme; see above) can be, without limitation, fluorescent, luminescent, or radioactive or they may absorb visible or ultraviolet light. Examples of detectors suitable for detecting such detectable labels include, without limitation, x-ray film, radioactivity counters, scintillation counters, spectrophotometers, colorimeters, fluorometers, luminometers, and densitometers.

Any of the methods for detection can be performed in any format that allows for any suitable preparation, processing, and analysis of the reactions. This can be, for example, in multi-well assay plates (e.g., 96 wells or 384 wells) or using any suitable array or microarray. Stock solutions for various agents can be made manually or robotically, and all subsequent pipetting, diluting, mixing, distribution, washing, incubating, sample readout, data collection and analysis can be done robotically using commercially available analysis software, robotics, and detection instrumentation capable of detecting a detectable label.

Hybridization Assays

Such applications are hybridization assays in which a nucleic acid that displays "probe" nucleic acids for each of the genes to be assayed/profiled in the profile to be generated is employed. In these assays, a sample of target nucleic acids is first prepared from the initial nucleic acid sample being assayed, where preparation may include labeling of the target nucleic acids with a label, e.g., a member of a signal producing system. Following target nucleic acid sample preparation, the sample is contacted with the array under hybridization conditions, whereby complexes are formed between target nucleic acids that are complementary to probe sequences attached to the array surface. The presence of hybridized complexes is then detected, either qualitatively or quantitatively. Specific hybridization technology which may be practiced to generate the expression profiles employed in the subject methods includes the technology described in U.S. Pat. Nos. 5,143,854; 5,288,644; 5,324, 633; 5,432,049; 5,470,710; 5,492,806; 5,503,980; 5,510, 270; 5,525,464; 5,547,839; 5,580,732; 5,661,028; 5,800, 992; the disclosures of which are herein incorporated by reference; as well as WO 95/21265; WO 96/31622; WO 97/10365; WO 97/27317; EP 373 203; and EP 785 280. In these methods, an array of "probe" nucleic acids that includes a probe for each of the biomarkers whose expression is being assayed is contacted with target nucleic acids as described above. Contact is carried out under hybridization conditions, e.g., stringent hybridization conditions as described above, and unbound nucleic acid is then removed. The resultant pattern of hybridized nucleic acids provides information regarding expression for each of the biomarkers that have been probed, where the expression information is in terms of whether or not the gene is expressed and, typically, at what level, where the expression data, i.e., expression profile, may be both qualitative and quantitative.

Optimal hybridization conditions will depend on the length (e.g., oligomer vs. polynucleotide greater than 200 bases) and type (e.g., RNA, DNA, PNA) of labeled probe and immobilized polynucleotide or oligonucleotide. General parameters for specific (i.e., stringent) hybridization conditions for nucleic acids are described in Sambrook et al., supra, and in Ausubel et al., "Current Protocols in Molecular Biology", Greene Publishing and Wiley-interscience, NY (1987), which is incorporated in its entirety for all purposes. When the cDNA microarrays are used, typical hybridization conditions are hybridization in 5×SSC plus 0.2% SDS at 65C for 4 hours followed by washes at 25° C. in low stringency wash buffer (1×SSC plus 0.2% SDS) followed by 10 minutes at 25° C. in high stringency wash buffer (0.1SSC plus 0.2% SDS) (see Shena et al., Proc. Natl. Acad. Sci. USA, Vol. 93, p. 10614 (1996)). Useful hybridization conditions are also provided in, e.g., Tijessen, Hybridization With Nucleic Acid Probes", Elsevier Science Publishers B. V. (1993) and Kricka, "Nonisotopic DNA Probe Techniques", Academic Press, San Diego, Calif. (1992).

CRISPR-Effector System-based Nucleic Acid Detection

In some embodiments, a molecular signature or biomarker is detected by a CRISPR-Effector system, such as any such system having collateral activity. In some embodiments, the CRISPR-Effector system can include a gRNA capable of binding a target polynucleotide and a Cas effector. In some embodiments, the Cas effector can have collateral polynucleotide activity and can be used to detect a replication-specific feature described herein. The CIRSPR-effector system or component thereof can be included in a composition with one or more other reagents (including but not limited to an amplification reagent), molecules, etc. to facilitate detection and/or measuring of one or more effects of the pool of target compounds. Such systems are also referred to as CRISPR diagnostics and can be configured to detect specific DNAs and RNAs and provide a detectable signal upon detection by capitalizing on the collateral effect of the CRISPR system. Such systems are described in e.g., Vangah et al Biol Proced Online. 2020. 22:22 doi: 10.1186/ s12575-020-00135-3, Patchsung et al. 2020. Nat Biomed Eng. Aug 26. doi: 10.1038/s41551-020-00603-x; Barnes et al. 2020 Nat. Commun. 11(1):4131; Iwasaki and Batey. 2020. Nuc. Acid Res. 2020 Sep. 25; 48(17):e101. doi: 10.1093/nar/gkaa673; Joung et al. 2020. medRxiv. 2020 May 8:2020.05.04.20091231. doi: 10.1101/ 2020.05.04.20091231; de Puig et al. Annu Rev Biomed Eng. 2020 Jun. 4; 22:371-386. doi: 10.1146/annurev-bioeng-060418-052240; Baerwald et al. 2020, Mol Ecol Resour. 2020 July;20(4):961-970. doi: 10.1111/1755-0998.13186; Ackerman et al., Nature. 2020 June;582(7811):277-282. doi: 10.1038/s41586-020-2279-8; Petri and Pattanayak et al., CRISPR J. 2018 June;1:209-211. doi: 10.1089/ crispr.2018.29018.kpe; Batista and Pacheco et al., J Microbiol Methods. 2018 September;152:98-104. doi: 10.1016/ j.mimet.2018.07.024; Gootenberg et al. Science. 2018 Apr. 27; 360(6387):439-444. doi: 10.1126/science.aaq0179; Gootenberg et al. Science. 2017 Apr. 28; 356(6336):438- 442. doi: 10.1126/science.aam9321; PCT/US18/054472 filed Oct. 22, 2018 at [0183]—[0327], incorporated herein by reference. Reference is made to WO 2017/219027, WO2018/107129, US20180298445, US 2018-0274017, US 2018-0305773, WO 2018/170340, U.S. application Ser. No. 15/922,837, filed Mar. 15, 2018 entitled "Devices for CRISPR Effector System Based Diagnostics", PCT/US18/ 50091, filed Sep. 7, 2018 "Multi-Effector CRISPR Based Diagnostic Systems", PCT/US18/66940 filed Dec. 20, 2018 entitled "CRISPR Effector System Based Multiplex Diagnostics", PCT/US18/054472 filed Oct. 4, 2018 entitled "CRISPR Effector System Based Diagnostic", U.S. Provisional Application No. 62/740,728 filed Oct. 3, 2018 entitled "CRISPR Effector System Based Diagnostics for Hemorrhagic Fever Detection", U.S. Provisional Application No. 62/690,278 filed Jun. 26, 2018 and U.S. Provisional Application No. 62/767,059 filed Nov. 14, 2018 both entitled "CRISPR Double Nickase Based Amplification, Compositions, Systems and Methods", U.S. Provisional Application Nos. 62/690,160 filed Jun. 26, 2018 and U.S. Pat. No. 62,767,077 filed Nov. 14, 2018, both entitled "CRISPR/CAS and Transposase Based Amplification Compositions, Systems, And Methods", U.S. Provisional Application Nos. 62/690,257 filed Jun. 26, 2018 and 62/767,052 filed Nov. 14, 2018 both entitled "CRISPR Effector System Based Amplification Methods, Systems, And Diagnostics", US Provisional Application Nos. 62/767,076 filed Nov. 14, 2018 entitled "Multiplexing Highly Evolving Viral Variants With SHERLOCK" and 62/767,070 filed Nov. 14, 2018 entitled "Droplet SHERLOCK." Reference is further made to WO2017/127807, WO2017/184786, WO 2017/184768, WO 2017/189308, WO 2018/035388, WO 2018/170333, WO 2018/191388, WO 2018/213708, WO 2019/005866, PCT/ US18/67328 filed Dec. 21, 2018 entitled "Novel CRISPR Enzymes and Systems", PCT/US18/67225 filed Dec. 21, 2018 entitled "Novel CRISPR Enzymes and Systems" and PCT/US18/67307 filed Dec. 21, 2018 entitled "Novel CRISPR Enzymes and Systems", U.S. Provisional Application No. 62/712,809 filed Jul. 31, 2018 entitled "Novel CRISPR Enzymes and Systems", U.S. Provisional Application No. 62/744,080 filed Oct. 10, 2018 entitled "Novel Cas12b Enzymes and Systems" and U.S. Provisional Application No. 62/751,196 filed Oct. 26, 2018 entitled "Novel Cas12b Enzymes and Systems", U.S. 715,640 filed Aug. 7, 2018 entitled "Novel CRISPR Enzymes and Systems", WO 2016/205711, U.S. Pat. No. 9,790,490, WO 2016/205749, WO 2016/205764, WO 2017/070605, WO 2017/106657, and WO 2016/149661, WO2018/035387, WO2018/194963, Cox DBT, et al., RNA editing with CRISPR-Cas13, Science. 2017 Nov. 24; 358(6366):1019-1027; Gootenberg J S, et al., Multiplexed and portable nucleic acid detection platform with Cas13, Cas12a, and Csm6., Science. 2018 Apr. 27; 360(6387):439-444; Gootenberg J S, et al., Nucleic acid detection with CRISPR-Cas13a/C2c2., Science. 2017 Apr. 28; 356(6336):438-442; Abudayyeh 00, et al., RNA targeting with CRISPR-Cas13, Nature. 2017 Oct. 12; 550(7675): 280-284; Smargon A A, et al., Cas13b Is a Type VI-B CRISPR-Associated RNA-Guided RNase Differentially Regulated by Accessory Proteins Csx27 and Csx28. Mol Cell. 2017 Feb. 16; 65(4):618-630.e7; Abudayyeh 00, et al., C2c2 is a single-component programmable RNA-guided RNA-targeting CRISPR effector, Science. 2016 Aug. 5; 353(6299):aaf5573; Yang L, et al., Engineering and optimising deaminase fusions for genome editing. Nat Commun. 2016 Nov. 2; 7:13330, Myrvhold et al., Field deployable viral diagnostics using CRISPR-Cas13, Science 2018 360, 444-448, Shmakov et al. "Diversity and evolution of class 2 CRISPR-Cas systems," Nat Rev Microbiol. 2017 15(3):169-182, each of which is incorporated herein by reference in its entirety and can be adapted for use with the methods described herein.

PCR-based Polynucleotide Detection

In some embodiments, a PCR-based polynucleotide detection can be used detect or measure a molecular signature or biomarker. In some embodiments, the PCR-based detection method selectively amplifies the target molecule, thus providing specific detection of the target molecule. Some techniques involve direct amplification of the polynucleotide. Other techniques involve amplification of a proxy for the original target molecule such as cDNA or cRNA. Exemplary PCR-based polynucleotide detection methods include, without limitation, semi-qualitative, semi-quantitative, or quantitative PCR, quantitative real-time PCR, reverse transcriptase PCR, real-time reverse transcriptase PCR (rt RT-PCR), nested PCR, strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Epigenome Analysis Techniques

As used herein the term "epigenome, epigenetics" and the like refer to changes, which can be heritable, in gene activity caused by something other than DNA (or genome) sequence changes, and include without limitation, DNA methylation, DNA-protein interactions, chromatin accessibility, and histone isoforms, modifications, and location (occupancy) in genome regions. In some embodiments, the molecular signature and/or molecular biomarker is an epigenetic signature or biomarker. In some embodiments, a sequencing- and/or an array-based technique is used to analyze DNA methylation and include methylation sequencing with a next-generation sequencing technique and the use of methylation microarrays both capable of analyzing the methylation state of various CpGs.

In some cases, the DNA methylation may be detected in a methylation assay utilizing next-generation sequencing. For example, DNA methylation may be detected by massive parallel sequencing with bisulfite conversion, e.g., whole-genome bisulfite sequencing or reduced representation bisulfite sequencing. Optionally, the DNA methylation is detected by microarray, such as a genome-wide microarray. Microarrays, and massively parallel sequencing, have enabled the interrogation of cytosine methylation on a genome-wide scale (Zilberman D, Henikoff S. 2007. Genome-wide analysis of DNA methylation patterns. Development 134(22): 3959-3965.). Genome wide methods have been described previously (Deng, et al. 2009. Targeted bisulfite sequencing reveals changes in DNA methylation associated with nuclear reprogramming. Nat Biotechnol 27(4): 353-360; Meissner, et al. 2005. Reduced representation bisulfite sequencing for comparative high-resolution DNA methylation analysis. Nucleic Acids Res 33(18): 5868-5877; Down, et al. 2008. A Bayesian deconvolution strategy for immunoprecipitation-based DNA methylome analysis. Nat Biotechnol 26(7): 779-785; Gu et al. 2011. Preparation of reduced representation bisulfite sequencing libraries for genome-scale DNA methylation profiling. Nat Protoc 6(4): 468-481).

In some embodiments, DNA methylation may be detected by whole genome bisulfite sequencing (WGBS) (Cokus, et al. 2008. Shotgun bisulphite sequencing of the *Arabidopsis* genome reveals DNA methylation patterning. Nature 452 (7184): 215-219; Lister, et al. 2009. Human DNA methylomes at base resolution show widespread epigenomic differences. Nature 462(7271): 315-322; Harris, et al. 2010. Comparison of sequencing-based methods to profile DNA methylation and identification of monoallelic epigenetic modifications. Nat Biotechnol 28(10): 1097-1105).

In certain cases, DNA methylation may be detected methylation-specific PCR, whole genome bisulfite sequence, the HELP assay and other methods using methylation-sensitive restriction endonucleases, ChiP-on-chip assays, restriction landmark genomic scanning, COBRA, Ms-SNuPE, methylated DNA immunoprecipitation (MeDip), pyrosequencing of bisulfite treated DNA, molecular break light assay for DNA adenine methyltransferase activity, methyl sensitive Southern blotting, methylCpG binding proteins, mass spectrometry, HPLC, and reduced representation bisulfite sequencing. In some embodiments, the DNA methylation is detected in a methylation assay utilizing next-generation sequencing. For example, DNA methylation may be detected by massive parallel sequencing with bisulfite conversion, e.g., whole-genome bisulfite sequencing or reduced representation bisulfite sequencing. Optionally, the DNA methylation is detected by microarray, such as a genome-wide microarray.

A methylation profile can be determined from the methods disclosed herein. In embodiments, determining the methylation profile comprises generating a genome-wide methylation profile of the cells. Neighborhood methylation profile analysis may be performed by analyzing the loci with which any given locus was in contact. Such analysis may be used to evaluate can how the chromatin neighborhood affected the methylation state of the DNA of that locus. Aggregate methylation profile may also be performed to sum the methylation profile at a large number of positions and to reveal subtle effects in WGBS data. In some examples, aggregate methylation analysis may be performed by plotting DNA methylation in the vicinity of selected sequences (e.g., motifs) and compare it to nucleosome occupancy data (e.g., from MNase-Seq). Methylation profile may comprise unmethylation, methylation and co-methylation at each end of the end-joined nucleic acid fragments.

In some embodiments, DNA-protein interactions can be evaluated using a ChIP assay, ChIP-Seq, DNA electrophoretic mobility shift assay, DNA pull down assays, a microplate capture and detection assay, or a reporter assay (such as a Luciferase-based reporter assay). Such assays are generally known in the art.

Histone analysis can include detection of histone isoforms, modifications, and/or location can be analyzed using techniques such as immunodetection assays (e.g. ELISA, Western Blot, ChIP, ChIP-Seq, immunofluorescence, Histone Acetyltransferase assay, histone deacetylase assay, Mitotic assays, mass spectrometry and others), Histone modifications that can be analyzed include, without limitation, acetylation, methylation, phosphorylation, ubiquitylation, glycosylation, ADP-ribosylation, carbonylation and SUMOylation.

The epigenome can also include the presence or level of non-translated RNAs such as RNAi. These can be detected by methods previously described in relation to nucleic acid and transcriptome detection and analysis.

Protein Analysis

In some embodiments, the molecular signature or biomarker can be or include a protein signature or protein biomarker. Proteins can be evaluated using a variety of techniques generally known to those of ordinary skill in the art. In some embodiments, the protein analysis includes analyzing the primary, secondary, tertiary, quaternary structure of the protein (or complex as the case may be). In some embodiments, the analysis includes analyzing one or more functionalities of the protein(s). Suitable techniques include, without limitation, protein sequencing (e.g. Edman, de novo, or peptide mass fingerprinting), mass-spectrometry, immunochemical techniques, histological techniques (e.g. staining techniques), immunofluorescent techniques, FACS, post-translation modification analysis (e.g. glycosylation analysis), a light scattering technique (e.g., batch dynamic light scattering, static light scattering, charge and zeta potential determination, circular dichroism spectrometry, isothermal titration calorimetry, size separation technique (e.g. gel electrophoresis), charge-based separation technique (e.g. isoelectric focusing), affinity-based separation technique, X-ray crystallography, SEM crystallography technique, a spatial proteomic technique, and any combination thereof.

Multiomic Analysis

In some embodiments, a molecular signature or biomarker can be measured or detected using a multiomic analysis. Multiomic analysis, or simply multiomics, refers to the analytical approach of a biological sample in which the data sets are from multiple "omes", such as the genome, transcriptome, proteome, epigenome, metabolome, microbiome, and the like. In some embodiments, such multiomic approach can be a single-cell multiomic approach, which includes multilevel single-cell data (such as that obtained from a single-cell genomic data and single-cell protein, epigenome transcriptome or other data from (e.g. a spatial proteomic technique (see e.g. proximity extension assays using e.g. DNA barcoded antibodies (see e.g., Assarsson, et al. 2014. "Homogenous 96-Plex PEA Immunoassay Exhibiting High Sensitivity, Specificity, and Excellent Scalability". PLoS ONE. 9 (4): e95192), mass cytometry for multiomics (see e.g. Gherardini, et al. 2016. "Highly multiplexed simultaneous detection of RNAs and proteins in single cells". Nature Methods. 13 (3): 269-275. doi:10.1038/nmeth.3742. ISSN 1548-7105), single-cell bisulfite sequencing (see e.g., Kelsey, et al. 2014. "Single-cell genome-wide bisulfite sequencing for assessing epigenetic heterogeneity". Nature Methods. 11 (8): 817-820)., sc-RNA Seq, scATAC-Seq and scHiC (see e.g., Fraser, et. al. 2013. "Single-cell Hi-C reveals cell-to-cell variability in chromosome structure". Nature. 502 (7469): 59-64).

Unique gene expression profiles related to specific biophysical properties and underlying cell biology. In some embodiments, a linked single-cell biophysical and molecular signature (such as gene expression signature) is validated. In some embodiments, linked single-cell biophysical and molecular signatures, such as for a hematopoietic malignancy, are validated as follows. First, two murine lymphoblast cell lines (L1210 and FL5.12) that have well-characterized mass and growth properties that are stable over the course of long-term propagation in bulk culture are measured. Single cells collected are downstream of the SMR (used for cell mass measurement) for scRNA-seq. ScRNA can be performed to yield high-quality cDNA libraries for individual L1210 cells and individual FL5.12 cells with paired biophysical data. They can be compared to an initial quality control for the cDNA library and used if they pass (e.g., number of genes detected greater than 4000).

In some embodiments, in order to determine the transcriptional signatures associated with the spectrum of biophysical states in these cells, genes are ranked by how strongly their expression levels correlated with single-cell biophysical data (Spearman's correlation coefficients). The GSEA Preranked tool is used in some embodiments to determine which gene sets showed significant enrichment at either end of these ranked lists (FDR <0.05). As demonstrated in the Working Examples below, using the validation method described herein, for both cell lines, genes ranked by correlation strength with single-cell mass (final mass measurement collected before cell lysis) were highly enriched for functional annotations relating to cell cycle progression (FDR <0.05). Both cell lines revealed a larger number of genes that showed a significant positive correlation with mass relative to the number of genes with a significant negative correlation.

In some embodiments, the biomarker for a hematopoietic malignancy and/or relapse can be composed of biophysical properties (e.g. cellular mass) and a molecular signature (e.g. a gene expression program) of cells at single-cell level. In some embodiments, the cells are leukemic cells, stromal cells, immune cells, or cells of tissue origin. In some embodiments, biophysical properties include cellular mass and cell shape. In some embodiments, the gene expression program is obtained by analyzing a variety of leukemic and other types of cells in tumor environment for the expression of whole genome or of a selected group of genes.

In some embodiments, the gene expression program of leukemic cells includes genes for specific signaling pathways. In some embodiments, the analysis is performed on log-transformed expression level measurements (ln(TPM+ 1)). Data pre-processing can be conducted with the Seurat package for R (Satija et al. Spatial reconstruction of single-cell gene expression data. Nat Biotechnol. 2015; 33:495-U206). All genes that are detected in >5% of cells can be included in the final analysis for each group of cells. In some embodiments, to define the null distribution of correlation coefficients, the Spearman correlation is determined between expression levels of genes involved in cell cycle, stemness, and quiescent programs and mass for randomly shuffled data sampled from the experimental values (i.e., mismatching single-cell mass and gene expression data). In some embodiments, after 10,000 iterations, the average mean and standard deviation values of these correlation coefficient distributions are used to define the null distributions presented. In some embodiments, the null distributions are computed for the correlation coefficients between either mass, MAR, or normalized MAR and the principal components for either the DMSO-treated, drug-treated, or combined transcriptomic data sets using a similar random shuffling of PC coordinates across single-cells. Following 10,000 iterations, the mean and standard deviation of these distributions are compared to the correlation of each biophysical parameter with all significant principal components (PCs). For each data set, the PCElbow plot and jackstraw functions in Seurat are used to select significant PCs whose explained variation preceded a precipitous drop in cumulative explained variation (elbow). In each data set, for consistency, the top 10 PCs are investigated, although in some cases fewer than 10 PCs preceded the elbow. In some embodiments, correlation coefficients are deemed insignificant if they are within two standard deviations of the mean determined from random shuffling.

Single-Cell RNA-Seq Data Processing

In some embodiments, expression levels are quantified as $E_{ij} = \log 2(TPM_{i,j}/10+1)$, where $TPM_{i,j}$ refers to transcript-per-million for gene i in sample j, as calculated by $RSEM_{31}$. TPM values are divided by 10, since it can be estimated that the complexity of single-cell libraries in the order of 100,000 transcripts and would like to avoid counting each transcript about 10 times, as would be the case with TPM, which may inflate the difference between the expression level of a gene in cells in which the gene is detected and those in which it is not detected.

For each cell, the two quality measures can be quantified: the number of genes for which at least one read was mapped, and the average expression level of a curated list of housekeeping genes. In some embodiments, all cells with either fewer than 3,000 detected genes or an average housekeeping expression (E, as defined above) below 2.5 are conservatively excluded. For the remaining cells after any exclusion, the aggregate expression of each gene as log 2(average $(TPM_{i,1 \ldots n})+1$) is calculated in some embodiments, and genes with an aggregate expression below 4 can be excluded. In the Working Examples herein, using this method resulted in a set of 8,008 analyzed genes. For the remaining cells and genes, relative expression can be defined by centering the expression levels, $Er_{i,j} = E_{i,j}$-average $[E_{i,1 \ldots n}]$. Centering can be performed within each tumor or other sample separately in order to decrease the impact of inter-tumoral variability on the combined analysis across tumors.

Gene Set Enrichment Analysis

In some embodiments, ranked gene lists are created for each cell population by determining the gene-wise correlation coefficient (Spearman) between log-transformed gene expression levels and either single-cell mass. Spearman and Pearson correlation coefficients yield similar results for all conditions measured. Gene set enrichment was computed for these ranked lists using the GSEA Preranked tool, implemented with the fgsea package in R. (Kimmerling et al. Genome Biology 2018, 19:207). Differential expression analysis for cell types is performed using the FindMarkers function of Seurat with the Wilcoxon rank sum test. All P values presented are Bonferroni corrected, as per Seurat documentation recommendation.

Dimensionality Reduction

In some embodiments, variable genes for the leukemic cells at MRD are identified using Seurat's FindVariableGenes. Principal components analysis (PCA) is performed over these genes for each cell, followed by non-linear dimensionality reduction by t-stochastic neighbor embedding (tSNE). Clusters are identified in the linear PC space using K-nearest neighbor (KNN) clustering, and cluster assignments are visualized on the non-linear tSNE space.

Ingenuity Pathway Analysis

In some embodiments, Ingenuity pathway analysis (IPA, Qiagen) is performed on canonical pathways using genes which significantly correlated positively and negatively with cellular mass. Briefly, correlation and P values for significant genes were uploaded into IPA and analyzed using the "Core Analysis" function. Correlations were input as "Expression: Other" measurements with range from-INF to INF.

Preclinical PDX Model and Other Xenograft or Synergy Models

In some embodiments, provided herein are preclinical patient-derived xenograft (PDX) animal models for analyzing the integrative approach for predicting and preventing relapse of B-cell ALL. PDX models used herein are especially useful for decipher the molecular characteristics and biophysical properties of leukemic cells at various stages, including MRD and relapse stages.

PDX models are created by implantation of tumor cells into immunodeficient mice.

These models maintain similar morphology and molecular profiling of the original tumors, and therefore have been extensively used in cancer research in both the basic and preclinical fields.

In some embodiments, the methods disclosed herein use PDX models. In some embodiments, syngeneic animal models can also be used for the present invention. A syngeneic animal model (e.g., 4T1 and MC38 cell lines) provides an effective approach for studying how cancer therapies perform in the presence of a functional immune system. In some embodiments, conventional animal models for observing and analyzing tumor growth, inhibition, and relapse can also be used for the present invention.

Signaling Pathways and Cell Stats Enriched

In some embodiments, the molecular signature includes one or more signaling pathways and/or cell states enriched in a hematopoietic malignant cell(s). In some embodiments, the hematopoietic malignant cell(s) is/are a leukemic cell(s) of B-cell ALL at the MRD phase. These enriched signaling pathways include, but are not limited to, cell cycling pathways, quiescence pathways, and senescent/quiescent pathway. The enriched cell states include G2/M, M, M/G1, G1/S, and S phases. In some embodiments, a phase-specific score is generated for each cell, across all five phases, using averaged normalized expression levels ($\log_2(TPM+1)$) of the genes in each set (Macosko et al., Cell 2015, 161:1202-1214). Cells are then ordered along the cell cycle by comparing the patterns of these five phase scores per cell. To identify cell cycle-regulated genes, a sliding window approach is used in some embodiments, and identified windows of maximal and minimal average expression, both for ordered cells, and for shuffled cells are used in some embodiments to evaluate the false-discovery rate.

Healthy Cellular Mass Distributions

In some embodiments, provided are cellular mass distributions in healthy bone marrow cells within a population. In some embodiments, cellular mass is binned at regular mass intervals for single cells, and each mass bin is correlated to cell state represented by the differential expression of genes.

In some embodiments, high cellular mass is correlated to G2/M score and S score. In some embodiments, the G2/M score is associated with high levels of expression of genes comprising AURKB, BIRC5, CDKI, HMGB2, PCNA, and TOP2A. In some embodiments, cells with mass greater than 20, 21, 22, 23, 24, 25, or 26 pg have high scores of G2/M and S. In some embodiments, cells with mass around or great than 40 pg have the highest G2/M score. In some embodiments, cells with mass less than 20, 21, 22, 23, 24, 25, or 26 pg have low scores of G2/M and S. In some embodiment, more cells have low G2/M and S scores than those with high scores in a population of healthy bone marrow cells.

In some embodiments, provided herein are cellular mass distribution of healthy bone marrow cells across developmental stages. The developmental stages of B cells comprise hematopoietic stem cells (HSC), CLP, pre-pro B cells, pro B cells, pre B-I (large) cells, pre B-II (small) cells, and early B cells. In some embodiments, these developmental stages are categorized into progenitor cell type (HSC, CLP, and pre-pro-B), pro B (pro B, pre B-I and pre B-II), and early B cells. For each category, a distinct cellular mass distribution can be obtained. Progenitor cells have the highest cellular masses, followed by pro B, and early B cells have the lowest cellular mass. The methods disclosed herein provide a clear mass distributions of healthy bone marrow cells across the developmental stages.

Mutations of Genes in STATS Pathway and ERK Pathway

In some embodiments, the molecular biomarker is or includes mutations of genes in STAT5 pathway and ERK pathway that are predictive of relapse risk for B-cell ALL. Gene mutations in leukemic cells can be determined using conventional gene sequencing techniques, including Sanger sequencing, next-generation sequencing, and pyrosequencing. In some embodiments, ABL1 gene mutations can be tracked to progenitor-like cells before or during treatment or at MRD phase. ABL1 mutations are associated with low-risk and/or late-onset relapse. In some embodiments, KRAS and NRAS gene mutations can be tracked to pre-B-like or early B-like cells. KRAS and NRAS mutations are associated with high-risk and/or early-onset relapse. In some embodiments, leukemic cells with KRAS and/or NRAS mutations have a high pre-BCR score and are at cycling state.

Linked Cellular Mass and Gene Expression Programs of Leukemic Cells

In some embodiments, provided herein are the match data of gene expression programs and cellular mass of single leukemic cells. In some embodiments, provided herein are the mapped data of gene expression programs and cell states of single leukemic cells. In some embodiments, a mass distribution of healthy bone marrow cells across developmental stages is correlated to the gene expression programs at single-cell level. In some embodiments, gene expression markers for progenitor cells are highly expressed in cells with higher cellular mass, and gene expression markers for early B cells are highly expressed in cells with lower cellular mass.

In some embodiments, provided herein are molecular signatures of leukemic cells leukemic cells from B-cell ALL before treatment. Prior to treatment such cells can have a high heterogeneity and can be contextualized with the normal developmental stages of B cells. Leukemic cells from different B-cell ALL patients can have distinct gene expression program and at corresponding cell development stages. Such individualized signatures can be used to definitively classify cells from different patients or animals, allowing for improved patient stratification and improved treatment efficacies. Methods of using such individualized signatures is described in greater detail elsewhere herein.

In some embodiments, the heterogeneity of pretreatment B-cell ALL cells at single-cell level is determined. Gene expression programs can be mapped to those of normal B cells at single-cell level. As demonstrated in the Working Examples herein, progenitor cell-like leukemic cells have higher cellular mass than early B cell-like leukemic cells. Most of leukemic cells resemble normal pro-B and pre-B cells in terms of gene expression programs. In some embodiments, progenitor-like leukemic cells have high expression of genes comprising SRGN, NR4A1, NR4A2, CDKNIA, ID1, ID2, MPO, GADD45B, and CD34. In some embodiments, Pro/pre-B-like leukemic cells have high expression of CD22, TCLIA, CD74, IGLL1, and MIE. The genes listed herein are representative and other genes may also be markers for progenitor-like or pro/pre-B-like cells. In some embodiments and as evidenced by the Working Examples herein, cells with high cellular mass have high levels of expression of genes belonging to progenitor-like cell markers and have high progenitor scores. Cells with low cellular mass have high levels of expression of genes belonging to pro B/early B cell markers and have high pro B and early B scores.

In some embodiments, pretreated B-cell ALL cells are mapped to different B-cell development stages. In some embodiments, leukemic cells with high levels of CD34 correlate to progenitor-like state, and cells with low levels of CD34 correlate to pro/pre-B or early B-like states.

In some embodiments, cellular mass distribution of leukemic cells obtained from PDX models is provided. Cells before treatment with a TKI have cellular masses from 10 to 46.6 pg while cells at MRD have cellular mass from 10 to 29.5 pg. These data indicate that TKI treatment has inhibited or killed most leukemic cells with high cellular mass, i.e., progenitor-like cells, and most of the cells existing at the MRD phase are of pro-B-like/pre-B-like/early B-like.

In some embodiments, biomarkers for a hematopoietic malignancy and/or relapse can include one or more measurements of biophysical parameters, transcriptomic profile, and mutation of genes involved in specific signaling pathways. In some embodiments, these measurements can be used individually or in combination for predicting the risk of relapse of hematopoietic malignance. In some embodiments, biophysical parameters such as cellular mass can be mapped to transcriptomic profile, molecular characteristics, transcriptomic profiling, genetic features, epigenetic modifications, genomic features, epigenomic features, proteomic features, metabolomic features, and any other biological, physiological, and/or pathological features, so the average cellular mass serves as an integrative biomarker.

Methods of Diagnosing, Prognosing, and/or Monitoring Hematopoietic Malignancy and/or Relapse Described herein are methods of diagnosing, prognosing, and/or monitoring hematopoietic malignancy and/or relapse thereof. The methods can also be used to identify a patient as having a high risk of and/or having hematopoietic malignancy relapse and/or early-onset relapse. The methods can also be used to identify a patient as having a low risk of hematopoietic malignancy relapse and/or having or being at risk for late-onset relapse. The methods can employ detection of a biophysical biomarker (e.g. cell mass) and/or a molecular biomarker (e.g. a molecular signature). In some embodiments, the biophysical biomarker is linked to a molecular biomarker. In some embodiments, the biophysical biomarker and a molecular biomarker are measured in the same individual cell.

In some embodiments, a method of diagnosing, prognosing, and/or monitoring hematopoietic malignancy and/or relapse in a subject in need thereof includes diagnosing, prognosing, and/or monitoring hematopoietic malignancy and/or relapse thereof in the subject in need thereof by determining an average cellular mass of the plurality of cells using the cellular mass of each individual cell of the plurality of cells, wherein an average cellular mass equal to or greater than a defined threshold indicates a low risk of hematopoietic malignancy relapse and an average cellular mass less than a defined threshold indicates a high risk of hematopoietic malignancy relapse.

In some embodiments, the method can include diagnosing, prognosing, and/or monitoring hematopoietic malignancy and/or relapse thereof in a subject in need thereof by performing one or both of the following on one or more cells in a plurality of cells present in a sample obtained from the subject in need thereof: determining an average cellular mass of the plurality of cells using the cellular mass of each individual cell of the plurality of cells, wherein an average cellular mass equal to or greater than a defined threshold indicates a low risk of hematopoietic malignancy relapse and an average cellular mass less than a defined threshold indicates a high risk of hematopoietic malignancy relapse; and/or determining a molecular signature of one or more cells in the plurality of cells, wherein the molecular signature comprises (a) a quiescent signature characterized by high TNF-a/NF-kB score and/or low HSF1/p38 score, and cycling signature characterized by high pre-BCR score, wherein a quiescent signature indicates a low risk of relapse, and a cycling signature indicates a high risk of relapse; (b) an ABL1, KRAS, and NRAS gene mutation status, wherein a mutation or mutations in ABL1 gene indicates low risk and/or late-onset of relapse, and a mutation or mutations in KRAS and/or NRAS genes indicate a high risk and/or early-onset of relapse; or (c) both.

In some embodiments, a method of diagnosing, prognosing, and/or monitoring hematopoietic malignancy and/or relapse thereof in a subject in need thereof includes determining a molecular signature of one or more cells in the plurality of cells, wherein the molecular signature comprises (a) a quiescent signature characterized by high TNF-a/NF-kB score and/or low HSF1/p38 score, and cycling signature characterized by high pre-BCR score, wherein a quiescent signature indicates a low risk of relapse, and a cycling signature indicates a high risk of relapse; (b) an ABL1, KRAS, and NRAS gene mutation status, wherein a mutation or mutations in ABL1 gene indicates low risk and/or late-onset of relapse, and a mutation or mutations in KRAS and/or NRAS genes indicate a high risk and/or early-onset of relapse; or (c) both.

In some embodiments, a method of diagnosing, prognosing, and/or monitoring hematopoietic malignancy and/or relapse in a subject in need thereof only includes determining a biophysical phenotype, such as cell mass (which can be reported as an average cell mass calculated from the individual measured cell masses of a population of cells), stiffness or other biophysical phenotype described elsewhere herein, and basing a diagnosis, prognosis, and/or disease stage or treatment efficacy based on the biophysical phenotype alone. It will be appreciated and as is discussed elsewhere herein that the biophysical phenotype is a proxy for and can be representative of an underlying molecular phenotype or cell state. In some embodiments, the biophysical phenotype is validated as a proxy or representation for a molecular signature and/or specific cell state.

In some embodiments, determining the average cellular mass of the plurality of cells comprises measuring a cellular mass of each individual cell in the plurality of cells and calculating an average cellular mass of the plurality cells based on the measured cellular mass of each of the individual cells in the plurality of cells.

In some embodiments, an average cellular mass of or between 20-80 pg indicates a low risk of relapse, and an average cellular mass of or between about 0-20 pg indicates a high risk of relapse. In some embodiments, an average cellular mass of or between 20-60 pg indicates a low risk of relapse, and an average cellular mass of or between about 5-20 pg indicates a high risk of relapse. In some embodiments, an average cellular mass of or between about 20-35 pg indicates a low risk of relapse.

The hematopoietic malignancy can be a lymphoid or myeloid malignancy. The hematopoietic malignancies may be any of lymphoid malignancies comprising B-cell ALL, T-cell ALL, chronic lymphoblastic leukemia (CLL), diffuse large B-cell lymphoma, follicular lymphoma, Burkitt's lymphoma, mantle cell lymphoma, marginal zone lymphoma, T-cell lymphoma, multiple myeloma, Hodgkin's lymphoma, and any other types of malignancies derived from lymphoid lineage. In some embodiments, the methods disclosed herein for predicting the risk of relapse can be used for any of the subtypes of the aforementioned lymphoid malignancies. In some embodiments, the hematopoietic malignancies can be any of myeloid malignancies comprising chronic myeloid leukemia (CML), acute myeloid leukemia (AML), myelodysplastic syndromes (MDS), myeloproliferative diseases (MPD), chronic neutrophilic leukemia, chronic eosinophilic leukemia, polycythemia vera, chronic idiopathic myelofibrosis, essential thrombocythemia, chronic myeloproliferative disease (unclassifiable), refractory anemia, refractory cytopenia with multilineage dysplasia (RCMD), mastocytosis, and any other types of malignancies derived from myeloid lineage. In some embodiments, the methods disclosed herein for predicting the risk of relapse can be used for any of the subtypes of the aforementioned myeloid malignancies.

In certain example embodiments, the hematopoietic malignancy is an acute lymphoblastic leukemia (ALL). In certain example embodiments, the ALL is a B-cell ALL. In certain other example embodiments, the ALL is a T-cell ALL.

In some embodiments, the hematopoietic malignancy is a B-cell malignancy, a T-cell malignancy, or a myeloid-cell malignancy. In some embodiments, the hematopoietic malignancy is acute lymphoblastic leukemia (ALL), chronic myeloid leukemia (CML), or both.

In some embodiments, one or more B-cell ALL cells have a BCR-ABL translocation.

In some embodiments, the average cellular mass of the plurality of cells is determined by measuring a cellular mass of each individual cell in the plurality of cells and calculating an average cellular mass of the plurality cells based on the measured cellular mass of each of the individual cells in the plurality of cells. In some embodiments, the cellular mass of each individual cell is measured using a suspended microchannel resonator (SMR). In some embodiments, the SMR is modified such that after determining a cellular mass or other biophysical characteristic, the cell is identified in a suitable fashion such that other characteristics measured (such as a molecular signature) in the same cell can be linked.

The terms "diagnosis" and "monitoring" are commonplace and well-understood in medical practice. By means of further explanation and without limitation the term "diagnosis" generally refers to the process or act of recognizing, deciding on or concluding on a disease or condition in a subject on the basis of symptoms and signs and/or from results of various diagnostic procedures (such as, for example, from knowing the presence, absence and/or quantity of one or more biomarkers characteristic of the diagnosed disease or condition). The term "monitoring" generally refers to the follow-up of a disease or a condition in a subject for any changes which may occur over time.

The terms "prognosing" or "prognosis" generally refer to an anticipation on the progression of a disease or condition and the prospect (e.g., the probability, duration, and/or extent) of recovery. A good prognosis of the diseases or conditions taught herein may generally encompass anticipation of a satisfactory partial or complete recovery from the diseases or conditions, preferably within an acceptable time period. A good prognosis of such may more commonly encompass anticipation of not further worsening or aggravating of such, preferably within a given time period. A poor prognosis of the diseases or conditions as taught herein may generally encompass anticipation of a substandard recovery and/or unsatisfactorily slow recovery, or to substantially no recovery or even further worsening of such. The term also encompasses prediction of a disease. The terms "predicting" or "prediction" generally refer to an advance declaration, indication or foretelling of a disease or condition in a subject not (yet) having said disease or condition. For example, a prediction of a disease or condition in a subject may indicate a probability, chance or risk that the subject will develop said disease or condition, for example within a certain time period or by a certain age. Said probability, chance or risk may be indicated inter alia as an absolute value, range or statistics, or may be indicated relative to a suitable control subject or subject population (such as, e.g., relative to a general, normal or healthy subject or subject population). Hence, the probability, chance or risk that a subject will develop a disease or condition may be advantageously indicated as increased or decreased, or as fold-increased or fold-decreased relative to a suitable control subject or subject population. As used herein, the term "prediction" of the conditions or diseases as taught herein in a subject may also particularly mean that the subject has a 'positive' prediction of such, i.e., that the subject is at risk of having such (e.g., the risk is significantly increased vis-à-vis a control subject or subject population). The term "prediction of no" diseases or conditions as taught herein as described herein in a subject may particularly mean that the subject has a 'negative' prediction of such, i.e., that the subject's risk of having such is not significantly increased vis-à-vis a control subject or subject population.

Hence, the methods may rely on comparing the quantity of biomarkers, or gene or gene product signatures measured in samples from patients with reference values, wherein said reference values represent known predictions, diagnoses and/or prognoses of diseases or conditions as taught herein.

For example, distinct reference values may represent the prediction of a risk (e.g., an abnormally elevated risk) of having a given disease or condition as taught herein vs. the prediction of no or normal risk of having said disease or condition. In another example, distinct reference values may represent predictions of differing degrees of risk of having such disease or condition.

In a further example, distinct reference values can represent the diagnosis of a given disease or condition as taught herein vs. the diagnosis of no such disease or condition (such as, e.g., the diagnosis of healthy, or recovered from said disease or condition, etc.). In another example, distinct reference values may represent the diagnosis of such disease or condition of varying severity.

In yet another example, distinct reference values may represent a good prognosis for a given disease or condition as taught herein vs. a poor prognosis for said disease or condition. In a further example, distinct reference values may represent varyingly favorable or unfavorable prognoses for such disease or condition.

Such comparison may generally include any means to determine the presence or absence of at least one difference and optionally of the size of such difference between values being compared. A comparison may include a visual inspection, an arithmetical or statistical comparison of measurements. Such statistical comparisons include, but are not limited to, applying a rule.

Reference values may be established according to known procedures previously employed for other cell populations, biomarkers and gene or gene product signatures. For example, a reference value may be established in an individual or a population of individuals characterized by a particular diagnosis, prediction and/or prognosis of said disease or condition (i.e., for whom said diagnosis, prediction and/or prognosis of the disease or condition holds true). Such population may comprise without limitation 2 or more, 10 or more, 100 or more, or even several hundred or more individuals.

A "deviation" of a first value from a second value may generally encompass any direction (e.g., increase: first value >second value; or decrease: first value <second value) and any extent of alteration.

For example, a deviation may encompass a decrease in a first value by, without limitation, at least about 10% (about 0.9-fold or less), or by at least about 20% (about 0.8-fold or less), or by at least about 30% (about 0.7-fold or less), or by at least about 40% (about 0.6-fold or less), or by at least about 50% (about 0.5-fold or less), or by at least about 60% (about 0.4-fold or less), or by at least about 70% (about 0.3-fold or less), or by at least about 80% (about 0.2-fold or less), or by at least about 90% (about 0.1-fold or less), relative to a second value with which a comparison is being made.

For example, a deviation may encompass an increase of a first value by, without limitation, at least about 10% (about 1.1-fold or more), or by at least about 20% (about 1.2-fold or more), or by at least about 30% (about 1.3-fold or more), or by at least about 40% (about 1.4-fold or more), or by at least about 50% (about 1.5-fold or more), or by at least about 60% (about 1.6-fold or more), or by at least about 70% (about 1.7-fold or more), or by at least about 80% (about 1.8-fold or more), or by at least about 90% (about 1.9-fold or more), or by at least about 100% (about 2-fold or more), or by at least about 150% (about 2.5-fold or more), or by at least about 200% (about 3-fold or more), or by at least about 500% (about 6-fold or more), or by at least about 700% (about 8-fold or more), or like, relative to a second value with which a comparison is being made.

Preferably, a deviation may refer to a statistically significant observed alteration. For example, a deviation may refer to an observed alteration which falls outside of error margins of reference values in a given population (as expressed, for example, by standard deviation or standard error, or by a predetermined multiple thereof, e.g., ±1xSD or ±2xSD or ±3xSD, or 1xSE or ±2xSE or ±3xSE). Deviation may also refer to a value falling outside of a reference range defined by values in a given population (for example, outside of a range which comprises ≥40%, 50%, ≥60%, ≥70%, ≥75% or ≥80% or ≥85% or ≥90% or ≥95% or even ≥100% of values in said population).

In a further embodiment, a deviation may be concluded if an observed alteration is beyond a given threshold or cut-off. Such threshold or cut-off may be selected as generally known in the art to provide for a chosen sensitivity and/or specificity of the prediction methods, e.g., sensitivity and/or specificity of at least 50%, or at least 60%, or at least 70%, or at least 80%, or at least 85%, or at least 90%, or at least 95%.

For example, receiver-operating characteristic (ROC) curve analysis can be used to select an optimal cut-off value of the quantity of a given immune cell population, biomarker or gene or gene product signatures, for clinical use of the present diagnostic tests, based on acceptable sensitivity and specificity, or related performance measures which are well-knownper se, such as positive predictive value (PPV), negative predictive value (NPV), positive likelihood ratio (LR+), negative likelihood ratio (LR−), Youden index, or similar.

Compositions and Formulations for Treating and/or or Preventing Hematopoietic Malignancy Relapse Small Molecules and Biologics In some embodiments, the composition for treating and/or preventing a hematopoietic malignancy or relapse thereof are small molecules or biologics.

Small Molecules

In certain embodiments, the one or more agents is a small molecule. The term "small molecule" refers to compounds, preferably organic compounds, with a size comparable to those organic molecules generally used in pharmaceuticals. The term excludes biological macromolecules (e.g., proteins, peptides, nucleic acids, etc.). Preferred small organic molecules range in size up to about 5000 Da, e.g., up to about 4000, preferably up to 3000 Da, more preferably up to 2000 Da, even more preferably up to about 1000 Da, e.g., up to about 900, 800, 700, 600 or up to about 500 Da. In certain embodiments, the small molecule may act as an antagonist or agonist (e.g., blocking an enzyme active site or activating a receptor by binding to a ligand binding site).

One type of small molecule applicable to the present invention is a degrader molecule. Proteolysis Targeting Chimera (PROTAC) technology is a rapidly emerging alternative therapeutic strategy with the potential to address many of the challenges currently faced in modern drug development programs. PROTAC technology employs small molecules that recruit target proteins for ubiquitination and removal by the proteasome (see, e.g., Zhou et al., Discovery of a Small-Molecule Degrader of Bromodomain and Extra-Terminal (BET) Proteins with Picomolar Cellular Potencies and Capable of Achieving Tumor Regression. J. Med. Chem. 2018, 61, 462-481; Bondeson and Crews, Targeted Protein Degradation by Small Molecules, Annu Rev Pharmacol Toxicol. 2017 Jan. 6; 57: 107-123; and Lai et al., Modular PROTAC Design for the Degradation of Oncogenic BCR-ABL Angew Chem Int Ed Engl. 2016 Jan. 11; 55(2): 807-810).

Antibodies

In certain embodiments, the one or more agents is an antibody. The term "antibody" is used interchangeably with the term "immunoglobulin" herein, and includes intact antibodies, fragments of antibodies, e.g., Fab, F(ab')2 fragments, and intact antibodies and fragments that have been mutated either in their constant and/or variable region (e.g., mutations to produce chimeric, partially humanized, or fully humanized antibodies, as well as to produce antibodies with a desired trait, e.g., enhanced binding and/or reduced FcR binding). The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')2, Fabc, Fd, dAb, $V_{HH}$ and scFv and/or Fv fragments.

As used herein, a preparation of antibody protein having less than about 50% of non-antibody protein (also referred to herein as a "contaminating protein"), or of chemical precursors, is considered to be "substantially free." 40%, 30%, 20%, 10% and more preferably 5% (by dry weight), of non-antibody protein, or of chemical precursors is considered to be substantially free. When the antibody protein or biologically active portion thereof is recombinantly produced, it is also preferably substantially free of culture medium, i.e., culture medium represents less than about 30%, preferably less than about 20%, more preferably less than about 10%, and most preferably less than about 5% of the volume or mass of the protein preparation.

The term "antigen-binding fragment" refers to a polypeptide fragment of an immunoglobulin or antibody that binds antigen or competes with intact antibody (i.e., with the intact antibody from which they were derived) for antigen binding (i.e., specific binding). As such these antibodies or fragments thereof are included in the scope of the invention, provided that the antibody or fragment binds specifically to a target molecule.

It is intended that the term "antibody" encompass any Ig class or any Ig subclass (e.g. the IgG1, IgG2, IgG3, and IgG4 subclasses of IgG) obtained from any source (e.g., humans and non-human primates, and in rodents, lagomorphs, caprines, bovines, equines, ovines, etc.).

The term "Ig class" or "immunoglobulin class", as used herein, refers to the five classes of immunoglobulin that have been identified in humans and higher mammals, IgG, IgM, IgA, IgD, and IgE. The term "Ig subclass" refers to the two subclasses of IgM (H and L), three subclasses of IgA (IgA1, IgA2, and secretory IgA), and four subclasses of IgG (IgG1, IgG2, IgG3, and IgG4) that have been identified in humans and higher mammals. The antibodies can exist in monomeric or polymeric form; for example, 1 gM antibodies exist in pentameric form, and IgA antibodies exist in monomeric, dimeric or multimeric form.

The term "IgG subclass" refers to the four subclasses of immunoglobulin class IgG-IgG1, IgG2, IgG3, and IgG4 that have been identified in humans and higher mammals by the heavy chains of the immunoglobulins, VI—74, respectively. The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind antigen. The term "domain" refers to a globular region of a heavy or light chain polypeptide comprising peptide loops (e.g., comprising 3 to 4 peptide loops) stabilized, for example, by β pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of an antibody light chain are referred to interchangeably as "light chain constant regions", "light chain constant domains", "CL" regions or "CL" domains. The "constant" domains of an antibody heavy chain are referred to interchangeably as "heavy chain constant regions", "heavy chain constant domains", "CH" regions or "CH" domains). The "variable" domains of an antibody light chain are referred to interchangeably as "light chain variable regions", "light chain variable domains", "VL" regions or "VL" domains). The "variable" domains of an antibody heavy chain are referred to interchangeably as "heavy chain constant regions", "heavy chain constant domains", "VH" regions or "VH" domains).

The term "region" can also refer to a part or portion of an antibody chain or antibody chain domain (e.g., a part or portion of a heavy or light chain or a part or portion of a constant or variable domain, as defined herein), as well as more discrete parts or portions of said chains or domains. For example, light and heavy chains or light and heavy chain variable domains include "complementarity determining regions" or "CDRs" interspersed among "framework regions" or "FRs", as defined herein.

The term "conformation" refers to the tertiary structure of a protein or polypeptide (e.g., an antibody, antibody chain, domain or region thereof). For example, the phrase "light (or heavy) chain conformation" refers to the tertiary structure of a light (or heavy) chain variable region, and the phrase "antibody conformation" or "antibody fragment conformation" refers to the tertiary structure of an antibody or fragment thereof.

The term "antibody-like protein scaffolds" or "engineered protein scaffolds" broadly encompasses proteinaceous non-immunoglobulin specific-binding agents, typically obtained by combinatorial engineering (such as site-directed random mutagenesis in combination with phage display or other molecular selection techniques). Usually, such scaffolds are derived from robust and small soluble monomeric proteins (such as Kunitz inhibitors or lipocalins) or from a stably folded extra-membrane domain of a cell surface receptor (such as protein A, fibronectin or the ankyrin repeat).

Such scaffolds have been extensively reviewed in Binz et al. (Engineering novel binding proteins from nonimmunoglobulin domains. Nat Biotechnol 2005, 23:1257-1268), Gebauer and Skerra (Engineered protein scaffolds as next-generation antibody therapeutics. Curr Opin Chem Biol. 2009, 13:245-55), Gill and Damle (Biopharmaceutical drug discovery using novel protein scaffolds. Curr Opin Biotechnol 2006, 17:653-658), Skerra (Engineered protein scaffolds for molecular recognition. J Mol Recognit 2000, 13:167-187), and Skerra (Alternative non-antibody scaffolds for molecular recognition. Curr Opin Biotechnol 2007, 18:295-304), and include without limitation affibodies, based on the Z-domain of staphylococcal protein A, a three-helix bundle of 58 residues providing an interface on two of its alpha-helices (Nygren, Alternative binding proteins: Affibody binding proteins developed from a small three-helix bundle scaffold. FEBS J 2008, 275:2668-2676); engineered Kunitz domains based on a small (ca. 58 residues) and robust, disulphide-crosslinked serine protease inhibitor, typically of human origin (e.g. LACI-D1), which can be engineered for different protease specificities (Nixon and Wood, Engineered protein inhibitors of proteases. Curr Opin Drug Discov Dev 2006, 9:261-268); monobodies or adnectins based on the 10th extracellular domain of human fibronectin III (10Fn3), which adopts an Ig-like beta-sandwich fold (94 residues) with 2-3 exposed loops, but lacks the central disulphide bridge (Koide and Koide, Monobodies: antibody mimics based on the scaffold of the fibronectin type III domain. Methods Mol Biol 2007, 352:95-109); anticalins derived from the lipocalins, a diverse family of eight-stranded beta-barrel proteins (ca. 180 residues) that naturally form binding sites for small ligands by means of four structurally variable loops at the open end, which are abundant in humans, insects, and many other organisms (Skerra, Alternative binding proteins: Anticalins harnessing the structural plasticity of the lipocalin ligand pocket to engineer novel binding activities. FEBS J 2008, 275:2677-2683); DARPins, designed ankyrin repeat domains (166 residues), which provide a rigid interface arising from typically three repeated beta-turns (Stumpp et al., DARPins: a new generation of protein therapeutics. Drug Discov Today 2008, 13:695-701); avimers (multimerized LDLR-A module) (Silverman et al., Multivalent avimer proteins evolved by exon shuffling of a family of human receptor domains. Nat Biotechnol 2005, 23:1556-1561); and cysteine-rich knottin peptides (Kolmar, Alternative binding proteins: biological activity and therapeutic potential of cystine-knot miniproteins. FEBS J 2008, 275:2684-2690).

"Specific binding" of an antibody means that the antibody exhibits appreciable affinity for a particular antigen or epitope and, generally, does not exhibit significant cross reactivity. "Appreciable" binding includes binding with an affinity of at least 25 μM. Antibodies with affinities greater than $1 \times 10^7$ $M^{-1}$ (or a dissociation coefficient of 1 M or less or a dissociation coefficient of 1 nm or less) typically bind with correspondingly greater specificity. Values intermediate of those set forth herein are also intended to be within the scope of the present invention and antibodies of the invention bind with a range of affinities, for example, 100 nM or less, 75 nM or less, 50 nM or less, 25 nM or less, for example 10 nM or less, SnM or less, 1 nM or less, or in embodiments 500 pM or less, 100 pM or less, 50 pM or less or 25 pM or less. An antibody that "does not exhibit significant crossreactivity" is one that will not appreciably bind to an entity other than its target (e.g., a different epitope or a different molecule). For example, an antibody that specifically binds to a target molecule will appreciably bind the target molecule but will not significantly react with non-target molecules or peptides. An antibody specific for a particular epitope will, for example, not significantly cross-react with remote epitopes on the same protein or peptide. Specific binding can be determined according to any art-recognized means for determining such binding. Preferably, specific binding is determined according to Scatchard analysis and/or competitive binding assays.

As used herein, the term "affinity" refers to the strength of the binding of a single antigen-combining site with an antigenic determinant. Affinity depends on the closeness of stereochemical fit between antibody combining sites and antigen determinants, on the size of the area of contact between them, on the distribution of charged and hydrophobic groups, etc. Antibody affinity can be measured by equilibrium dialysis or by the kinetic BIACORE™ method. The dissociation constant, Kd, and the association constant, Ka, are quantitative measures of affinity.

As used herein, the term "monoclonal antibody" refers to an antibody derived from a clonal population of antibody-producing cells (e.g., B lymphocytes or B cells) which is homogeneous in structure and antigen specificity. The term "polyclonal antibody" refers to a plurality of antibodies originating from different clonal populations of antibody-producing cells which are heterogeneous in their structure and epitope specificity but which recognize a common antigen. Monoclonal and polyclonal antibodies may exist within bodily fluids, as crude preparations, or may be purified, as described herein.

The term "binding portion" of an antibody (or "antibody portion") includes one or more complete domains, e.g., a pair of complete domains, as well as fragments of an antibody that retain the ability to specifically bind to a target molecule. It has been shown that the binding function of an antibody can be performed by fragments of a full-length antibody. Binding fragments are produced by recombinant DNA techniques, or by enzymatic or chemical cleavage of intact immunoglobulins. Binding fragments include Fab, Fab', F(ab')2, Fabc, Fd, dAb, Fv, single chains, single-chain antibodies, e.g., scFv, and single domain antibodies.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, FR residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin.

Examples of portions of antibodies or epitope-binding proteins encompassed by the present definition include: (i) the Fab fragment, having $V_L$, $C_L$, $V_H$ and $C_H 1$ domains; (ii) the Fab' fragment, which is a Fab fragment having one or more cysteine residues at the C-terminus of the $C_H 1$ domain; (iii) the Fd fragment having $V_H$ and $C_H 1$ domains; (iv) the Fd' fragment having $V_H$ and $C_H 1$ domains and one or more cysteine residues at the C-terminus of the CHI domain; (v) the Fv fragment having the $V_L$ and VH domains of a single arm of an antibody; (vi) the dAb fragment (Ward et al., 341 Nature 544 (1989)) which consists of a VH domain or a $V_L$ domain that binds antigen; (vii) isolated CDR regions or isolated CDR regions presented in a functional framework; (viii) F(ab')$_2$ fragments which are bivalent fragments including two Fab' fragments linked by a disulphide bridge at the hinge region; (ix) single chain antibody molecules (e.g., single chain Fv; scFv) (Bird et al., 242 Science 423 (1988); and Huston et al., 85 PNAS 5879 (1988)); (x) "diabodies" with two antigen-binding sites, comprising a heavy chain variable domain (VH) connected to a light chain variable domain ($V_L$) in the same polypeptide chain (see, e.g., EP 404,097; WO 93/11161; Hollinger et al., 90 PNAS 6444 (1993)); (xi) "linear antibodies" comprising a pair of tandem Fd segments ($V_H$-$C_h 1$-$V_H$-$C_h 1$) which, together with complementary light chain polypeptides, form a pair of antigen-binding regions (Zapata et al., Protein Eng. 8(10): 1057-62 (1995); and U.S. Pat. No. 5,641,870).

As used herein, a "blocking" antibody or an antibody "antagonist" is one which inhibits or reduces biological activity of the antigen(s) it binds. In certain embodiments, the blocking antibodies or antagonist antibodies or portions thereof described herein completely inhibit the biological activity of the antigen(s).

Antibodies may act as agonists or antagonists of the recognized polypeptides. For example, the present invention includes antibodies which disrupt receptor/ligand interactions either partially or fully. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or of one of its down-stream substrates by immunoprecipitation followed by western blot analysis. In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex. Likewise, encompassed by the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides disclosed herein. The antibody agonists and antagonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16): 3668-3678 (1998); Harrop et al., J. Immunol. 161(4):1786-1794 (1998); Zhu et al., Cancer Res. 58(15):3209-3214 (1998); Yoon et al., J. Immunol. 160(7):3170-3179 (1998); Prat et al., J. Cell. Sci. III (Pt2):237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4): 755-762 (1995); Muller et al., Structure 6(9):1153-1167 (1998); Bartunek et al., Cytokine 8(1):14-20 (1996).

The antibodies as defined for the present invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

Simple binding assays can be used to screen for or detect agents that bind to a target protein, or disrupt the interaction between proteins (e.g., a receptor and a ligand). Because certain targets of the present invention are transmembrane proteins, assays that use the soluble forms of these proteins rather than full-length protein can be used, in some embodiments. Soluble forms include, for example, those lacking the transmembrane domain and/or those comprising the IgV domain or fragments thereof which retain their ability to bind their cognate binding partners. Further, agents that inhibit or enhance protein interactions for use in the compositions and methods described herein, can include recombinant peptidomimetics.

Detection methods useful in screening assays include antibody-based methods, detection of a reporter moiety, detection of cytokines as described herein, and detection of a gene signature as described herein.

Another variation of assays to determine binding of a receptor protein to a ligand protein is through the use of affinity biosensor methods. Such methods may be based on the piezoelectric effect, electrochemistry, or optical methods, such as ellipsometry, optical wave guidance, and surface plasmon resonance (SPR).

Aptamers

In certain embodiments, the one or more agents is an aptamer. Nucleic acid aptamers are nucleic acid species that have been engineered through repeated rounds of in vitro selection or equivalently, SELEX (systematic evolution of ligands by exponential enrichment) to bind to various molecular targets such as small molecules, proteins, nucleic acids, cells, tissues and organisms. Nucleic acid aptamers have specific binding affinity to molecules through interactions other than classic Watson-Crick base pairing. Aptamers are useful in biotechnological and therapeutic applications as they offer molecular recognition properties similar to antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications. In certain embodiments, RNA aptamers may be expressed from a DNA construct. In other embodiments, a nucleic acid aptamer may be linked to another polynucleotide sequence. The polynucleotide sequence may be a double stranded DNA polynucleotide sequence. The aptamer may be covalently linked to one strand of the polynucleotide sequence. The aptamer may be ligated to the polynucleotide sequence. The polynucleotide sequence may be configured, such that the polynucleotide sequence may be linked to a solid support or ligated to another polynucleotide sequence.

Aptamers, like peptides generated by phage display or monoclonal antibodies ("mAbs"), are capable of specifically binding to selected targets and modulating the target's activity, e.g., through binding, aptamers may block their target's ability to function. A typical aptamer is 10-15 kDa in size (30-45 nucleotides), binds its target with sub-nanomolar affinity, and discriminates against closely related targets (e.g., aptamers will typically not bind other proteins from the same gene family). Structural studies have shown that aptamers are capable of using the same types of binding interactions (e.g., hydrogen bonding, electrostatic complementarity, hydrophobic contacts, steric exclusion) that drives affinity and specificity in antibody-antigen complexes.

Aptamers have a number of desirable characteristics for use in research and as therapeutics and diagnostics including high specificity and affinity, biological efficacy, and excellent pharmacokinetic properties. In addition, they offer specific competitive advantages over antibodies and other protein biologics. Aptamers are chemically synthesized and are readily scaled as needed to meet production demand for research, diagnostic or therapeutic applications. Aptamers are chemically robust. They are intrinsically adapted to regain activity following exposure to factors such as heat and denaturants and can be stored for extended periods (>1 yr) at room temperature as lyophilized powders. Not being bound by a theory, aptamers bound to a solid support or beads may be stored for extended periods.

Oligonucleotides in their phosphodiester form may be quickly degraded by intracellular and extracellular enzymes such as endonucleases and exonucleases. Aptamers can include modified nucleotides conferring improved characteristics on the ligand, such as improved in vivo stability or improved delivery characteristics. Examples of such modifications include chemical substitutions at the ribose and/or phosphate and/or base positions. SELEX identified nucleic acid ligands containing modified nucleotides are described, e.g., in U.S. Pat. No. 5,660,985, which describes oligonucleotides containing nucleotide derivatives chemically modified at the 2' position of ribose, 5 position of pyrimidines, and 8 position of purines, U.S. Pat. No. 5,756,703 which describes oligonucleotides containing various 2'-modified pyrimidines, and U.S. Pat. No. 5,580,737 which describes highly specific nucleic acid ligands containing one or more nucleotides modified with 2'-amino (2'-$NH_2$), 2'-fluoro (2'-F), and/or 2'-O-methyl (2'-OMe) substituents. Modifications of aptamers may also include, modifications at exocyclic amines, substitution of 4-thiouridine, substitution of 5-bromo or 5-iodo-uracil; backbone modifications, phosphorothioate or allyl phosphate modifications, methylations, and unusual base-pairing combinations such as the isobases isocytidine and isoguanosine. Modifications can also include 3' and 5' modifications such as capping. As used herein, the term phosphorothioate encompasses one or more non-bridging oxygen atoms in a phosphodiester bond replaced by one or more sulfur atoms. In further embodiments, the oligonucleotides comprise modified sugar groups, for example, one or more of the hydroxyl groups is replaced with halogen, aliphatic groups, or functionalized as ethers or amines. In one embodiment, the 2'-position of the furanose residue is substituted by any of an O-methyl, O-alkyl, 0-allyl, S-alkyl, S-allyl, or halo group. Methods of synthesis of 2'-modified sugars are described, e.g., in Sproat, et al., Nucl. Acid Res. 19:733-738 (1991); Cotten, et al, Nucl. Acid Res. 19:2629-2635 (1991); and Hobbs, et al, Biochemistry 12:5138-5145 (1973). Other modifications are known to one of ordinary skill in the art. In certain embodiments, aptamers include aptamers with improved off-rates as described in International Patent Publication No. WO 2009012418, "Method for generating aptamers with improved off-rates," incorporated herein by reference in its entirety. In certain embodiments aptamers are chosen from a library of aptamers. Such libraries include, but are not limited to, those described in Rohloff et al., "Nucleic Acid Ligands With Protein-like Side Chains: Modified Aptamers and Their Use as Diagnostic and Therapeutic Agents," Molecular Therapy Nucleic Acids (2014) 3, e201. Aptamers are also commercially available (see, e.g., SomaLogic, Inc., Boulder, Colorado). In certain embodiments, the present invention may utilize any aptamer containing any modification as described herein.

Genetic Modifying Agents

In some embodiments, genetic modifying agents can be used for inhibiting pre-BCR signaling pathway and/or p38 MAPK pathway. In some embodiments, the genetic modifying agent can be used to inhibit, degrade, and/or delete one or more polynucleotide components in the pre-BCR and/or p38 MAPK pathway. In certain embodiments, the one or more modulating agents may be a genetic modifying agent (e.g., modifies a transcription factor). The genetic modifying agent may comprise a CRISPR system, a zinc finger nuclease system, a TALEN, a meganuclease or RNAi system. In certain embodiments, a target gene is genetically modified. In certain embodiments, a target gene RNA is modified, such that the modification is temporary. Methods of modifying RNA is discussed further herein.

CRISPR-Cas Modification

In some embodiments, a polynucleotide of the present invention described elsewhere herein can be modified using a CRISPR-Cas and/or Cas-based system.

In general, a CRISPR-Cas or CRISPR system as used in herein and in documents, such as International Patent Publication No. WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). See, e.g., Shmakov et al. (2015) "Discovery and Functional Characterization of Diverse Class 2 CRISPR-Cas Systems", Molecular Cell, DOI: dx.doi.org/10.1016/j.molcel.2015.10.008.

CRISPR-Cas systems can generally fall into two classes based on their architectures of their effector molecules, which are each further subdivided by type and subtype. The two class are Class 1 and Class 2. Class 1 CRISPR-Cas systems have effector modules composed of multiple Cas proteins, some of which form crRNA-binding complexes, while Class 2 CRISPR-Cas systems include a single, multi-domain crRNA-binding protein.

In some embodiments, the CRISPR-Cas system that can be used to modify a polynucleotide of the present invention described herein can be a Class 1 CRISPR-Cas system. In some embodiments, the CRISPR-Cas system that can be used to modify a polynucleotide of the present invention described herein can be a Class 2 CRISPR-Cas system.

Class 1 CRISPR-Cas Systems

Figure 5A:
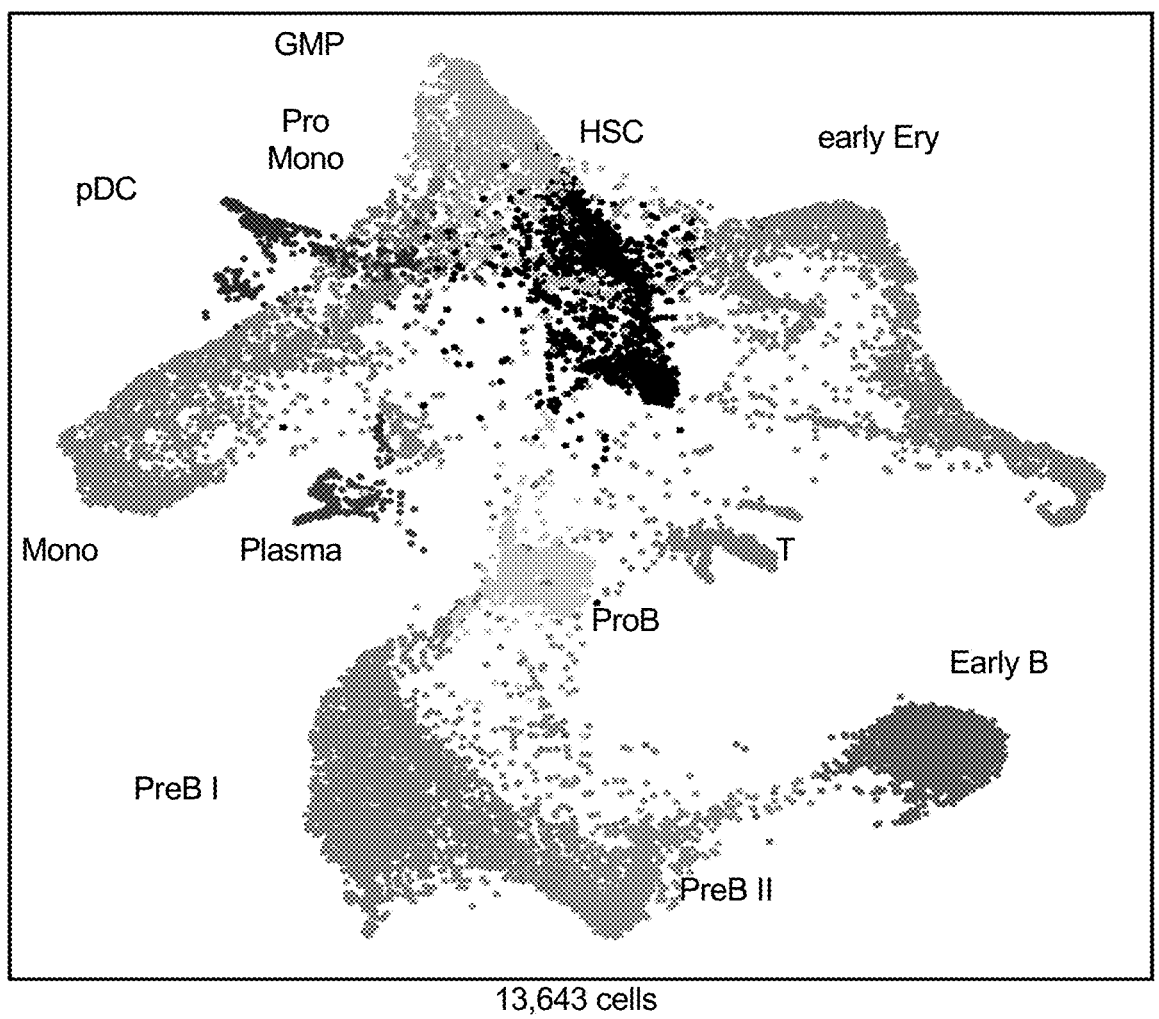
FIGS. 5A-5C—A map of early hematopoiesis from healthy bone marrow donors.
Figure 5B:
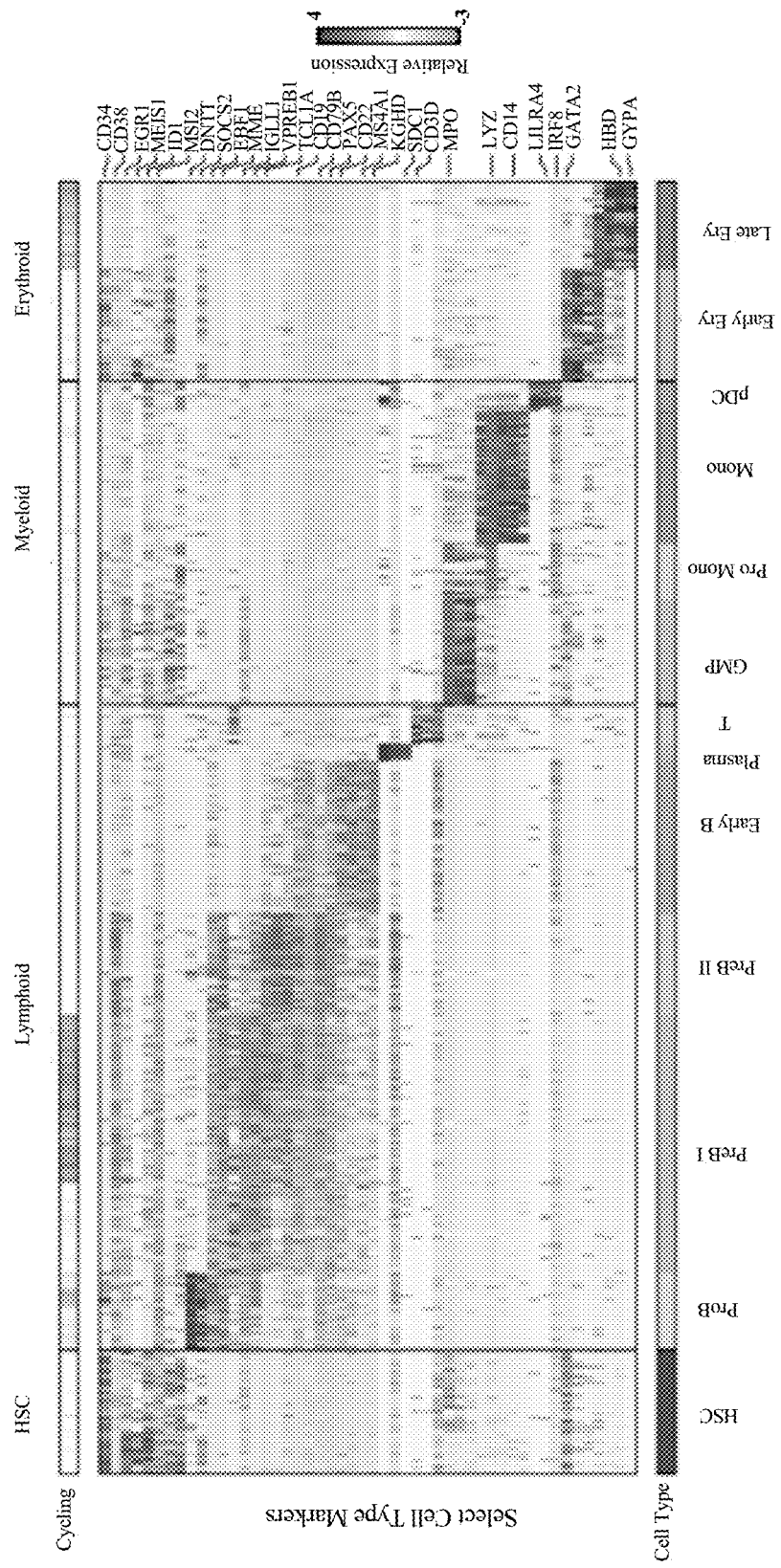
Figure 5C:
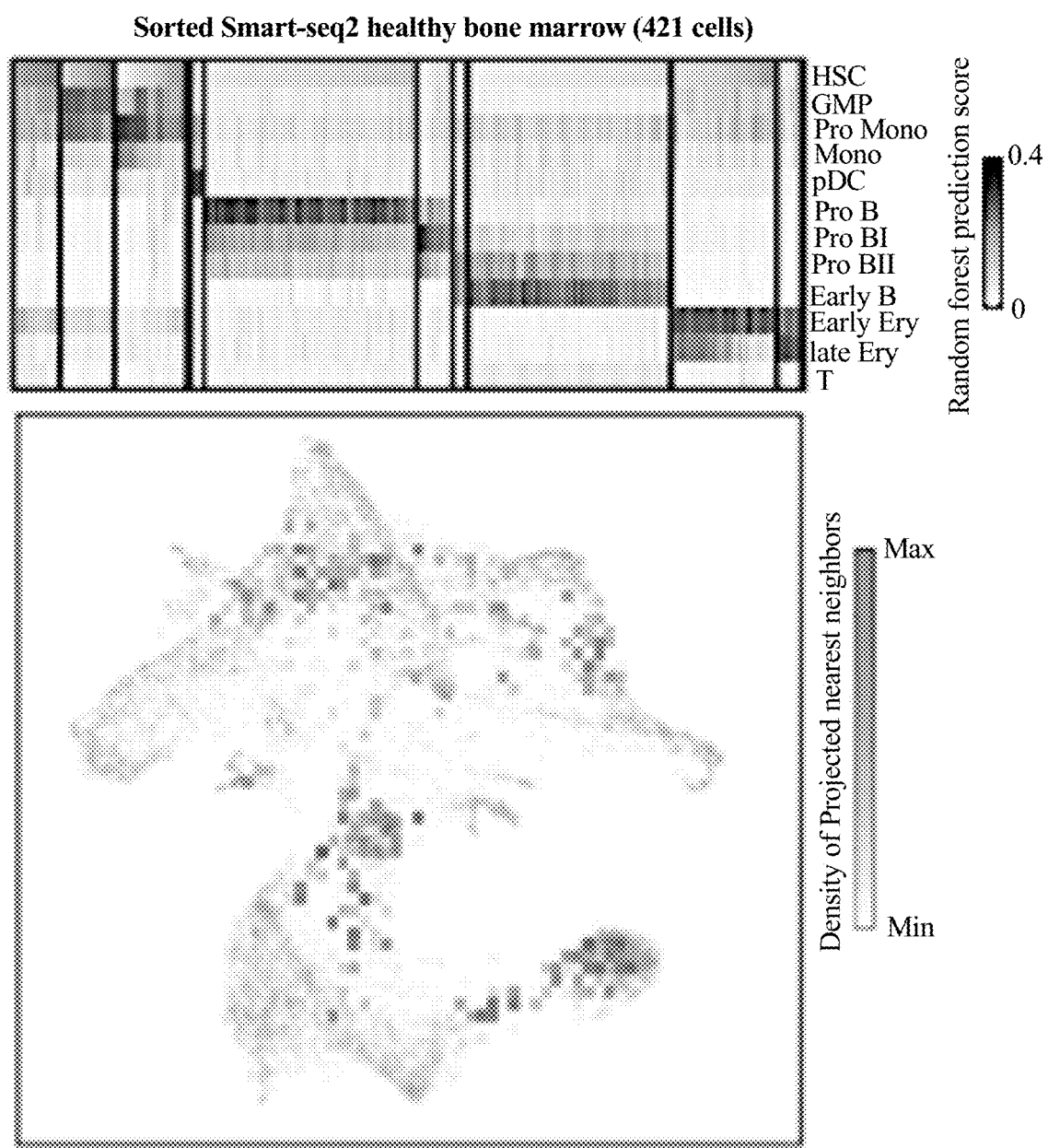
Figure 6B:
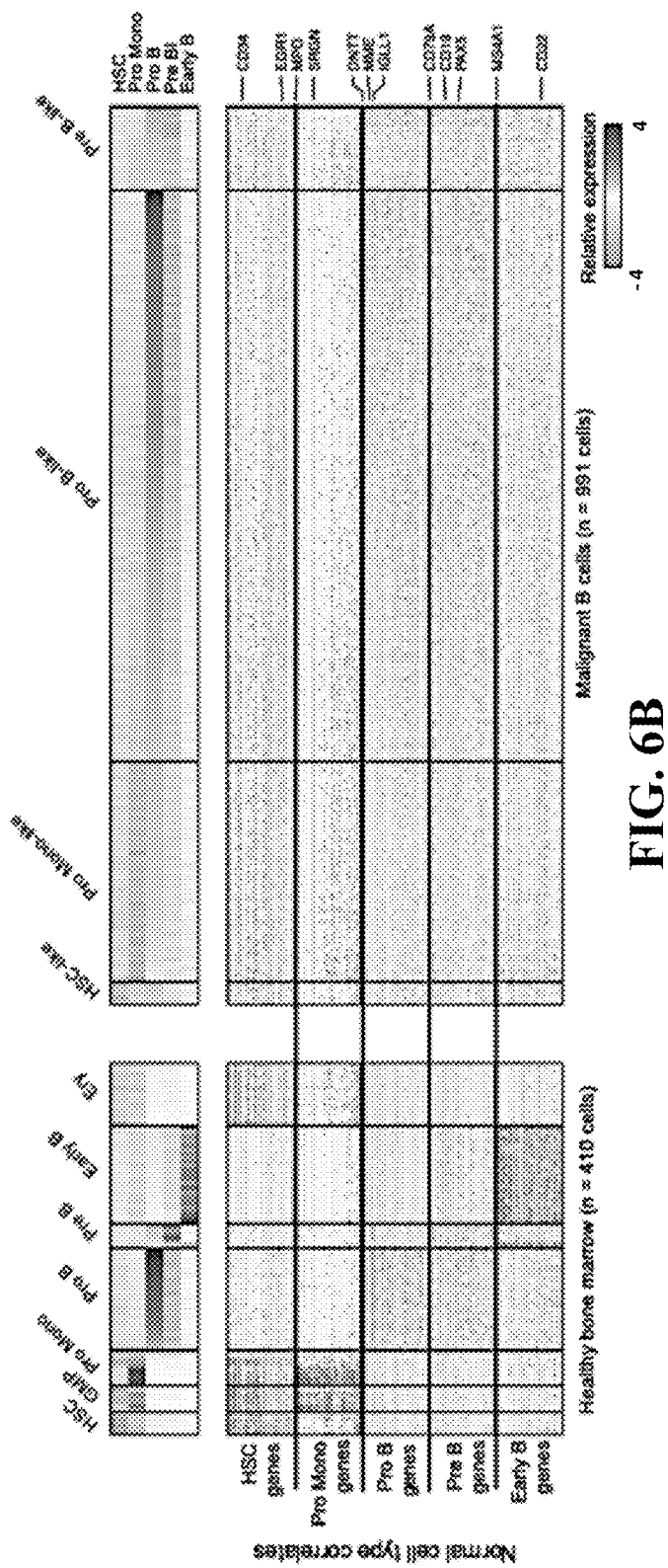
Figure 6C:
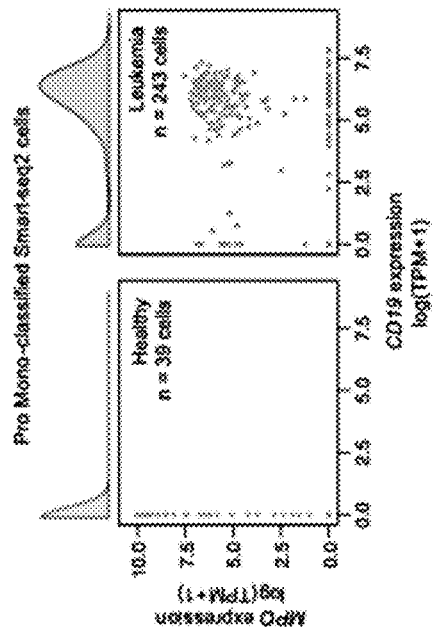
Figure 7C:
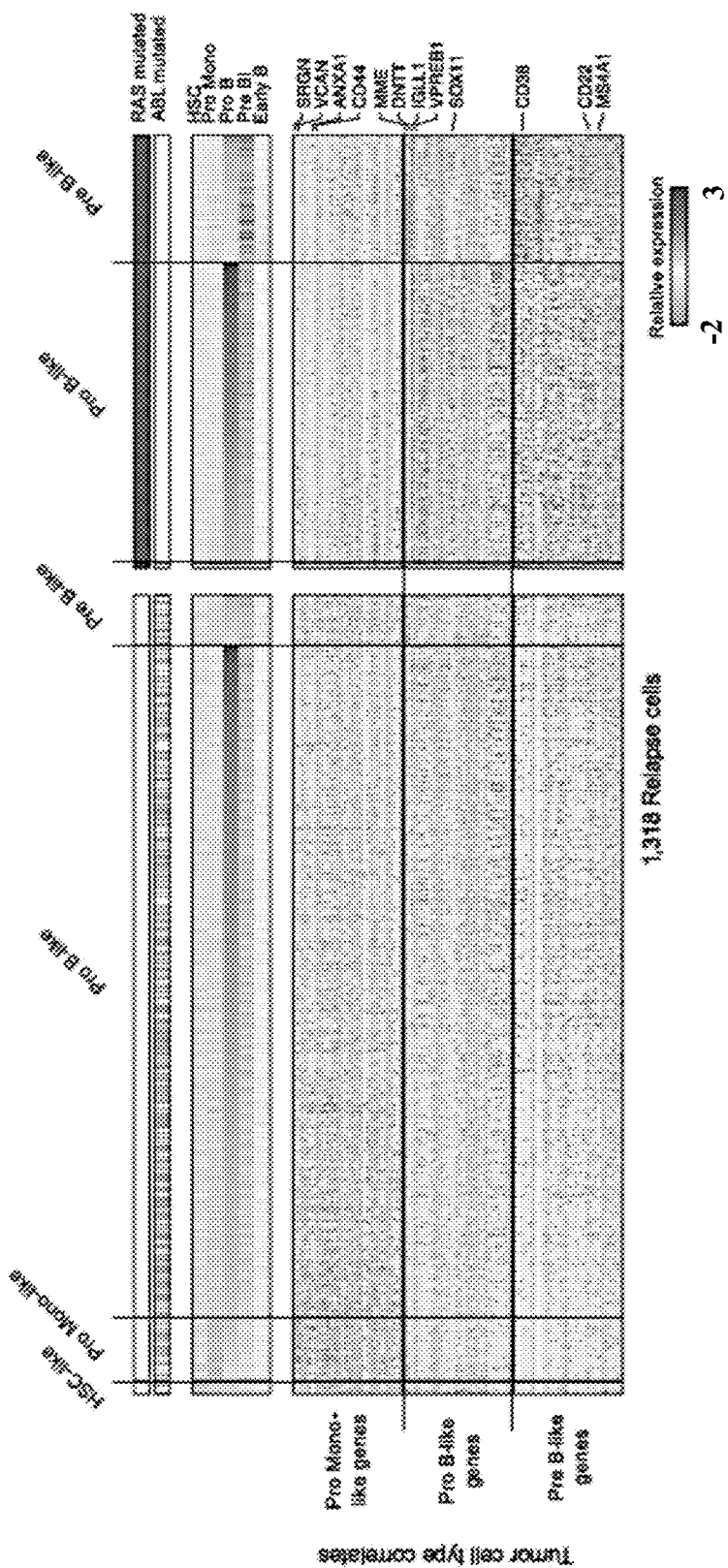
Figure 8A:
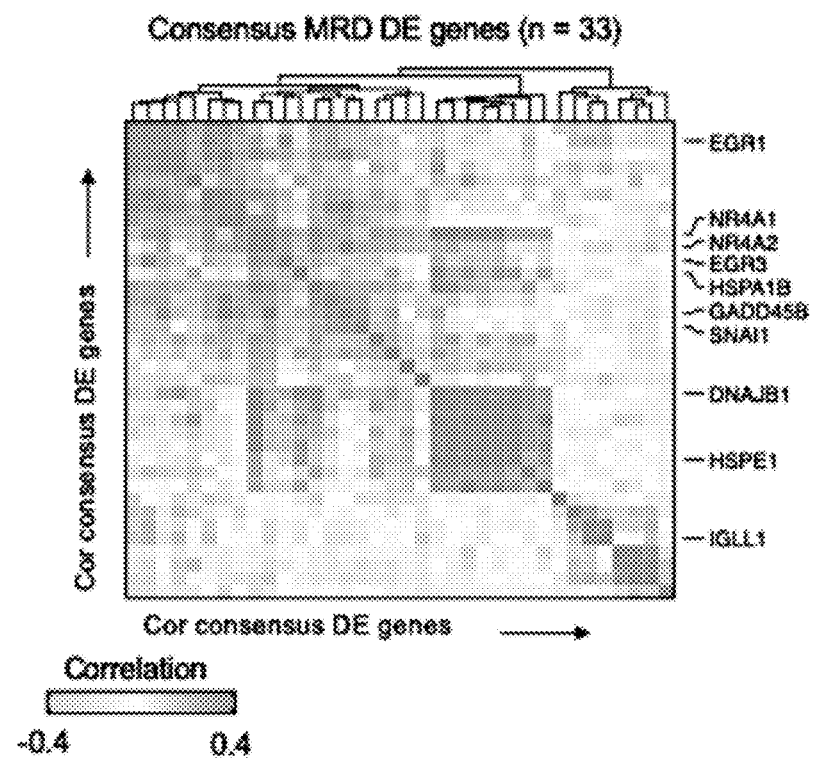
FIGS. 8A-8B—MRD cells adopt quiescent/dormant phenotypes, cycling cells have more differentiated phenotypes.
Figure 8B:
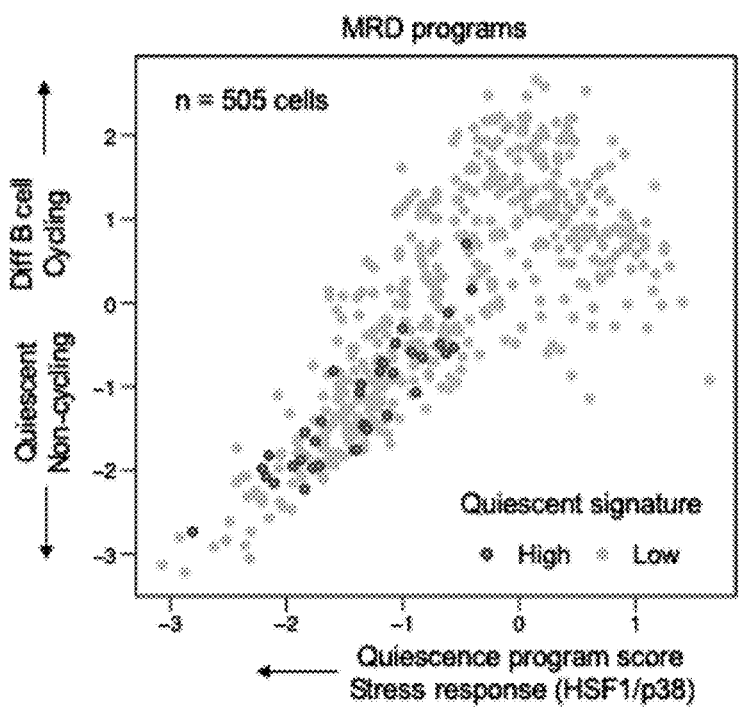
Figure 9:
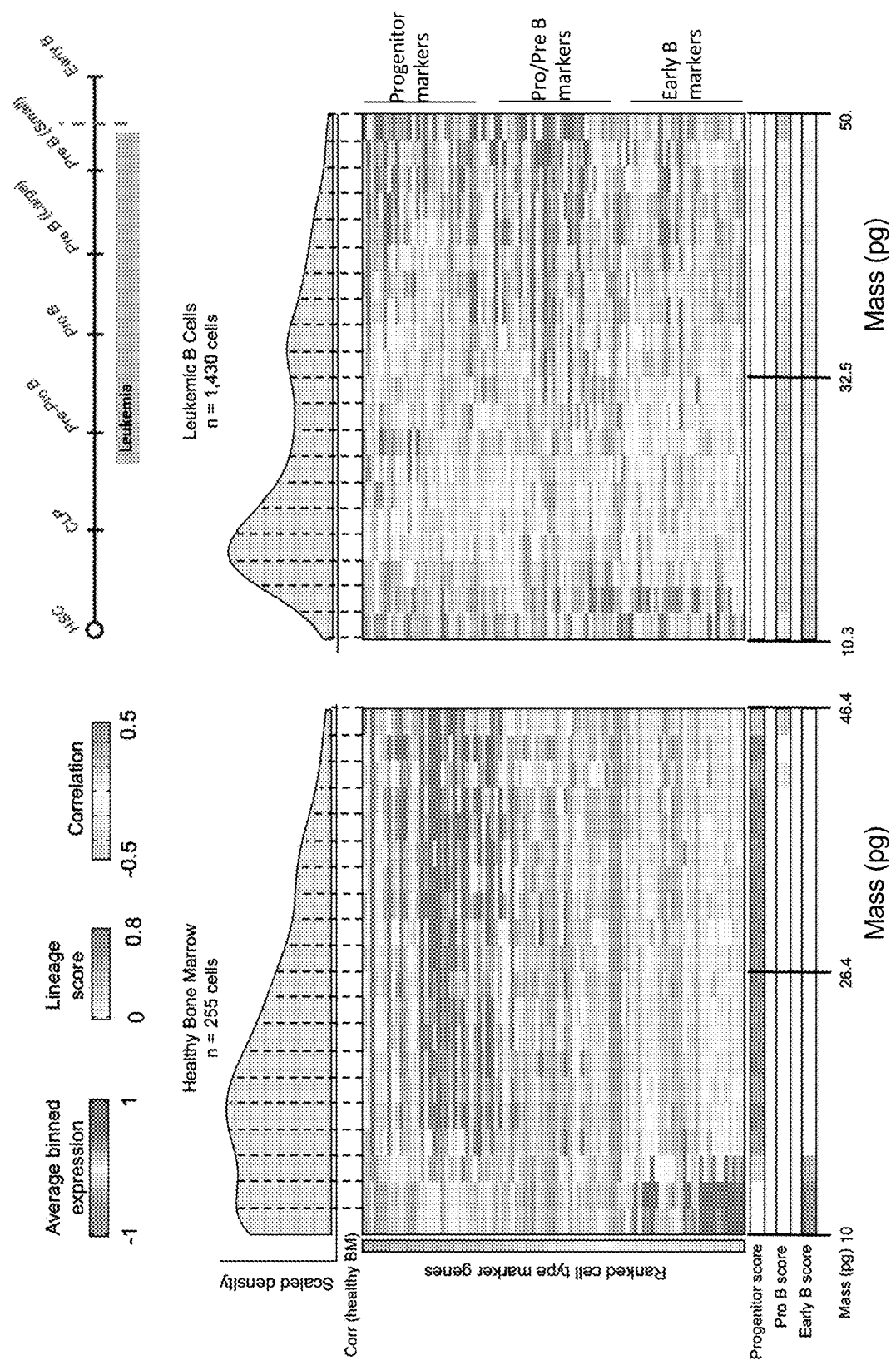
FIG. 9—Pretreatment ALL heterogeneity maps to B-Cell developmental stages. Most leukemic cells resemble normal pro/pre B cells. Cellular mass and gene expression levels for healthy bone marrow cells (left) and leukemic cell (right) at single-cell level are shown. Each column represents a cell and each row represents a selected gene.

In some embodiments, the CRISPR-Cas system that can be used to modify a polynucleotide of the present invention described herein can be a Class 1 CRISPR-Cas system. Class 1 CRISPR-Cas systems are divided into types I, II, and IV. Makarova et al. 2020. Nat. Rev. 18: 67-83., particularly as described in FIG. 1. Type I CRISPR-Cas systems are divided into 9 subtypes (I-A, I-B, I-C, I-D, I-E, I-F1, I-F2, I-F3, and IG). Makarova et al., 2020. Class 1, Type I CRISPR-Cas systems can contain a Cas3 protein that can have helicase activity. Type III CRISPR-Cas systems are divided into 6 subtypes (III-A, III-B, III-C, III-D, III-E, and III-F). Type III CRISPR-Cas systems can contain a Cas10 that can include an RNA recognition motif called Palm and a cyclase domain that can cleave polynucleotides. Makarova et al., 2020. Type IV CRISPR-Cas systems are divided into 3 subtypes. (IV-A, IV-B, and IV-C). Makarova et al., 2020. Class 1 systems also include CRISPR-Cas variants, including Type I-A, I-B, I-E, I-F and I-U variants, which can include variants carried by transposons and plasmids, including versions of subtype I-F encoded by a large family of Tn7-like transposon and smaller groups of Tn7-like transposons that encode similarly degraded subtype I-B systems. Peters et al., PNAS 114 (35) (2017); DOI: 10.1073/pnas.1709035114; see also, Makarova et al. 2018. The CRISPR Journal, v. 1, n5, FIG. 5.

The Class 1 systems typically comprise a multi-protein effector complex, which can, in some embodiments, include ancillary proteins, such as one or more proteins in a complex referred to as a CRISPR-associated complex for antiviral defense (Cascade), one or more adaptation proteins (e.g., Cas1, Cas2, RNA nuclease), and/or one or more accessory proteins (e.g., Cas 4, DNA nuclease), CRISPR associated Rossman fold (CARF) domain containing proteins, and/or RNA transcriptase.

The backbone of the Class 1 CRISPR-Cas system effector complexes can be formed by RNA recognition motif domain-containing protein(s) of the repeat-associated mysterious proteins (RAMPs) family subunits (e.g., Cas 5, Cas6, and/or Cas7). RAMP proteins are characterized by having one or more RNA recognition motif domains. In some embodiments, multiple copies of RAMPs can be present. In some embodiments, the Class I CRISPR-Cas system can include 1, 2, 3, 4, 5, 6, 7, 8, 9, 10, 11, 12 or more Cas5, Cas6, and/or Cas 7 proteins. In some embodiments, the Cas6 protein is an RNAse, which can be responsible for pre-crRNA processing. When present in a Class 1 CRISPR-Cas system, Cas6 can be optionally physically associated with the effector complex.

Figure 2:
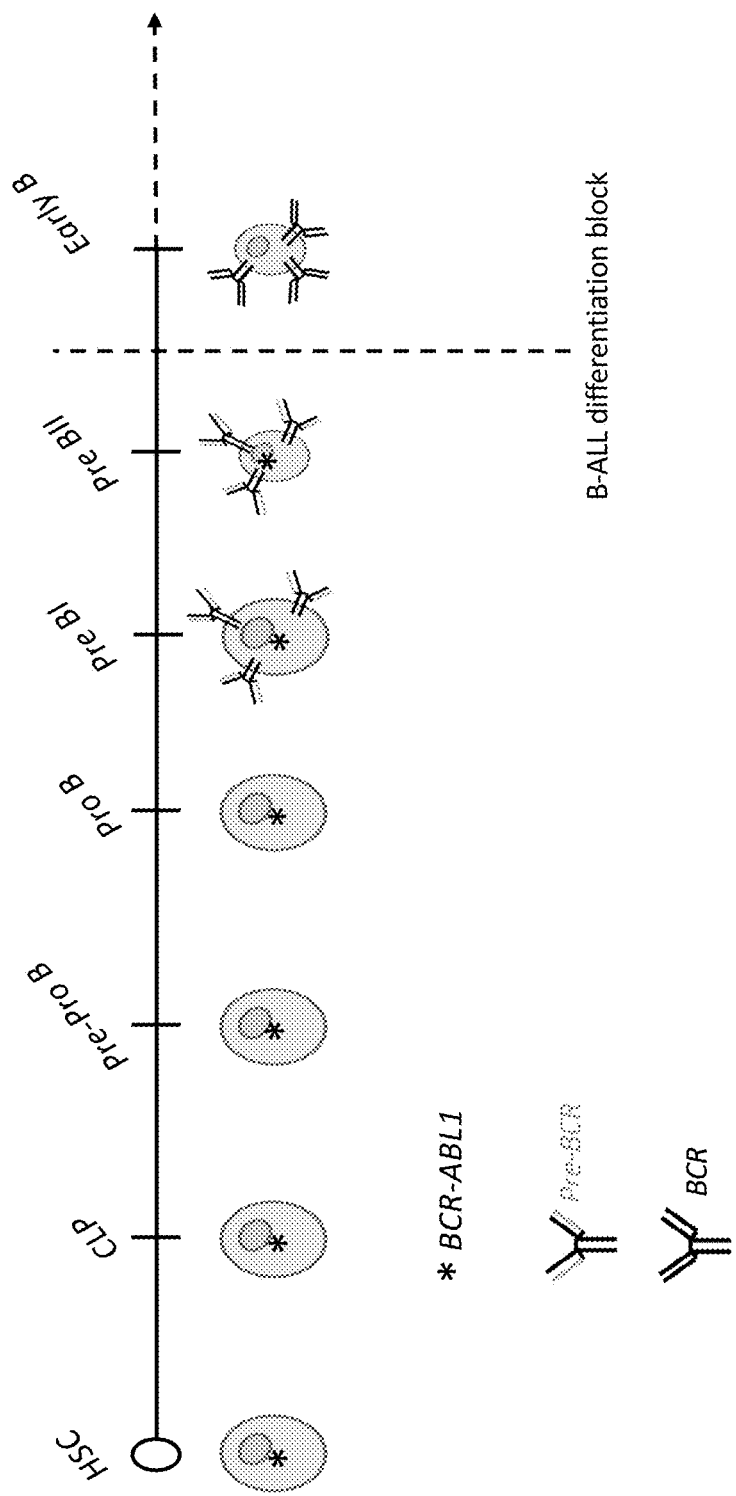
FIG. 2—A schematic showing the developmental stages of normal B cells as well as the corresponding B-cell ALL at each stage. Approximately 25 percent of B-cell acute lymphoblastic Leukemia (B-ALL) patients have "Philadelphia" chromosomal rearrangements resulting in a BCR-ABL fusion protein that drives growth and survival. It is thus a disease of defective B cell development. Translocation usually occur primarily in B cell precursors. A treatment approach to this disease is to treat with kinase inhibitors that target the overactive BCR-ABL oncogene. Relapse is typical with current treatment approaches such as current generation tyrosine kinase inhibitors.
Figure 3A:
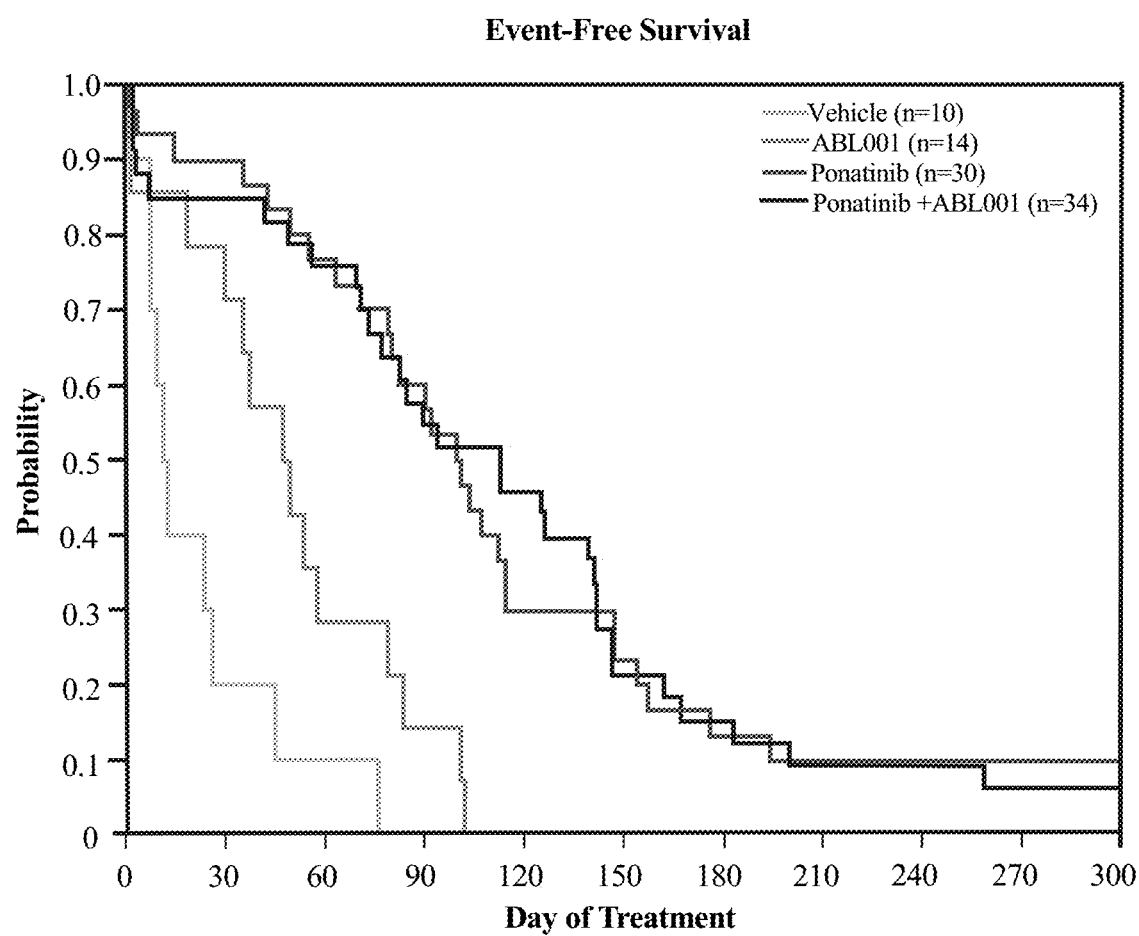
FIGS. 3A-3C—Prolonged remission mediated by ponatinib in BCR-ABL+B-cell ALL.
Figure 3B:
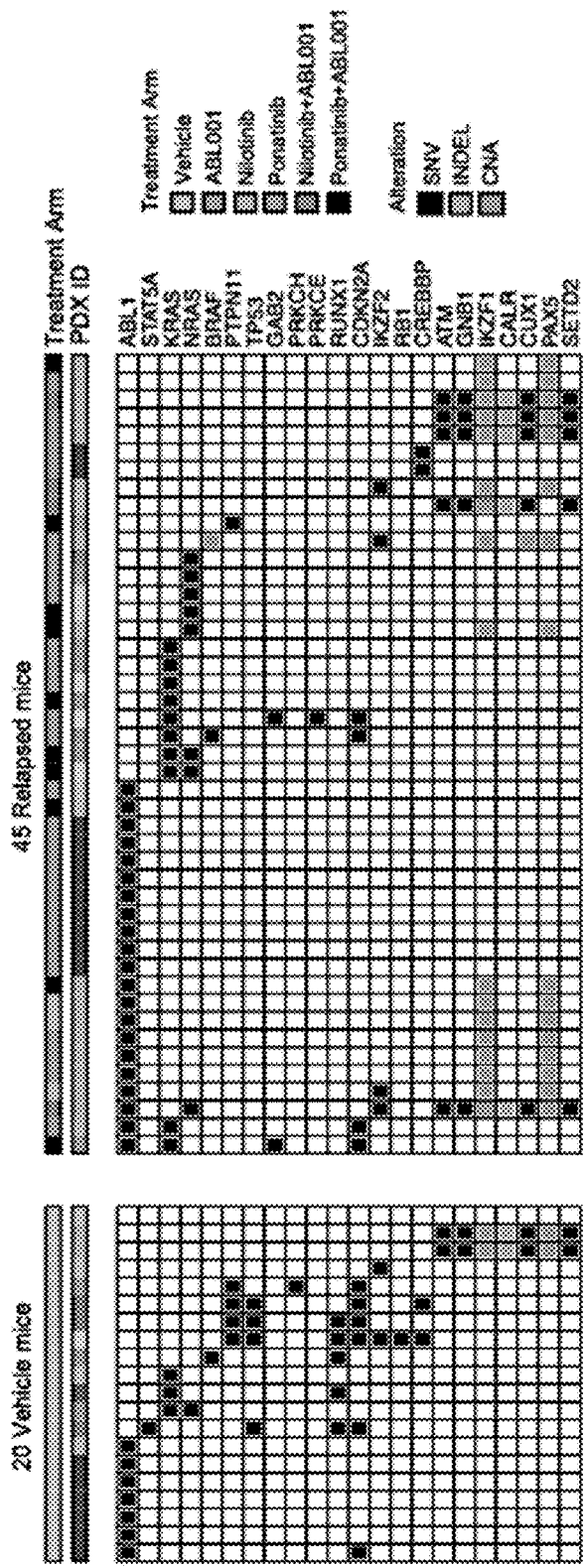
Figure 3C:
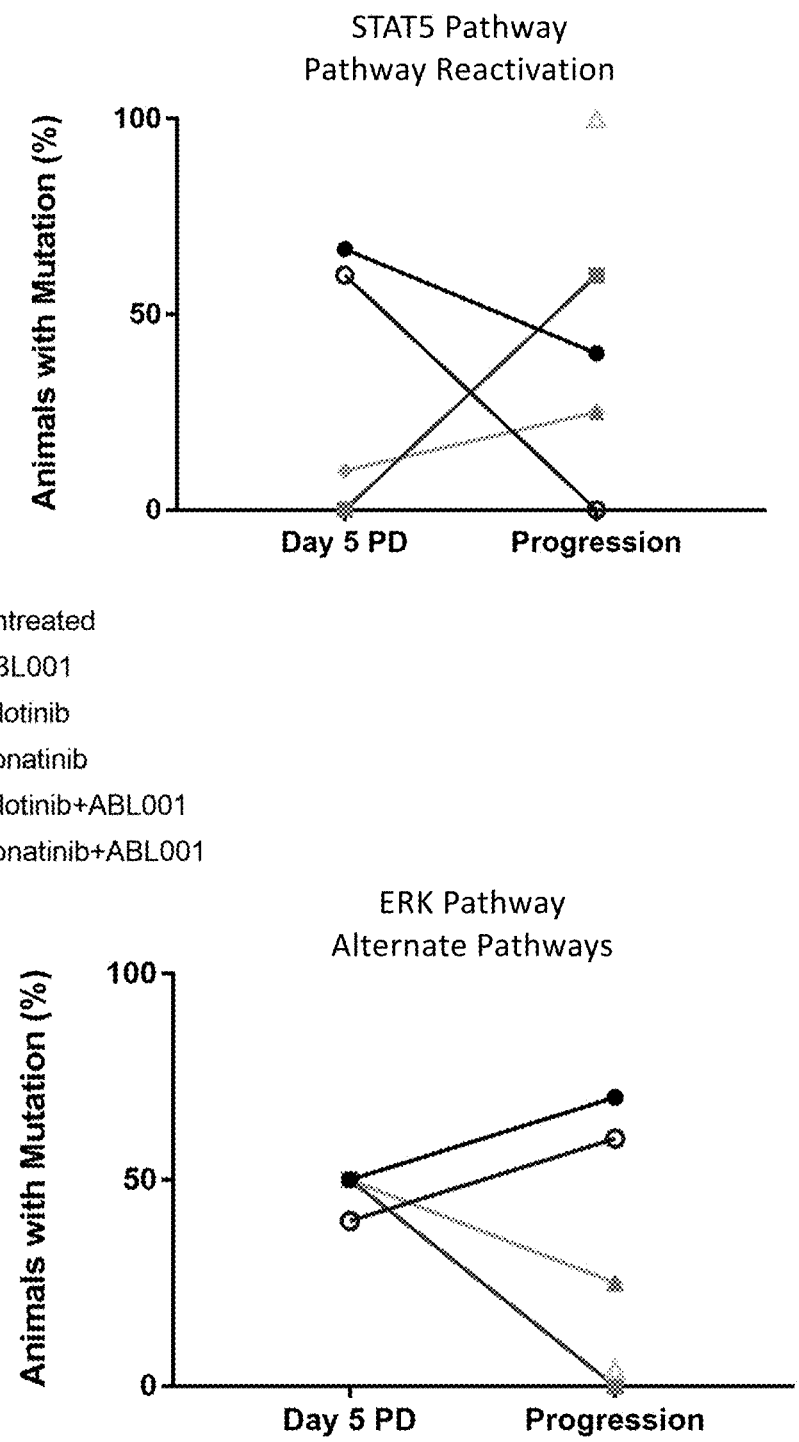

Class 1 CRISPR-Cas system effector complexes can, in some embodiments, also include a large subunit. The large subunit can be composed of or include a Cas8 and/or Cas10 protein. See, e.g., FIGS. 1 and 2. Koonin E V, Makarova K S. 2019. Phil. Trans. R. Soc. B 374: 20180087, DOI: 10.1098/rstb.2018.0087 and Makarova et al. 2020.

Class 1 CRISPR-Cas system effector complexes can, in some embodiments, include a small subunit (for example, Cas11). See, e.g., FIGS. 1 and 2. Koonin E V, Makarova K S. 2019 Origins and Evolution of CRISPR-Cas systems. Phil. Trans. R. Soc. B 374: 20180087, DOI: 10.1098/rstb.2018.0087.

In some embodiments, the Class 1 CRISPR-Cas system can be a Type I CRISPR-Cas system. In some embodiments, the Type I CRISPR-Cas system can be a subtype I-A CRISPR-Cas system. In some embodiments, the Type I CRISPR-Cas system can be a subtype I-B CRISPR-Cas system. In some embodiments, the Type I CRISPR-Cas system can be a subtype I-C CRISPR-Cas system. In some embodiments, the Type I CRISPR-Cas system can be a subtype I-D CRISPR-Cas system. In some embodiments, the Type I CRISPR-Cas system can be a subtype I-E CRISPR-Cas system. In some embodiments, the Type I CRISPR-Cas system can be a subtype I-F1 CRISPR-Cas system. In some embodiments, the Type I CRISPR-Cas system can be a subtype I-F2 CRISPR-Cas system. In some embodiments, the Type I CRISPR-Cas system can be a subtype I-F3 CRISPR-Cas system. In some embodiments, the Type I CRISPR-Cas system can be a subtype I-G CRISPR-Cas system. In some embodiments, the Type I CRISPR-Cas system can be a CRISPR-Cas variant, such as a Type I-A, I-B, I-E, I-F and I-U variants, which can include variants carried by transposons and plasmids, including versions of subtype I-F encoded by a large family of Tn7-like transposon and smaller groups of Tn7-like transposons that encode similarly degraded subtype I-B systems as previously described.

In some embodiments, the Class 1 CRISPR-Cas system can be a Type III CRISPR-Cas system. In some embodiments, the Type III CRISPR-Cas system can be a subtype III-A CRISPR-Cas system. In some embodiments, the Type III CRISPR-Cas system can be a subtype III-B CRISPR-Cas system. In some embodiments, the Type III CRISPR-Cas system can be a subtype III-C CRISPR-Cas system. In some embodiments, the Type III CRISPR-Cas system can be a subtype III-D CRISPR-Cas system. In some embodiments, the Type III CRISPR-Cas system can be a subtype III-E CRISPR-Cas system. In some embodiments, the Type III CRISPR-Cas system can be a subtype III-F CRISPR-Cas system.

In some embodiments, the Class 1 CRISPR-Cas system can be a Type IV CRISPR-Cas-system. In some embodiments, the Type IV CRISPR-Cas system can be a subtype IV-A CRISPR-Cas system. In some embodiments, the Type IV CRISPR-Cas system can be a subtype IV-B CRISPR-Cas system. In some embodiments, the Type IV CRISPR-Cas system can be a subtype IV-C CRISPR-Cas system.

The effector complex of a Class 1 CRISPR-Cas system can, in some embodiments, include a Cas3 protein that is optionally fused to a Cas2 protein, a Cas4, a Cas5, a Cas6, a Cas7, a Cas8, a Cas10, a Cas11, or a combination thereof. In some embodiments, the effector complex of a Class 1 CRISPR-Cas system can have multiple copies, such as 1, 2, 3, 4, 5, 6, 7, 8, 9, 10, 11, 12, 13, or 14, of any one or more Cas proteins.

Class 2 CRISPR-Cas Systems

The compositions, systems, and methods described in greater detail elsewhere herein can be designed and adapted for use with Class 2 CRISPR-Cas systems. Thus, in some embodiments, the CRISPR-Cas system is a Class 2 CRISPR-Cas system. Class 2 systems are distinguished from Class 1 systems in that they have a single, large, multi-domain effector protein. In certain example embodiments, the Class 2 system can be a Type II, Type V, or Type VI system, which are described in Makarova et al. "Evolutionary classification of CRISPR-Cas systems: a burst of class 2 and derived variants" Nature Reviews Microbiology, 18:67-81 (Feb 2020), incorporated herein by reference. Each type of Class 2 system is further divided into subtypes. See Markova et al. 2020, particularly at Figure. 2. Class 2, Type II systems can be divided into 4 subtypes: II-A, II-B, II-C1, and II-C2. Class 2, Type V systems can be divided into 17 subtypes: V-A, V-B1, V-B2, V-C, V-D, V-E, V-F1, V-F1(V-U3), V-F2, V-F3, V-G, V-H, V-I, V-K (V-U5), V-U1, V-U2, and V-U4. Class 2, Type IV systems can be divided into 5 subtypes: VI-A, VI-B1, VI-B2, VI-C, and VI-D.

The distinguishing feature of these types is that their effector complexes consist of a single, large, multi-domain protein. Type V systems differ from Type II effectors (e.g., Cas9), which contain two nuclear domains that are each responsible for the cleavage of one strand of the target DNA, with the HNH nuclease inserted inside the Ruv-C like nuclease domain sequence. The Type V systems (e.g., Cas12) only contain a RuvC-like nuclease domain that cleaves both strands. Type VI (Cas13) are unrelated to the effectors of Type II and V systems and contain two HEPN domains and target RNA. Cas13 proteins also display collateral activity that is triggered by target recognition. Some Type V systems have also been found to possess this collateral activity with two single-stranded DNA in in vitro contexts.

In some embodiments, the Class 2 system is a Type II system. In some embodiments, the Type II CRISPR-Cas system is a II-A CRISPR-Cas system. In some embodiments, the Type II CRISPR-Cas system is a II-B CRISPR-Cas system. In some embodiments, the Type II CRISPR-Cas system is a II-C1 CRISPR-Cas system. In some embodiments, the Type II CRISPR-Cas system is a II-C2 CRISPR-Cas system. In some embodiments, the Type II system is a Cas9 system. In some embodiments, the Type II system includes a Cas9.

In some embodiments, the Class 2 system is a Type V system. In some embodiments, the Type V CRISPR-Cas system is a V-A CRISPR-Cas system. In some embodiments, the Type V CRISPR-Cas system is a V-B1 CRISPR-Cas system. In some embodiments, the Type V CRISPR-Cas system is a V-B2 CRISPR-Cas system. In some embodiments, the Type V CRISPR-Cas system is a V-C CRISPR-Cas system. In some embodiments, the Type V CRISPR-Cas system is a V-D CRISPR-Cas system. In some embodiments, the Type V CRISPR-Cas system is a V-E CRISPR-Cas system. In some embodiments, the Type V CRISPR-Cas system is a V-F1 CRISPR-Cas system. In some embodiments, the Type V CRISPR-Cas system is a V-F1 (V-U3) CRISPR-Cas system. In some embodiments, the Type V CRISPR-Cas system is a V-F2 CRISPR-Cas system. In some embodiments, the Type V CRISPR-Cas system is a V-F3 CRISPR-Cas system. In some embodiments, the Type V CRISPR-Cas system is a V-G CRISPR-Cas system. In some embodiments, the Type V CRISPR-Cas system is a V-H CRISPR-Cas system. In some embodiments, the Type V CRISPR-Cas system is a V-I CRISPR-Cas system. In some embodiments, the Type V CRISPR-Cas system is a V-K (V-U5) CRISPR-Cas system. In some embodiments, the Type V CRISPR-Cas system is a V-U1 CRISPR-Cas system. In some embodiments, the Type V CRISPR-Cas system is a V-U2 CRISPR-Cas system. In some embodiments, the Type V CRISPR-Cas system is a V-U4 CRISPR-Cas system. In some embodiments, the Type V CRISPR-Cas system includes a Cas12a (Cpf1), Cas12b (C2c1), Cas12c (C2c3), Cas12d (CasY), Cas12e (CasX), and/or Cas14.

In some embodiments the Class 2 system is a Type VI system. In some embodiments, the Type VI CRISPR-Cas system is a VI-A CRISPR-Cas system. In some embodiments, the Type VI CRISPR-Cas system is a VI-B1 CRISPR-Cas system. In some embodiments, the Type VI CRISPR-Cas system is a VI-B2 CRISPR-Cas system. In some embodiments, the Type VI CRISPR-Cas system is a VI-C CRISPR-Cas system. In some embodiments, the Type VI CRISPR-Cas system is a VI-D CRISPR-Cas system. In some embodiments, the Type VI CRISPR-Cas system includes a Cas13a (C2c2), Cas13b (Group 29/30), Cas13c, and/or Cas13d.

Specialized Cas-based Systems

In some embodiments, the system is a Cas-based system that is capable of performing a specialized function or activity. For example, the Cas protein may be fused, operably coupled to, or otherwise associated with one or more functionals domains. In certain example embodiments, the Cas protein may be a catalytically dead Cas protein ("dCas") and/or have nickase activity. A nickase is a Cas protein that cuts only one strand of a double stranded target. In such embodiments, the dCas or nickase provide a sequence-specific targeting functionality that delivers the functional domain to or proximate a target sequence. Example functional domains that may be fused to, operably coupled to, or otherwise associated with a Cas protein can be or include, but are not limited to a nuclear localization signal (NLS)

domain, a nuclear export signal (NES) domain, a translational activation domain, a transcriptional activation domain (e.g. VP64, p65, MyoD1, HSF1, RTA, and SET7/9), a translation initiation domain, a transcriptional repression domain (e.g., a KRAB domain, NuE domain, NcoR domain, and a SID domain such as a SID4X domain), a nuclease domain (e.g., FokI), a histone modification domain (e.g., a histone acetyltransferase), a light inducible/controllable domain, a chemically inducible/controllable domain, a transposase domain, a homologous recombination machinery domain, a recombinase domain, an integrase domain, and combinations thereof. Methods for generating catalytically dead Cas9 or a nickase Cas9 (WO 2014/204725, Ran et al. Cell. 2013 Sept 12; 154(6):1380-1389), Cas12 (Liu et al. Nature Communications, 8, 2095 (2017), and Cas13 (International Patent Publication Nos. WO 2019/005884 and WO2019/060746) are known in the art and incorporated herein by reference.

In some embodiments, the functional domains can have one or more of the following activities: methylase activity, demethylase activity, translation activation activity, translation initiation activity, translation repression activity, transcription activation activity, transcription repression activity, transcription release factor activity, histone modification activity, nuclease activity, single-strand RNA cleavage activity, double-strand RNA cleavage activity, single-strand DNA cleavage activity, double-strand DNA cleavage activity, molecular switch activity, chemical inducibility, light inducibility, and nucleic acid binding activity. In some embodiments, the one or more functional domains may comprise epitope tags or reporters. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporters include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and auto-fluorescent proteins including blue fluorescent protein (BFP).

The one or more functional domain(s) may be positioned at, near, and/or in proximity to a terminus of the effector protein (e.g., a Cas protein). In embodiments having two or more functional domains, each of the two can be positioned at or near or in proximity to a terminus of the effector protein (e.g., a Cas protein). In some embodiments, such as those where the functional domain is operably coupled to the effector protein, the one or more functional domains can be tethered or linked via a suitable linker (including, but not limited to, GlySer linkers) to the effector protein (e.g., a Cas protein). When there is more than one functional domain, the functional domains can be same or different. In some embodiments, all the functional domains are the same. In some embodiments, all of the functional domains are different from each other. In some embodiments, at least two of the functional domains are different from each other. In some embodiments, at least two of the functional domains are the same as each other.

Other suitable functional domains can be found, for example, in International Patent Publication No. WO 2019/018423.

Split CRISPR-Cas systems

In some embodiments, the CRISPR-Cas system is a split CRISPR-Cas system. See e.g., Zetche et al., 2015. Nat. Biotechnol. 33(2): 139-142 and International Patent Publication WO 2019/018423, the compositions and techniques of which can be used in and/or adapted for use with the present invention. Split CRISPR-Cas proteins are set forth herein and in documents incorporated herein by reference in further detail herein. In certain embodiments, each part of a split CRISPR protein are attached to a member of a specific binding pair, and when bound with each other, the members of the specific binding pair maintain the parts of the CRISPR protein in proximity. In certain embodiments, each part of a split CRISPR protein is associated with an inducible binding pair. An inducible binding pair is one which is capable of being switched "on" or "off" by a protein or small molecule that binds to both members of the inducible binding pair. In some embodiments, CRISPR proteins may preferably split between domains, leaving domains intact. In particular embodiments, said Cas split domains (e.g., RuvC and HNH domains in the case of Cas9) can be simultaneously or sequentially introduced into the cell such that said split Cas domain(s) process the target nucleic acid sequence in the algae cell. The reduced size of the split Cas compared to the wild type Cas allows other methods of delivery of the systems to the cells, such as the use of cell penetrating peptides as described herein.

DNA and RNA Base Editing

In some embodiments, a polynucleotide of the present invention described elsewhere herein can be modified using a base editing system. In some embodiments, a Cas protein is connected or fused to a nucleotide deaminase. Thus, in some embodiments the Cas-based system can be a base editing system. As used herein, "base editing" refers generally to the process of polynucleotide modification via a CRISPR-Cas-based or Cas-based system that does not include excising nucleotides to make the modification. Base editing can convert base pairs at precise locations without generating excess undesired editing byproducts that can be made using traditional CRISPR-Cas systems.

In certain example embodiments, the nucleotide deaminase may be a DNA base editor used in combination with a DNA-binding Cas protein such as, but not limited to, Class 2 Type II and Type V systems. Two classes of DNA base editors are generally known: cytosine base editors (CBEs) and adenine base editors (ABEs). CBEs convert a C•G base pair into a T•A base pair (Komor et al. 2016. Nature. 533:420-424; Nishida et al. 2016. Science. 353; and Li et al. Nat. Biotech. 36:324-327) and ABEs convert an A•T base pair to a G•C base pair. Collectively, CBEs and ABEs can mediate all four possible transition mutations (C to T, A to G, T to C, and G to A). Rees and Liu. 2018.Nat. Rev. Genet. 19(12): 770-788, particularly at FIGS. 1*b*, 2*a*-2*c*, 3*a*-3*f*, and Table 1. In some embodiments, the base editing system includes a CBE and/or an ABE. In some embodiments, a polynucleotide of the present invention described elsewhere herein can be modified using a base editing system. Rees and Liu. 2018. Nat. Rev. Gent. 19(12):770-788. Base editors also generally do not need a DNA donor template and/or rely on homology-directed repair. Komor et al. 2016. Nature. 533: 420-424; Nishida et al. 2016. Science. 353; and Gaudeli et al. 2017. Nature. 551:464-471. Upon binding to a target locus in the DNA, base pairing between the guide RNA of the system and the target DNA strand leads to displacement of a small segment of ssDNA in an "R-loop". Nishimasu et al. Cell. 156:935-949. DNA bases within the ssDNA bubble are modified by the enzyme component, such as a deaminase. In some systems, the catalytically disabled Cas protein can be a variant or modified Cas can have nickase functionality and can generate a nick in the non-edited DNA strand to induce cells to repair the non-edited strand using the edited strand as a template. Komor et al. 2016. Nature.

533:420-424; Nishida et al. 2016. Science. 353; and Gaudeli et al. 2017. Nature. 551:464-471.

Other Example Type V base editing systems are described in International Patent Publication Nos. WO 2018/213708, WO 2018/213726, and International Patent Applications No. PCT/US2018/067207, PCT/US2018/067225, and PCT/US2018/067307, each of which is incorporated herein by reference.

In certain example embodiments, the base editing system may be an RNA base editing system. As with DNA base editors, a nucleotide deaminase capable of converting nucleotide bases may be fused to a Cas protein. However, in these embodiments, the Cas protein will need to be capable of binding RNA. Example RNA binding Cas proteins include, but are not limited to, RNA-binding Cas9s such as *Francisella novicida* Cas9 ("FnCas9"), and Class 2 Type VI Cas systems. The nucleotide deaminase may be a cytidine deaminase or an adenosine deaminase, or an adenosine deaminase engineered to have cytidine deaminase activity. In certain example embodiments, the RNA base editor may be used to delete or introduce a post-translation modification site in the expressed mRNA. In contrast to DNA base editors, whose edits are permanent in the modified cell, RNA base editors can provide edits where finer, temporal control may be needed, for example in modulating a particular immune response. Example Type VI RNA-base editing systems are described in Cox et al. 2017. Science 358: 1019-1027, International Patent Publication Nos. WO 2019/005884, WO 2019/005886, and WO 2019/071048, and International Patent Application Nos. PCT/US20018/05179 and PCT/US2018/067207, which are incorporated herein by reference. An example FnCas9 system that may be adapted for RNA base editing purposes is described in International Patent Publication No. WO 2016/106236, which is incorporated herein by reference.

An example method for delivery of base-editing systems, including use of a split-intein approach to divide CBE and ABE into reconstitutable halves, is described in Levy et al. Nature Biomedical Engineering doi.org/10.1038/s41441-019-0505-5 (2019), which is incorporated herein by reference.

Prime Editors

In some embodiments, a polynucleotide of the present invention described elsewhere herein can be modified using a prime editing system. See e.g. Anzalone et al. 2019. Nature. 576: 149-157. Like base editing systems, prime editing systems can be capable of targeted modification of a polynucleotide without generating double stranded breaks and does not require donor templates. Further prime editing systems can be capable of all 12 possible combination swaps. Prime editing can operate via a "search-and-replace" methodology and can mediate targeted insertions, deletions, all 12 possible base-to-base conversion and combinations thereof. Generally, a prime editing system, as exemplified by PE1, PE2, and PE3 (Id.), can include a reverse transcriptase fused or otherwise coupled or associated with an RNA-programmable nickase and a prime-editing extended guide RNA (pegRNA) to facility direct copying of genetic information from the extension on the pegRNA into the target polynucleotide. Embodiments that can be used with the present invention include these and variants thereof. Prime editing can have the advantage of lower off-target activity than traditional CRIPSR-Cas systems along with few byproducts and greater or similar efficiency as compared to traditional CRISPR-Cas systems.

In some embodiments, the prime editing guide molecule can specify both the target polynucleotide information (e.g., sequence) and contain a new polynucleotide cargo that replaces target polynucleotides. To initiate transfer from the guide molecule to the target polynucleotide, the PE system can nick the target polynucleotide at a target side to expose a 3'hydroxyl group, which can prime reverse transcription of an edit-encoding extension region of the guide molecule (e.g. a prime editing guide molecule or peg guide molecule) directly into the target site in the target polynucleotide. See e.g. Anzalone et al. 2019. Nature. 576: 149-157, particularly at FIGS. 1b, 1c, related discussion, and Supplementary discussion.

In some embodiments, a prime editing system can be composed of a Cas polypeptide having nickase activity, a reverse transcriptase, and a guide molecule. The Cas polypeptide can lack nuclease activity. The guide molecule can include a target binding sequence as well as a primer binding sequence and a template containing the edited polynucleotide sequence. The guide molecule, Cas polypeptide, and/or reverse transcriptase can be coupled together or otherwise associate with each other to form an effector complex and edit a target sequence. In some embodiments, the Cas polypeptide is a Class 2, Type V Cas polypeptide. In some embodiments, the Cas polypeptide is a Cas9 polypeptide (e.g. is a Cas9 nickase). In some embodiments, the Cas polypeptide is fused to the reverse transcriptase. In some embodiments, the Cas polypeptide is linked to the reverse transcriptase.

Figure 4A:
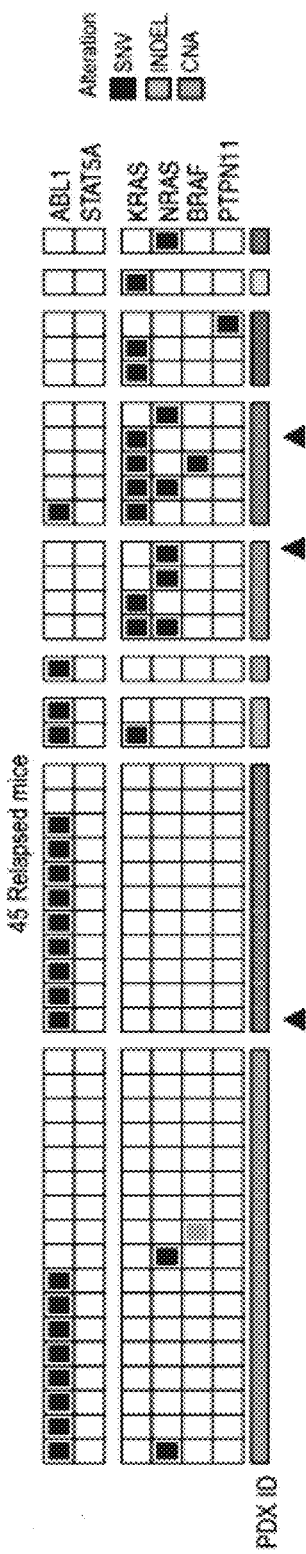
FIGS. 4A-4B—Mutational skew by differentiation state.
Figure 4B:
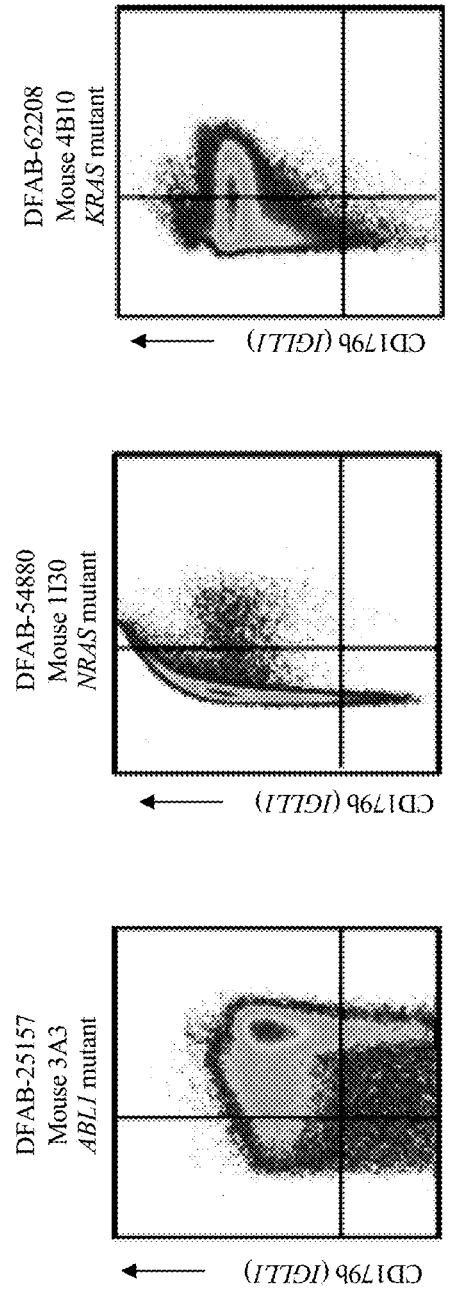

In some embodiments, the prime editing system can be a PE1 system or variant thereof, a PE2 system or variant thereof, or a PE3 (e.g. PE3, PE3b) system. See e.g., Anzalone et al. 2019. Nature. 576: 149-157, particularly at pgs. 2-3, FIGS. 2a, 3a-3f, 4a-4b, Extended data FIGS. 3a-3b, 4.

The peg guide molecule can be about 10 to about 200 or more nucleotides in length, such as 10 to/or 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 or more nucleotides in length. Optimization of the peg guide molecule can be accomplished as described in Anzalone et al. 2019. Nature. 576: 149-157, particularly at pg. 3, FIG. 2a-2b, and Extended Data FIGS. 5a-c.

CRISPR Associated Transposase (CAST) Systems

In some embodiments, a polynucleotide of the present invention described elsewhere herein can be modified using a CRISPR Associated Transposase ("CAST") system. CAST system can include a Cas protein that is catalytically inactive, or engineered to be catalytically active, and further comprises a transposase (or subunits thereof) that catalyze RNA-guided DNA transposition. Such systems are able to insert DNA sequences at a target site in a DNA molecule without relying on host cell repair machinery. CAST systems can be Class1 or Class 2 CAST systems. An example Class 1 system is described in Klompe et al. Nature, doi: 10.1038/s41586-019-1323, which is in incorporated herein by reference. An example Class 2 system is described in Strecker et al. Science. 10/1126/science. aax9181 (2019), and PCT/US2019/066835 which are incorporated herein by reference.

Guide Molecules

The CRISPR-Cas or Cas-Based system described herein can, in some embodiments, include one or more guide molecules. The terms guide molecule, guide sequence and guide polynucleotide refer to polynucleotides capable of guiding Cas to a target genomic locus and are used interchangeably as in foregoing cited documents such as International Patent Publication No. WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. The guide molecule can be a polynucleotide.

The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay (Qui et al. 2004. BioTechniques. 36(4)702-707). Similarly, cleavage of a target nucleic acid sequence may be evaluated in a test tube by providing the target nucleic acid sequence, components of a nucleic acid-targeting complex, including the guide sequence to be tested and a control guide sequence different from the test guide sequence, and comparing binding or rate of cleavage at the target sequence between the test and control guide sequence reactions. Other assays are possible and will occur to those skilled in the art.

In some embodiments, the guide molecule is an RNA. The guide molecule(s) (also referred to interchangeably herein as guide polynucleotide and guide sequence) that are included in the CRISPR-Cas or Cas-based system can be any polynucleotide sequence having sufficient complementarity with a target nucleic acid sequence to hybridize with the target nucleic acid sequence and direct sequence-specific binding of a nucleic acid-targeting complex to the target nucleic acid sequence. In some embodiments, the degree of complementarity, when optimally aligned using a suitable alignment algorithm, can be about or more than about 50%, 60%, 75%, 80%, 85%, 90%, 95%, 97.5%, 99%, or more. Optimal alignment may be determined with the use of any suitable algorithm for aligning sequences, non-limiting examples of which include the Smith-Waterman algorithm, the Needleman-Wunsch algorithm, algorithms based on the Burrows-Wheeler Transform (e.g., the Burrows Wheeler Aligner), Clustal W, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net).

A guide sequence, and hence a nucleic acid-targeting guide, may be selected to target any target nucleic acid sequence. The target sequence may be DNA. The target sequence may be any RNA sequence. In some embodiments, the target sequence may be a sequence within an RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmatic RNA (scRNA). In some preferred embodiments, the target sequence may be a sequence within an RNA molecule selected from the group consisting of mRNA, pre-mRNA, and rRNA. In some preferred embodiments, the target sequence may be a sequence within an RNA molecule selected from the group consisting of ncRNA, and lncRNA. In some more preferred embodiments, the target sequence may be a sequence within an mRNA molecule or a pre-mRNA molecule.

In some embodiments, a nucleic acid-targeting guide is selected to reduce the degree secondary structure within the nucleic acid-targeting guide. In some embodiments, about or less than about 75%, 50%, 40%, 30%, 25%, 20%, 15%, 10%, 5%, 1%, or fewer of the nucleotides of the nucleic acid-targeting guide participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and P A Carr and G M Church, 2009, Nature Biotechnology 27(12): 1151-62).

In certain embodiments, a guide RNA or crRNA may comprise, consist essentially of, or consist of a direct repeat (DR) sequence and a guide sequence or spacer sequence. In certain embodiments, the guide RNA or crRNA may comprise, consist essentially of, or consist of a direct repeat sequence fused or linked to a guide sequence or spacer sequence. In certain embodiments, the direct repeat sequence may be located upstream (i.e., 5') from the guide sequence or spacer sequence. In other embodiments, the direct repeat sequence may be located downstream (i.e., 3') from the guide sequence or spacer sequence.

In certain embodiments, the crRNA comprises a stem loop, preferably a single stem loop. In certain embodiments, the direct repeat sequence forms a stem loop, preferably a single stem loop.

In certain embodiments, the spacer length of the guide RNA is from 15 to 35 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27 to 30 nt, e.g., 27, 28, 29, or 30 nt, from 30 to 35 nt, e.g., 30, 31, 32, 33, 34, or 35 nt, or 35 nt or longer.

The "tracrRNA" sequence or analogous terms includes any polynucleotide sequence that has sufficient complementarity with a crRNA sequence to hybridize. In some embodiments, the degree of complementarity between the tracrRNA sequence and crRNA sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and crRNA sequence are contained within a single transcript, such that hybridization between the two produces a transcript having a secondary structure, such as a hairpin.

In general, degree of complementarity is with reference to the optimal alignment of the sca sequence and tracr sequence, along the length of the shorter of the two sequences. Optimal alignment may be determined by any suitable alignment algorithm and may further account for secondary structures, such as self-complementarity within either the sca sequence or tracr sequence. In some embodiments, the degree of complementarity between the tracr sequence and sca sequence along the length of the shorter of the two when optimally aligned is about or more than about 25%, 30%, 40%, 50%, 60%, 70%, 80%, 90%, 95%, 97.5%, 99%, or higher.

In some embodiments, the degree of complementarity between a guide sequence and its corresponding target sequence can be about or more than about 50%, 60%, 75%, 80%, 85%, 90%, 95%, 97.5%, 99%, or 100%; a guide or RNA or sgRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length; or guide or RNA or sgRNA can be less than about 75, 50, 45, 40, 35, 30, 25, 20, 15, 12, or fewer nucleotides in length; and tracr RNA can be 30 or 50 nucleotides in length. In some embodiments, the degree of complementarity between a guide sequence and its corresponding target sequence is greater than 94.5% or 95% or 95.5% or 96% or 96.5% or 97% or 97.5% or 98% or 98.5% or 99% or 99.5% or 99.9%, or 100%. Off target is less than 100% or 99.9% or 99.5% or 99% or 99% or 98.5% or 98% or 97.5% or 97% or 96.5% or 96% or 95.5% or 95% or 94.5% or 94% or 93% or 92% or 91% or 90% or 89% or 88% or 87% or 86% or 85% or 84% or 83% or 82% or 81% or 80% complementarity between the sequence and the guide, with it being advantageous that off target is 100% or 99.9% or 99.5% or 99% or 99% or 98.5% or 98% or 97.5% or 97% or 96.5% or 96% or 95.5% or 95% or 94.5% complementarity between the sequence and the guide.

In some embodiments according to the invention, the guide RNA (capable of guiding Cas to a target locus) may comprise (1) a guide sequence capable of hybridizing to a genomic target locus in the eukaryotic cell; (2) a tracr sequence; and (3) a tracr mate sequence. All (1) to (3) may reside in a single RNA, i.e., an sgRNA (arranged in a 5' to 3' orientation), or the tracr RNA may be a different RNA than the RNA containing the guide and tracr sequence. The tracr hybridizes to the tracr mate sequence and directs the CRISPR/Cas complex to the target sequence. Where the tracr RNA is on a different RNA than the RNA containing the guide and tracr sequence, the length of each RNA may be optimized to be shortened from their respective native lengths, and each may be independently chemically modified to protect from degradation by cellular RNase or otherwise increase stability.

Many modifications to guide sequences are known in the art and are further contemplated within the context of this invention. Various modifications may be used to increase the specificity of binding to the target sequence and/or increase the activity of the Cas protein and/or reduce off-target effects. Example guide sequence modifications are described in International Patent Application No. PCT US2019/045582, specifically paragraphs [0178]-[0333]. which is incorporated herein by reference.

Target Sequences, PAMs, and PFSs
Target Sequences

In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to an RNA polynucleotide being or comprising the target sequence. In other words, the target polynucleotide can be a polynucleotide or a part of a polynucleotide to which a part of the guide sequence is designed to have complementarity with and to which the effector function mediated by the complex comprising the CRISPR effector protein and a guide molecule is to be directed. In some embodiments, a target sequence is located in the nucleus or cytoplasm of a cell.

The guide sequence can specifically bind a target sequence in a target polynucleotide. The target polynucleotide may be DNA. The target polynucleotide may be RNA. The target polynucleotide can have one or more (e.g., 1, 2, 3, 4, 5, 6, 7, 8, 9, 10, etc. or more) target sequences. The target polynucleotide can be on a vector. The target polynucleotide can be genomic DNA. The target polynucleotide can be episomal. Other forms of the target polynucleotide are described elsewhere herein.

The target sequence may be DNA. The target sequence may be any RNA sequence. In some embodiments, the target sequence may be a sequence within an RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmatic RNA (scRNA). In some preferred embodiments, the target sequence (also referred to herein as a target polynucleotide) may be a sequence within an RNA molecule selected from the group consisting of mRNA, pre-mRNA, and rRNA. In some preferred embodiments, the target sequence may be a sequence within an RNA molecule selected from the group consisting of ncRNA, and lncRNA. In some more preferred embodiments, the target sequence may be a sequence within an mRNA molecule or a pre-mRNA molecule.

PAM and PFS Elements

PAM elements are sequences that can be recognized and bound by Cas proteins. Cas proteins/effector complexes can then unwind the dsDNA at a position adjacent to the PAM element. It will be appreciated that Cas proteins and systems that include them that target RNA do not require PAM sequences (Marraffini et al. 2010. Nature. 463:568-571). Instead, many rely on PFSs, which are discussed elsewhere herein. In certain embodiments, the target sequence should be associated with a PAM (protospacer adjacent motif) or PFS (protospacer flanking sequence or site), that is, a short sequence recognized by the CRISPR complex. Depending on the nature of the CRISPR-Cas protein, the target sequence should be selected, such that its complementary sequence in the DNA duplex (also referred to herein as the non-target sequence) is upstream or downstream of the PAM. In the embodiments, the complementary sequence of the target sequence is downstream or 3' of the PAM or upstream or 5' of the PAM. The precise sequence and length requirements for the PAM differ depending on the Cas protein used, but PAMs are typically 2-5 base pair sequences adjacent the protospacer (that is, the target sequence). Examples of the natural PAM sequences for different Cas proteins are provided herein below and the skilled person will be able to identify further PAM sequences for use with a given Cas protein.

The ability to recognize different PAM sequences depends on the Cas polypeptide(s) included in the system. See e.g., Gleditzsch et al. 2019. RNA Biology. 16(4):504-517. Table 1 (from Gleditzsch et al. 2019) below shows several Cas polypeptides and the PAM sequence they recognize.

TABLE 1

Example PAM Sequences

| Cas Protein | PAM Sequence |
| --- | --- |
| SpCas9 | NGG/NRG |
| SaCas9 | NGRRT (SEQ ID NO: 1) or NGRRN (SEQ ID NO: 2) |
| NmeCas9 | NNNNGATT (SEQ ID NO: 3) |
| CjCas9 | NNNNRYAC (SEQ ID NO: 4) |
| StCas9 | NNAGAAW (SEQ ID NO: 5) |
| Cas12a (Cpf1) (including LbCpf1 and AsCpf1) | TTTV (SEQ ID NO: 6) |
| Cas12b (C2c1) | TTT, TTA, and TTC |
| Cas12c (C2c3) | TA |
| Cas12d (CasY) | TA |
| Cas12e (CasX) | 5'-TTCN-3' (SEQ ID NO: 7) |

In a preferred embodiment, the CRISPR effector protein may recognize a 3' PAM. In certain embodiments, the CRISPR effector protein may recognize a 3' PAM which is 5'H, wherein H is A, C or U.

Further, engineering of the PAM Interacting (PI) domain on the Cas protein may allow programing of PAM specificity, improve target site recognition fidelity, and increase the versatility of the CRISPR-Cas protein, for example as described for Cas9 in Kleinstiver B P et al. Engineered CRISPR-Cas9 nucleases with altered PAM specificities. Nature. 2015 Jul. 23; 523(7561):481-5. doi: 10.1038/nature 14592. As further detailed herein, the skilled person will understand that Cas13 proteins may be modified analogously. Gao et al, "Engineered Cpf1 Enzymes with Altered PAM Specificities," bioRxiv 091611; doi: http://dx.doi.org/ 10.1101/091611 (Dec. 4, 2016). Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

PAM sequences can be identified in a polynucleotide using an appropriate design tool, which are commercially available as well as online. Such freely available tools include, but are not limited to, CRISPRFinder and CRISPRTarget. Mojica et al. 2009. Microbiol. 155(Pt. 3):733-740; Atschul et al. 1990. J. Mol. Biol. 215:403-410; Biswass et al. 2013 RNA Biol. 10:817-827; and Grissa et al. 2007. Nucleic Acid Res. 35:W52-57. Experimental approaches to PAM identification can include, but are not limited to, plasmid depletion assays (Jiang et al. 2013. Nat. Biotechnol. 31:233-239; Esvelt et al. 2013. Nat. Methods. 10:1116-1121; Kleinstiver et al. 2015. Nature. 523:481-485), screened by a high-throughput in vivo model called PAM-SCNAR (Pattanayak et al. 2013. Nat. Biotechnol. 31:839-843 and Leenay et al. 2016.Mol. Cell. 16:253), and negative screening (Zetsche et al. 2015. Cell. 163:759-771).

As previously mentioned, CRISPR-Cas systems that target RNA do not typically rely on PAM sequences. Instead such systems typically recognize protospacer flanking sites (PFSs) instead of PAMs Thus, Type VI CRISPR-Cas systems typically recognize protospacer flanking sites (PFSs) instead of PAMs. PFSs represents an analogue to PAMs for RNA targets. Type VI CRISPR-Cas systems employ a Cas13. Some Cas13 proteins analyzed to date, such as Cas13a (C2c2) identified from Leptotrichia shahii (LShCAs13a) have a specific discrimination against G at the 3'end of the target RNA. The presence of a C at the corresponding crRNA repeat site can indicate that nucleotide pairing at this position is rejected. However, some Cas13 proteins (e.g., LwaCAs13a and PspCas13b) do not seem to have a PFS preference. See e.g., Gleditzsch et al. 2019. RNA Biology. 16(4):504-517.

Some Type VI proteins, such as subtype B, have 5'-recognition of D (G, T, A) and a 3'-motif requirement of NAN or NNA. One example is the Cas13b protein identified in Bergeyella zoohelcum (BzCas13b). See e.g., Gleditzsch et al. 2019. RNA Biology. 16(4):504-517.

Overall Type VI CRISPR-Cas systems appear to have less restrictive rules for substrate (e.g., target sequence) recognition than those that target DNA (e.g., Type V and type II).

Zinc Finger Nucleases

In some embodiments, the polynucleotide is modified using a Zinc Finger nuclease or system thereof. One type of programmable DNA-binding domain is provided by artificial zinc-finger (ZF) technology, which involves arrays of ZF modules to target new DNA-binding sites in the genome. Each finger module in a ZF array targets three DNA bases. A customized array of individual zinc finger domains is assembled into a ZF protein (ZFP).

ZFPs can comprise a functional domain. The first synthetic zinc finger nucleases (ZFNs) were developed by fusing a ZF protein to the catalytic domain of the Type IIS restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to FokI cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms. Exemplary methods of genome editing using ZFNs can be found for example in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, all of which are specifically incorporated by reference.

TALE Nucleases

In some embodiments, a TALE nuclease or TALE nuclease system can be used to modify a polynucleotide. In some embodiments, the methods provided herein use isolated, non-naturally occurring, recombinant or engineered DNA-binding proteins that comprise TALE monomers or TALE monomers or half monomers as a part of their organizational structure that enable the targeting of nucleic acid sequences with improved efficiency and expanded specificity.

Naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", "TALE monomers" or "monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA-binding domain is $X_{1-11}(X_{12}X_{13})-X_{14-33}$ or $_{34}$ or $_{35}$, where the subscript indicates the amino acid position and X represents any amino acid. $X_{12}X_{13}$ indicate the RVDs. In some polypeptide monomers, the variable amino acid at position 13 is missing or absent and in such monomers, the RVD consists of a single amino acid. In such cases the RVD may be alternatively represented as X*, where X represents $X_{12}$ and (*) indicates that $X_{13}$ is absent. The DNA-binding domain comprises several repeats of TALE monomers and this may be represented as $(X_{1-11}(X_{12}X_{13})-X_{14-33}$ or $_{34}$ or $_{35})_z$, where in an advantageous embodiment, z is at least 5 to 40. In a further advantageous embodiment, z is at least 10 to 26.

The TALE monomers can have a nucleotide binding affinity that is determined by the identity of the amino acids in its RVD. For example, polypeptide monomers with an RVD of NI can preferentially bind to adenine (A), monomers with an RVD of NG can preferentially bind to thymine (T), monomers with an RVD of HD can preferentially bind to cytosine (C) and monomers with an RVD of NN can preferentially bind to both adenine (A) and guanine (G). In some embodiments, monomers with an RVD of IG can preferentially bind to T. Thus, the number and order of the polypeptide monomer repeats in the nucleic acid binding domain of a TALE determines its nucleic acid target specificity. In some embodiments, monomers with an RVD of NS can recognize all four base pairs and can bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011).

The polypeptides used in methods of the invention can be isolated, non-naturally occurring, recombinant or engineered nucleic acid-binding proteins that have nucleic acid or DNA-binding regions containing polypeptide monomer repeats that are designed to target specific nucleic acid sequences.

As described herein, polypeptide monomers having an RVD of HN or NH preferentially bind to guanine and thereby allow the generation of TALE polypeptides with high binding specificity for guanine containing target nucleic acid sequences. In some embodiments, polypeptide monomers having RVDs RN, NN, NK, SN, NH, KN, HN, NQ, HH, RG, KH, RH and SS can preferentially bind to guanine. In some embodiments, polypeptide monomers having RVDs RN, NK, NQ, HH, KH, RH, SS and SN preferentially bind to guanine and can thus allow the generation of TALE polypeptides with high binding specificity for guanine containing target nucleic acid sequences. In some embodiments, polypeptide monomers having RVDs HH, KH, NH, NK, NQ, RH, RN and SS can preferentially bind to guanine and thereby allow the generation of TALE polypeptides with high binding specificity for guanine containing target nucleic acid sequences. In some embodiments, the RVDs that have high binding specificity for guanine are RN, NH RH and KH. Furthermore, polypeptide monomers having an RVD of NV can preferentially bind to adenine and guanine. In some embodiments, monomers having RVDs of H*, HA, KA, N*, NA, NC, NS, RA, and S* bind to adenine, guanine, cytosine and thymine with comparable affinity.

The predetermined N-terminal to C-terminal order of the one or more polypeptide monomers of the nucleic acid or DNA-binding domain determines the corresponding predetermined target nucleic acid sequence to which the polypeptides of the invention will bind. As used herein the monomers and at least one or more half monomers are "specifically ordered to target" the genomic locus or gene of interest. In plant genomes, the natural TALE-binding sites always begin with a thymine (T), which may be specified by a cryptic signal within the non-repetitive N-terminus of the TALE polypeptide; in some cases, this region may be referred to as repeat 0. In animal genomes, TALE binding sites do not necessarily have to begin with a thymine (T) and polypeptides of the invention may target DNA sequences that begin with T, A, G or C. The tandem repeat of TALE monomers always ends with a half-length repeat or a stretch of sequence that may share identity with only the first 20 amino acids of a repetitive full-length TALE monomer and this half repeat may be referred to as a half-monomer. Therefore, it follows that the length of the nucleic acid or DNA being targeted is equal to the number of full monomers plus two.

As described in Zhang et al., Nature Biotechnology 29:149-153 (2011), TALE polypeptide binding efficiency may be increased by including amino acid sequences from the "capping regions" that are directly N-terminal or C-terminal of the DNA-binding region of naturally occurring TALEs into the engineered TALEs at positions N-terminal or C-terminal of the engineered TALE DNA-binding region. Thus, in certain embodiments, the TALE polypeptides described herein further comprise an N-terminal capping region and/or a C-terminal capping region.

An exemplary amino acid sequence of a N-terminal capping region is:

(SEQ ID NO: 88)
M D P I R S R T P S P A R E L L S G P Q

P D G V Q P T A D R G V S P P A G G P L

D G L P A R R T M S R T R L P S P P A P

S P A F S A D S F S D L L R Q F D P S L

F N T S L F D S L P P F G A H H T E A A

T G E W D E V Q S G L R A A D A P P P T

M R V A V T A A R P P R A K P A P R R R

A A Q P S D A S P A A Q V D L R T L G Y

S Q Q Q Q E K I K P K V R S T V A Q H H

E A L V G H G F T H A H I V A L S Q H P

A A L G T V A V K Y Q D M I A A L P E A

```
                    -continued
        T H E A I V G V G K Q W S G A R A L E A

L L T V A G E L R G P P L Q L D T G Q L

L K I A K R G G V T A V E A V H A W R N

A L T G A P L N
```

An exemplary amino acid sequence of a C-terminal capping region is:

```
                                        (SEQ ID NO: 99)
        R P A L E S I V A Q L S R P D P A L A A L

T N D H L V A L A C L G G R P A L D A V K

K G L P H A P A L I K R T N R R I P E R T

S H R V A D H A Q V V R V L G F F Q C H S

H P A Q A F D D A M T Q F G M S R H G L L

Q L F R R V G V T E L E A R S G T L P P A

S Q R W D R I L Q A S G M K R A K P S P T

S T Q T P D Q A S L H A F A D S L E R D L

D A P S P M H E G D Q T R A S
```

As used herein the predetermined "N-terminus" to "C terminus" orientation of the N-terminal capping region, the DNA-binding domain comprising the repeat TALE monomers and the C-terminal capping region provide structural basis for the organization of different domains in the d-TALEs or polypeptides of the invention.

The entire N-terminal and/or C-terminal capping regions are not necessary to enhance the binding activity of the DNA-binding region. Therefore, in certain embodiments, fragments of the N-terminal and/or C-terminal capping regions are included in the TALE polypeptides described herein.

In certain embodiments, the TALE polypeptides described herein contain a N-terminal capping region fragment that included at least 10, 20, 30, 40, 50, 54, 60, 70, 80, 87, 90, 94, 100, 102, 110, 117, 120, 130, 140, 147, 150, 160, 170, 180, 190, 200, 210, 220, 230, 240, 250, 260 or 270 amino acids of an N-terminal capping region. In certain embodiments, the N-terminal capping region fragment amino acids are of the C-terminus (the DNA-binding region proximal end) of an N-terminal capping region. As described in Zhang et al., Nature Biotechnology 29:149-153 (2011), N-terminal capping region fragments that include the C-terminal 240 amino acids enhance binding activity equal to the full length capping region, while fragments that include the C-terminal 147 amino acids retain greater than 80% of the efficacy of the full length capping region, and fragments that include the C-terminal 117 amino acids retain greater than 50% of the activity of the full-length capping region.

In some embodiments, the TALE polypeptides described herein contain a C-terminal capping region fragment that included at least 6, 10, 20, 30, 37, 40, 50, 60, 68, 70, 80, 90, 100, 110, 120, 127, 130, 140, 150, 155, 160, 170, 180 amino acids of a C-terminal capping region. In certain embodiments, the C-terminal capping region fragment amino acids are of the N-terminus (the DNA-binding region proximal end) of a C-terminal capping region. As described in Zhang et al., Nature Biotechnology 29:149-153 (2011), C-terminal capping region fragments that include the C-terminal 68 amino acids enhance binding activity equal to the full-length capping region, while fragments that include the C-terminal 20 amino acids retain greater than 50% of the efficacy of the full-length capping region.

In certain embodiments, the capping regions of the TALE polypeptides described herein do not need to have identical sequences to the capping region sequences provided herein. Thus, in some embodiments, the capping region of the TALE polypeptides described herein have sequences that are at least 50%, 60%, 70%, 80%, 85%, 90%, 91%, 92%, 93%, 94%, 95%, 96%, 97%, 98% or 99% identical or share identity to the capping region amino acid sequences provided herein. Sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the TALE polypeptides described herein have sequences that are at least 95% identical or share identity to the capping region amino acid sequences provided herein.

Sequence homologies can be generated by any of a number of computer programs known in the art, which include but are not limited to BLAST or FASTA. Suitable computer programs for carrying out alignments like the GCG Wisconsin Bestfit package may also be used. Once the software has produced an optimal alignment, it is possible to calculate % homology, preferably % sequence identity. The software typically does this as part of the sequence comparison and generates a numerical result.

In some embodiments described herein, the TALE polypeptides of the invention include a nucleic acid binding domain linked to the one or more effector domains. The terms "effector domain" or "regulatory and functional domain" refer to a polypeptide sequence that has an activity other than binding to the nucleic acid sequence recognized by the nucleic acid binding domain. By combining a nucleic acid binding domain with one or more effector domains, the polypeptides of the invention may be used to target the one or more functions or activities mediated by the effector domain to a particular target DNA sequence to which the nucleic acid binding domain specifically binds.

In some embodiments of the TALE polypeptides described herein, the activity mediated by the effector domain is a biological activity. For example, in some embodiments the effector domain is a transcriptional inhibitor (i.e., a repressor domain), such as an mSin interaction domain (SID). SID4X domain or a Kruppel-associated box (KRAB) or fragments of the KRAB domain. In some embodiments, the effector domain is an enhancer of transcription (i.e., an activation domain), such as the VP16, VP64 or p65 activation domain. In some embodiments, the nucleic acid binding is linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal.

In some embodiments, the effector domain is a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination of the activities described herein.

Meganucleases

In some embodiments, a meganuclease or system thereof can be used to modify a polynucleotide. Meganucleases, which are endodeoxyribonucleases characterized by a large recognition site (double-stranded DNA sequences of 12 to 40 base pairs). Exemplary methods for using meganucleases can be found in U.S. Pat. Nos. 8,163,514, 8,133,697, 8,021,867, 8,119,361, 8,119,381, 8,124,369, and 8,129,134, which are specifically incorporated herein by reference.

RNAi

In certain embodiments, the genetic modifying agent is RNAi (e.g., shRNA). As used herein, "gene silencing" or "gene silenced" in reference to an activity of an RNAi molecule, for example a siRNA or miRNA refers to a decrease in the mRNA level in a cell for a target gene by at least about 5%, about 10%, about 20%, about 30%, about 40%, about 50%, about 60%, about 70%, about 80%, about 90%, about 95%, about 99%, about 100% of the mRNA level found in the cell without the presence of the miRNA or RNA interference molecule. In one preferred embodiment, the mRNA levels are decreased by at least about 70%, about 80%, about 90%, about 95%, about 99%, about 100%.

As used herein, the term "RNAi" refers to any type of interfering RNA, including but not limited to, siRNAi, shRNAi, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein). The term "RNAi" can include both gene silencing RNAi molecules, and also RNAi effector molecules which activate the expression of a gene.

As used herein, a "siRNA" refers to a nucleic acid that forms a double stranded RNA, which double stranded RNA has the ability to reduce or inhibit expression of a gene or target gene when the siRNA is present or expressed in the same cell as the target gene. The double stranded RNA siRNA can be formed by the complementary strands. In one embodiment, a siRNA refers to a nucleic acid that can form a double stranded siRNA. The sequence of the siRNA can correspond to the full-length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The terms "microRNA" or "miRNA" are used interchangeably herein are endogenous RNAs, some of which are known to regulate the expression of protein-coding genes at the posttranscriptional level. Endogenous microRNAs are small RNAs naturally present in the genome that are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated herein by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and/or RNAi pathways.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 1 16:281-297), comprises a dsRNA molecule.

Sequences Related to Nucleus Targeting and Transportation

In some embodiments, one or more gene modifying agents or system components (e.g., the Cas protein and/or deaminase) can include one or more sequences related to nucleus targeting and transportation. Such sequence may facilitate the one or more components in the composition for targeting a sequence within a cell. In order to improve targeting of the CRISPR-Cas protein and/or the nucleotide deaminase protein or catalytic domain thereof used genetic modifying agent to the nucleus, it may be advantageous to provide one or both of these components with one or more nuclear localization sequences (NLSs).

In some embodiments, the NLSs used in the context of the present disclosure are heterologous to the proteins. Non-limiting examples of NLSs include an NLS sequence derived from: the NLS of the SV40 virus large T-antigen, having the amino acid sequence PKKKRKV (SEQ ID NO:10) or PKKKRKVEAS (SEQ ID NO:11); the NLS from nucleoplasmin (e.g., the nucleoplasmin bipartite NLS with the sequence KRPAATKKAGQAKKKK (SEQ ID NO: 12)); the c-myc NLS having the amino acid sequence PAAKRVKLD (SEQ ID NO:13) or RQRRNELKRSP (SEQ ID NO: 14); the hRNPA1 M9 NLS having the sequence NQSSNFGPMKGGNFGGRSSGPYGGGGQYFAK-PRNQGGY (SEQ ID NO:15); the sequence RMRIZFKNKGKDTAELRRRRVEVSVELRKAKKD-EQILKRRNV (SEQ ID NO: 16) of the IBB domain from importin-alpha; the sequences VSRKRPRP (SEQ ID NO:17) and PPKKARED (SEQ ID NO:18) of the myoma T protein; the sequence PQPKKKPL (SEQ ID NO:19) of human p53; the sequence SALIKKKKKMAP (SEQ ID NO:20) of mouse c-abl IV; the sequences DRLRR (SEQ ID NO:21) and PKQKKRK (SEQ ID NO:22) of the influenza virus NS1; the sequence RKLKKKIKKL (SEQ ID NO:23) of the Hepatitis virus delta antigen; the sequence REKKKFLKRR (SEQ ID NO:24) of the mouse Mx1 protein; the sequence KRKGDEVDGVDEVAKKKSKK (SEQ ID NO:25) of the human poly(ADP-ribose) polymerase; and the sequence RKCLQAGMNLEARKTKK (SEQ ID NO:26) of the steroid hormone receptors (human) glucocorticoid. In general, the one or more NLSs are of sufficient strength to drive accumulation of the DNA-targeting Cas protein (or other genetic modifying agent) in a detectable amount in the nucleus of a eukaryotic cell. In general, strength of nuclear localization activity may derive from the number of NLSs in the genetic modifying agent, the particular NLS(s) used, or a combination of these factors. Detection of accumulation in the nucleus may be performed by any suitable technique. For example, a detectable marker may be fused to the nucleic acid-targeting protein, such that location within a cell may be visualized, such as in combination with a means for detecting the location of the nucleus (e.g., a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of nucleic acid-targeting complex formation (e.g., assay for deaminase activity) at the target sequence, or assay for altered gene expression activity affected by DNA-targeting complex formation and/or DNA-targeting), as compared to a control not exposed to the CRISPR-Cas protein and deaminase protein, or exposed to a CRISPR-Cas and/or deaminase protein lacking the one or more NLSs.

The genetic modifying agent can include 1 or more, such as 2, 3, 4, 5, 6, 7, 8, 9, 10, or more heterologous NLSs. In some embodiments, the genetic modifying agent comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g., zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. In preferred embodiments of the genetic modifying agent, an NLS is attached to the C-terminal of a protein component of the genetic modifying agent.

In certain embodiments, the CRISPR-Cas protein and another component of the system (e.g. a deaminase) are delivered to the cell or expressed within the cell as separate proteins. In these embodiments, each of the CRISPR-Cas and additional protein can include one or more NLSs as described herein. Where the nucleotide deaminase is fused to an adaptor protein (such as MS2) as described above, the one or more NLS can be provided on the adaptor protein, provided that this does not interfere with aptamer binding. In particular embodiments, the one or more NLS sequences may also function as linker sequences between the nucleotide deaminase or other additional protein or domain and the CRISPR-Cas protein.

In some embodiments, a component (e.g., the dead Cas protein, the nucleotide deaminase protein or catalytic domain thereof, or a combination thereof) in the systems may comprise one or more nuclear export signals (NES), one or more nuclear localization signals (NLS), or any combinations thereof. In some cases, the NES may be an HIV Rev NES. In certain cases, the NES may be MAPK NES. When the component is a protein, the NES or NLS may be at the C terminus of the component. Alternatively or additionally, the NES or NLS may be at the N-terminus of the component. In some examples, the Cas protein and optionally said nucleotide deaminase protein or catalytic domain thereof comprise one or more heterologous nuclear export signal(s) (NES(s)) or nuclear localization signal(s) (NLS(s)), preferably an HIV Rev NES or MAPK NES, preferably C-terminal.

Templates

In some embodiments, the genetic modifying agent or system thereof includes a template, e.g., a recombination template. A template may be a component of another vector as described herein, contained in a separate vector, or provided as a separate polynucleotide. In some embodiments, a recombination template is designed to serve as a template in homologous recombination, such as within or near a target sequence nicked or cleaved by a nucleic acid-targeting effector protein as a part of a nucleic acid-targeting complex.

In an embodiment, the template nucleic acid alters the sequence of the target position. In an embodiment, the template nucleic acid results in the incorporation of a modified, or non-naturally occurring base into the target nucleic acid.

The template sequence may undergo a breakage mediated or catalyzed recombination with the target sequence. In an embodiment, the template nucleic acid may include sequence that corresponds to a site on the target sequence that is cleaved by a Cas protein mediated cleavage event. In an embodiment, the template nucleic acid may include a sequence that corresponds to both, a first site on the target sequence that is cleaved in a first Cas protein mediated event, and a second site on the target sequence that is cleaved in a second Cas protein mediated event.

In certain embodiments, the template nucleic acid can include a sequence which results in an alteration in the coding sequence of a translated sequence, e.g., one which results in the substitution of one amino acid for another in a protein product, e.g., transforming a mutant allele into a wild type allele, transforming a wild type allele into a mutant allele, and/or introducing a stop codon, insertion of an amino acid residue, deletion of an amino acid residue, or a nonsense mutation. In certain embodiments, the template nucleic acid can include a sequence which results in an alteration in a non-coding sequence, e.g., an alteration in an exon or in a 5' or 3' non-translated or non-transcribed region. Such alterations include an alteration in a control element, e.g., a promoter, enhancer, and an alteration in a cis-acting or trans-acting control element.

A template nucleic acid having homology with a target position in a target gene may be used to alter the structure of a target sequence. The template sequence may be used to alter an unwanted structure, e.g., an unwanted or mutant nucleotide. The template nucleic acid may include a sequence which, when integrated, results in decreasing the activity of a positive control element; increasing the activity of a positive control element; decreasing the activity of a negative control element; increasing the activity of a negative control element; decreasing the expression of a gene; increasing the expression of a gene; increasing resistance to a disorder or disease; increasing resistance to viral entry; correcting a mutation or altering an unwanted amino acid residue conferring, increasing, abolishing or decreasing a biological property of a gene product, e.g., increasing the enzymatic activity of an enzyme, or increasing the ability of a gene product to interact with another molecule.

The template nucleic acid may include a sequence which results in a change in sequence of 1, 2, 3, 4, 5, 6, 7, 8, 9, 10, 11, 12 or more nucleotides of the target sequence.

A template polynucleotide may be of any suitable length, such as about or more than about 10, 15, 20, 25, 50, 75, 100, 150, 200, 500, 1000, or more nucleotides in length. In an embodiment, the template nucleic acid may be 20+/−10, 30+/−10, 40+/−10, 50+/−10, 60+/−10, 70+/−10, 80+/−10, 90+/−10, 100+/−10, 110+/−10, 120+/−10, 130+/−10, 140+/−10, 150+/−10, 160+/−10, 170+/−10, 180+/−10, 190+/−10, 200+/−10, 210+/−10, of 220+/−10 nucleotides in length. In an embodiment, the template nucleic acid may be 30+/−20, 40+/−20, 50+/−20, 60+/−20, 70+/−20, 80+/−20, 90+/−20, 100+/−20, 110+/−20, 120+/−20, 130+/−20, 140+/−20, 150+/−20, 160+/−20, 170+/−20, 180+/−20, 190+/−20, 200+/−20, 210+/−20, of 220+/−20 nucleotides in length. In an embodiment, the template nucleic acid is 10 to 1,000, 20 to 900, 30 to 800, 40 to 700, 50 to 600, 50 to 500, 50 to 400, 50 to 300, 50 to 200, or 50 to 100 nucleotides in length.

In some embodiments, the template polynucleotide is complementary to a portion of a polynucleotide comprising the target sequence. When optimally aligned, a template polynucleotide might overlap with one or more nucleotides of a target sequences (e.g. about or more than about 1, 5, 10, 15, 20, 25, 30, 35, 40, 45, 50, 60, 70, 80, 90, 100 or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence.

The exogenous polynucleotide template comprises a sequence to be integrated (e.g., a mutated gene). The sequence for integration may be a sequence endogenous or exogenous to the cell. Examples of a sequence to be integrated include polynucleotides encoding a protein or a non-coding RNA (e.g., a microRNA). Thus, the sequence for integration may be operably linked to an appropriate control sequence or sequences. Alternatively, the sequence to be integrated may provide a regulatory function.

An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000.

An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000.

In certain embodiments, one or both homology arms may be shortened to avoid including certain sequence repeat elements. For example, a 5' homology arm may be shortened to avoid a sequence repeat element. In other embodiments, a 3' homology arm may be shortened to avoid a sequence repeat element. In some embodiments, both the 5' and the 3' homology arms may be shortened to avoid including certain sequence repeat elements.

In some methods, the exogenous polynucleotide template may further comprise a marker. Such a marker may make it easy to screen for targeted integrations. Examples of suitable markers include restriction sites, fluorescent proteins, or selectable markers. The exogenous polynucleotide template of the disclosure can be constructed using recombinant techniques (see, for example, Sambrook et al., 2001 and Ausubel et al., 1996).

In certain embodiments, a template nucleic acid for correcting a mutation may designed for use as a single-stranded oligonucleotide. When using a single-stranded oligonucleotide, 5' and 3' homology arms may range up to about 200 base pairs (bp) in length, e.g., at least 25, 50, 75, 100, 125, 150, 175, or 200 bp in length.

Suzuki et al. describe in vivo genome editing via CRISPR/Cas9 mediated homology-independent targeted integration (2016, Nature 540:144-149).

Modified Cells for Adoptive Cell Therapies

Described herein are cells, such as cells obtained from or within a subject in need of treatment, that are modified using a genetic modifying agent described herein. In some embodiments, the cells can be modified such that one or more components of a pre-BCR and/or p38MAPK pathway are inhibited, deleted, or otherwise rendered non-functional. Other modified cells such as modified T cells, such as for CAR T-cell therapy are described in greater detail elsewhere herein. Methods of genetically modifying cells using the genetic modifying agents described herein are generally known in the art and generally include delivery of a genetic modifying agent to a cell to be modified using a suitable method, selecting modified cells, and optionally culturing and expanding said cells prior to using them in, for example, an adoptive cell therapy. Modification can occur in vivo (i.e. by direct delivery of a gene modifying agent to a cell or cells within a subject), ex vivo, or in vitro.

Delivery

The present disclosure also provides delivery systems for introducing components of the systems and compositions herein to cells, tissues, organs, or organisms. A delivery system may comprise one or more delivery vehicles and/or cargos. Exemplary delivery systems and methods include those described in paragraphs [00117] to [00278] of Feng Zhang et al., (WO2016106236A1), and pages 1241-1251 and Table 1 of Lino C A et al., Delivering CRISPR: a review of the challenges and approaches, DRUG DELIVERY, 2018, VOL. 25, NO. 1, 1234-1257, which are incorporated by reference herein in their entireties.

Physical Delivery

In some embodiments, the cargos may be introduced to cells by physical delivery methods. Examples of physical methods include microinjection, electroporation, and hydrodynamic delivery. Both nucleic acid and proteins may be delivered using such methods. For example, Cas protein may be prepared in vitro, isolated, (refolded, purified if needed), and introduced to cells. Suitable physical delivery methods include, but are not limited to, microinjection, electroporation, hydrodynamic delivery, transfection, transduction, biolistics, and implantable devices.

Vehicle Delivery

In some embodiments, delivery of the genetic modifying agent or component thereof can include delivery medicated by a vehicle. The delivery vehicles may deliver the cargo (e.g. a genetic modifying agent or component thereof) into cells, tissues, organs, or organisms (e.g., animals or plants). The cargos may be packaged, carried, or otherwise associated with the delivery vehicles. The delivery vehicles may be selected based on the types of cargo to be delivered, and/or the delivery is in vitro and/or in vivo. Examples of delivery vehicles include vectors, viruses (e.g. virus particles), non-viral vehicles, and other delivery reagents described herein. Suitable delivery vehicles include, but are not limited to, particles (e.g. nanoparticles), vectors and vector systems (such as viral and non-viral vectors), and non-vector delivery vehicles (e.g. lipid particles, lipoplexes, polyplexes, sugar-based particles, cell penetrating peptides, DNA nanoclews, metal nanoparticles, iTOP, polymer-based particles, streptolysin O (SLO), multifunctional envelope-type nanodevices (MEND), lipid-coated mesoporous silica particles, inorganic nanoparticles, exosomes, spherical nucleic acids, self-assembling nanoparticles, and super-charged proteins.

Delivery can be targeted. In some embodiments, the delivery vehicle can allow for targeted delivery to a specific cell, tissue, organ, or system. In such embodiments, the delivery vehicle can include one or more targeting moieties that can direct targeted delivery of the cargo(s). In an embodiment, the delivery vehicle comprises a targeting moiety, such as active targeting of a lipid entity of the invention, e.g., lipid particle or nanoparticle or liposome or lipid bilayer of the invention comprising a targeting moiety for active targeting. Targeting moieties for a variety of cell types are generally known. Exemplary hemopoietic cell targeting moieties include CD-19 (B-cell marker) and CD-20 (B-cells).

Delivery can be responsive. In some embodiments, the delivery vehicle can allow for responsive delivery of the cargo(s). Responsive delivery, as used in this context herein, refers to delivery of cargo(s) by the delivery vehicle in response to an external stimuli. Examples of suitable stimuli include, without limitation, an energy (light, heat, cold, and the like), a chemical stimuli (e.g. chemical composition, etc.), and a biologic or physiologic stimuli (e.g. environmental pH, osmolarity, salinity, biologic molecule, etc.). In some embodiments, the targeting moiety can be responsive to an external stimuli and facilitate responsive delivery. In other embodiments, responsiveness is determined by a non-targeting moiety component of the delivery vehicle.

Pharmaceutical Formulations

Also described herein are pharmaceutical formulations that can contain an amount, effective amount, and/or least effective amount, and/or therapeutically effective amount of one or more compounds, molecules, compositions, vectors, vector systems, cells, or a combination thereof (which are also referred to as the primary active agent or ingredient elsewhere herein) described in greater detail elsewhere herein a pharmaceutically acceptable carrier or excipient.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo. As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient. When present, the compound can optionally be present in the pharmaceutical formulation as a pharmaceutically acceptable salt.

In some embodiments, the pharmaceutical formulation can include, such as an active ingredient, one or more BCR-ABL tyrosine kinase inhibitors or a pharmaceutical formulation thereof; one or more pre-BCR signaling pathway inhibitors or a pharmaceutical formulation thereof; one or more p38 MAPK inhibitors or a pharmaceutical formulation thereof; or any combination thereof. In some embodiments, the one or more BCR-ABL tyrosine kinase inhibitors is or includes imatinib, dasatinib, nilotinib, bosutinib, ponatinib, bafetinib, rebastinib, tozasertib, danusertib, HG-7-85-01, GNF-2, GNF-5, Compound 2, asciminib, or a combination thereof. In some embodiments, the one or more pre-BCR signaling inhibitors is or includes fostamatinib, ibrutinib, duvelisib, idelalisib, dasatinib, entospletinib, cerdulatinib, TAK-659, RG7666, apitolisib, LY3023414, gedatolisib, bimiralisib, SF-1126, copanlisib, buparlisib, tenalisib, taselisib, KA2237, alpelisib, parsaclisib, umbralisib, fimepinostat, rigosertib, dactolisib, BGT-226, DS-7423, PF-04691502, PKI-179, pictilisib, PX-866, TG100-115, AZD8835, WX-037, a genetic modifying agent capable of inhibiting or deleting one or more components of the pre-BCR signaling pathway, or a combination thereof. In some embodiments, the one or more p38 MAPK inhibitors comprise losmapimod, talmapimod, SB203580, VX-702, VX-745, pamapimod, dilmapimod, doramapimod, BMS-582949, ARRY-797, PH797804, SCIO-469, SD-0006, AMG-548, ralimetinib (LY2228820), SB239063, Skepinone-L, SB202190, TAK715, a genetic modifying agent capable of inhibiting or deleting one or more components of the p38 signaling pathway, or a combination thereof.

In some embodiments, the pharmaceutical formulation includes, such as an active ingredient, one or more modified cells, where the modified cells have a modified pre-BCR and/or p38 MAPK pathway or a component thereof. The modification can be such that the pre-BCR and/or p38 MAPK pathway or a component thereof is inhibited, deleted, or otherwise rendered non-functional. Such cells are described in greater detail elsewhere herein.

In some embodiments, the pharmaceutical formulation includes, such as an active ingredient, an anti-CD20 molecule, such as anti-CD20 antibody or fragment thereof. In some embodiments, the anti-CD20 antibody is or is composed of rituximab, ofatumumab, obinutuzumab, ibritunonab tiuxetan, ocrelizumab, tositumomab, or a combination thereof.

In some embodiments, the pharmaceutical formulation includes, such as an active ingredient, a gene modifying agent capable of modifying a pre-BCR and/or p38 MAPK pathway or component thereof in a cell such that the pre-BCR and/or p38 MAPK pathway or component thereof is inhibited, degraded, deleted, or otherwise rendered non-functional. Exemplary genetic modifying agents are described in greater detail elsewhere herein.

In some embodiments, the active ingredient is present as a pharmaceutically acceptable salt of the active ingredient. As used herein, "pharmaceutically acceptable salt" refers to any acid or base addition salt whose counter-ions are non-toxic to the subject to which they are administered in pharmaceutical doses of the salts. Suitable salts include, hydrobromide, iodide, nitrate, bisulfate, phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, camphorsulfonate, napthalenesulfonate, propionate, malonate, mandelate, malate, phthalate, and pamoate.

The pharmaceutical formulations described herein can be administered to a subject in need thereof via any suitable method or route to a subject in need thereof. Suitable administration routes can include, but are not limited to auricular (otic), buccal, conjunctival, cutaneous, dental, electro-osmosis, endocervical, endosinusial, endotracheal, enteral, epidural, extra-amniotic, extracorporeal, hemodialysis, infiltration, interstitial, intra-abdominal, intra-amniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronal (dental), intracoronary, intracorporus cavernosum, intradermal, intradiscal, intraductal, intraduodenal, intradural, intraepidermal, intraesophageal, intragastric, intragingival, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intravenous bolus, intravenous drip, intraventricular, intravesical, intravitreal, iontophoresis, irrigation, laryngeal, nasal, nasogastric, occlusive dressing technique, ophthalmic, oral, oropharyngeal, other, parenteral, percutaneous, periarticular, peridural, perineural, periodontal, rectal, respiratory (inhalation), retrobulbar, soft tissue, subarachnoid, subconjunctival, subcutaneous, sublingual, submucosal, topical, transdermal, transmucosal, transplacental, transtracheal, transtympanic, ureteral, urethral, and/or vaginal administration, and/or any combination of the above administration routes, which typically depends on the disease to be treated and/or the active ingredient(s).

Where appropriate, compounds, molecules, compositions, vectors, vector systems, cells, or a combination thereof described in greater detail elsewhere herein can be provided to a subject in need thereof as an ingredient, such as an active ingredient or agent, in a pharmaceutical formulation. As such, also described are pharmaceutical formulations containing one or more of the compounds and salts thereof, or pharmaceutically acceptable salts thereof described herein. Suitable salts include, hydrobromide, iodide, nitrate, bisulfate, phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, napthalenesulfonate, propionate, malonate, mandelate, malate, phthalate, and pamoate.

In some embodiments, the subject in need thereof has or is suspected of having a hematopoietic disease, such as a hematopoietic malignancy or relapse, or a symptom thereof. In some embodiments, the subject is identified, such as by using a method described in greater detail elsewhere herein, as having a high risk of a hematopoietic malignancy relapse. In some embodiments, the subject in need thereof is in the acute response phase of a treatment for a hematopoietic malignancy. In some embodiments, the subject in need thereof is in the MRD phase of a hematopoietic malignancy. The hematopoietic malignancy can be a lymphoid or myeloid malignancy. The hematopoietic malignancies may be any of lymphoid malignancies comprising B-cell ALL, T-cell ALL, chronic lymphoblastic leukemia (CLL), diffuse large B-cell lymphoma, follicular lymphoma, Burkitt's lymphoma, mantle cell lymphoma, marginal zone lymphoma, T-cell lymphoma, multiple myeloma, Hodgkin's lymphoma, and any other types of malignancies derived from lymphoid lineage. In some embodiments, the methods disclosed herein for predicting the risk of relapse can be used for any of the subtypes of the aforementioned lymphoid malignancies. In some embodiments, the hematopoietic malignancies can be any of myeloid malignancies comprising chronic myeloid leukemia (CML), acute myeloid leukemia (AML), myelodysplastic syndromes (MD), myeloproliferative diseases (MPD), chronic neutrophilic leukemia, chronic eosinophilic leukemia, polycythemia vera, chronic idiopathic myelofibrosis, essential thrombocythemia, chronic myeloproliferative disease (unclassifiable), refractory anemia, refractory cytopenia with multilineage dysplasia (RCMD), mastocytosis, and any other types of malignancies derived from myeloid lineage. In some embodiments, the methods disclosed herein for predicting the risk of relapse can be used for any of the subtypes of the aforementioned myeloid malignancies. In certain example embodiments, the hematopoietic malignancy is an acute lymphoblastic leukemia (ALL). In certain example embodiments, the ALL is a B-cell ALL.

As used herein, "agent" refers to any substance, compound, molecule, and the like, which can be biologically active or otherwise can induce a biological and/or physiological effect on a subject to which it is administered to. As used herein, "active agent" or "active ingredient" refers to a substance, compound, or molecule, which is biologically active or otherwise, induces a biological or physiological effect on a subject to which it is administered to. In other words, "active agent" or "active ingredient" refers to a component or components of a composition to which the whole or part of the effect of the composition is attributed. An agent can be a primary active agent, or in other words, the component(s) of a composition to which the whole or part of the effect of the composition is attributed. An agent can be a secondary agent, or in other words, the component(s) of a composition to which an additional part and/or other effect of the composition is attributed.

Pharmaceutically Acceptable Carriers and Secondary Ingredients and Agents

The pharmaceutical formulation can include a pharmaceutically acceptable carrier. Suitable pharmaceutically acceptable carriers include, but are not limited to water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, and polyvinyl pyrrolidone, which do not deleteriously react with the active composition.

The pharmaceutical formulations can be sterilized, and if desired, mixed with agents, such as lubricants, preservatives, stabilizers, wetting agents, emulsifiers, salts for influencing osmotic pressure, buffers, coloring, flavoring and/or aromatic substances, and the like which do not deleteriously react with the active compound.

In some embodiments, the pharmaceutical formulation can also include an effective amount of secondary active agents, including but not limited to, biologic agents or molecules including, but not limited to, e.g. polynucleotides, amino acids, peptides, polypeptides, antibodies, aptamers, ribozymes, hormones, immunomodulators, antipyretics, anxiolytics, antipsychotics, analgesics, antispasmodics, anti-inflammatories, anti-histamines, anti-infectives, chemotherapeutics, and combinations thereof. In some embodiments, the secondary active agent is an anti-cancer or chemotherapeutic. In some embodiments, the secondary active agent is an anti-CD20 molecule. In some embodiments, the anti-CD20 molecule is an anti-CD20 antibody or fragment thereof. In some embodiments, the anti-CD20 antibody is or is composed of rituximab, ofatumumab, obinutuzumab, ibritumomab tiuxetan, ocrelizumab, tositumomab, or a combination thereof.

Effective Amounts

In some embodiments, the amount of the primary active agent and/or optional secondary agent can be an effective amount, least effective amount, and/or therapeutically effective amount. As used herein, "effective amount" refers to the amount of the primary and/or optional secondary agent included in the pharmaceutical formulation that achieve one or more therapeutic effects or desired effect. As used herein, "least effective" amount refers to the lowest amount of the primary and/or optional secondary agent that achieves the one or more therapeutic or other desired effects. As used herein, "therapeutically effective amount" refers to the amount of the primary and/or optional secondary agent included in the pharmaceutical formulation that achieves one or more therapeutic effects. In some embodiments, the one or more therapeutic effects are inhibiting or otherwise rendering a pre-BCR and/or p38MAPK pathway or a component thereof non-functional.

The effective amount, least effective amount, and/or therapeutically effective amount of the primary and optional secondary active agent described elsewhere herein contained in the pharmaceutical formulation can range from about 0 to 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 pg, ng, g, mg, or g or be any numerical value with any of these ranges.

In some embodiments, the effective amount, least effective amount, and/or therapeutically effective amount can be an effective concentration, least effective concentration, and/or therapeutically effective concentration, which can each range from about 0 to 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 pM, nM, M, mM, or M or be any numerical value with any of these ranges.

In other embodiments, the effective amount, least effective amount, and/or therapeutically effective amount of the primary and optional secondary active agent can range from about 0 to 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 IU or be any numerical value with any of these ranges.

In some embodiments, the primary and/or the optional secondary active agent present in the pharmaceutical formulation can range from about 0 to 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.9, to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9% w/w, v/v, or w/v of the pharmaceutical formulation.

In some embodiments where a cell population is present in the pharmaceutical formulation (e.g., as a primary and/or or secondary active agent), the effective amount of cells can range from about 2 cells to $1\times10^1$/mL, $1\times10^{20}$/mL or more, such as about $1\times10^1$/mL, $1\times10^2$/mL, $1\times10^3$/mL, $1\times10^4$/mL, $1\times10^5$/mL, $1\times10^6$/mL, $1\times10^7$/mL, $1\times10^8$/mL, $1\times10^9$/mL, $1\times10^{10}$/mL, $1\times10^{11}$/mL, $1\times10^{12}$/mL, $1\times10^{13}$/mL, $1\times10^{14}$/mL, $1\times10^{15}$/mL, $1\times10^{16}$/mL, $1\times10^{17}$/mL, $1\times10^{18}$/mL, $1\times10^{19}$/mL, to/or about $1\times10^{20}$/mL.

In some embodiments, the amount or effective amount, particularly where an infective particle is being delivered (e.g. a virus particle having the primary or secondary agent as a cargo), the effective amount of virus particles can be expressed as a titer (plaque forming units per unit of volume) or as a MOI (multiplicity of infection). In some embodiments, the effective amount can be $1\times10^1$ particles per pL, nL, μL, mL, or L to $1\times10^{20}$/particles per pL, nL, μL, mL, or L or more, such as about $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, $1\times10^{16}$, $1\times10^{17}$, $1\times10^{18}$, $1\times10^{19}$, to/or about $1\times10^{20}$ particles per pL, nL, μL, mL, or L. In some embodiments, the effective titer can be about $1\times10^1$ transforming units per pL, nL, μL, mL, or L to $1\times10^{20}$/transforming units per pL, nL, μL, mL, or L or more, such as about $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, $1\times10^{16}$, $1\times10^{17}$, $1\times10^{18}$, $1\times10^{19}$, to/or about $1\times10^{20}$ transforming units per pL, nL, μL, mL, or L. In some embodiments, the MOI of the pharmaceutical formulation can range from about 0.1 to 10 or more, such as 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10 or more.

In some embodiments, the amount or effective amount of the one or more of the active agent(s) described herein contained in the pharmaceutical formulation can range from about 1 pg/kg to about 10 mg/kg based upon the bodyweight of the subject in need thereof or average bodyweight of the specific patient population to which the pharmaceutical formulation can be administered.

In embodiments where there is a secondary agent contained in the pharmaceutical formulation, the effective amount of the secondary active agent will vary depending on the secondary agent, the primary agent, the administration route, subject age, disease, stage of disease, among other things, which will be one of ordinary skill in the art.

When optionally present in the pharmaceutical formulation, the secondary active agent can be included in the pharmaceutical formulation or can exist as a stand-alone compound or pharmaceutical formulation that can be administered contemporaneously or sequentially with the compound, derivative thereof, or pharmaceutical formulation thereof.

In some embodiments, the effective amount of the secondary active agent can range from about 0 to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9% w/w, v/v, or w/v of the total secondary active agent in the pharmaceutical formulation. In additional embodiments, the effective amount of the secondary active agent can range from about 0 to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9% w/w, v/v, or w/v of the total pharmaceutical formulation.

In some embodiments, ponatinib is used at a therapeutic effective dosage based on the approval information by the FDA. In these embodiments, the therapeutically effective amount of ponatinib is 45 mg. In some of these embodiments, the therapeutically effective amount of ponatinib is administered orally. In some of these embodiments, the therapeutically effective amount of ponatinib is administered once daily. Treatment can be continued in some embodiments, as long as the patient does not show evidence of disease progression or unacceptable toxicity. In some embodiments, fostamatinib can be used at dosage and administration route as approved by the FDA. In some embodiments, a starting amount of fostamatinib is 100 mg administered orally twice daily with or without food. In some embodiments, after 4 weeks at the starting amount, the amount of fostamatinib is increased to 150 mg twice daily, if needed, to achieve platelet count at least $50 \times 10^9$/L as necessary to reduce the risk of bleeding. In some embodiments, ibrutinib can be used at dosage and administration route as approved by the FDA. In some embodiments, the therapeutically effective amount of ibrutinib is 560 mg administered orally once daily or is 420 mg administered orally once daily. In some embodiments, the dosage is administered orally with a glass of water. In some embodiments, the dosage should not be opened, broken, chewed, crushed, or cut. In some embodiments, the therapeutically effective amount, dosage form, and administration route of duvelisib is as approved by the FDA. In some embodiments, the therapeutically effective amount of duvelisib is 25 mg administered orally, twice daily. Dosage can be modified based on toxicity. In some embodiments, p38 MAPK inhibitors can be used based on the dosages and administration route being reported as effective treatment in various clinical trial results.

In some embodiments, a therapeutically effective amount of ponatinib is combined with a therapeutically effective amount of one or more pre-BCR inhibitors and one or more a therapeutically effective amount of p38 MAPK inhibitors. In some embodiments, a therapeutically effective amount of ponatinib is combined with a therapeutically effective amount of one or more pre-BCR inhibitors. In some embodiments, a therapeutically effective amount of ponatinib is combined with a therapeutically effective amount of one or more p38 MAPK inhibitors. In some embodiments, the agents are administered concurrently to a patient. In some embodiments, the agents are administered separately or sequentially to a patient.

Dosage Forms

In some embodiments, the pharmaceutical formulations described herein can be provided in a dosage form. The dosage form can be administered to a subject in need thereof. The dosage form can be effective generate specific concentration, such as an effective concentration, at a given site in the subject in need thereof. As used herein, "dose," "unit dose," or "dosage" can refer to physically discrete units suitable for use in a subject, each unit containing a predetermined quantity of the primary active agent, and optionally present secondary active ingredient, and/or a pharmaceutical formulation thereof calculated to produce the desired response or responses in association with its administration. In some embodiments, the given site is proximal to the administration site. In some embodiments, the given site is distal to the administration site. In some cases, the dosage form contains a greater amount of one or more of the active ingredients present in the pharmaceutical formulation than the final intended amount needed to reach a specific region or location within the subject to account for loss of the active components such as via first and second pass metabolism.

The dosage forms can be adapted for administration by any appropriate route. Appropriate routes include, but are not limited to, oral (including buccal or sublingual), rectal, intraocular, inhaled, intranasal, topical (including buccal, sublingual, or transdermal), vaginal, parenteral, subcutaneous, intramuscular, intravenous, internasal, and intradermal. Other appropriate routes are described elsewhere herein. Such formulations can be prepared by any method known in the art.

Dosage forms adapted for oral administration can discrete dosage units such as capsules, pellets or tablets, powders or granules, solutions, or suspensions in aqueous or non-aqueous liquids; edible foams or whips, or in oil-in-water liquid emulsions or water-in-oil liquid emulsions. In some embodiments, the pharmaceutical formulations adapted for oral administration also include one or more agents which flavor, preserve, color, or help disperse the pharmaceutical formulation. Dosage forms prepared for oral administration can also be in the form of a liquid solution that can be delivered as a foam, spray, or liquid solution. The oral dosage form can be administered to a subject in need thereof. Where appropriate, the dosage forms described herein can be microencapsulated.

The dosage form can also be prepared to prolong or sustain the release of any ingredient. In some embodiments, compounds, molecules, compositions, vectors, vector systems, cells, or a combination thereof described herein can be the ingredient whose release is delayed. In some embodiments the primary active agent is the ingredient whose release is delayed. In some embodiments, an optional secondary agent can be the ingredient whose release is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, M D, 2000, and "Pharmaceutical dosage forms and drug delivery systems", 6th Edition, Ansel et al., (Media, PA: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Weiterstadt, Germany), zein, shellac, and polysaccharides.

Coatings may be formed with a different ratio of water-soluble polymer, water insoluble polymers, and/or pH dependent polymers, with or without water insoluble/water soluble non-polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Where appropriate, the dosage forms described herein can be a liposome. In these embodiments, primary active ingredient(s), and/or optional secondary active ingredient(s), and/or pharmaceutically acceptable salt thereof where appropriate are incorporated into a liposome. In embodiments where the dosage form is a liposome, the pharmaceutical formulation is thus a liposomal formulation. The liposomal formulation can be administered to a subject in need thereof.

Dosage forms adapted for topical administration can be formulated as ointments, creams, suspensions, lotions, powders, solutions, pastes, gels, sprays, aerosols, or oils. In some embodiments for treatments of the eye or other external tissues, for example the mouth or the skin, the pharmaceutical formulations are applied as a topical ointment or cream. When formulated in an ointment, a primary active ingredient, optional secondary active ingredient, and/or pharmaceutically acceptable salt thereof where appropriate can be formulated with a paraffinic or water-miscible ointment base. In other embodiments, the primary and/or secondary active ingredient can be formulated in a cream with an oil-in-water cream base or a water-in-oil base. Dosage forms adapted for topical administration in the mouth include lozenges, pastilles, and mouth washes.

Dosage forms adapted for nasal or inhalation administration include aerosols, solutions, suspension drops, gels, or dry powders. In some embodiments, a primary active ingredient, optional secondary active ingredient, and/or pharmaceutically acceptable salt thereof where appropriate can be in a dosage form adapted for inhalation is in a particle-size-reduced form that is obtained or obtainable by micronization. In some embodiments, the particle size of the size reduced (e.g. micronized) compound or salt or solvate thereof, is defined by a $D_{50}$ value of about 0.5 to about 10 microns as measured by an appropriate method known in the art. Dosage forms adapted for administration by inhalation also include particle dusts or mists. Suitable dosage forms wherein the carrier or excipient is a liquid for administration as a nasal spray or drops include aqueous or oil solutions/suspensions of an active (primary and/or secondary) ingredient, which may be generated by various types of metered dose pressurized aerosols, nebulizers, or insufflators. The nasal/inhalation formulations can be administered to a subject in need thereof.

In some embodiments, the dosage forms are aerosol formulations suitable for administration by inhalation. In some of these embodiments, the aerosol formulation contains a solution or fine suspension of a primary active ingredient, secondary active ingredient, and/or pharmaceutically acceptable salt thereof where appropriate and a pharmaceutically acceptable aqueous or non-aqueous solvent. Aerosol formulations can be presented in single or multi-dose quantities in sterile form in a sealed container. For some of these embodiments, the sealed container is a single dose or multi-dose nasal or an aerosol dispenser fitted with a metering valve (e.g. metered dose inhaler), which is intended for disposal once the contents of the container have been exhausted.

Where the aerosol dosage form is contained in an aerosol dispenser, the dispenser contains a suitable propellant under pressure, such as compressed air, carbon dioxide, or an organic propellant, including but not limited to a hydrofluorocarbon. The aerosol formulation dosage forms in other embodiments are contained in a pump-atomizer. The pressurized aerosol formulation can also contain a solution or a suspension of a primary active ingredient, optional secondary active ingredient, and/or pharmaceutically acceptable salt thereof. In further embodiments, the aerosol formulation also contains co-solvents and/or modifiers incorporated to improve, for example, the stability and/or taste and/or fine particle mass characteristics (amount and/or profile) of the formulation. Administration of the aerosol formulation can be once daily or several times daily, for example 2, 3, 4, or 8 times daily, in which 1, 2, 3 or more doses are delivered each time. The aerosol formulations can be administered to a subject in need thereof.

For some dosage forms suitable and/or adapted for inhaled administration, the pharmaceutical formulation is a dry powder inhalable-formulations. In addition to a primary active agent, optional secondary active ingredient, and/or pharmaceutically acceptable salt thereof where appropriate, such a dosage form can contain a powder base such as lactose, glucose, trehalose, mannitol, and/or starch. In some of these embodiments, a primary active agent, secondary active ingredient, and/or pharmaceutically acceptable salt thereof where appropriate is in a particle-size reduced form. In further embodiments, a performance modifier, such as L-leucine or another amino acid, cellobiose octaacetate, and/or metals salts of stearic acid, such as magnesium or calcium stearate. In some embodiments, the aerosol formulations are arranged so that each metered dose of aerosol contains a predetermined amount of an active ingredient, such as the one or more of the compositions, compounds, vector(s), molecules, cells, and combinations thereof described herein.

Dosage forms adapted for vaginal administration can be presented as pessaries, tampons, creams, gels, pastes, foams, or spray formulations. Dosage forms adapted for rectal administration include suppositories or enemas. The vaginal formulations can be administered to a subject in need thereof.

Dosage forms adapted for parenteral administration and/or adapted for injection can include aqueous and/or non-aqueous sterile injection solutions, which can contain antioxidants, buffers, bacteriostats, solutes that render the composition isotonic with the blood of the subject, and aqueous and non-aqueous sterile suspensions, which can include suspending agents and thickening agents. The dosage forms adapted for parenteral administration can be presented in a single-unit dose or multi-unit dose containers, including but not limited to sealed ampoules or vials. The doses can be lyophilized and re-suspended in a sterile carrier to reconstitute the dose prior to administration. Extemporaneous injection solutions and suspensions can be prepared in some embodiments, from sterile powders, granules, and tablets. The parenteral formulations can be administered to a subject in need thereof.

For some embodiments, the dosage form contains a predetermined amount of a primary active agent, secondary active ingredient, and/or pharmaceutically acceptable salt thereof where appropriate per unit dose. In an embodiment, the predetermined amount of primary active agent, secondary active ingredient, and/or pharmaceutically acceptable salt thereof where appropriate can be an effective amount, a least effect amount, and/or a therapeutically effective amount. In other embodiments, the predetermined amount of a primary active agent, secondary active agent, and/or pharmaceutically acceptable salt thereof where appropriate, can be an appropriate fraction of the effective amount of the active ingredient.

Co-Therapies and Combination Therapies

In some embodiments, the pharmaceutical formulation(s) described herein can be part of a combination treatment or combination therapy. The combination treatment can include the pharmaceutical formulation described herein and an additional treatment modality. The additional treatment modality can be a chemotherapeutic, a biological therapeutic, surgery, radiation, diet modulation, environmental modulation, a physical activity modulation, and combinations thereof.

In some embodiments, the co-therapy or combination therapy can additionally include but not limited to, polynucleotides, amino acids, peptides, polypeptides, antibodies, aptamers, ribozymes, hormones, immunomodulators, antipyretics, anxiolytics, antipsychotics, analgesics, antispasmodics, anti-inflammatories, anti-histamines, anti-infectives, chemotherapeutics, and combinations thereof.

In some embodiments a combination therapy includes a BCR-ABL tyrosine kinase inhibitor pathway and an inhibitor of the pre-BCR pathway or a component thereof. In some embodiments a combination therapy includes a BCR-ABL tyrosine kinase inhibitor and an inhibitor of the p38 MAPK pathway or a component thereof.

Administration of the Pharmaceutical Formulations

The pharmaceutical formulations or dosage forms thereof described herein can be administered one or more times hourly, daily, monthly, or yearly (e.g. 1, 2, 3, 4, 5, 6, 7, 8, 9, 10, 11, 12, 13, 14, 15, 16, 17, 18, 19, 20, or more times hourly, daily, monthly, or yearly). In some embodiments, the pharmaceutical formulations or dosage forms thereof described herein can be administered continuously over a period of time ranging from minutes to hours to days. Devices and dosages forms are known in the art and described herein that are effective to provide continuous administration of the pharmaceutical formulations described herein. In some embodiments, the first one or a few initial amount(s) administered can be a higher dose than subsequent doses. This is typically referred to in the art as a loading dose or doses and a maintenance dose, respectively. In some embodiments, the pharmaceutical formulations can be administered such that the doses over time are tapered (increased or decreased) over time so as to wean a subject gradually off of a pharmaceutical formulation or gradually introduce a subject to the pharmaceutical formulation.

As previously discussed, the pharmaceutical formulation can contain a predetermined amount of a primary active agent, secondary active agent, and/or pharmaceutically acceptable salt thereof where appropriate. In some of these embodiments, the predetermined amount can be an appropriate fraction of the effective amount of the active ingredient. Such unit doses may therefore be administered once or more than once a day, month, or year (e.g. 1, 2, 3, 4, 5, 6, or more times per day, month, or year). Such pharmaceutical formulations may be prepared by any of the methods well known in the art.

Where co-therapies or multiple pharmaceutical formulations are to be delivered to a subject, the different therapies or formulations can be administered sequentially or simultaneously. Sequential administration is administration where an appreciable amount of time occurs between administrations, such as more than about 15, 20, 30, 45, 60 minutes or more. The time between administrations in sequential administration can be on the order of hours, days, months, or even years, depending on the active agent present in each administration. Simultaneous administration refers to administration of two or more formulations at the same time or substantially at the same time (e.g. within seconds or just a few minutes apart), where the intent is that the formulations be administered together at the same time.

Methods of Treating and/or Preventing Hematopoietic Malignancy Relapse

Described herein are methods of treating and/or preventing a hematopoietic malignancy or relapse thereof. In some embodiments, the method can include identifying a subject to be treated as being at high risk for a hematopoietic malignancy relapse. In some embodiments, the method can include identifying a subject as having or at risk for early-onset relapse. In some embodiments, the method can include identifying a subject as having a low risk for a hematopoietic malignancy relapse. In some embodiments, the method can include identifying a subject having or at risk for late-onset relapse. The methods can include administering a treatment to the subject in need thereof, such as one or more pharmaceutical compositions described in greater detail elsewhere herein. In some embodiments, treatment includes an adoptive cell therapy.

In some embodiments, a method of treating or preventing hematopoietic malignancy and/or hematopoietic malignancy relapse in a subject in need thereof includes prognosing, diagnosing, and/or monitoring hematopoietic malignancy and/or hematopoietic malignancy relapse in the subject in need thereof by determining an average cellular mass of the plurality of cells using the cellular mass of each individual cell of the plurality of cells, wherein an average cellular mass equal to or greater than a defined threshold indicates a low risk of hematopoietic malignancy relapse and an average cellular mass less than a defined threshold indicates a high risk of hematopoietic malignancy relapse and administering, to a subject in need thereof of having a high risk of hematopoietic malignancy relapse a therapeutically effective amount of (a) one or more BCR-ABL tyrosine kinase inhibitors or a pharmaceutical formulation thereof, (b) one or more pre-BCR signaling pathway inhibitors or a pharmaceutical formulation thereof; (c) one or more p38 MAPK inhibitors or a pharmaceutical formulation thereof, or (d) any combination thereof.

In some embodiments, a method of treating or preventing hematopoietic malignancy and/or hematopoietic malignancy relapse in a subject in need thereof includes prognosing, diagnosing, and/or monitoring hematopoietic malignancy and/or hematopoietic malignancy relapse in the subject in need thereof by determining a molecular signature of one or more cells in the plurality of cells, wherein the molecular signature comprises (a) a quiescent signature characterized by high TNF-a/NF-kB score and/or low HSF1/p38 score, and cycling signature characterized by high pre-BCR score, wherein a quiescent signature indicates a low risk of relapse, and a cycling signature indicates a high risk of relapse; (b) an ABL1, KRAS, and NRAS gene mutation status, wherein a mutation or mutations in ABL1 gene indicates low risk and/or late-onset of relapse, and a mutation or mutations in KRAS and/or NRAS genes indicate a high risk of and/or early-onset of relapse; or (c) both; and administering, to a subject in need thereof having a high risk of hematopoietic malignancy relapse and/or an early-onset of relapse a therapeutically effective amount of (a) one or more BCR-ABL tyrosine kinase inhibitors or a pharmaceutical formulation thereof, (b) one or more pre-BCR signaling pathway inhibitors or a pharmaceutical formulation thereof; (c) one or more p38 MAPK inhibitors or a pharmaceutical formulation thereof; or (d) any combination thereof.

In some embodiments, a method of treating or preventing hematopoietic malignancy and/or hematopoietic malignancy relapse in a subject in need thereof includes prognosing, diagnosing, and/or monitoring hematopoietic malignancy and/or hematopoietic malignancy relapse by only determining a biophysical phenotype, such as cell mass (which can be reported as an average cell mass calculated from the individual measured cell masses of a population of cells), stiffness or other biophysical phenotype described elsewhere herein, and identifying high risk individuals in need of treatment, identify suitable treatment agents, dosing amounts and/or regimens, or any combination thereof based on the biophysical phenotype alone. It will be appreciated and as is discussed elsewhere herein that the biophysical phenotype is a proxy for and can be representative of an underlying molecular phenotype or cell state. In some embodiments, the biophysical phenotype is validated as a proxy or representation for a molecular signature and/or specific cell state.

In some embodiments, a method of treating or preventing hematopoietic malignancy and/or hematopoietic malignancy relapse in a subject in need thereof includes prognosing, diagnosing, and/or monitoring hematopoietic malignancy and/or hematopoietic malignancy relapse in the subject in need thereof by performing one or both of the following on one or more cells in a plurality of cells present in a sample obtained from the subject in need thereof; determining an average cellular mass of the plurality of cells using the cellular mass of each individual cell of the plurality of cells, wherein an average cellular mass equal to or greater than a defined threshold indicates a low risk of hematopoietic malignancy relapse and an average cellular mass less than a defined threshold indicates a high risk of hematopoietic malignancy relapse; determining a molecular signature of one or more cells in the plurality of cells, wherein the molecular signature comprises (a) a quiescent signature characterized by high TNF-α/NF-kB score and/or low HSF1/p38 score, and cycling signature characterized by high pre-BCR score, wherein a quiescent signature indicates a low risk of relapse, and a cycling signature indicates a high risk of relapse; (b) an ABL1, KRAS, and NRAS gene mutation status, wherein a mutation or mutations in ABL1 gene indicates low risk and/or late-onset of relapse, and a mutation or mutations in KRAS and/or NRAS genes indicate a high risk and/or early-onset of relapse; or (c) both; and administering, to a subject in need thereof of having a high risk of, a risk of early-onset hematopoietic malignancy relapse, or both, a therapeutically effective amount of (a) one or more BCR-ABL tyrosine kinase inhibitors or a pharmaceutical formulation thereof; (b) one or more pre-BCR signaling pathway inhibitors or a pharmaceutical formulation thereof; (c) one or more p38 MAPK inhibitors or a pharmaceutical formulation thereof; or (d) any combination thereof.

In some embodiments, determining the average cellular mass of the plurality of cells comprises measuring a cellular mass of each individual cell in the plurality of cells and calculating an average cellular mass of the plurality cells based on the measured cellular mass of each of the individual cells in the plurality of cells. In some embodiments, the cellular mass of each individual cell is measured using a suspended microchannel resonator. In some embodiments, the cellular mass of each individual cell is measured using a suspended microchannel resonator (SMR). In some embodiments, the SMR is modified such that after determining a cellular mass or other biophysical characteristic, the cell is identified in a suitable fashion such that other characteristics measured (such as a molecular signature) in the same cell can be linked.

In some embodiments, an average cellular mass between 20-80 pg indicates a low risk of relapse, and an average cellular mass between 0-20 pg indicates a high risk of relapse. In some embodiments, an average cellular mass between 20-60 pg indicates a low risk of relapse, and an average cellular mass between 5-20 pg indicates a high risk of relapse. In some embodiments, an average cellular mass between 20-35 pg indicates a low risk of relapse.

The hematopoietic malignancy can be a lymphoid or myeloid malignancy. The hematopoietic malignancies may be any of lymphoid malignancies comprising B-cell ALL, T-cell ALL, chronic lymphoblastic leukemia (CLL), diffuse large B-cell lymphoma, follicular lymphoma, Burkitt's lymphoma, mantle cell lymphoma, marginal zone lymphoma, T-cell lymphoma, multiple myeloma, Hodgkin's lymphoma, and any other types of malignancies derived from lymphoid lineage. In some embodiments, the methods disclosed herein for predicting the risk of relapse can be used for any of the subtypes of the aforementioned lymphoid malignancies. In some embodiments, the hematopoietic malignancies can be any of myeloid malignancies comprising chronic myeloid leukemia (CML), acute myeloid leukemia (AML), myelodysplastic syndromes (MDS), myeloproliferative diseases (MPD), chronic neutrophilic leukemia, chronic eosinophilic leukemia, polycythemia vera, chronic idiopathic myelofibrosis, essential thrombocythemia, chronic myeloproliferative disease (unclassifiable), refractory anemia, refractory cytopenia with multilineage dysplasia (RCMD), mastocytosis, and any other types of malignancies derived from myeloid lineage. In some embodiments, the methods disclosed herein for predicting the risk of relapse can be used for any of the subtypes of the aforementioned myeloid malignancies.

In certain example embodiments, the hematopoietic malignancy is an acute lymphoblastic leukemia (ALL). In certain example embodiments, the ALL is a B-cell ALL. In certain other example embodiments, the ALL is a T-cell ALL.

In some embodiments, the hematopoietic malignancy is a B-cell malignancy, a T-cell malignancy, or a myeloid-cell malignancy. In some embodiments, the hematopoietic malignancy is acute lymphoblastic leukemia (ALL), chronic myeloid leukemia (CML), or both.

In some embodiments, one or more B-cell ALL cells have a BCR-ABL translocation. A "BCR-ABL translocation" is a term of art used to describe a translocation event between two chromosomes or a region thereof that results in the formation of a BCR-ABL fusion gene, whose gene product has been identified as being relevant to the pathology of ALL and/or CML in at least a subset of patients. See e.g., Nowell P, Hungerford D. 1960 Science 132: 1497; Salesse and Verfaillie. 2002. Oncogene. 21:8547-8559; Byun et al. 2017. Haematologica. 102(5):e187-e190; Sugapriya et al. 2012 Indian J Hematol Blood Transfus. 28(1):37-41; Jabbour and Kantarjian. 2018. Am J Hematol. 93(3): 442-459; Zhou and Xu. 2015 Protein Cell. 6(6):403-412; and Jain and Abraham. 2020. Arch Pathol Lab Med. 144(2):150-155.

In some embodiments, the one or more BCR-ABL tyrosine kinase inhibitors comprise imatinib, dasatinib, nilotinib, bosutinib, ponatinib, bafetinib, rebastinib, tozasertib, danusertib, HG-7-85-01, GNF-2, GNF-5, Compound 2, asciminib, or a combination thereof.

In some embodiments, the one or more pre-BCR signaling inhibitors comprise fostamatinib, ibrutinib, duvelisib, idelalisib, dasatinib, entospletinib, cerdulatinib, TAK-659, RG7666, apitolisib, LY3023414, gedatolisib, bimiralisib, SF-1126, copanlisib, buparlisib, tenalisib, taselisib, KA2237, alpelisib, parsaclisib, umbralisib, fimepinostat, rigosertib, dactolisib, BGT-226, DS-7423, PF-04691502, PKI-179, pictilisib, PX-866, TG100-115, AZD8835, WX-037, a genetic modifying agent capable of inhibiting or deleting one or more components of the pre-BCR signaling pathway, or a combination thereof.

In some embodiments, the one or more p38 MAPK inhibitors comprise losmapimod, talmapimod, SB203580, VX-702, VX-745, pamapimod, dilmapimod, doramapimod, BMS-582949, ARRY-797, PH797804, SCIO-469, SD-0006, AMG-548, ralimetinib (LY2228820), SB239063, Skepinone-L, SB202190, TAK715, a genetic modifying agent capable of inhibiting or deleting one or more components of the p38 signaling pathway, or a combination thereof.

In some embodiments, the sample is obtained from peripheral blood or bone marrow of the subject in need thereof.

In some embodiments, the subject in need thereof is in the acute response phase of treatment for the hematopoietic malignancy. In some embodiments, the subject in need thereof is in the minimal residual disease phase of the hematopoietic malignancy.

In some embodiments, the method of treating or preventing haemopoietic malignancy relapse comprises administering, to a subject identified as having a high risk of or early-onset of haemopoietic malignancy relapse, a therapeutically effective amount of one or more BCR-ABL tyrosine kinase inhibitors or a pharmaceutical formulation thereof; one or more pre-BCR signaling pathway inhibitors or a pharmaceutical formulation thereof, one or more p38 MAPK inhibitors or a pharmaceutical formulation thereof, or any combination thereof. Exemplary pre-BCR signaling pathway and p38 MAPK inhibitors are described in greater detail elsewhere herein.

Methods of identifying a subject as having a high or low risk of hematopoietic malignancy relapse are described in greater detail elsewhere herein. Methods of identifying subjects as being at risk for or having early-onset or late-onset relapse are described in greater detail elsewhere herein.

In some embodiments, a method of treating a hematopoietic malignancy or preventing a relapse thereof in subject having or having had a hematopoietic malignancy includes administering, to the subject, (a) a therapeutically effective amount of one or more BCR-ABL inhibitors or a pharmaceutical formulation thereof; (b) a therapeutically effective amount of one or more pre-BCR inhibitors or a pharmaceutical formulation thereof, (c) a therapeutically effective amount of one or more p38 MAPK inhibitors or a pharmaceutical formulation thereof, or (d) a combination thereof.

In some embodiments administering includes administering a therapeutically effective amount of one or more BCR-ABL inhibitors or a pharmaceutical formulation thereof and a therapeutically effective amount of one or more pre-BCR inhibitors or a pharmaceutical formulation thereof.

In some embodiments, administering comprises administering a therapeutically effective amount of one or more BCR-ABL inhibitors or a pharmaceutical formulation thereof and a therapeutically effective amount of one or more p38 MAPK inhibitors or a pharmaceutical formulation thereof.

In some embodiments, the method further includes administering an additional therapeutic agent or an anti-cancer treatment to the subject. In some embodiments, the additional therapeutic agent is an anti-CD 20 composition. In some embodiments, the anti-CD20 composition is an anti-CD20 antibody. In some embodiments, the anti-CD20 antibody is or includes rituximab, ofatumurnab, obinutuzurnab, ibritumomab tiuxetan, ocrelizumab, tositumomab, or a combination thereof.

Adoptive Cell Transfer

In some embodiments, a method of treating a hematopoietic malignancy or relapse thereof includes adoptive cell transfer. In some embodiments, the cells that are modified ex vivo and reintroduced to the subject are cells that are genetically modified to have an inhibited pre-BCR and p38 MAPK pathway or a component thereof. Such cells are described in greater detail elsewhere herein.

In some embodiments, the cells used in an adoptive cell therapy are T cells, such as modified T cells. In certain embodiments, the T cells modified to have decreased expression, activity, and/or function of one or more exhaustion regulators may be used in adoptive cell transfer. In certain embodiments, the T cells are modified and expanded. In certain embodiments, the T cells are formulated into a pharmaceutical composition. The modified T cells may be resistant to exhaustion induced by a tumor or tumor microenvironment and have enhanced ant-tumor activity. In other words, a tumor may target immune cells or the tumor microenvironment to induce a dysfunctional immune state. In certain embodiments, modulating one or more identified therapeutic targets in an immune cell shifts the immune cell to be resistant to dysfunction or have increased effector function. Such immune cells may be used to increase the effectiveness of adoptive cell transfer. In certain embodiments, immune cells are modulated using a genetic modifying agent, antibody or small molecule, described further herein.

As used herein, "ACT", "adoptive cell therapy" and "adoptive cell transfer" may be used interchangeably. In certain embodiments, Adoptive cell therapy (ACT) can refer to the transfer of cells to a patient with the goal of transferring the functionality and characteristics into the new host by engraftment of the cells (see, e.g., Mettananda et al., Editing an a-globin enhancer in primary human hematopoietic stem cells as a treatment for P-thalassemia, Nat Commun. 2017 Sep. 4; 8(1):424). As used herein, the term "engraft" or "engraftment" refers to the process of cell incorporation into a tissue of interest in vivo through contact with existing cells of the tissue. Adoptive cell therapy (ACT) can refer to the transfer of cells, most commonly immune-derived cells, back into the same patient or into a new recipient host with the goal of transferring the immunologic functionality and characteristics into the new host. If possible, use of autologous cells helps the recipient by minimizing GVHD issues. The adoptive transfer of autologous tumor infiltrating lymphocytes (TIL) (Zacharakis et al., (2018) Nat Med. 2018 June;24(6):724-730; Besser et al., (2010) Clin. Cancer Res 16 (9) 2646-55; Dudley et al., (2002) Science 298 (5594): 850-4; and Dudley et al., (2005) Journal of Clinical Oncology 23 (10): 2346-57.) or genetically re-directed peripheral blood mononuclear cells (Johnson et al., (2009) Blood 114 (3): 535-46; and Morgan et al., (2006) Science 314(5796) 126-9) has been used to successfully treat patients with advanced solid tumors, including melanoma, metastatic breast cancer and colorectal carcinoma, as well as patients with CD19-expressing hematologic malignancies (Kalos et al., (2011) Science Translational Medicine 3 (95): 95ra73). In certain embodiments, allogenic cells immune cells are transferred (see, e.g., Ren et al., (2017) Clin Cancer Res 23 (9) 2255-2266). As described further herein, allogenic cells can be edited to reduce alloreactivity and prevent graft-versus-host disease. Thus, use of allogenic cells allows for cells to be obtained from healthy donors and prepared for use in patients as opposed to preparing autologous cells from a patient after diagnosis.

Embodiments of the invention involve the adoptive transfer of immune system cells, such as T cells, specific for selected antigens, such as tumor associated antigens or tumor specific neoantigens (see, e.g., Maus et al., 2014, Adoptive Immunotherapy for Cancer or Viruses, Annual Review of Immunology, Vol. 32: 189-225; Rosenberg and Restifo, 2015, Adoptive cell transfer as personalized immunotherapy for human cancer, Science Vol. 348 no. 6230 pp. 62-68; Restifo et al., 2015, Adoptive immunotherapy for cancer: harnessing the T-cell response. Nat. Rev. Immunol. 12(4): 269-281; and Jenson and Riddell, 2014, Design and implementation of adoptive therapy with chimeric antigen receptor-modified T cells. Immunol Rev. 257(1): 127-144; and Rajasagi et al., 2014, Systematic identification of personal tumor-specific neoantigens in chronic lymphocytic leukemia. Blood. 2014 Jul. 17; 124(3):453-62).

In certain embodiments, an antigen (such as a tumor antigen) to be targeted in adoptive cell therapy (such as particularly CAR or TCR T-cell therapy) of a disease (such as particularly of tumor or cancer) may be selected from a group consisting of: B-cell maturation antigen (BCMA) (see, e.g., Friedman et al., Effective Targeting of Multiple BCMA-Expressing Hematological Malignancies by Anti-BCMA CAR T Cells, Hum Gene Ther. 2018 Mar. 8; Berdeja J G, et al. Durable clinical responses in heavily pretreated patients with relapsed/refractory multiple myeloma: updated results from a multicenter study of bb2121 anti-Bcma CAR T-cell therapy. Blood. 2017; 130:740; and Mouhieddine and Ghobrial, Immunotherapy in Multiple Myeloma: The Era of CAR T-Cell Therapy, Hematologist, May-June 2018, Volume 15, issue 3); PSA (prostate-specific antigen); prostate-specific membrane antigen (PSMA); PSCA (Prostate stem cell antigen); Tyrosine-protein kinase transmembrane receptor ROR1; fibroblast activation protein (FAP); Tumor-associated glycoprotein 72 (TAG72); Carcinoembryonic antigen (CEA); Epithelial cell adhesion molecule (EPCAM); Mesothelin; Human Epidermal growth factor Receptor 2 (ERBB2 (Her2/neu)); Prostase; Prostatic acid phosphatase (PAP); elongation factor 2 mutant (ELF2M); Insulin-like growth factor 1 receptor (IGF-1R); gp lOO; BCR-ABL (breakpoint cluster region-Abelson); tyrosinase; New York esophageal squamous cell carcinoma 1 (NY-ESO-1); x-light chain, LAGE (L antigen); MAGE (melanoma antigen); Melanoma-associated antigen 1 (MAGE-A1); MAGE A3; MAGE A6; legumain; Human papillomavirus (HPV) E6; HPV E7; prostein; survivin; PCTA1 (Galectin 8); Melan-A/MART-1; Ras mutant; TRP-1 (tyrosinase related protein 1, or gp75); Tyrosinase-related Protein 2 (TRP2); TRP-2/INT2 (TRP-2/intron 2); RAGE (renal antigen); receptor for advanced glycation end products 1 (RAGE1); Renal ubiquitous 1, 2 (RU1, RU2); intestinal carboxyl esterase (iCE); Heat shock protein 70-2 (HSP70-2) mutant; thyroid stimulating hormone receptor (TSHR); CD123; CD171; CD19; CD20; CD22; CD26; CD30; CD33; CD44v7/8 (cluster of differentiation 44, exons 7/8); CD53; CD92; CD100; CD148; CD150; CD200; CD261; CD262; CD362; CS-1 (CD2 subset 1, CRACC, SLAMF7, CD319, and 19A24); C-type lectin-like molecule-1 (CLL-1); ganglioside GD3 (aNeu5Ac (2-8)aNeu5Ac(2-3)bDGalp(1-4)bDGlcp(1-1)Cer); Tn antigen (Tn Ag); Fms-Like Tyrosine Kinase 3 (FLT3); CD38; CD138; CD44v6; B7H3 (CD276); KIT (CD117); Interleukin-13 receptor subunit alpha-2 (IL-13Ra2); Interleukin 11 receptor alpha (IL-11Ra); prostate stem cell antigen (PSCA); Protease Serine 21 (PRSS21); vascular endothelial growth factor receptor 2 (VEGFR2); Lewis(Y) antigen; CD24; Platelet-derived growth factor receptor beta (PDGFR-beta); stage-specific embryonic antigen-4 (SSEA-4); Mucin 1, cell surface associated (MUC1); mucin 16 (MUC16); epidermal growth factor receptor (EGFR); epidermal growth factor receptor variant III (EGFRvIII); neural cell adhesion molecule (NCAM); carbonic anhydrase IX (CAIX); Proteasome (Prosome, Macropain) Subunit, Beta Type, 9 (LMP2); ephrin type-A receptor 2 (EphA2); Ephrin B2; Fucosyl GMi; sialyl Lewis adhesion molecule (sLe); ganglioside GM3 (aNeu5Ac(2-3)bDGalp(1-4)bDGlcp(1-1) Cer); TGS5; high molecular weight-melanoma-associated antigen (HMWMAA); o-acetyl-GD2 ganglioside (OAcGD2); Folate receptor alpha; Folate receptor beta; tumor endothelial marker 1 (TEM1/CD248); tumor endothelial marker 7-related (TEM7R); claudin 6 (CLDN6); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexa-saccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); CT (cancer/testis (antigen)); melanoma cancer testis antigen-1 (MAD-CT-1); melanoma cancer testis antigen-2 (MAD-CT-2); Fos-related antigen 1; p53; p53 mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; Cyclin D1; v-myc avian myelocytomatosis viral oncogene neuroblastoma derived homolog (MYCN); Ras Homolog Family Member C (RhoC); Cytochrome P450 1B1 (CYP1B1); CCCTC-Binding Factor (Zinc Finger Protein)-Like (BORIS); Squamous Cell Carcinoma Antigen Recognized By T Cells-1 or 3 (SART1, SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint -1 , -2 , -3 or -4 (SSX1, SSX2, SSX3, SSX4); CD79a; CD79b; CD72; Leukocyte-associated immunoglobulin-like receptor 1 (LAIR1); Fc fragment of IgA receptor (FCAR); Leukocyte immunoglobulin-like receptor subfamily A member 2 (LILRA2); CD300 molecule-like family member f (CD300LF); C-type lectin domain family 12 member A (CLECi2A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); mouse double minute 2 homolog (MDM2); livin; alphafetoprotein (AFP); transmembrane activator and CAML Interactor (TACI); B-cell activating factor receptor (BAFF-R); V-Ki-ras2 Kirsten rat sarcoma viral oncogene homolog (KRAS); immunoglobulin lambda-like polypeptide 1 (IGLL1); 707-AP (707 alanine proline); ART-4 (adenocarcinoma antigen recognized by T4 cells); BAGE (B antigen; b-catenin/m, b-catenin/mutated); CAMEL (CTL-recognized antigen on melanoma); CAPi (carcinoembryonic antigen peptide 1); CASP-8 (caspase-8); CDC27m (cell-division cycle 27 mutated); CDK4/m (cycline-dependent kinase 4 mutated); Cyp-B (cyclophilin B); DAM (differentiation antigen melanoma); EGP-2 (epithelial glycoprotein 2); EGP-40 (epithelial glycoprotein 40); Erbb2, 3, 4 (erythroblastic leukemia viral oncogene homolog -2 , -3, 4); FBP (folate binding protein); fAchR (Fetal acetylcholine receptor); G250 (glycoprotein 250); GAGE (G antigen); GnT-V (N-acetylglucosaminyltransferase V); HAGE (helicase antigen); ULA-A (human leukocyte antigen-A); HST2 (human signet ring tumor 2); KIAA0205; KDR (kinase insert domain receptor); LDLR/FUT (low density lipid receptor/GDP L-fucose: b-D-galactosidase 2-a-L fucosyltransferase); L1CAM (L1 cell adhesion molecule); MC1R (melanocortin 1 receptor); Myosin/m (myosin mutated); MUM-1 , -2 , -3 (melanoma ubiquitous mutated 1, 2, 3); NA88-A (NA cDNA clone of patient M88); KG2D (Natural killer group 2, member D) ligands; oncofetal antigen (h5T4); p190 minor bcr-abl (protein of 190 KD bcr-abl); Pml/RARa (promyelocytic leukemia/retinoic acid receptor a); PRAME (preferentially expressed antigen of melanoma); SAGE (sarcoma antigen); TEL/AML1 (translocation Ets-family leukemia/acute myeloid leukemia 1); TPI/m (triose-phosphate isomerase mutated); CD70; and any combination thereof.

In certain embodiments, an antigen to be targeted in adoptive cell therapy (such as particularly CAR or TCR T-cell therapy) of a disease (such as particularly of tumor or cancer) is a tumor-specific antigen (TSA).

In certain embodiments, an antigen to be targeted in adoptive cell therapy (such as particularly CAR or TCR T-cell therapy) of a disease (such as particularly of tumor or cancer) is a neoantigen.

In certain embodiments, an antigen to be targeted in adoptive cell therapy (such as particularly CAR or TCR T-cell therapy) of a disease (such as particularly of tumor or cancer) is a tumor-associated antigen (TAA).

In certain embodiments, an antigen to be targeted in adoptive cell therapy (such as particularly CAR or TCR T-cell therapy) of a disease (such as particularly of tumor or cancer) is a universal tumor antigen. In certain preferred embodiments, the universal tumor antigen is selected from the group consisting of: a human telomerase reverse transcriptase (hTERT), survivin, mouse double minute 2 homolog (MDM2), cytochrome P450 1B 1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53, cyclin (D1), and any combinations thereof.

In certain embodiments, an antigen (such as a tumor antigen) to be targeted in adoptive cell therapy (such as particularly CAR or TCR T-cell therapy) of a disease (such as particularly of tumor or cancer) may be selected from a group consisting of: CD19, BCMA, CD70, CLL-1, MAGE A3, MAGE A6, HPV E6, HPV E7, WT1, CD22, CD171, ROR1, MUC16, and SSX2. In certain preferred embodiments, the antigen may be CD19. For example, CD19 may be targeted in hematologic malignancies, such as in lymphomas, more particularly in B-cell lymphomas, such as without limitation in diffuse large B-cell lymphoma, primary mediastinal B-cell lymphoma, transformed follicular lymphoma, marginal zone lymphoma, mantle cell lymphoma, acute lymphoblastic leukemia including adult and pediatric ALL, non-Hodgkin lymphoma, indolent non-Hodgkin lymphoma, or chronic lymphocytic leukemia. For example, BCMA may be targeted in multiple myeloma or plasma cell leukemia (see, e.g., 2018 American Association for Cancer Research (AACR) Annual meeting Poster: Allogeneic Chimeric Antigen Receptor T Cells Targeting B-CellMaturation Antigen). For example, CLL1 may be targeted in acute myeloid leukemia. For example, MAGE A3, MAGE A6, SSX2, and/or KRAS may be targeted in solid tumors. For example, HPV E6 and/or HPV E7 may be targeted in cervical cancer or head and neck cancer. For example, WT1 may be targeted in acute myeloid leukemia (AML), myelodysplastic syndromes (MDS), chronic myeloid leukemia (CML), non-small cell lung cancer, breast, pancreatic, ovarian or colorectal cancers, or mesothelioma. For example, CD22 may be targeted in B-cellmalignancies, including non-Hodgkin lymphoma, diffuse large B-cell lymphoma, or acute lymphoblastic leukemia. For example, CD171 may be targeted in neuroblastoma, glioblastoma, or lung, pancreatic, or ovarian cancers. For example, ROR1 may be targeted in ROR1+ malignancies, including non-small cell lung cancer, triple negative breast cancer, pancreatic cancer, prostate cancer, ALL, chronic lymphocytic leukemia, or mantle cell lymphoma. For example, MUC16 may be targeted in MUC16ecto+ epithelial ovarian, fallopian tube or primary peritoneal cancer. For example, CD70 may be targeted in both hematologic malignancies as well as in solid cancers such as renal cell carcinoma (RCC), gliomas (e.g., GBM), and head and neck cancers (HNSCC). CD70 is expressed in both hematologic malignancies as well as in solid cancers, while its expression in normal tissues is restricted to a subset of lymphoid cell types (see, e.g., 2018 American Association for Cancer Research (AACR) Annual meeting Poster: Allogeneic CRISPR Engineered Anti-CD70 CAR T Cells Demonstrate Potent Preclinical Activity Against Both Solid and Hematological Cancer Cells).

Various strategies may for example be employed to genetically modify T cells by altering the specificity of the T-cell receptor (TCR) for example by introducing new TCR a and R chains with selected peptide specificity (see U.S. Pat. No. 8,697,854; PCT Patent Publications: WO2003020763, WO2004033685, WO2004044004, WO2005114215, WO2006000830, WO2008038002, WO2008039818, WO2004074322, WO2005113595, WO2006125962, WO2013166321, WO2013039889, WO2014018863, WO2014083173; U.S. Pat. No. 8,088, 379).

As an alternative to, or addition to, TCR modifications, chimeric antigen receptors (CARs) may be used in order to generate immunoresponsive cells, such as T cells, specific for selected targets, such as malignant cells, with a wide variety of receptor chimera constructs having been described (see U.S. Pat. Nos. 5,843,728; 5,851,828; 5,912,170; 6,004,811; 6,284,240; 6,392,013; 6,410,014; 6,753,162; 8,211,422; and PCT Publication WO9215322).

In general, CARs are comprised of an extracellular domain, a transmembrane domain, and an intracellular domain, wherein the extracellular domain comprises an antigen-binding domain that is specific for a predetermined target. While the antigen-binding domain of a CAR is often an antibody or antibody fragment (e.g., a single chain variable fragment, scFv), the binding domain is not particularly limited so long as it results in specific recognition of a target. For example, in some embodiments, the antigen-binding domain may comprise a receptor, such that the CAR is capable of binding to the ligand of the receptor. Alternatively, the antigen-binding domain may comprise a ligand, such that the CAR is capable of binding the endogenous receptor of that ligand.

The antigen-binding domain of a CAR is generally separated from the transmembrane domain by a hinge or spacer. The spacer is also not particularly limited, and it is designed to provide the CAR with flexibility. For example, a spacer domain may comprise a portion of a human Fc domain, including a portion of the CH3 domain, or the hinge region of any immunoglobulin, such as IgA, IgD, IgE, IgG, or IgM, or variants thereof. Furthermore, the hinge region may be modified so as to prevent off-target binding by FcRs or other potential interfering objects. For example, the hinge may comprise an IgG4 Fc domain with or without a S228P, L235E, and/or N297Q mutation (according to Kabat numbering) in order to decrease binding to FcRs. Additional spacers/hinges include, but are not limited to, CD4, CD8, and CD28 hinge regions.

The transmembrane domain of a CAR may be derived either from a natural or from a synthetic source. Where the source is natural, the domain may be derived from any membrane bound or transmembrane protein. Transmembrane regions of particular use in this disclosure may be derived from CD8, CD28, CD3, CD45, CD4, CD5, CD8, CD9, CD 16, CD22, CD33, CD37, CD64, CD80, CD86, CD 134, CD137, CD 154, TCR. Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Alternative CAR constructs may be characterized as belonging to successive generations. First-generation CARs typically consist of a single-chain variable fragment of an antibody specific for an antigen, for example comprising a VL linked to a VH of a specific antibody, linked by a flexible linker, for example by a CD8α hinge domain and a CD8α transmembrane domain, to the transmembrane and intracellular signaling domains of either CD3ζ or FcRγ (scFv-CD3ζ or scFv-FcRγ; see U.S. Pat. Nos. 7,741,465; 5,912,172; U.S. Pat. No. 5,906,936). Second-generation CARs incorporate the intracellular domains of one or more co-stimulatory molecules, such as CD28, OX40 (CD134), or 4-1BB (CD137) within the endodomain (for example scFv-CD28/OX40/4-1BB-CD3ζ; see U.S. Pat. Nos. 8,911,993; 8,916,381; 8,975,071; 9,101,584; 9,102,760; 9,102,761). Third-generation CARs include a combination of co-stimulatory endodomains, such a CD3ζ-chain, CD97, GDI 1a-CD18, CD2, ICOS, CD27, CD154, CDS, OX40, 4-1BB, CD2, CD7, LIGHT, LFA-1, NKG2C, B7-H3, CD30, CD40, PD-1, or CD28 signaling domains (for example scFv-CD28-4-1BB-CD3ζ or scFv-CD28-OX40-CD3ζ; see U.S. Pat. Nos. 8,906,682; 8,399,645; 5,686,281; PCT Publication No. WO2014134165; PCT Publication No. WO2012079000). In certain embodiments, the primary signaling domain comprises a functional signaling domain of a protein selected from the group consisting of CD3 zeta, CD3 gamma, CD3 delta, CD3 epsilon, common FcR gamma (FCERIG), FcR beta (Fc Epsilon Rib), CD79a, CD79b, Fe gamma RIIa, DAP10, and DAP12. In certain preferred embodiments, the primary signaling domain comprises a functional signaling domain of CD3ζ or FcRγ. In certain embodiments, the one or more co-stimulatory signaling domains comprise a functional signaling domain of a protein selected, each independently, from the group consisting of: CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8 alpha, CD8 beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD1ib, ITGAX, CD11c, ITGB1, CD29, ITGB2, CD18, ITGB7, TNFR2, TRANCE/RANKL, DNAM1 (CD226), SLAMF4 (CD244, 2B4), CD84, CD96 (Tactile), CEACAMI, CRTAM, Ly9 (CD229), CD160 (BY55), PSGL1, CD100 (SEMA4D), CD69, SLAMF6 (NTB-A, Lyl08), SLAM (SLAMFI, CD150, IPO-3), BLAME (SLAMF8), SELPLG (CD162), LTBR, LAT, GADS, SLP-76, PAG/Cbp, NKp44, NKp30, NKp46, and NKG2D. In certain embodiments, the one or more co-stimulatory signaling domains comprise a functional signaling domain of a protein selected, each independently, from the group consisting of: 4-1BB, CD27, and CD28. In certain embodiments, a chimeric antigen receptor may have the design as described in U.S. Pat. No. 7,446,190, comprising an intracellular domain of CD3ζ chain (such as amino acid residues 52-163 of the human CD3 zeta chain, as shown in SEQ ID NO: 14 of U.S. Pat. No. 7,446,190), a signaling region from CD28 and an antigen-binding element (or portion or domain; such as scFv). The CD28 portion, when between the zeta chain portion and the antigen-binding element, may suitably include the transmembrane and signaling domains of CD28 (such as amino acid residues 114-220 of SEQ ID NO: 10, full sequence shown in SEQ ID NO: 6 of U.S. Pat. No. 7,446,190; these can include the following portion of CD28 as set forth in Genbank identifier NM_006139 (sequence version 1, 2 or 3): IEVMYPPPYLD-NEKSNGTIIHVKGKHLCPSPLFPGPSKPFWVLVVVGGV-LACYSLLVTVA FIIFWVRSKRSRLLHSDYMNMT-PRRPGPTRKHYQPYAPPRDFAAYRS)) (SEQ. I.D. No. 27). Alternatively, when the zeta sequence lies between the CD28 sequence and the antigen-binding element, intracellular domain of CD28 can be used alone (such as amino sequence set forth in SEQ ID NO: 9 of U.S. Pat. No. 7,446,190). Hence, certain embodiments employ a CAR comprising (a) a zeta chain portion comprising the intracellular domain of human CD3ζ chain, (b) a co-stimulatory signaling region, and (c) an antigen-binding element (or portion or domain), wherein the co-stimulatory signaling region comprises the amino acid sequence encoded by SEQ ID NO: 6 of U.S. Pat. No. 7,446,190.

Alternatively, co-stimulation may be orchestrated by expressing CARs in antigen-specific T cells, chosen so as to be activated and expanded following engagement of their native αβTCR, for example by antigen on professional antigen-presenting cells, with attendant co-stimulation. In addition, additional engineered receptors may be provided on the immunoresponsive cells, for example to improve targeting of a T-cell attack and/or minimize side effects.

By means of an example and without limitation, Kochenderfer et al., (2009) J Immunother. 32 (7): 689-702 described anti-CD19 chimeric antigen receptors (CAR). FMC63-28Z CAR contained a single chain variable region moiety (scFv) recognizing CD19 derived from the FMC63 mouse hybridoma (described in Nicholson et al., (1997) Molecular Immunology 34: 1157-1165), a portion of the human CD28 molecule, and the intracellular component of the human TCR-ζ molecule. FMC63-CD828BBZ CAR contained the FMC63 scFv, the hinge and transmembrane regions of the CD8 molecule, the cytoplasmic portions of CD28 and 4-1BB, and the cytoplasmic component of the TCR-ζ molecule. The exact sequence of the CD28 molecule included in the FMC63-28Z CAR corresponded to Genbank identifier NM_006139; the sequence included all amino acids starting with the amino acid sequence IEVMYPPPY (SEQ. I.D. No. 28) and continuing all the way to the carboxy-terminus of the protein. To encode the anti-CD19 scFv component of the vector, the authors designed a DNA sequence which was based on a portion of a previously published CAR (Cooper et al., (2003) Blood 101: 1637-1644). This sequence encoded the following components in frame from the 5' end to the 3' end: an XhoI site, the human granulocyte-macrophage colony-stimulating factor (GM-CSF) receptor α-chain signal sequence, the FMC63 light chain variable region (as in Nicholson et al., supra), a linker peptide (as in Cooper et al., supra), the FMC63 heavy chain variable region (as in Nicholson et al., supra), and a NotI site. A plasmid encoding this sequence was digested with XhoI and NotI. To form the MSGV-FMC63-28Z retroviral vector, the XhoI and NotI-digested fragment encoding the FMC63 scFv was ligated into a second XhoI and NotI-digested fragment that encoded the MSGV retroviral backbone (as in Hughes et al., (2005) Human Gene Therapy 16: 457-472) as well as part of the extracellular portion of human CD28, the entire transmembrane and cytoplasmic portion of human CD28, and the cytoplasmic portion of the human TCR-ζ molecule (as in Maher et al., 2002) Nature Biotechnology 20: 70-75). The FMC63-28Z CAR is included in the KTE-C19 (axicabtagene ciloleucel) anti-CD19 CAR-T therapy product in development by Kite Pharma, Inc. for the treatment of inter alia patients with relapsed/refractory aggressive B-cell non-Hodgkin lymphoma (NHL). Accordingly, in certain embodiments, cells intended for adoptive cell therapies, more particularly immunoresponsive cells such as T cells, may express the FMC63-28Z CAR as described by Kochenderfer et al. (supra). Hence, in certain embodiments, cells intended for adoptive cell therapies, more particularly immunoresponsive cells such as T cells, may comprise a CAR comprising an extracellular antigen-binding element (or portion or domain; such as scFv) that specifically binds to an antigen, an intracellular signaling domain comprising an intracellular domain of a CD3ζ chain, and a co-stimulatory signaling region comprising a signaling domain of CD28. Preferably, the CD28 amino acid sequence is as set forth in Genbank identifier NM_006139 (sequence version 1, 2 or 3) starting with the amino acid sequence IEVMYPPPY (SEQ ID NO: 28) and continuing all the way to the carboxy-terminus of the protein. The sequence is reproduced herein:

```
                                        (SEQ ID NO: 29)
IEVMYPPPYLDNEKSNGTIIHVKGKHLCPSPLFPGPS

KPFWVLVVVGGVLACYSLLVTVAFIIFWVRSKRSRLL

HSDYMNMTPRRPGPTRKHYQPYAPPRDFAAYRS.
```

Preferably, the antigen is CD19, more preferably the antigen-binding element is an anti-CD19 scFv, even more preferably the anti-CD19 scFv as described by Kochenderfer et al. (supra).

Additional anti-CD19 CARs are further described in WO2015187528. More particularly Example 1 and Table 1 of WO2015187528, incorporated by reference herein, demonstrate the generation of anti-CD19 CARs based on a fully human anti-CD19 monoclonal antibody (47G4, as described in US20100104509) and murine anti-CD19 monoclonal antibody (as described in Nicholson et al. and explained above). Various combinations of a signal sequence (human CD8-alpha or GM-CSF receptor), extracellular and transmembrane regions (human CD8-alpha) and intracellular T-cell signaling domains (CD28-CD3ζ; 4-1BB-CD3ζ; CD27-CD3ζ; CD28-CD27-CD3ζ, 4-1BB-CD27-CD3ζ; CD27-4-1BB-CD3ζ; CD28-CD27-FcεRI gamma chain; or CD28-FcεRI gamma chain) were disclosed. Hence, in certain embodiments, cells intended for adoptive cell therapies, more particularly immunoresponsive cells such as T cells, may comprise a CAR comprising an extracellular antigen-binding element that specifically binds to an antigen, an extracellular and transmembrane region as set forth in Table 1 of WO2015187528 and an intracellular T-cell signaling domain as set forth in Table 1 of International Patent Publication No. WO2015187528. Preferably, the antigen is CD19, more preferably the antigen-binding element is an anti-CD19 scFv, even more preferably the mouse or human anti-CD19 scFv as described in Example 1 of WO2015187528. In certain embodiments, the CAR comprises, consists essentially of or consists of an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13 as set forth in Table 1 of WO2015187528.

By means of an example and without limitation, chimeric antigen receptor that recognizes the CD70 antigen is described in International Patent Publication No. WO2012058460A2 (see also, Park et al., CD70 as a target for chimeric antigen receptor T cells in head and neck squamous cell carcinoma, Oral Oncol. 2018 March;78:145-150; and Jin et al., CD70, a novel target of CAR T-cell therapy for gliomas, Neuro Oncol. 2018 Jan. 10; 20(1):55-65). CD70 is expressed by diffuse large B-cell and follicular lymphoma and also by the malignant cells of Hodgkin's lymphoma, Waldenstrom's macroglobulinemia and multiple myeloma, and by HTLV-1—and EBV-associated malignancies. (Agathanggelou et al. Am. J. Pathol. 1995;147: 1152-1160; Hunter et al., Blood 2004; 104:4881. 26; Lens et al., J Immunol. 2005; 174:6212-6219; Baba et al., J Virol. 2008; 82:3843-3852.) In addition, CD70 is expressed by non-hematological malignancies such as renal cell carcinoma and glioblastoma. (Junker et al., J Urol. 2005; 173:2150-2153; Chahlavi et al., Cancer Res 2005; 65:5428-5438)

Physiologically, CD70 expression is transient and restricted to a subset of highly activated T, B, and dendritic cells.

By means of an example and without limitation, chimeric antigen receptor that recognizes BCMA has been described (see, e.g., US20160046724A1; WO2016014789A2; WO2017211900A1; WO2015158671A1; US20180085444A1; WO2018028647A1; US20170283504A1; and WO2013154760A1).

In certain embodiments, the immune cell may, in addition to a CAR or exogenous TCR as described herein, further comprise a chimeric inhibitory receptor (inhibitory CAR) that specifically binds to a second target antigen and is capable of inducing an inhibitory or immunosuppressive or repressive signal to the cell upon recognition of the second target antigen. In certain embodiments, the chimeric inhibitory receptor comprises an extracellular antigen-binding element (or portion or domain) configured to specifically bind to a target antigen, a transmembrane domain, and an intracellular immunosuppressive or repressive signaling domain. In certain embodiments, the second target antigen is an antigen that is not expressed on the surface of a cancer cell or infected cell or the expression of which is downregulated on a cancer cell or an infected cell. In certain embodiments, the second target antigen is an MHC-class I molecule. In certain embodiments, the intracellular signaling domain comprises a functional signaling portion of an immune checkpoint molecule, such as for example PD-1 or CTLA4. Advantageously, the inclusion of such inhibitory CAR reduces the chance of the engineered immune cells attacking non-target (e.g., non-cancer) tissues.

Alternatively, T cells expressing CARs may be further modified to reduce or eliminate expression of endogenous TCRs in order to reduce off-target effects. Reduction or elimination of endogenous TCRs can reduce off-target effects and increase the effectiveness of the T cells (U.S. Pat. No. 9,181,527). T cells stably lacking expression of a functional TCR may be produced using a variety of approaches. T cells internalize, sort, and degrade the entire T-cell receptor as a complex, with a half-life of about 10 hours in resting T cells and 3 hours in stimulated T cells (von Essen, M. et al. 2004. J. Immunol. 173:384-393). Proper functioning of the TCR complex requires the proper stoichiometric ratio of the proteins that compose the TCR complex. TCR function also requires two functioning TCR zeta proteins with ITAM motifs. The activation of the TCR upon engagement of its MHC-peptide ligand requires the engagement of several TCRs on the same T cell, which all must signal properly. Thus, if a TCR complex is destabilized with proteins that do not associate properly or cannot signal optimally, the T cell will not become activated sufficiently to begin a cellular response.

Accordingly, in some embodiments, TCR expression may be eliminated using RNA interference (e.g., shRNA, siRNA, miRNA, etc.), CRISPR, or other methods that target the nucleic acids encoding specific TCRs (e.g., TCR-α and TCR-β) and/or CD3 chains in primary T cells. By blocking expression of one or more of these proteins, the T cell will no longer produce one or more of the key components of the TCR complex, thereby destabilizing the TCR complex and preventing cell surface expression of a functional TCR.

In some instances, CAR may also comprise a switch mechanism for controlling expression and/or activation of the CAR. For example, a CAR may comprise an extracellular, transmembrane, and intracellular domain, in which the extracellular domain comprises a target-specific binding element that comprises a label, binding domain, or tag that is specific for a molecule other than the target antigen that is expressed on or by a target cell. In such embodiments, the specificity of the CAR is provided by a second construct that comprises a target antigen-binding domain (e.g., an scFv or a bispecific antibody that is specific for both the target antigen and the label or tag on the CAR) and a domain that is recognized by or binds to the label, binding domain, or tag on the CAR. See, e.g., WO 2013/044225, WO 2016/000304, WO 2015/057834, WO 2015/057852, WO 2016/070061, U.S. Pat. No. 9,233,125, US 2016/0129109. In this way, a T cell that expresses the CAR can be administered to a subject, but the CAR cannot bind its target antigen until the second composition comprising an antigen-specific binding domain is administered.

Alternative switch mechanisms include CARs that require multimerization in order to activate their signaling function (see, e.g., US Patent Publication Nos. 2015/0368342, US 2016/0175359, US 2015/0368360) and/or an exogenous signal, such as a small molecule drug (US 2016/0166613, Yung et al., Science, 2015), in order to elicit a T-cell response. Some CARs may also comprise a "suicide switch" to induce cell death of the CAR T cells following treatment (Buddee et al., PLoS One, 2013) or to downregulate expression of the CAR following binding to the target antigen (WO 2016/011210).

Alternative techniques may be used to transform target immunoresponsive cells, such as protoplast fusion, lipofection, transfection or electroporation. A wide variety of vectors may be used, such as retroviral vectors, lentiviral vectors, adenoviral vectors, adeno-associated viral vectors, plasmids or transposons, such as a Sleeping Beauty transposon (see U.S. Pat. Nos. 6,489,458; 7,148,203; 7,160,682; 7,985,739; 8,227,432), may be used to introduce CARs, for example using 2nd generation antigen-specific CARs signaling through CD3ζ and either CD28 or CD137. Viral vectors may for example include vectors based on HIV, SV40, EBV, HSV or BPV.

Cells that are targeted for transformation may for example include T cells, Natural Killer (NK) cells, cytotoxic T lymphocytes (CTL), regulatory T cells, human embryonic stem cells, tumor-infiltrating lymphocytes (TIL) or a pluripotent stem cell from which lymphoid cells may be differentiated. T cells expressing a desired CAR may for example be selected through co-culture with γ-irradiated activating and propagating cells (AaPC), which co-express the cancer antigen and co-stimulatory molecules. The engineered CAR T cells may be expanded, for example by co-culture on AaPC in presence of soluble factors, such as IL-2 and IL-21. This expansion may for example be carried out so as to provide memory CAR+ T cells (which may for example be assayed by non-enzymatic digital array and/or multi-panel flow cytometry). In this way, CAR T cells may be provided that have specific cytotoxic activity against antigen-bearing tumors (optionally in conjunction with production of desired chemokines such as interferon-γ). CAR T cells of this kind may for example be used in animal models, for example to treat tumor xenografts.

In certain embodiments, ACT includes co-transferring CD4+ Th1 cells and CD8+ CTLs to induce a synergistic antitumour response (see, e.g., Li et al., Adoptive cell therapy with CD4+ T helper 1 cells and CD8+ cytotoxic T cells enhances complete rejection of an established tumour, leading to generation of endogenous memory responses to non-targeted tumour epitopes. Clin Transl Immunology. 2017 October; 6(10): e160).

In certain embodiments, Th17 cells are transferred to a subject in need thereof. Th17 cells have been reported to directly eradicate melanoma tumors in mice to a greater extent than Th1 cells (Muranski P, et al., Tumor-specific Th17-polarized cells eradicate large established melanoma. Blood. 2008 Jul. 15; 112(2):362-73; and Martin-Orozco N, et al., T helper 17 cells promote cytotoxic T cell activation in tumor immunity. Immunity. 2009 Nov. 20; 31(5):787-98). Those studies involved an adoptive T cell transfer (ACT) therapy approach, which takes advantage of CD4+ T cells that express a TCR recognizing tyrosinase tumor antigen. Exploitation of the TCR leads to rapid expansion of Th17 populations to large numbers ex vivo for reinfusion into the autologous tumor-bearing hosts.

In certain embodiments, ACT may include autologous iPSC-based vaccines, such as irradiated iPSCs in autologous anti-tumor vaccines (see e.g., Kooreman, Nigel G. et al., Autologous iPSC-Based Vaccines Elicit Anti-tumor Responses In Vivo, Cell Stem Cell 22, 1-13, 2018, doi.org/10.1016/j.stem.2018.01.016).

Unlike T-cell receptors (TCRs) that are MHC restricted, CARs can potentially bind any cell surface-expressed antigen and can thus be more universally used to treat patients (see Irving et al., Engineering Chimeric Antigen Receptor T cells for Racing in Solid Tumors: Don't Forget the Fuel, Front. Immunol., 3 Apr. 2017, doi.org/10.3389/fimmu.2017.00267). In certain embodiments, in the absence of endogenous T-cell infiltrate (e.g., due to aberrant antigen processing and presentation), which precludes the use of TIL therapy and immune checkpoint blockade, the transfer of CAR T cells may be used to treat patients (see, e.g., Hinrichs C S, Rosenberg S A. Exploiting the curative potential of adoptive T-cell therapy for cancer. Immunol Rev (2014) 257(1):56-71. doi:10.1111/imr.12132).

Approaches such as the foregoing may be adapted to provide methods of treating and/or increasing survival of a subject having a disease, such as a neoplasia, for example by administering an effective amount of an immunoresponsive cell comprising an antigen recognizing receptor that binds a selected antigen, wherein the binding activates the immunoresponsive cell, thereby treating or preventing the disease (such as a neoplasia, a pathogen infection, an autoimmune disorder, or an allogeneic transplant reaction).

In certain embodiments, the treatment can be administered after lymphodepleting pretreatment in the form of chemotherapy (typically a combination of cyclophosphamide and fludarabine) or radiation therapy. Initial studies in ACT had short lived responses and the transferred cells did not persist in vivo for very long (Houot et al., T-cell-based immunotherapy: adoptive cell transfer and checkpoint inhibition. Cancer Immunol Res (2015) 3(10):1115-22; and Kamta et al., Advancing Cancer Therapy with Present and Emerging Immuno-Oncology Approaches. Front. Oncol. (2017) 7:64). Immune suppressor cells like Tregs and MDSCs may attenuate the activity of transferred cells by outcompeting them for the necessary cytokines. Not being bound by a theory lymphodepleting pretreatment may eliminate the suppressor cells allowing the TILs to persist.

In one embodiment, the treatment can be administrated into patients undergoing an immunosuppressive treatment (e.g., glucocorticoid treatment). The cells or population of cells, may be made resistant to at least one immunosuppressive agent due to the inactivation of a gene encoding a receptor for such immunosuppressive agent. In certain embodiments, the immunosuppressive treatment provides for the selection and expansion of the immunoresponsive T cells within the patient.

In certain embodiments, the treatment can be administered before primary treatment (e.g., surgery or radiation therapy) to shrink a tumor before the primary treatment. In another embodiment, the treatment can be administered after primary treatment to remove any remaining cancer cells.

In certain embodiments, immunometabolic barriers can be targeted therapeutically prior to and/or during ACT to enhance responses to ACT or CAR T-cell therapy and to support endogenous immunity (see, e.g., Irving et al., Engineering Chimeric Antigen Receptor T cells for Racing in Solid Tumors: Don't Forget the Fuel, Front. Immunol., 3 Apr. 2017, doi.org/10.3389/fimmu.2017.00267).

The administration of cells or population of cells, such as immune system cells or cell populations, such as more particularly immunoresponsive cells or cell populations, as disclosed herein may be carried out in any convenient manner, including by aerosol inhalation, injection, ingestion, transfusion, implantation or transplantation. The cells or population of cells may be administered to a patient subcutaneously, intradermally, intratumorally, intranodally, intramedullary, intramuscularly, intrathecally, by intravenous or intralymphatic injection, or intraperitoneally. In some embodiments, the disclosed CARs may be delivered or administered into a cavity formed by the resection of tumor tissue (i.e. intracavity delivery) or directly into a tumor prior to resection (i.e. intratumoral delivery). In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. Dosing in CAR T-cell therapies may for example involve administration of from $10^6$ to $10^9$ cells/kg, with or without a course of lymphodepletion, for example with cyclophosphamide. The cells or population of cells can be administrated in one or more doses. In another embodiment, the effective amount of cells are administrated as a single dose. In another embodiment, the effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions are within the skill of one in the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, the effective amount of cells or composition comprising those cells are administrated parenterally. The administration can be an intravenous administration. The administration can be directly done by injection within a tumor.

To guard against possible adverse reactions, engineered immunoresponsive cells may be equipped with a transgenic safety switch, in the form of a transgene that renders the cells vulnerable to exposure to a specific signal. For example, the herpes simplex viral thymidine kinase (TK) gene may be used in this way, for example by introduction into allogeneic T lymphocytes used as donor lymphocyte infusions following stem cell transplantation (Greco, et al., Improving the safety of cell therapy with the TK-suicide gene. Front. Pharmacol. 2015; 6: 95). In such cells, administration of a nucleoside prodrug such as ganciclovir or acyclovir causes cell death. Alternative safety switch constructs include inducible caspase 9, for example triggered by administration of a small-molecule dimerizer that brings together two nonfunctional icasp9 molecules to form the active enzyme. A wide variety of alternative approaches to implementing cellular proliferation controls have been described (see U.S. Patent Publication No. 20130071414; PCT Patent Publication WO2011146862; PCT Patent Publication WO2014011987; PCT Patent Publication WO2013040371; Zhou et al. BLOOD, 2014, 123/25:3895-3905; Di Stasi et al., The New England Journal of Medicine 2011; 365:1673-1683; Sadelain M, The New England Journal of Medicine 2011; 365:1735-173; Ramos et al., Stem Cells 28(6):1107-15 (2010)).

In a further refinement of adoptive therapies, genome editing may be used to tailor immunoresponsive cells to alternative implementations, for example providing edited CAR T cells (see Poirot et al., 2015, Multiplex genome edited T-cell manufacturing platform for "off-the-shelf" adoptive T-cell immunotherapies, Cancer Res 75 (18): 3853; Ren et al., 2017, Multiplex genome editing to generate universal CAR T cells resistant to PD1 inhibition, Clin Cancer Res. 2017 May 1;23(9):2255-2266. doi: 10.1158/1078-0432.CCR-16-1300. Epub 2016 Nov 4; Qasim et al., 2017, Molecular remission of infant B-ALL after infusion of universal TALEN gene-edited CAR T cells, Sci Transl Med. 2017 Jan. 25; 9(374); Legut, et al., 2018, CRISPR-mediated TCR replacement generates superior anticancer transgenic T cells. Blood, 131(3), 311-322; and Georgiadis et al., Long Terminal Repeat CRISPR-CAR-Coupled "Universal" T Cells Mediate Potent Anti-leukemic Effects, Molecular Therapy, In Press, Corrected Proof, Available online 6 Mar. 2018). Cells may be edited using any CRISPR system and method of use thereof as described herein. CRISPR systems may be delivered to an immune cell by any method described herein. In preferred embodiments, cells are edited ex vivo and transferred to a subject in need thereof. Immunoresponsive cells, CAR T cells or any cells used for adoptive cell transfer may be edited. Editing may be performed for example to insert or knock-in an exogenous gene, such as an exogenous gene encoding a CAR or a TCR, at a preselected locus in a cell (e.g. TRAC locus); to eliminate potential alloreactive T-cell receptors (TCR) or to prevent inappropriate pairing between endogenous and exogenous TCR chains, such as to knock-out or knock-down expression of an endogenous TCR in a cell; to disrupt the target of a chemotherapeutic agent in a cell; to block an immune checkpoint, such as to knock-out or knock-down expression of an immune checkpoint protein or receptor in a cell; to knock-out or knock-down expression of other gene or genes in a cell, the reduced expression or lack of expression of which can enhance the efficacy of adoptive therapies using the cell; to knock-out or knock-down expression of an endogenous gene in a cell, said endogenous gene encoding an antigen targeted by an exogenous CAR or TCR; to knock-out or knock-down expression of one or more MHC constituent proteins in a cell; to activate a T cell; to modulate cells such that the cells are resistant to exhaustion or dysfunction; and/or increase the differentiation and/or proliferation of functionally exhausted or dysfunctional CD8+ T cells (see PCT Patent Publications: WO2013176915, WO2014059173, WO2014172606, WO2014184744, and WO2014191128).

In certain embodiments, editing may result in inactivation of a gene. By inactivating a gene, it is intended that the gene of interest is not expressed in a functional protein form. In a particular embodiment, the CRISPR system specifically catalyzes cleavage in one targeted gene thereby inactivating said targeted gene. The nucleic acid strand breaks caused are commonly repaired through the distinct mechanisms of homologous recombination or non-homologous end joining (NHEJ). However, NHEJ is an imperfect repair process that often results in changes to the DNA sequence at the site of the cleavage. Repair via non-homologous end joining (NHEJ) often results in small insertions or deletions (Indel) and can be used for the creation of specific gene knockouts. Cells in which a cleavage induced mutagenesis event has occurred can be identified and/or selected by well-known methods in the art. In certain embodiments, homology directed repair (HDR) is used to concurrently inactivate a gene (e.g., TRAC) and insert an endogenous TCR or CAR into the inactivated locus.

Hence, in certain embodiments, editing of cells (such as by CRISPR/Cas), particularly cells intended for adoptive cell therapies, more particularly immunoresponsive cells such as T cells, may be performed to insert or knock-in an exogenous gene, such as an exogenous gene encoding a CAR or a TCR, at a preselected locus in a cell. Conventionally, nucleic acid molecules encoding CARs or TCRs are transfected or transduced to cells using randomly integrating vectors, which, depending on the site of integration, may lead to clonal expansion, oncogenic transformation, variegated transgene expression and/or transcriptional silencing of the transgene. Directing of transgene(s) to a specific locus in a cell can minimize or avoid such risks and advantageously provide for uniform expression of the transgene(s) by the cells. Without limitation, suitable 'safe harbor' loci for directed transgene integration include CCR5 or AAVS1. Homology-directed repair (HDR) strategies are known and described elsewhere in this specification allowing to insert transgenes into desired loci (e.g., TRAC locus).

Further suitable loci for insertion of transgenes, in particular CAR or exogenous TCR transgenes, include without limitation loci comprising genes coding for constituents of endogenous T-cell receptor, such as T-cell receptor alpha locus (TRA) or T-cell receptor beta locus (TRB), for example T-cell receptor alpha constant (TRAC) locus, T-cell receptor beta constant 1 (TRBC1) locus or T-cell receptor beta constant 2 (TRBC1) locus. Advantageously, insertion of a transgene into such locus can simultaneously achieve expression of the transgene, potentially controlled by the endogenous promoter, and knock-out expression of the endogenous TCR. This approach has been exemplified in Eyquem et al., (2017) Nature 543: 113-117, wherein the authors used CRISPR/Cas9 gene editing to knock-in a DNA molecule encoding a CD19-specific CAR into the TRAC locus downstream of the endogenous promoter; the CAR T cells obtained by CRISPR were significantly superior in terms of reduced tonic CAR signaling and exhaustion.

T-cell receptors (TCR) are cell surface receptors that participate in the activation of T cells in response to the presentation of antigen. The TCR is generally made from two chains, $\alpha$ and $\beta$, which assemble to form a heterodimer and associates with the CD3-transducing subunits to form the T-cell receptor complex present on the cell surface. Each $\alpha$ and $\beta$ chain of the TCR consists of an immunoglobulin-like N-terminal variable (V) and constant (C) region, a hydrophobic transmembrane domain, and a short cytoplasmic region. As for immunoglobulin molecules, the variable region of the $\alpha$ and $\beta$ chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction.

Recognition of MHC disparities between the donor and recipient through the T-cell receptor leads to T cell proliferation and the potential development of graft versus host disease (GVHD). The inactivation of TCRα or TCRβ can result in the elimination of the TCR from the surface of T cells preventing recognition of alloantigen and thus GVHD. However, TCR disruption generally results in the elimination of the CD3 signaling component and alters the means of further T cell expansion.

Hence, in certain embodiments, editing of cells (such as by CRISPR/Cas), particularly cells intended for adoptive cell therapies, more particularly immunoresponsive cells such as T cells, may be performed to knock-out or knock-down expression of an endogenous TCR in a cell. For example, NHEJ-based or HDR-based gene editing approaches can be employed to disrupt the endogenous TCR alpha and/or beta chain genes. For example, gene editing system or systems, such as CRISPR/Cas system or systems, can be designed to target a sequence found within the TCR beta chain conserved between the beta 1 and beta 2 constant region genes (TRBC1 and TRBC2) and/or to target the constant region of the TCR alpha chain (TRAC) gene.

Allogeneic cells are rapidly rejected by the host immune system. It has been demonstrated that allogeneic leukocytes present in non-irradiated blood products will persist for no more than 5 to 6 days (Boni, Muranski et al. 2008 Blood 1;112(12):4746-54). Thus, to prevent rejection of allogeneic cells, the host's immune system usually has to be suppressed to some extent. However, in the case of adoptive cell transfer the use of immunosuppressive drugs also have a detrimental effect on the introduced therapeutic T cells. Therefore, to effectively use an adoptive immunotherapy approach in these conditions, the introduced cells would need to be resistant to the immunosuppressive treatment. Thus, in a particular embodiment, the present invention further comprises a step of modifying T cells to make them resistant to an immunosuppressive agent, preferably by inactivating at least one gene encoding a target for an immunosuppressive agent. An immunosuppressive agent is an agent that suppresses immune function by one of several mechanisms of action. An immunosuppressive agent can be, but is not limited to a calcineurin inhibitor, a target of rapamycin, an interleukin-2 receptor α-chain blocker, an inhibitor of inosine monophosphate dehydrogenase, an inhibitor of dihydrofolic acid reductase, a corticosteroid or an immunosuppressive antimetabolite. The present invention allows conferring immunosuppressive resistance to T cells for immunotherapy by inactivating the target of the immunosuppressive agent in T cells. As non-limiting examples, targets for an immunosuppressive agent can be a receptor for an immunosuppressive agent such as: CD52, glucocorticoid receptor (GR), a FKBP family gene member and a cyclophilin family gene member.

In certain embodiments, editing of cells (such as by CRISPR/Cas), particularly cells intended for adoptive cell therapies, more particularly immunoresponsive cells such as T cells, may be performed to block an immune checkpoint, such as to knock-out or knock-down expression of an immune checkpoint protein or receptor in a cell. Immune checkpoints are inhibitory pathways that slow down or stop immune reactions and prevent excessive tissue damage from uncontrolled activity of immune cells. In certain embodiments, the immune checkpoint targeted is the programmed death-1 (PD-1 or CD279) gene (PDCD1). In other embodiments, the immune checkpoint targeted is cytotoxic T-lymphocyte-associated antigen (CTLA-4). In additional embodiments, the immune checkpoint targeted is another member of the CD28 and CTLA4 Ig superfamily such as BTLA, LAG3, ICOS, PDL1 or KIR. In further additional embodiments, the immune checkpoint targeted is a member of the TNFR superfamily such as CD40, OX40, CD137, GITR, CD27 or TIM-3.

Kits

Any of the compounds, compositions, formulations, particles, cells, described herein or a combination thereof can be presented as a combination kit. As used herein, the terms "combination kit" or "kit of parts" refers to the compounds, compositions, formulations, particles, cells and any additional components that are used to package, sell, market, deliver, and/or administer the combination of elements or a single element, such as the active ingredient, contained therein. Such additional components include, but are not limited to, packaging, syringes, blister packages, bottles, and the like. When one or more of the compounds, compositions, formulations, particles, cells, described herein or a combination thereof (e.g., agents) contained in the kit are administered simultaneously, the combination kit can contain the active agents in a single formulation, such as a pharmaceutical formulation, (e.g., a tablet) or in separate formulations. When the compounds, compositions, formulations, particles, and cells described herein or a combination thereof and/or kit components are not administered simultaneously, the combination kit can contain each agent or other component in separate pharmaceutical formulations. The separate kit components can be contained in a single package or in separate packages within the kit.

In some embodiments, the combination kit also includes instructions printed on or otherwise contained in a tangible medium of expression. The instructions can provide information regarding the content of the compounds, compositions, formulations, particles, cells, described herein or a combination thereof contained therein, safety information regarding the content of the compounds, compositions, formulations (e.g., pharmaceutical formulations), particles, and cells described herein or a combination thereof contained therein, information regarding the dosages, indications for use, and/or recommended treatment regimen(s) for the compound(s) and/or pharmaceutical formulations contained therein. In some embodiments, the instructions can provide directions for administering the compounds, compositions, formulations, particles, and cells described herein or a combination thereof to a subject in need thereof. In some embodiments, the subject in need thereof can be in need of a treatment or prevention of a hematopoietic malignancy or a relapse thereof. The hematopoietic malignancies may be any of lymphoid malignancies comprising B-cell ALL, T-cell ALL, chronic lymphoblastic leukemia (CLL), diffuse large B-cell lymphoma, follicular lymphoma, Burkitt's lymphoma, mantle cell lymphoma, marginal zone lymphoma, T-cell lymphoma, multiple myeloma, Hodgkin's lymphoma, and any other types of malignancies derived from lymphoid lineage. In some embodiments, the methods disclosed herein for predicting the risk of relapse can be used for any of the subtypes of the aforementioned lymphoid malignancies. In some embodiments, the hematopoietic malignancies can be any of myeloid malignancies comprising chronic myeloid leukemia (CML), acute myeloid leukemia (AML), myelodysplastic syndromes (MDS), myeloproliferative diseases (MPD), chronic neutrophilic leukemia, chronic eosinophilic leukemia, polycythemia vera, chronic idiopathic myelofibrosis, essential thrombocythemia, chronic myeloproliferative disease (unclassifiable), refractory anemia, refractory cytopenia with multilineage dysplasia (RCMD), mastocytosis, and any other types of malignancies derived from myeloid lineage. In some embodiments, the methods disclosed herein for predicting the risk of relapse can be used for any of the subtypes of the aforementioned myeloid malignancies. In certain example embodiments, the hematopoietic malignancy is an acute lymphoblastic leukemia (ALL). In certain example embodiments, the ALL is a B-cell ALL.

In some embodiments, the instructions provide that the subject in need thereof has or is suspected of having a hematopoietic disease, such as a hematopoietic malignancy or relapse, or a symptom thereof. In some embodiments, the instructions provide that the subject is identified, such as by using a method described in greater detail elsewhere herein, as having a high risk of a hematopoietic malignancy relapse. In some embodiments, the instructions provide that the subject in need thereof is in the acute response phase of a treatment for a hematopoietic malignancy. In some embodiments, the subject in need thereof is in the MRD phase of a hematopoietic malignancy.

In some embodiments, the instructions provide direction to identify a subject as being at a high risk for relapse and/or having early-onset of relapse of a hematopoietic malignancy when a plurality of cells from a suitable sample has (a) an average cellular mass less than a defined threshold; (b) when one or more cells from the plurality of cells has a cycling signature characterized by high pre-BCR score; (c) when one or more cells from the plurality of cells have one or more mutations in KRAS and/or NRAS genes indicate a high risk and/or early-onset of relapse; or (d) a combination thereof. In some embodiments, the instructions provide that the threshold for an average cell mass for a high risk individual is between 0-20 pg, between 5-20 pg, or between 10-20 pg.

In some embodiments, the instructions provide direction to identify a subject as being at low risk for relapse and/or having late-onset of relapse a hematopoietic malignancy when a plurality of cells from a suitable sample has (a) an average cellular mass equal to or greater than a defined threshold; (b) when one or more cells from the plurality of cells has a quiescent signature characterized by high TNF-a/NF-kB score and/or low HSF1/p38 score; (c) when one or more cells in the plurality of cells has one or more mutations in the ABL1 gene; or (d) a combination thereof. n some embodiments, the instructions provide that the threshold for an average cell mass for a low risk individual is between 20-80 pg, 20-60 pg, or 20-35 pg.

In some embodiments, the instructions provide direction to administer one or more BCR-ABL tyrosine kinase inhibitors or a pharmaceutical formulation thereof; one or more pre-BCR signaling pathway inhibitors or a pharmaceutical formulation thereof; one or more p38 MAPK inhibitors or a pharmaceutical formulation thereof; or any combination thereof to a subject in need thereof. In some embodiments, the instructions provide that the subject in need thereof is identified as being at high risk for hematopoietic malignancy relapse or at risk or having early-onset relapse. In some embodiments, the instructions provide direct to administer one or more BCR-ABL tyrosine kinase inhibitors and one or more pre-BCR or p38 MAPK inhibitors to a subject having a hematopoietic malignancy or being at risk for relapse.

In some embodiments, the instructions provide direction to administer an anti-CD20 molecule to the subject in need thereof as a co-therapy to the BCR-ABL tyrosine kinase inhibitor, the pre-BCR inhibitor, and/or the p38 MAPK inhibitor.

Further embodiments are illustrated in the following Examples which are given for illustrative purposes only and are not intended to limit the scope of the invention.

EXAMPLES

Example 1-Methods for Measuring Cellular Mass

This example describes the methods for measuring cellular mass of leukemic cells, a biophysical property used for composing an MRD module.

Leukemic cells are prepared from peripheral blood or bone marrow as previously described (Fisher I N et al. Transforming activities of the NUP98-KMT2A fusion gene associated with myelodysplasia and acute myeloid leukemia. Haematologica. 2019 Sep 26. pii: haematol.2019.219188. doi: 10.3324/haematol.2019.219188). For all experiments, cells were adjusted to a final concentration of $2.5 \times 10^5$ cells/mL to load single cells into the mass sensor array. Single-cell growth measurements were conducted as described previously (Kimmerling et al. Genome Biology 2018, 19:207) (FIG. 1). In order to exchange buffer and flush individual cells from the system, the release side of the device was constantly flushed with PBS at a rate of 15 µL per minute. Upon detection of a single-cell at the final cantilever of the serial SMR (sSMR), as indicated by a supra-threshold shift in resonant frequency, a set of three-dimensional motorized stages was triggered to move a custom PCR-tube strip mount from a waste collection position to a sample collection position. The location of these motors was written to a file for the duration of the experiment in order to annotate single-cell mass with well position, and thus transcriptional profiles, downstream. Each cell was collected in 5 µl of PBS directly in to a PCR tube containing 5 µl of 2× TCL lysis buffer (Qiagen) with 2% v/v 2-mercaptoethanol (Sigma) for a total final reaction volume of 10 1 µl. After each 8-tube PCR strip was filled with cells, the strip was spun down at 1000 g for 30 s and placed immediately on dry ice. Following collection, samples were stored at −80° C. prior to library preparation and scRNA sequencing.

Example 2—Measurement of Gene Transcription of Leukemic Cells

This example describes the methods of measuring gene transcription of leukemic cells at single-cell level that can be used for predicting the risk of relapse of B-cell ALL.

Leukemic cells with cellular mass determined are collected at the single-cell level and subjected to scRNA sequencing as described previously (Kimmerling et al. Genome Biology 2018, 19:207 Page 9 of 13). Gene expression analysis is performed on log-transformed expression level measurements (ln(TPM+1)). Data pre-processing was conducted with the Seurat package for R (Satija R, Farrell J A, Gennert D, Schier A F, Regev A. Spatial reconstruction of single-cell gene expression data. Nat Biotechnol. 2015; 33:495-U206). All genes that were detected in >5% of cells were included in the final analysis for each group of cells. To define the null distribution of correlation coefficients, the applicants determined the Spearman correlation between cell cycle gene expression levels, quiescent gene expression levels, and senescence/stemness gene expression levels and cellular mass for randomly shuffled data sampled from the experimental values (i.e., mismatching single-cell mass and gene expression data). After 10,000 iterations, the applicants used the average mean and standard deviation values of these correlation coefficient distributions to define the null distributions presented. The applicants computed the null distributions for the correlation coefficients between cellular mass and the principal components for each leukemic cell's transcriptomic data sets using a similar random shuffling of PC coordinates across single-cells. Following 10,000 iterations, the mean and standard deviation of these distributions were compared to the correlation of each biophysical parameter with all significant principal components (PCs). For each data set, the PCElbow plot and jackstraw functions in Seurat were used to select significant PCs whose explained variation preceded a precipitous drop in cumulative explained variation (elbow). In each data set, for consistency, the top 10 PCs were investigated, although in some cases fewer than 10 PCs preceded the elbow. Correlation coefficients were deemed insignificant if they were within two standard deviations of the mean determined from random shuffling.

Figure 10:
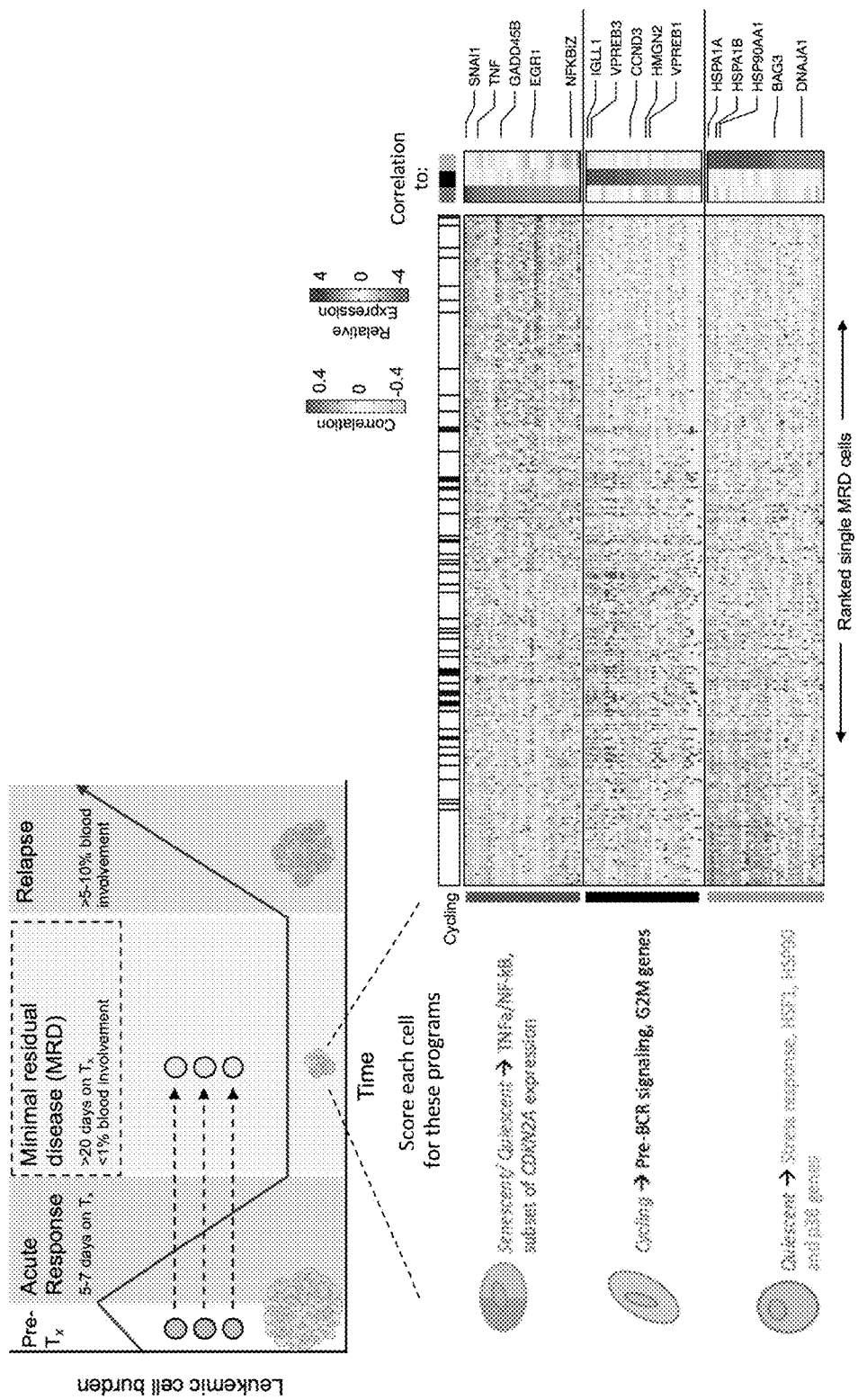
FIG. 10—Three common gene expression programs at MRD. Three consensus gene expression programs at MRD are shown. Also shown are representative genes for each program.
Figure 11:
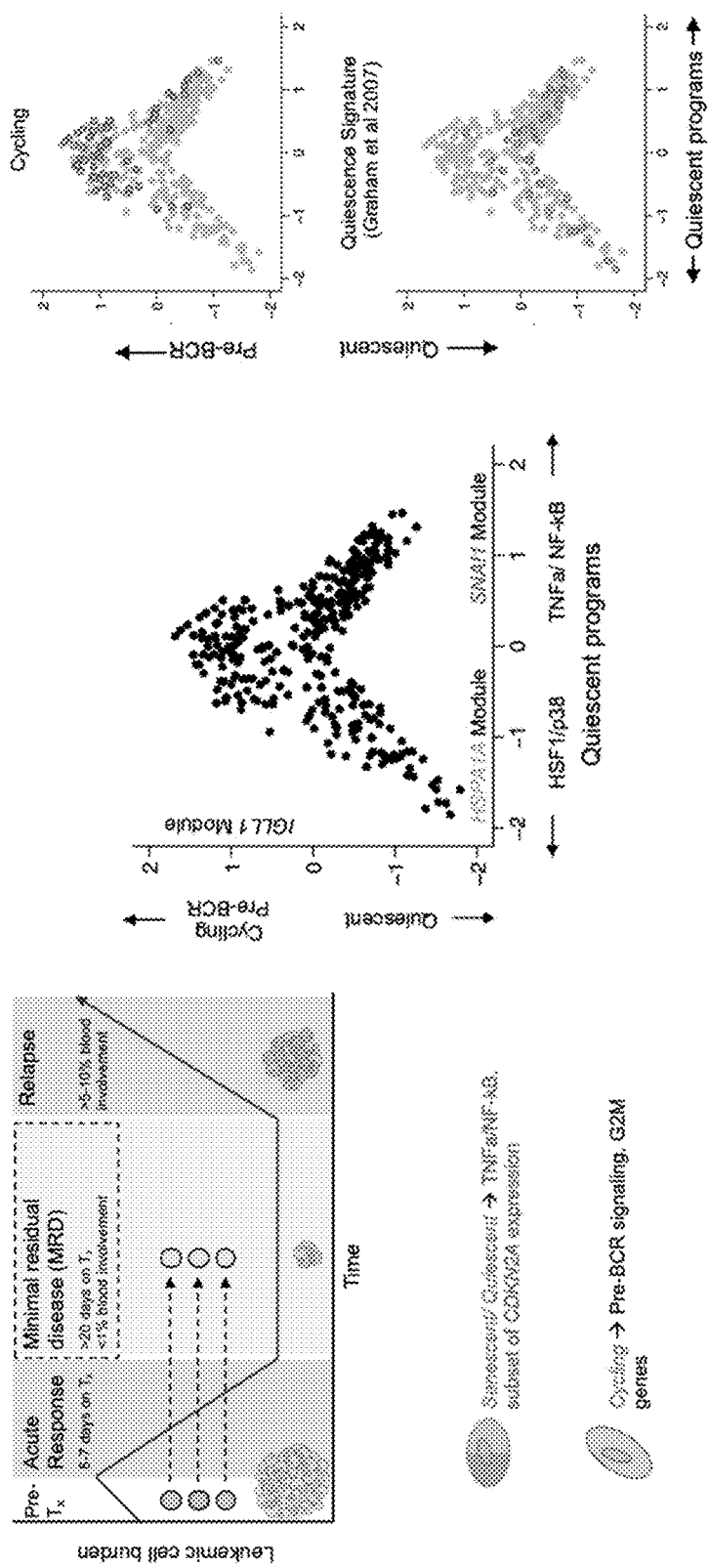
FIG. 11—Distribution of leukemic cells among the three gene expression programs at MRD. Leukemic cells with high scores of cycling prgram (pre-BCR pathway activity), high scores of senescence/stemness (quiescent) program (TNFa/NF-kB), and high scores of stress response program (HSF1/p38) are shown.
Figure 12:
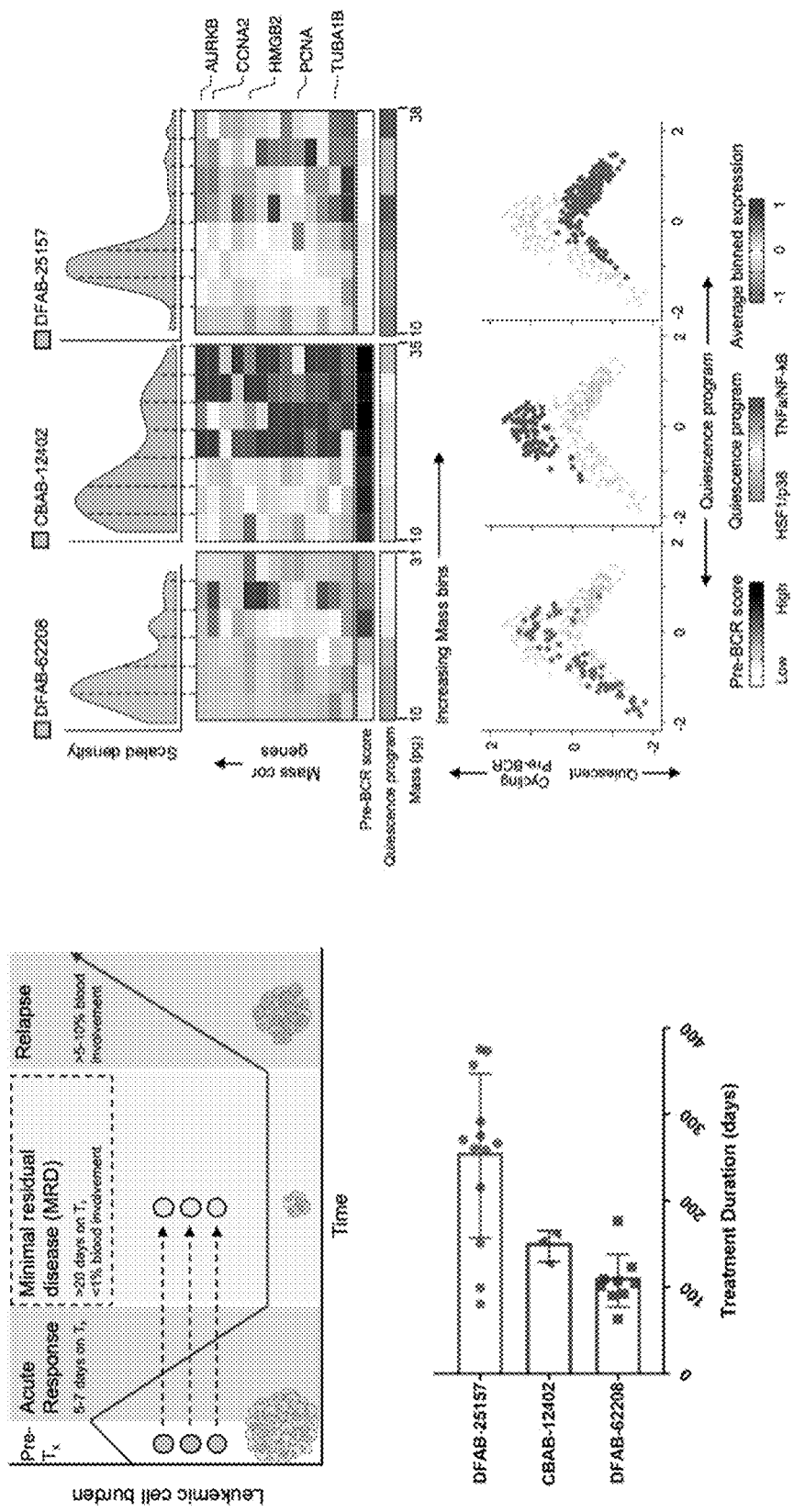
FIG. 12—Distinct MRD modules for three different PDX models. B-cell ALL leukemic cells from bone marrow obtained from three PDX mouse models show distinct MRD modules. DFAB-25157 has an MRD Module A (green, high sore of senescence/stemness score). CBAB-12402 has an MRD Module B (blue, high score of cycling/pre-BCR). DFAB-62208 has an MRD Module C (purple, high score of stress response program).
Figure 13A:
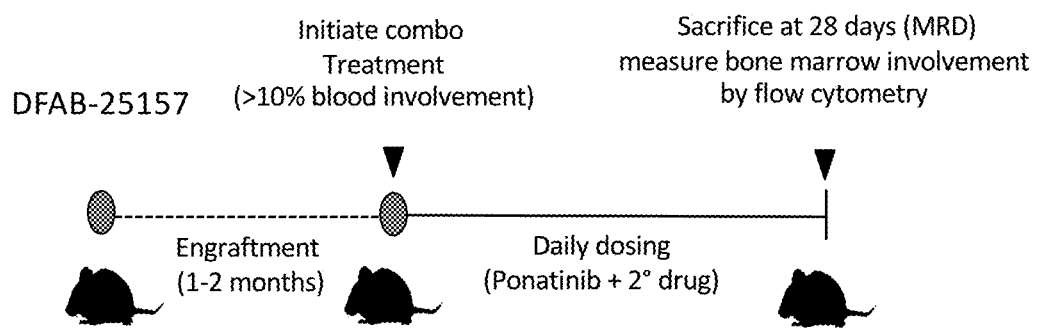
FIGS. 13A-13D—MRD expression states can be targeted to reduce leukemic burden.
Figure 13B:
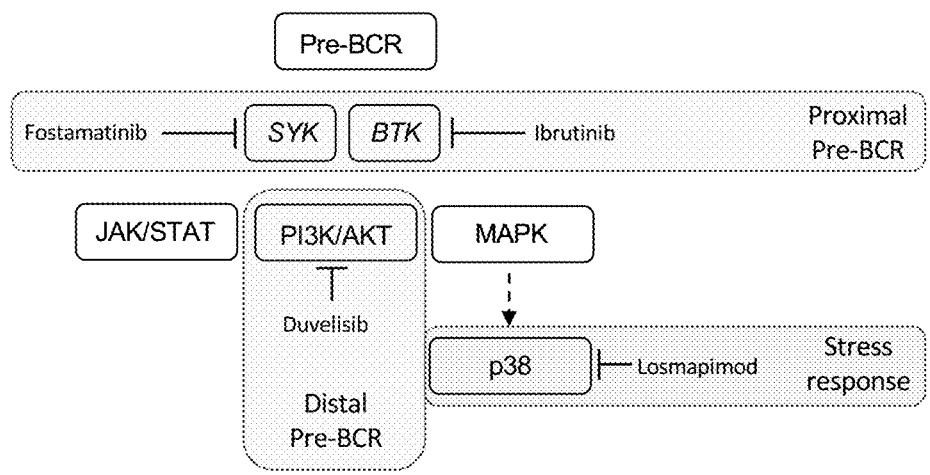
Figure 13C:
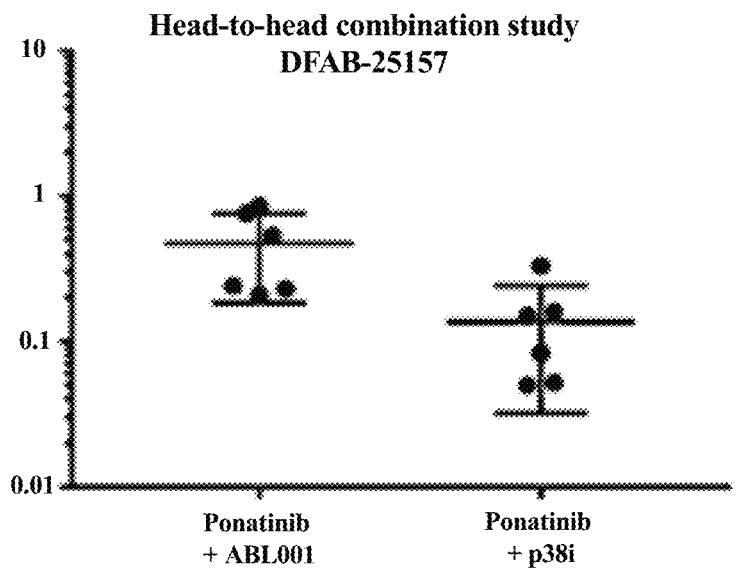
Figure 13D:
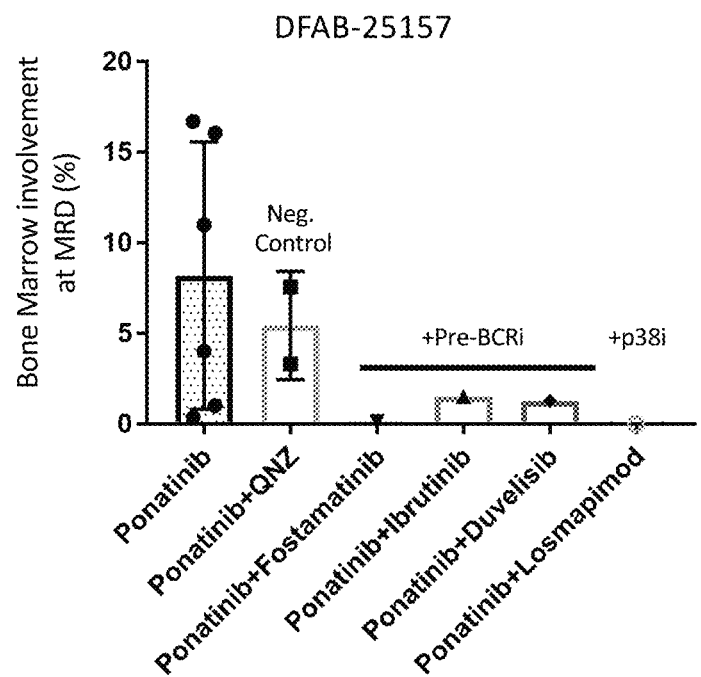

Based on the measurements of gene expression levels, leukemic cells with high expression levels of TNF-alpha, NF-kB, and CDKN2A are classified into quiescent program. Leukemic cells with high pre-BCR score as well as high expression levels of IGLL1, VPREB3, CCND3, HMGN2, VPREB1, AURKB, CCNA2, HMGB2, PCNA, and TUBA1B are classified into cycling program. Leukemic cells with high expression levels of HSPA1A, HSPA1B, HSP90AA1, BAG3, and DNAJA1 are classified into stress response program. (FIGS. 10, 11, 12).

Example 3—Calculation of Scores for Pre-BCR, HSF1/p38, and TNF-α/NF-kB Signaling pathways The pre-BCR, HSF1/p38, and TNF-α/NF-kB scores are calculated as the average relative expression of the gene set in each signaling pathway minus the average relative expression of a control gene set as described in Tirosh et al., Nature 2016, 539:309-313. Briefly, the score is calculated as $X_{i,j}$=average$[Er(G_{j,i})]$−average$[Er(Gj^{cont},i)]$ where $X_{i,j}$ is the score of cell i for pathway j, Er is relative expression, Gj is the gene set for pathway j, and $Gj^{cont}$ is a control gene set for the pathway j. The control gene set was defined by first binning all 8,008 analyzed genes into 25 bins of aggregate expression levels and then, for each gene in the lineage gene set, randomly selecting 100 genes from the same expression bin. In this way, the control gene set has a comparable distribution of expression levels to that of the lineage gene set and the control gene set is 100-fold larger, such that its average expression is analogous to averaging over 100 randomly selected gene sets of the same size as the lineage gene set. The final pathway score of each cell was defined as the maximal score over the three pathways, $X_i$=max($X_i$ pre-BCR, $X_i$ HSF1/p38, $X_i$ TNF-a/NF-kB). For visualization purposes where the p38/HSF and TNF-α/NF-kB scores are shown in a single axis, random scores within (0-0.15) were first assigned to all cells with X<0, to avoid having many overlapping cells at x=0. Second, negative scores were assigned to the cells with higher TNF-a/NF-kB than HSF/p38 scores (that is, a cell with TNF-a/NF-kB and HSF1/p38 scores of 0.1 and 1, respectively, would be assigned a lineage score of 1, whereas a cell with TNF-a/NF-kB and HSF1/p38 scores of 1 and 0.1 would be assigned a lineage score of −1).

Example 4—Methods for Treating B-Cell ALL

This example describes methods of using combination therapies for treating B-cell ALL.

PDX mice models for B-cell ALL are prepared as previously reported (Yang L. et al., Purinostat Mesylate is a uniquely potent and selective inhibitor of HDACs for the treatment of BCR-ABL-induced B-cell acute lymphoblastic leukemia. Clin Cancer Res. 2019 pii: clincanres.0516.2019. doi: 10.1158/1078-0432.CCR-19-0516). Mice are treated with ponatinib alone, ponatinib in combination with QNZ (a TNF-alpha inhibitor), ponatinib in combination with fostamatinib (a proximal pre-BCR pathway inhibitor), ponatinib in combination with ibrutinib (a proximal pre-BCR pathway inhibitor), ponatinib in combination with duvelisib (a distal pre-BCR inhibitor), or ponatinib in combination with losmapimod (a p38 MAPK inhibitor) for 28 days. Bone marrow aspirates are obtained, and leukemic cells are isolated using conventional Ficoll centrifugation and FACS sorting methods. The leukemic cells are counted as bone marrow involvement at MRD, and it is compared to that before treatment. The reduction of leukemic cells (%) as a result of the treatments is used as treatment efficacy.

The results show that ponatinib monotherapy has an 8% of bone marrow involvement at MRD (FIG. 13). The combination therapy of ponatinib and QNZ has a 5% of bone marrow involvement at MRD (FIG. 13). Surprisingly, the combination therapy of ponatinib and fostamatinib has completely killed leukemic cells in bone marrow. No leukemic cells can be detected in the bone marrow of mice treated with this combination therapy (FIG. 13). Similarly, the combination therapy of ponatinib and p38 MAPK inhibitor losmapimod also produce a complete remission with no leukemic cells being detectable in the bone marrow at MRD (FIG. 13). The combination therapies of ponatinib and ibrutinib or duvelisib result in a substantial reduction in bone marrow involvement at MRD (FIG. 13).

In a head-to-head comparison study, B-cell ALL PDX mice are treated with either a combination of ponatinib and ABL001 (a BCR-ABL1 kinase inhibitor targeting myristate binding site) or a combination of ponatinib and p38 MAPK inhibitor losmapimod. The bone marrow leukemic cells at MRD are counted as described above. The results show that the bone marrow from mice treated with ponatinib and p38 MAPK inhibitor losmapimod has substantially lesser number of leukemic cells than that from mice treated with ponatinib and ABL001 (FIG. 13).

REFERENCES

The following references apply to the above descriptions and examples are incorporated herein by reference:

Godin M, Delgado F F, Son S, Grover W H, Bryan A K, Tzur A, Jorgensen P, Payer K, Grossman A D, Kirschner M W, Manalis S R. Using buoyant mass to measure the growth of single cells. Nat Methods. 2010 May; 7(5):387-90. doi: 10.1038/nmeth.1452. Epub 2010 Apr 11.

U.S. Pat. No. 9,134,294. Method and apparatus for high throughput diagnosis of diseased cells with microchannel devices.

U.S. Pat. No. 9,027,388. Method and apparatus for measuring particle characteristics through mass detection.

Yinghui Guan, Brigitte Gerhard and Donna E. Hogge Detection, isolation, and stimulation of quiescent primitive leukemic progenitor cells from patients with acute myeloid leukemia (AML) doi: https://doi.org/10.1182/blood-2002-10-3062.

Trombetta J J, Gennert D, Lu D, Satija R, Shalek A K, Regev A. Preparation of Single-Cell RNA-Seq Libraries for Next Generation Sequencing. Curr Protoc Mol Biol. 2014,107:4.22.1-17. doi: 10.1002/0471142727.mb0422s107.

Satija R, Farrell J A, Gennert D, Schier A F, Regev A. Spatial reconstruction of single-cell gene expression data. Nat Biotechnol. 2015 May; 33(5):495-502. doi: 10.1038/nbt.3192.

Hsu P D, Lander E S, Zhang F. Development and applications of CRISPR-Cas9 for genome engineering. Cell. 2014 Jun. 5; 157(6):1262-78. doi: 10.1016/j.cell.2014.05.010.

Fisher I N, Thanasopoulou A, Juge S, Tzankov A, Bagger F O, Mendez M A, Peters A H F M, Schwaller J. Transforming activities of the NUP98-KMT2A fusion gene associated with myelodysplasia and acute myeloid leukemia. Haematologica. 2019 Sep 26. pii: haematol.2019.219188. doi: 10.3324/haematol.2019.219188.

Yang L, Qiu Q, Tang M, Wang F, Yi Y, Yi D, Yang Z, Zhu Z, Zheng S, Yang J, Pei H, Zheng L, Chen Y, Gou L, Luo L, Deng X, Ye H, Hu Y, Niu T, Chen L. Purinostat Mesylate is a uniquely potent and selective inhibitor of HDACs for the treatment of BCR-ABL-induced B-cell acute lymphoblastic leukemia. Clin Cancer Res. 2019 pii: clincanres.0516.2019. doi: 10.1 158/1078-0432.CCR-19-0516.

Kimmerling R J, Prakadan S M, Gupta A J, Calistri N L, Stevens M M, Olcum S, Cermak N, Drake R S, Pelton K, De Smet F, Ligon K L, Shalek A K, Manalis S R. Linking single-cell measurements of mass, growth rate, and gene expression. Genome Biol. 2018 Nov. 27; 19(1):207. doi: 10.1186/s13059-018-1576-0.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method of treating or preventing hematopoietic malignancy relapse in a subject in need thereof, comprising:
   (a) prognosing hematopoietic malignancy relapse in the subject in need thereof by determining an average cellular mass of the plurality of cells using the cellular mass of each individual cell of the plurality of cells, wherein an average cellular mass equal to or greater than a defined threshold indicates a low risk of hematopoietic malignancy relapse and an average cellular mass less than a defined threshold indicates a high risk of hematopoietic malignancy relapse; and
   administering, to a subject in need thereof of having a high risk of early onset hematopoietic malignancy relapse a therapeutically effective amount of
   (i) one or more BCR-ABL tyrosine kinase inhibitors or a pharmaceutical formulation thereof,
   (ii) one or more pre-BCR signaling pathway inhibitors or a pharmaceutical formulation thereof;
   (iii) one or more p38 MAPK inhibitors or a pharmaceutical formulation thereof; or
   (iv) any combination thereof.

2. The method of claim 1, wherein determining the average cellular mass of the plurality of cells comprises measuring a cellular mass of each individual cell in the plurality of cells and calculating an average cellular mass of the plurality cells based on the measured cellular mass of each of the individual cells in the plurality of cells.

3. The method of claim 2, wherein the cellular mass of each individual cell is measured using a suspended microchannel resonator.

4. The method of claim 1, wherein
   (a) an average cellular mass of 20-80 pg indicates a low risk of relapse, and an average cellular mass between about 0-20 pg indicates a high risk of relapse;

(b) an average cellular mass of 20-60 pg indicates a low risk of relapse, and an average cellular mass between about 5-20 pg indicates a high risk of relapse; or
(c) an average cellular mass of 20-35 pg indicates a low risk of relapse, and an average cellular mass between about 10-20 pg indicates a high risk of relapse.

5. The method of claim 1, wherein the hematopoietic malignancy is a B-cell malignancy, a T-cell malignancy, or a myeloid-cell malignancy.

6. The method of claim 5, wherein the hematopoietic malignancy is acute lymphoblastic leukemia (ALL), chronic myeloid leukemia (CML), or both.

7. The method of claim 6, wherein the ALL is B-cell ALL.

8. The method of claim 7, wherein one or more B-cell ALL cells have a BCR-ABL translocation.

9. The method of claim 1, wherein
(a) the one or more BCR-ABL tyrosine kinase inhibitors comprise imatinib, dasatinib, nilotinib, bosutinib, ponatinib, bafetinib, rebastinib, tozasertib, danusertib, HG-7-85-01, GNF-2, GNF-5, Compound 2, asciminib, or a combination thereof;
(b) the one or more pre-BCR signaling inhibitors comprise fostamatinib, ibrutinib, duvelisib, idelalisib, dasatinib, entospletinib, cerdulatinib, TAK-659, RG7666, apitolisib, LY3023414, gedatolisib, bimiralisib, SF-1126, copanlisib, buparlisib, tenalisib, taselisib, KA2237, alpelisib, parsaclisib, umbralisib, fimepinostat, rigosertib, dactolisib, BGT-226, DS-7423, PF-04691502, PKI-179, pictilisib, PX-866, TG100-115, AZD8835, WX-037, a genetic modifying agent capable of inhibiting or deleting one or more components of the pre-BCR signaling pathway, or a combination thereof;
(c) the one or more p38 MAPK inhibitors comprise losmapimod, talmapimod, SB203580, VX-702, VX-745, pamapimod, dilmapimod, doramapimod, BMS-582949, ARRY-797, PH797804, SCIO-469, SD-0006, AMG-548, ralimetinib (LY2228820), SB239063, Skepinone-L, SB202190, TAK715, a genetic modifying agent capable of inhibiting or deleting one or more components of the p38 signaling pathway, or a combination thereof; or
(d) any combination thereof.

10. The method of claim 1, wherein the sample is obtained from peripheral blood or bone marrow of the subject in need thereof.

11. The method of claim 1, wherein the subject in need thereof is in the minimal residual disease phase of the hematopoietic malignancy.

* * * * *

SEQUENCE LISTING

```
<160> NUMBER OF SEQ ID NOS: 29

<210> SEQ ID NO 1
<211> LENGTH: 5
<212> TYPE: PRT
<213> ORGANISM: Artificial Sequence
<220> FEATURE:
<223> OTHER INFORMATION: Synthetic

<400> SEQUENCE: 1

Asn Gly Arg Arg Thr
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic

<400> SEQUENCE: 2

Asn Gly Arg Arg Asn
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic

<400> SEQUENCE: 3

Asn Asn Asn Asn Gly Ala Thr Thr
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic
```

<400> SEQUENCE: 4

Asn Asn Asn Asn Arg Tyr Ala Cys
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

Asn Asn Ala Gly Ala Ala Trp
1               5

<210> SEQ ID NO 6
<211> LENGTH: 4
<212> TYPE: PRT
<213> ORGANISM: Artificial Sequence
<220> FEATURE:
<223> OTHER INFORMATION: Synthetic

<400> SEQUENCE: 6

Thr Thr Thr Val
1

<210> SEQ ID NO 7
<211> LENGTH: 4
<212> TYPE: PRT
<213> ORGANISM: Artificial Sequence
<220> FEATURE:
<223> OTHER INFORMATION: Synthetic

<400> SEQUENCE: 7

Thr Thr Cys Asn
1

<210> SEQ ID NO 8
<211> LENGTH: 288
<212> TYPE: PRT
<213> ORGANISM: Artificial Sequence
<220> FEATURE:
<223> OTHER INFORMATION: Synthetic

<400> SEQUENCE: 8

Met Asp Pro Ile Arg Ser Arg Thr Pro Ser Pro Ala Arg Glu Leu Leu
1               5                   10                  15

Ser Gly Pro Gln Pro Asp Gly Val Gln Pro Thr Ala Asp Arg Gly Val
            20                  25                  30

Ser Pro Pro Ala Gly Gly Pro Leu Asp Gly Leu Pro Ala Arg Arg Thr
        35                  40                  45

Met Ser Arg Thr Arg Leu Pro Ser Pro Ala Pro Ser Pro Ala Phe
    50                  55                  60

Ser Ala Asp Ser Phe Ser Asp Leu Leu Arg Gln Phe Asp Pro Ser Leu
65                  70                  75                  80

Phe Asn Thr Ser Leu Phe Asp Ser Leu Pro Pro Phe Gly Ala His His
                85                  90                  95

Thr Glu Ala Ala Thr Gly Glu Trp Asp Glu Val Gln Ser Gly Leu Arg
            100                 105                 110

Ala Ala Asp Ala Pro Pro Pro Thr Met Arg Val Ala Val Thr Ala Ala
        115                 120                 125

```
Arg Pro Pro Arg Ala Lys Pro Ala Pro Arg Arg Ala Ala Gln Pro
    130                 135                 140

Ser Asp Ala Ser Pro Ala Ala Gln Val Asp Leu Arg Thr Leu Gly Tyr
145                 150                 155                 160

Ser Gln Gln Gln Glu Lys Ile Lys Pro Lys Val Arg Ser Thr Val
            165                 170                 175

Ala Gln His His Glu Ala Leu Val Gly His Gly Phe Thr His Ala His
            180                 185                 190

Ile Val Ala Leu Ser Gln His Pro Ala Leu Gly Thr Val Ala Val
            195                 200                 205

Lys Tyr Gln Asp Met Ile Ala Ala Leu Pro Glu Ala Thr His Glu Ala
210                 215                 220

Ile Val Gly Val Gly Lys Gln Trp Ser Gly Ala Arg Ala Leu Glu Ala
225                 230                 235                 240

Leu Leu Thr Val Ala Gly Glu Leu Arg Gly Pro Pro Leu Gln Leu Asp
                245                 250                 255

Thr Gly Gln Leu Leu Lys Ile Ala Lys Arg Gly Val Thr Ala Val
            260                 265                 270

Glu Ala Val His Ala Trp Arg Asn Ala Leu Thr Gly Ala Pro Leu Asn
            275                 280                 285
```

<210> SEQ ID NO 9
<211> LENGTH: 183
<212> TYPE: PRT
<213> ORGANISM: Artificial Sequence
<220> FEATURE:
<223> OTHER INFORMATION: Synthetic

<400> SEQUENCE: 9

```
Arg Pro Ala Leu Glu Ser Ile Val Ala Gln Leu Ser Arg Pro Asp Pro
1               5                   10                  15

Ala Leu Ala Ala Leu Thr Asn Asp His Leu Val Ala Leu Ala Cys Leu
                20                  25                  30

Gly Gly Arg Pro Ala Leu Asp Ala Val Lys Lys Gly Leu Pro His Ala
            35                  40                  45

Pro Ala Leu Ile Lys Arg Thr Asn Arg Arg Ile Pro Glu Arg Thr Ser
    50                  55                  60

His Arg Val Ala Asp His Ala Gln Val Val Arg Val Leu Gly Phe Phe
65                  70                  75                  80

Gln Cys His Ser His Pro Ala Gln Ala Phe Asp Asp Ala Met Thr Gln
                85                  90                  95

Phe Gly Met Ser Arg His Gly Leu Leu Gln Leu Phe Arg Arg Val Gly
            100                 105                 110

Val Thr Glu Leu Glu Ala Arg Ser Gly Thr Leu Pro Pro Ala Ser Gln
        115                 120                 125

Arg Trp Asp Arg Ile Leu Gln Ala Ser Gly Met Lys Arg Ala Lys Pro
    130                 135                 140

Ser Pro Thr Ser Thr Gln Thr Pro Asp Gln Ala Ser Leu His Ala Phe
145                 150                 155                 160

Ala Asp Ser Leu Glu Arg Asp Leu Asp Ala Pro Ser Pro Met His Glu
                165                 170                 175

Gly Asp Gln Thr Arg Ala Ser
            180
```

<210> SEQ ID NO 10
<211> LENGTH: 7

```
<212> TYPE: PRT
<213> ORGANISM: Artificial Sequence
<220> FEATURE:
<223> OTHER INFORMATION: Synthetic

<400> SEQUENCE: 10

Pro Lys Lys Lys Arg Lys Val
1               5

<210> SEQ ID NO 11
<211> LENGTH: 10
<212> TYPE: PRT
<213> ORGANISM: Artificial Sequence
<220> FEATURE:
<223> OTHER INFORMATION: Synthetic

<400> SEQUENCE: 11

Pro Lys Lys Lys Arg Lys Val Glu Ala Ser
1               5                   10

<210> SEQ ID NO 12
<211> LENGTH: 16
<212> TYPE: PRT
<213> ORGANISM: Artificial Sequence
<220> FEATURE:
<223> OTHER INFORMATION: Synthetic

<400> SEQUENCE: 12

Lys Arg Pro Ala Ala Thr Lys Lys Ala Gly Gln Ala Lys Lys Lys Lys
1               5                   10                  15

<210> SEQ ID NO 13
<211> LENGTH: 9
<212> TYPE: PRT
<213> ORGANISM: Artificial Sequence
<220> FEATURE:
<223> OTHER INFORMATION: Synthetic

<400> SEQUENCE: 13

Pro Ala Ala Lys Arg Val Lys Leu Asp
1               5

<210> SEQ ID NO 14
<211> LENGTH: 11
<212> TYPE: PRT
<213> ORGANISM: Artificial Sequence
<220> FEATURE:
<223> OTHER INFORMATION: Synthetic

<400> SEQUENCE: 14

Arg Gln Arg Arg Asn Glu Leu Lys Arg Ser Pro
1               5                   10

<210> SEQ ID NO 15
<211> LENGTH: 38
<212> TYPE: PRT
<213> ORGANISM: Artificial Sequence
<220> FEATURE:
<223> OTHER INFORMATION: Synthetic

<400> SEQUENCE: 15

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
```

-continued

<210> SEQ ID NO 16
<211> LENGTH: 42
<212> TYPE: PRT
<213> ORGANISM: Artificial Sequence
<220> FEATURE:
<223> OTHER INFORMATION: Synthetic

<400> SEQUENCE: 16

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 17
<211> LENGTH: 8
<212> TYPE: PRT
<213> ORGANISM: Artificial Sequence
<220> FEATURE:
<223> OTHER INFORMATION: Synthetic

<400> SEQUENCE: 17

Val Ser Arg Lys Arg Pro Arg Pro
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic

<400> SEQUENCE: 18

Pro Pro Lys Lys Ala Arg Glu Asp
1               5

<210> SEQ ID NO 19
<211> LENGTH: 8
<212> TYPE: PRT
<213> ORGANISM: Homo sapiens

<400> SEQUENCE: 19

Pro Gln Pro Lys Lys Lys Pro Leu
1               5

<210> SEQ ID NO 20
<211> LENGTH: 12
<212> TYPE: PRT
<213> ORGANISM: Mus sp.

<400> SEQUENCE: 20

Ser Ala Leu Ile Lys Lys Lys Lys Lys Met Ala Pro
1               5                   10

<210> SEQ ID NO 21
<211> LENGTH: 5
<212> TYPE: PRT
<213> ORGANISM: Influenza virus

<400> SEQUENCE: 21

Asp Arg Leu Arg Arg
1               5

<210> SEQ ID NO 22
<211> LENGTH: 7
<212> TYPE: PRT
<213> ORGANISM: Influenza virus

<400> SEQUENCE: 22

Pro Lys Gln Lys Lys Arg Lys
1               5

<210> SEQ ID NO 23
<211> LENGTH: 10
<212> TYPE: PRT
<213> ORGANISM: Hepatitis virus

<400> SEQUENCE: 23

Arg Lys Leu Lys Lys Ile Lys Lys Leu
1               5                   10

<210> SEQ ID NO 24
<211> LENGTH: 10
<212> TYPE: PRT
<213> ORGANISM: Mus sp.

<400> SEQUENCE: 24

Arg Glu Lys Lys Lys Phe Leu Lys Arg Arg
1               5                   10

<210> SEQ ID NO 25
<211> LENGTH: 20
<212> TYPE: PRT
<213> ORGANISM: Homo sapiens

<400> SEQUENCE: 25

Lys Arg Lys Gly Asp Glu Val Asp Gly Val Asp Glu Val Ala Lys Lys
1               5                   10                  15

Lys Ser Lys Lys
            20

<210> SEQ ID NO 26
<211> LENGTH: 17
<212> TYPE: PRT
<213> ORGANISM: Homo sapiens

<400> SEQUENCE: 26

Arg Lys Cys Leu Gln Ala Gly Met Asn Leu Glu Ala Arg Lys Thr Lys
1               5                   10                  15

Lys

<210> SEQ ID NO 27
<211> LENGTH: 107
<212> TYPE: PRT
<213> ORGANISM: Artificial Sequence
<220> FEATURE:
<223> OTHER INFORMATION: Synthetic

<400> SEQUENCE: 27

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

```
Val Leu Ala Cys Tyr Ser Leu Leu Val Thr Val Ala Phe Ile Ile Phe
    50                  55                  60

Trp Val Arg Ser Lys Arg Ser Arg Leu Leu His Ser Asp Tyr Met Asn
65                  70                  75                  80

Met Thr Pro Arg Arg Pro Gly Pro Thr Arg Lys His Tyr Gln Pro Tyr
                85                  90                  95

Ala Pro Pro Arg Asp Phe Ala Ala Tyr Arg Ser
                100                 105

<210> SEQ ID NO 28
<211> LENGTH: 9
<212> TYPE: PRT
<213> ORGANISM: Artificial Sequence
<220> FEATURE:
<223> OTHER INFORMATION: Synthetic

<400> SEQUENCE: 28

Ile Glu Val Met Tyr Pro Pro Pro Tyr
1               5

<210> SEQ ID NO 29
<211> LENGTH: 107
<212> TYPE: PRT
<213> ORGANISM: Artificial Sequence
<220> FEATURE:
<223> OTHER INFORMATION: Synthetic

<400> SEQUENCE: 29

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
            35                  40                  45

Val Leu Ala Cys Tyr Ser Leu Leu Val Thr Val Ala Phe Ile Ile Phe
    50                  55                  60

Trp Val Arg Ser Lys Arg Ser Arg Leu Leu His Ser Asp Tyr Met Asn
65                  70                  75                  80

Met Thr Pro Arg Arg Pro Gly Pro Thr Arg Lys His Tyr Gln Pro Tyr
                85                  90                  95

Ala Pro Pro Arg Asp Phe Ala Ala Tyr Arg Ser
                100                 105
```